(12) United States Patent
Papkoff et al.

(10) Patent No.: US 8,080,650 B2
(45) Date of Patent: Dec. 20, 2011

(54) PRO104 ANTIBODY COMPOSITIONS AND METHODS OF USE

(75) Inventors: Jackie Papkoff, San Francisco, CA (US); Glenn Pilkington, Rye (AU); Gilbert-Andre Keller, Belmont, CA (US); Wenlu Li, South San Francisco, CA (US); Laura Corral, Belmont, MA (US); Iris Simon, Amsterdam (NL); Muriel Kmet, Palo Alto, CA (US); Jianwen Tang, Freemont, CA (US)

(73) Assignee: diaDexus, Inc., South San Francisco, CA (US)

( * ) Notice: Subject to any disclaimer, the term of this patent is extended or adjusted under 35 U.S.C. 154(b) by 139 days.

(21) Appl. No.: 12/354,047

(22) Filed: Jan. 15, 2009

(65) Prior Publication Data

US 2009/0220424 A1 Sep. 3, 2009

Related U.S. Application Data

(63) Continuation of application No. 10/562,259, filed as application No. PCT/JP2004/020741 on Jun. 28, 2004, now Pat. No. 7,479,546.

(60) Provisional application No. 60/485,346, filed on Jun. 27, 2003, provisional application No. 60/523,271, filed on Nov. 17, 2003.

(51) Int. Cl.
*C07H 21/04* (2006.01)
(52) U.S. Cl. .................................... 536/24.5
(58) Field of Classification Search ................... 536/24.5
See application file for complete search history.

(56) References Cited

U.S. PATENT DOCUMENTS

| | | | |
|---|---|---|---|
| 6,180,370 B1 | 1/2001 | Queen et al. | |
| 6,203,979 B1 | 3/2001 | Bandman et al. | 435/6 |
| 6,333,410 B1 | 12/2001 | Chari et al. | 540/456 |
| 6,479,274 B1 | 11/2002 | Antalis et al. | 435/252.3 |
| 7,618,814 B2 * | 11/2009 | Bentwich | 435/320.1 |
| 7,709,616 B2 * | 5/2010 | Bentwich et al. | 536/23.1 |
| 2004/0146862 A1 | 7/2004 | Mack et al. | 435/6 |
| 2007/0031844 A1 * | 2/2007 | Khvorova et al. | 435/6 |

FOREIGN PATENT DOCUMENTS

WO WO 98/36054 8/1998

OTHER PUBLICATIONS

Bass (2001, Nature, v.411:428-9).*
Elbashir, et al. (2001, Nature, v.411:494-8).*
Elbashir, et al. (2001, EMBO J., v.20:6877-88).*
Hooper et al. Biochim Biophys Acta. 2000 1492, 63-71.*
EMBL Accession No. AA525010 Jul. 19, 1997.
Blok et al., "Isolation of cDNAs That Are Differentially Expressed Between Androgen-Dependent and Androgen-Independent Prostate Carcinoma Cells Using Differential Display PCT", The Prostate 1995 26:213-224.
Chang et al., "Differentially Expressed Genes in Androgen-dependent and -independent Prostate Carcinomas", Cancer Research 1997 57:4075-4081.
Friedrich et al., "Differentiation-Stage Specific Expression of Oncoprotein 18 in Human and Rat Prostatic Adenocarcinoma", The Prostate 1995 27:102-109.
Hooper et al., "Testisin, a New Human Serine Proteinase Expressed by Premeiotic Testicular Germ Cells and Lost in Testicular Germ Cell Tumors", Cancer Research 1999 59:3199-3205.
Inoue et al., "Cloning and Tissue Distribution of a Novel Serine Protease esp-1 from Human Eosinophils", Biochemical and Biophysical Research Communications 1998 252:307-312.
Fundamental Immunology 242 William E. Paul, M.D. ed., 3d ed. p. 242, 1993.

* cited by examiner

*Primary Examiner* — Brian Whiteman
(74) *Attorney, Agent, or Firm* — Licata & Tyrrell, P.C.; Keith R McCollum

(57) ABSTRACT

The invention provides isolated anti-ovarian, pancreatic, lung or breast cancer antigen (Pro104) antibodies that bind to Pro104 on a mammalian cell in vivo. The invention also encompasses compositions comprising an anti-Pro104 antibody and a carrier. These compositions can be provided in an article of manufacture or a kit. Another aspect of the invention is an isolated nucleic acid encoding an anti-Pro104 antibody, as well as an expression vector comprising the isolated nucleic acid. Also provided are cells that produce the anti-Pro104 antibodies. The invention encompasses a method of producing the anti-Pro104 antibodies. Other aspects of the invention are a method of killing a Pro104-expressing cancer cell, comprising contacting the cancer cell with an anti-Pro104 antibody and a method of alleviating or treating a Pro104-expressing cancer in a mammal, comprising administering a therapeutically effective amount of the anti-Pro104 antibody to the mammal.

12 Claims, 35 Drawing Sheets

FIGURE 1. Pro104.D116.1 MAb Binds to 293F Cells Transiently Transfected with Pro104

No Fill: Pro104.D116.1 MAb
Shaded: Ovr110.A57.1 Control MAb

FIGURE 2. Pro104.D118.1 MAb Binds to 293F Cells Transiently Transfected with Pro104

Untransfected 293F Cells

Pro104-Transfected 293F Cells

No Fill: Pro104.D118.1 MAb
Shaded: Ovr110.A57.1 Control MAb

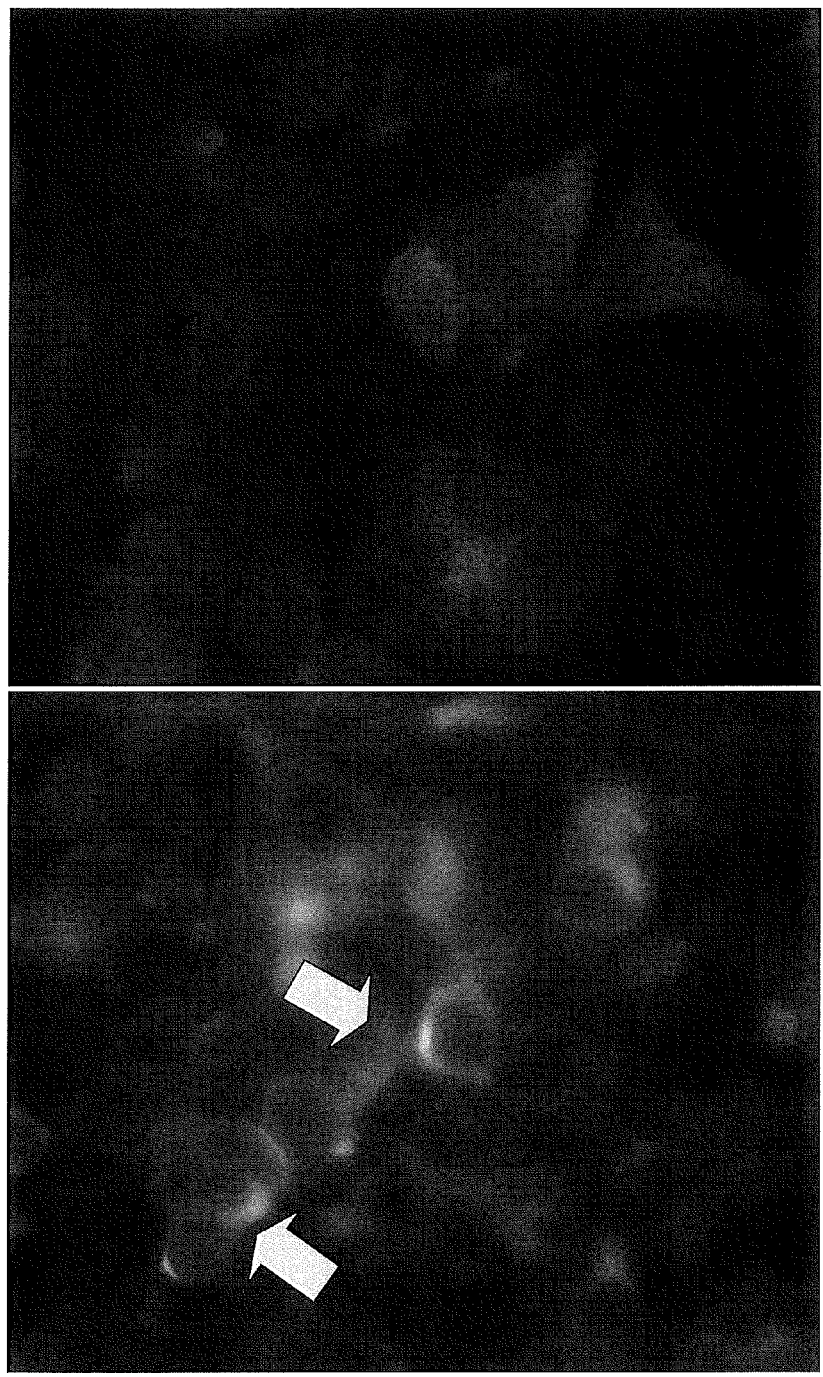
FIGURE 3. Pro104.C19.1 binds to live HeLa Cancer Cells Expressing Pro104
Fig. 3A. HeLa Cells    N= Nuclei    Fig. 3B. SKOV-3 cells

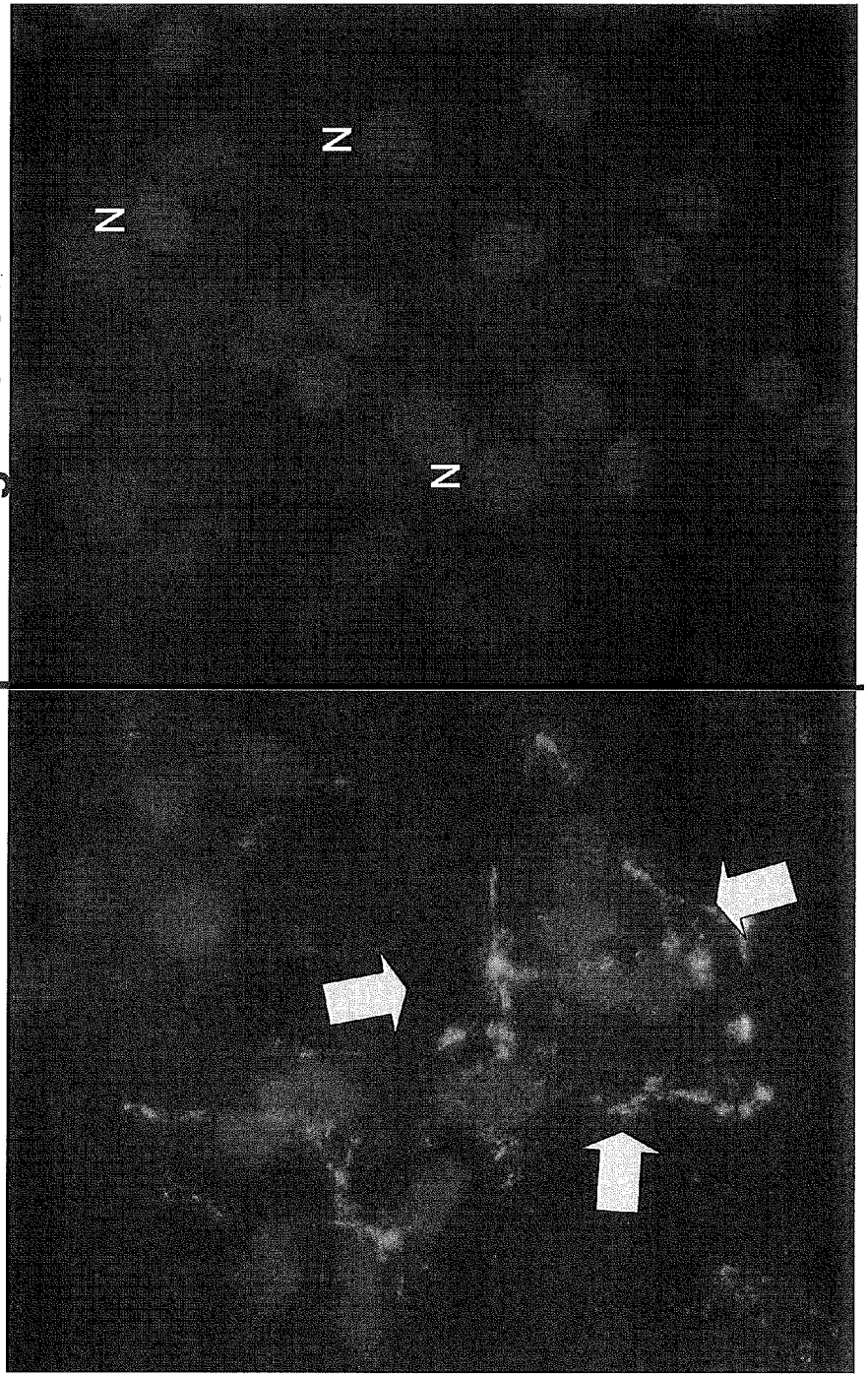
FIGURE 4. Cy3-Pro104.C25.1 binds to live HeLa Cancer Cells Expressing Pro104
Fig. 4A. HeLa Cells    N= Nuclei    Fig. 4B. SKOV-3 cells

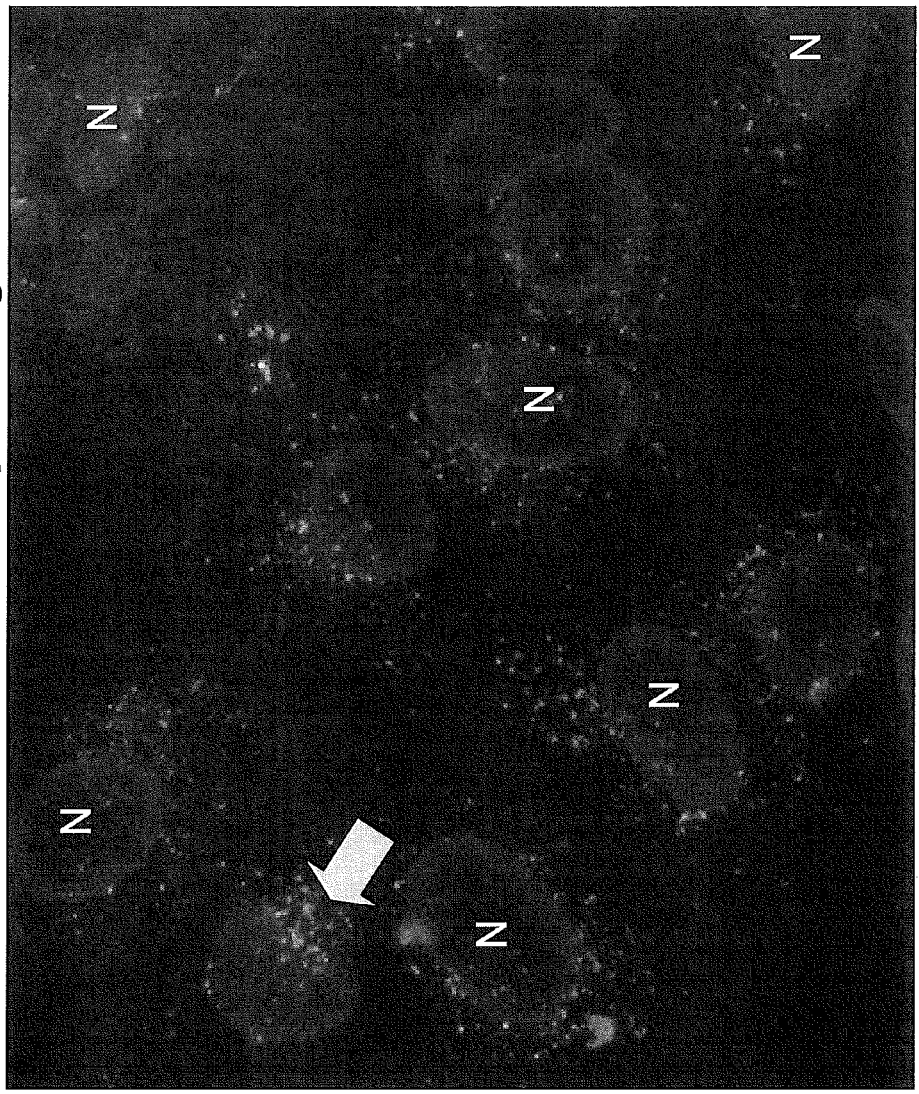
FIGURE 5. Cy3-Pro104.C25.1 binds to and is Internalized in live HeLa Cancer Cells Expressing Pro104
N= Nuclei

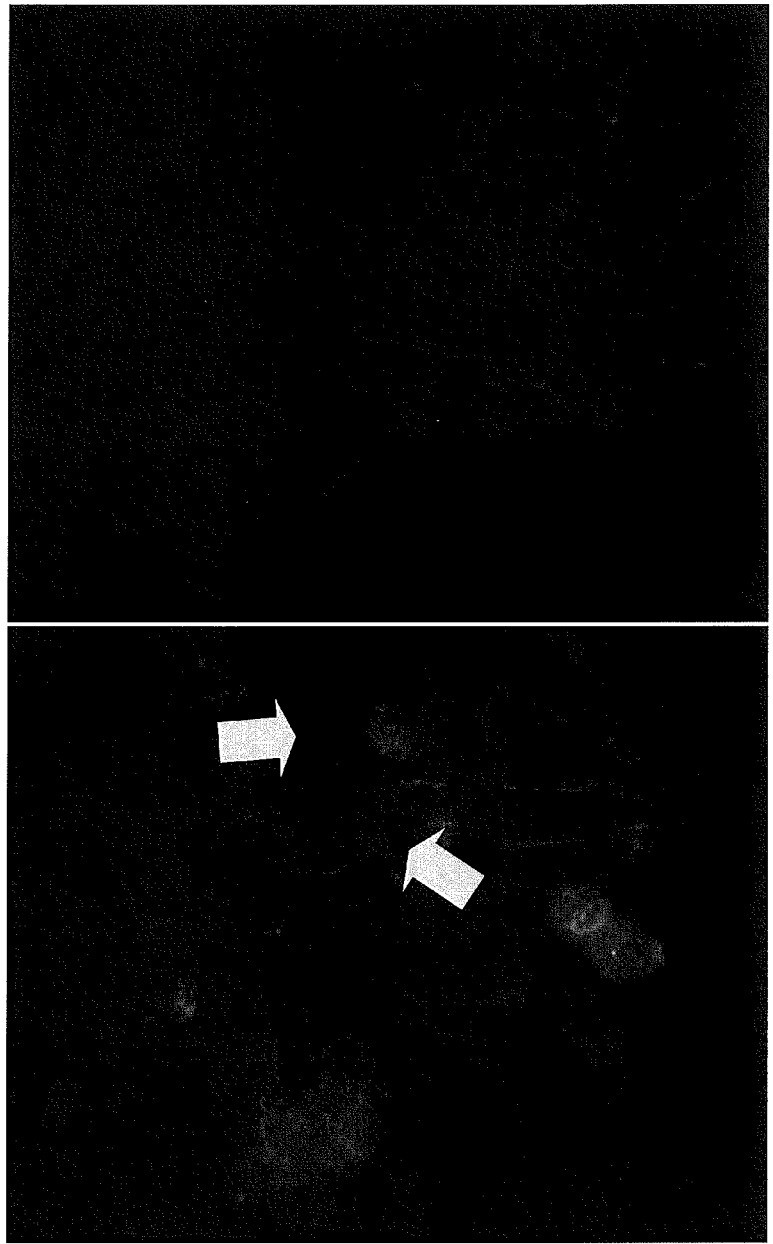
FIGURE 6. Cy3-Pro104.C19.1 binds to and is Internalized in Pancreatic Cancer Cells Expressing Pro104
Fig. 6A. MIA PaCa-2 Cells
Fig. 6B. HCT-116 cells
N= Nuclei

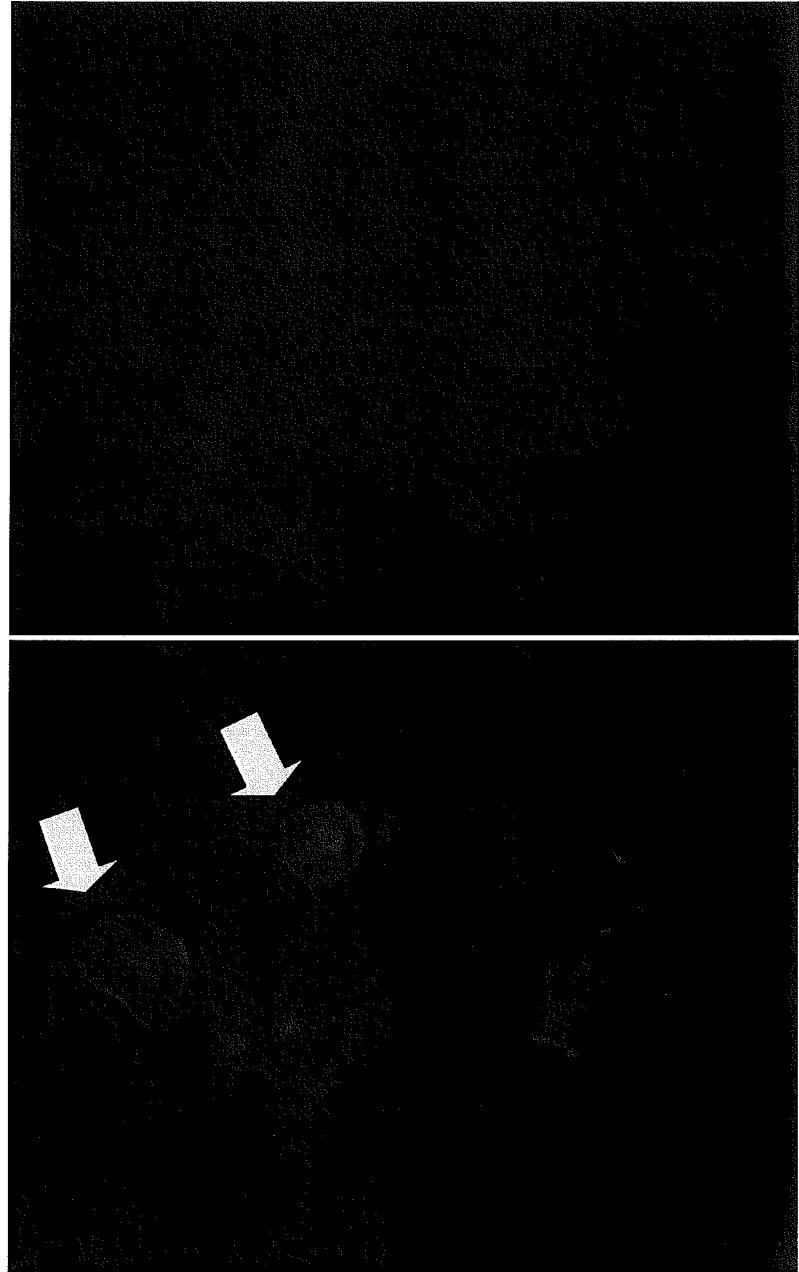
FIGURE 7. Cy3-Pro104.C55.1 binds to and is Internalized in Pancreatic Cancer Cells Expressing Pro104
Fig. 7A. MIA PaCa-2 Cells     Fig. 7B. HCT-116 cells
N= Nuclei FIGURE 8. Pro104.C25.1 binds to Pro104 on Cancer Cells in Ovarian Tumors
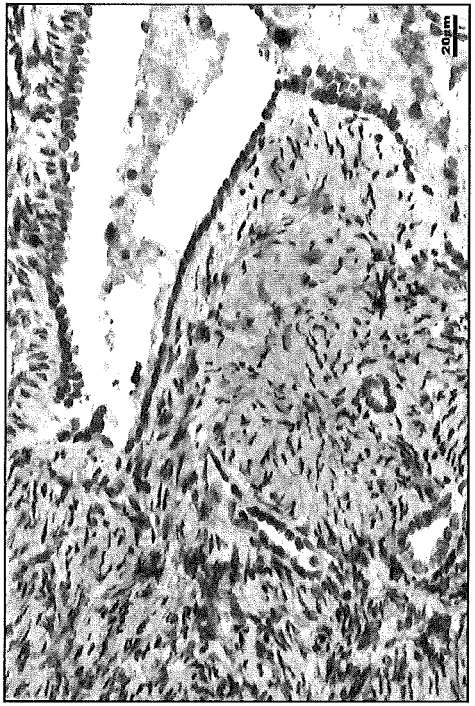
Fig. 8A ovarian cancer 1
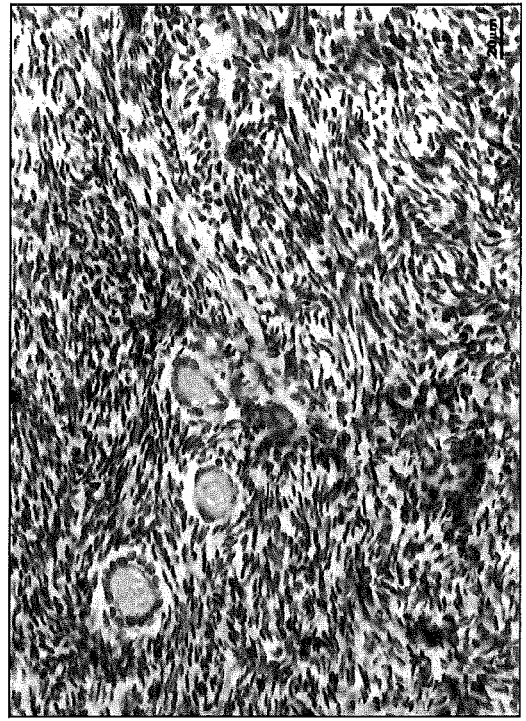
Fig. 8B normal ovary 1
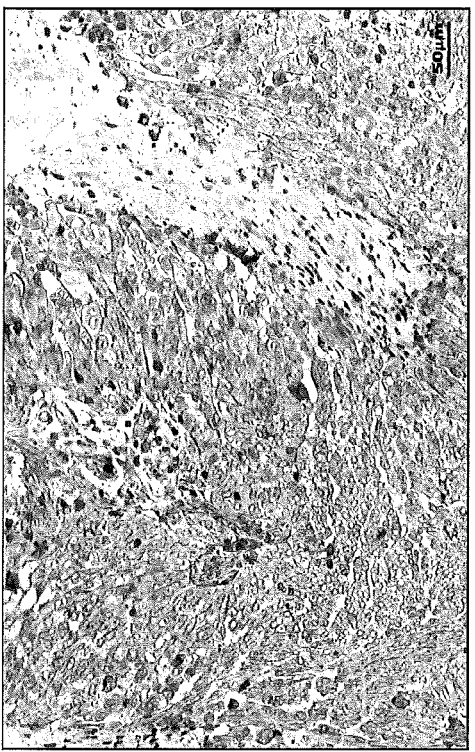
Fig. 8C ovarian cancer 2
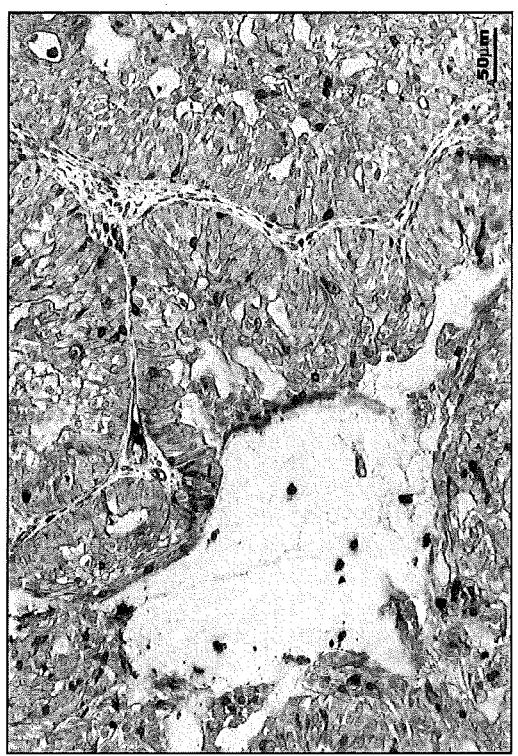
Fig. 8D normal ovary 2

FIGURE 9. Pro104.C25.1 binds to Pro104 on the Cell Membrane of Ovarian Cancer Cells

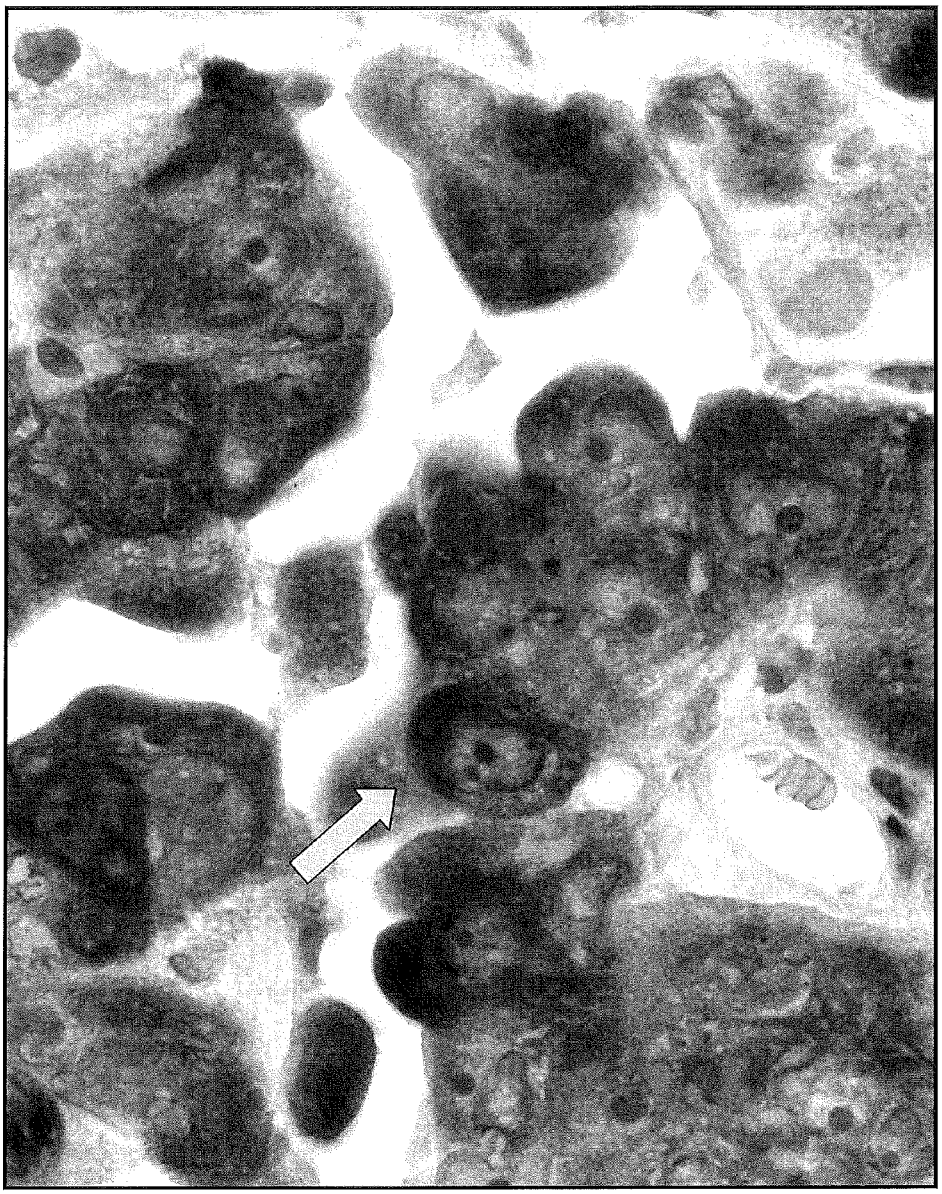
FIGURE 10. Pro104.D9 binds to Pro104 on the Cell Membrane of Ovarian Cancer Cells

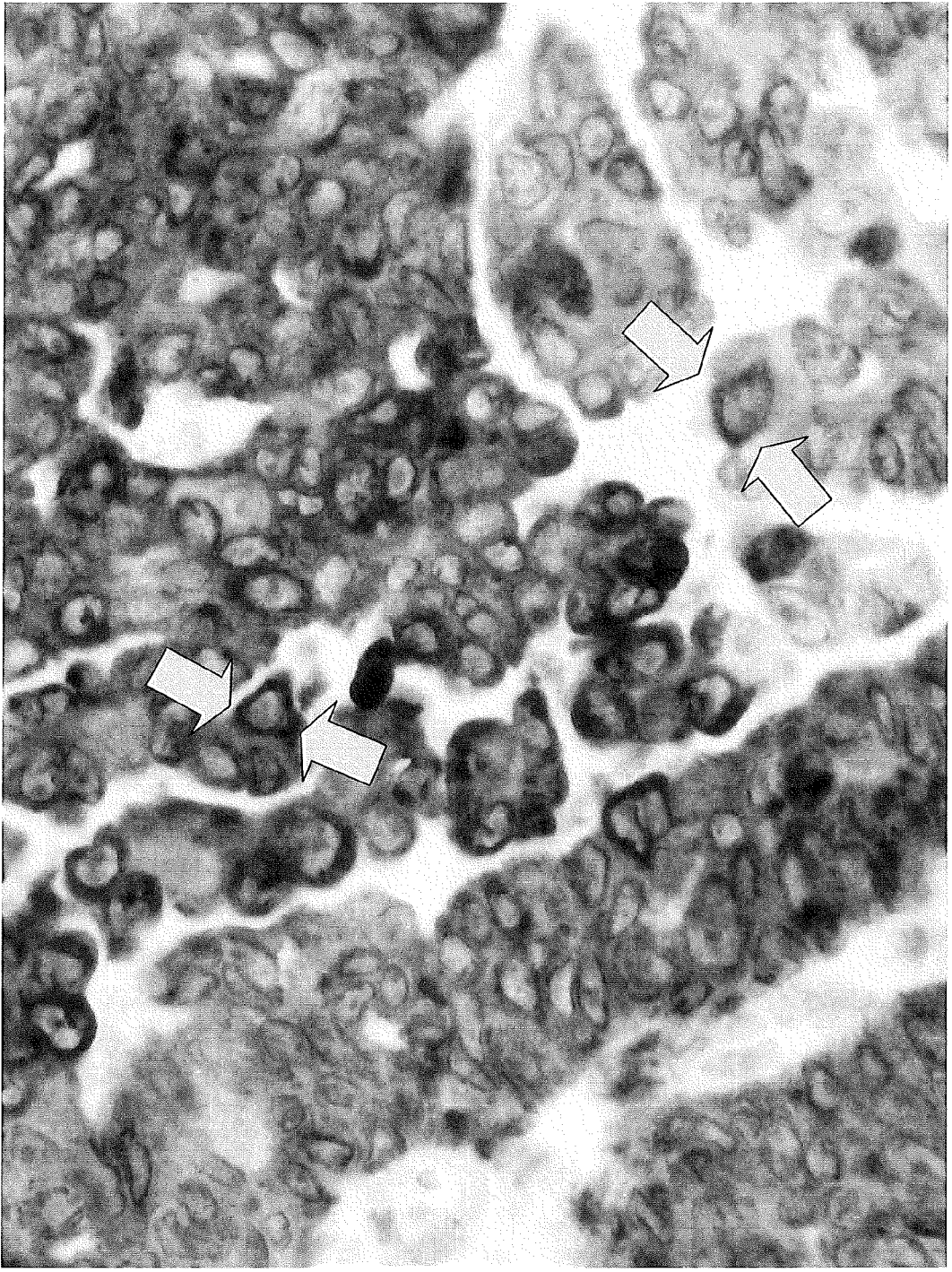
FIGURE 11. Pro104.D133 binds to Pro104 on the Cell Membrane of Serous Ovarian Cancer Cells

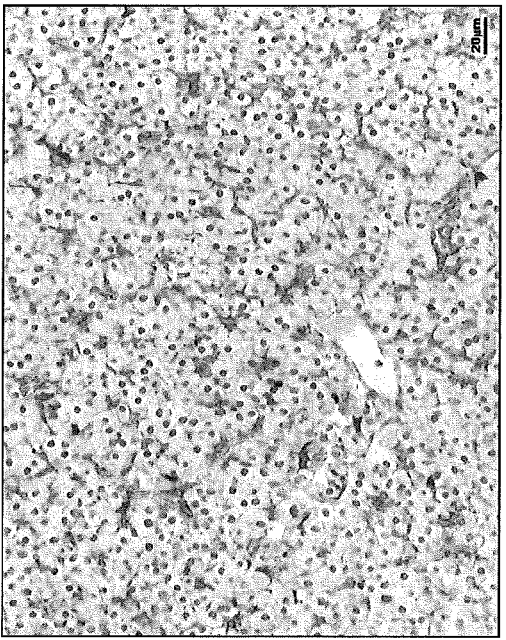
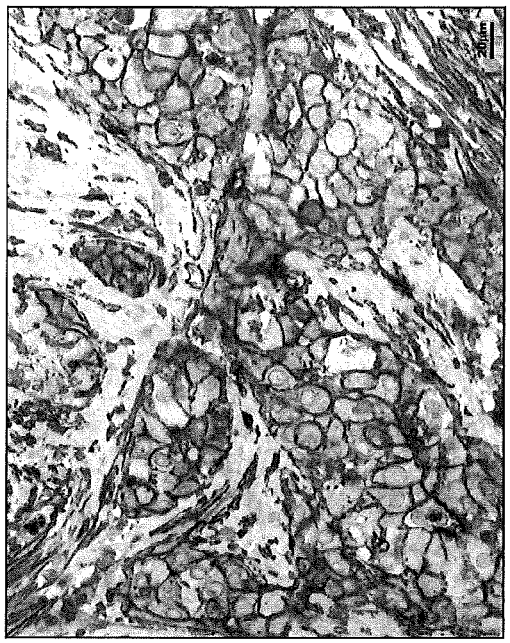
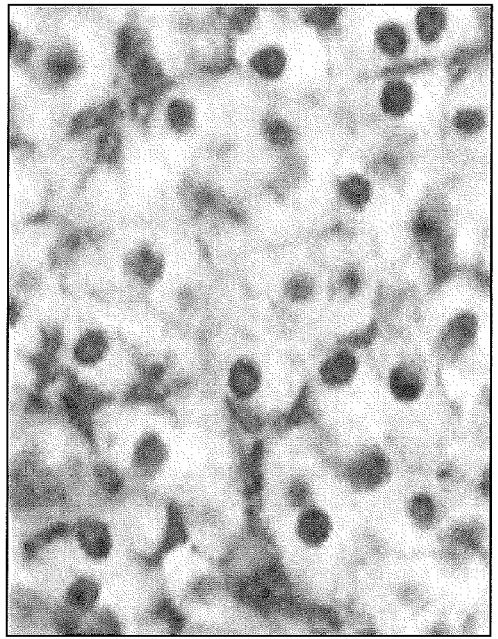
FIGURE 12. Pro104.C25.1 binds to Pro104 on Cancer Cells in Pancreatic Tumors
Fig. 12A Pancreatic cancer 1
Fig. 12B Normal pancreas 1
Fig. 12C Pancreatic cancer 2
Fig. 12D Normal pancreas 2

FIGURE 13. Controls Demonstrating Pro104 MAb Immunolabeling Specificity
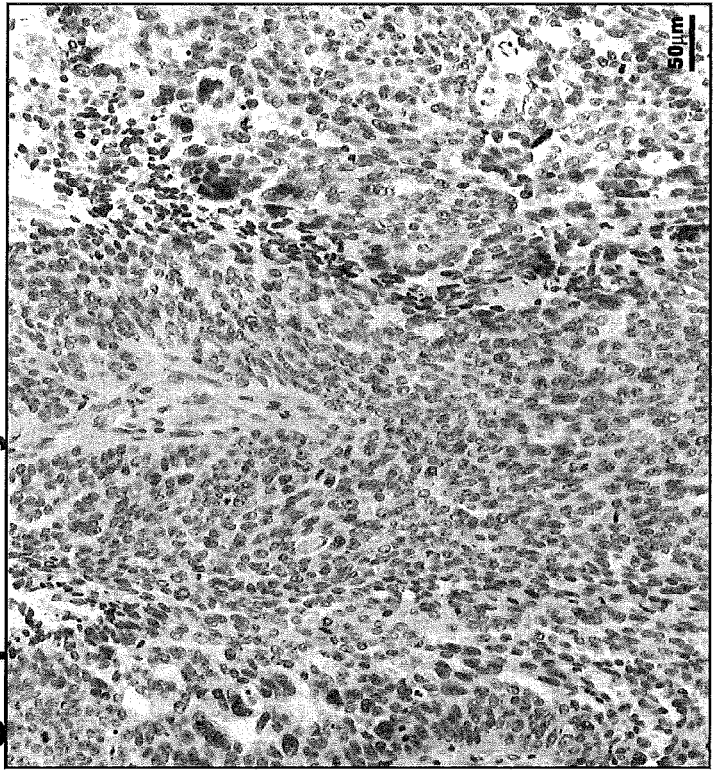
Fig. 13B Absorption with Pro104 Antigen
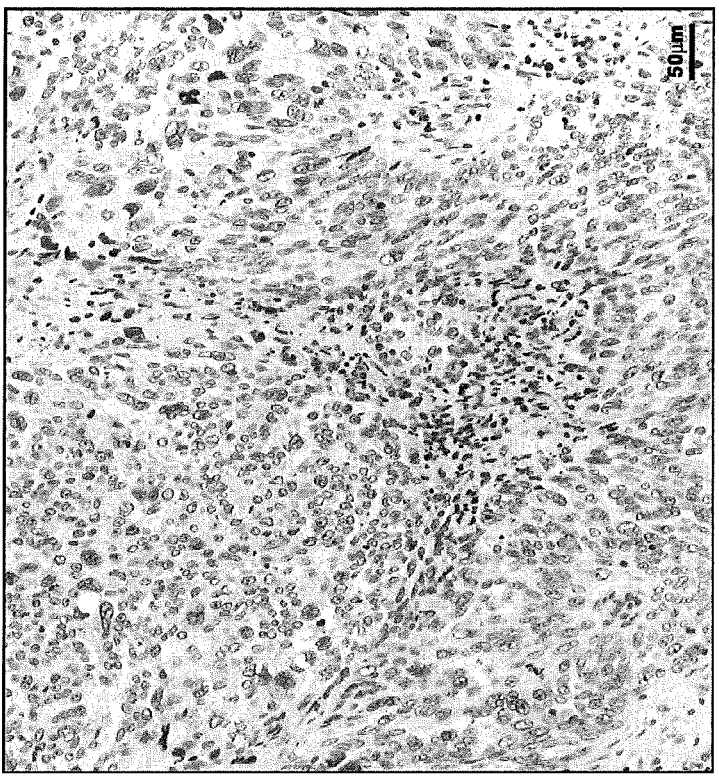
Fig. 13A Mouse IgG

Figure 14: Epitope Map of Pro104 MAbs
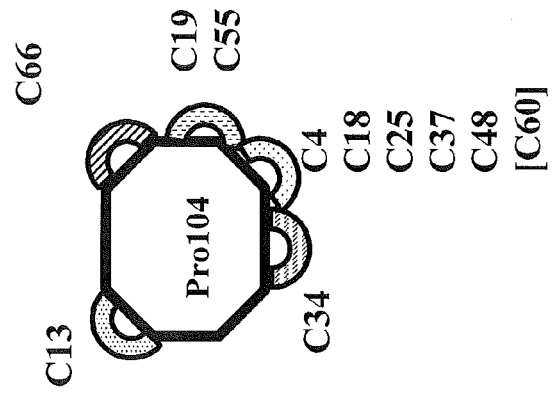
Pairs tested on Training Serum and Cell Line Panel:
C4/ C13; C48/ C13; C13/ C18; C19/ C48; C55/ C34; C66/ C18; C19/C25; C55/C25

FIGURE 15
Western Blot Showing Detection of Pro104 Protein in mRNA+ Cell Lines and Ovarian Tumor Tissue (T) but not Normal Adjacent Tissue (N)
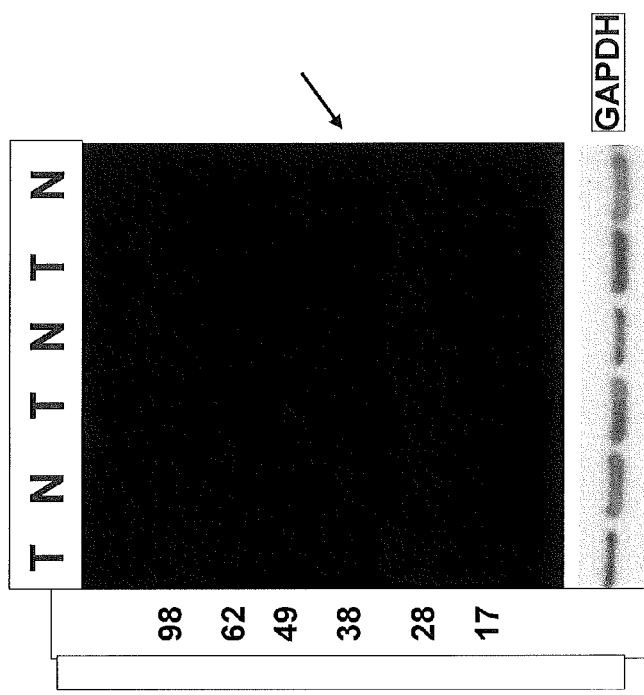
Fig. 15A
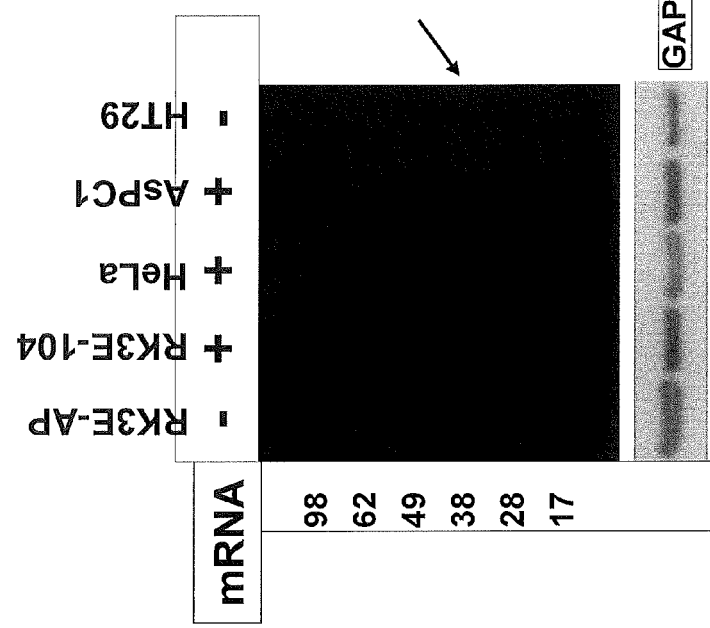
Fig. 15B
Arrow indicates location of Pro104 band

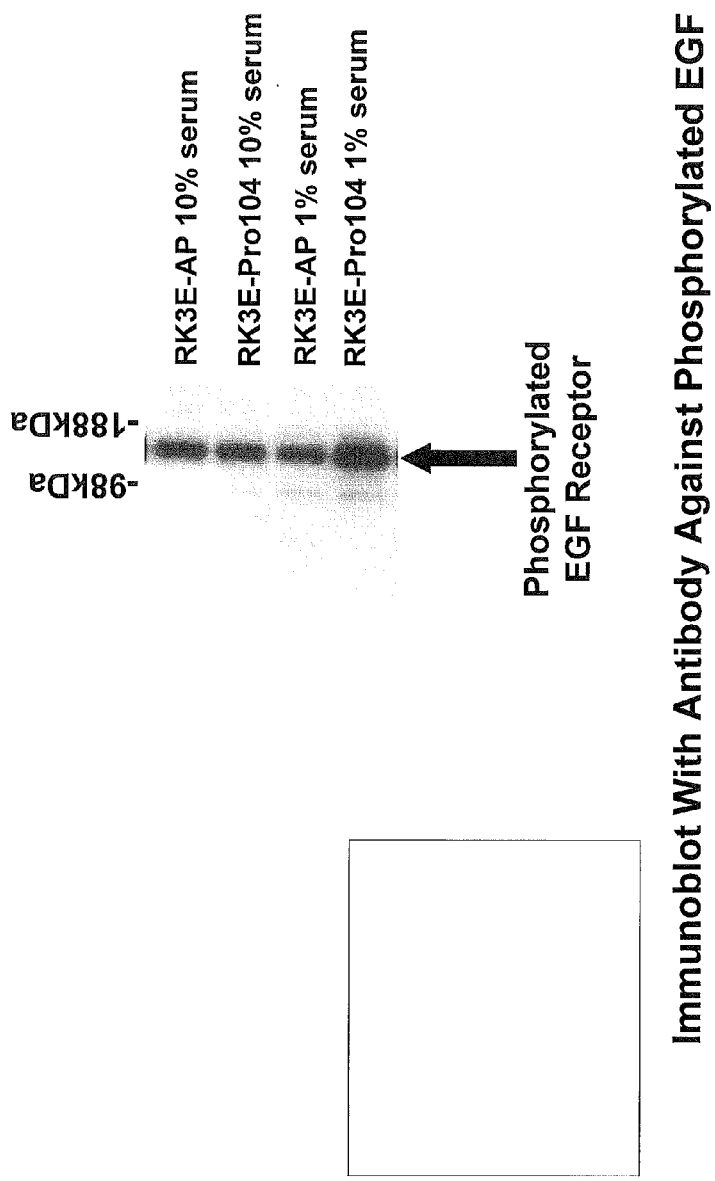

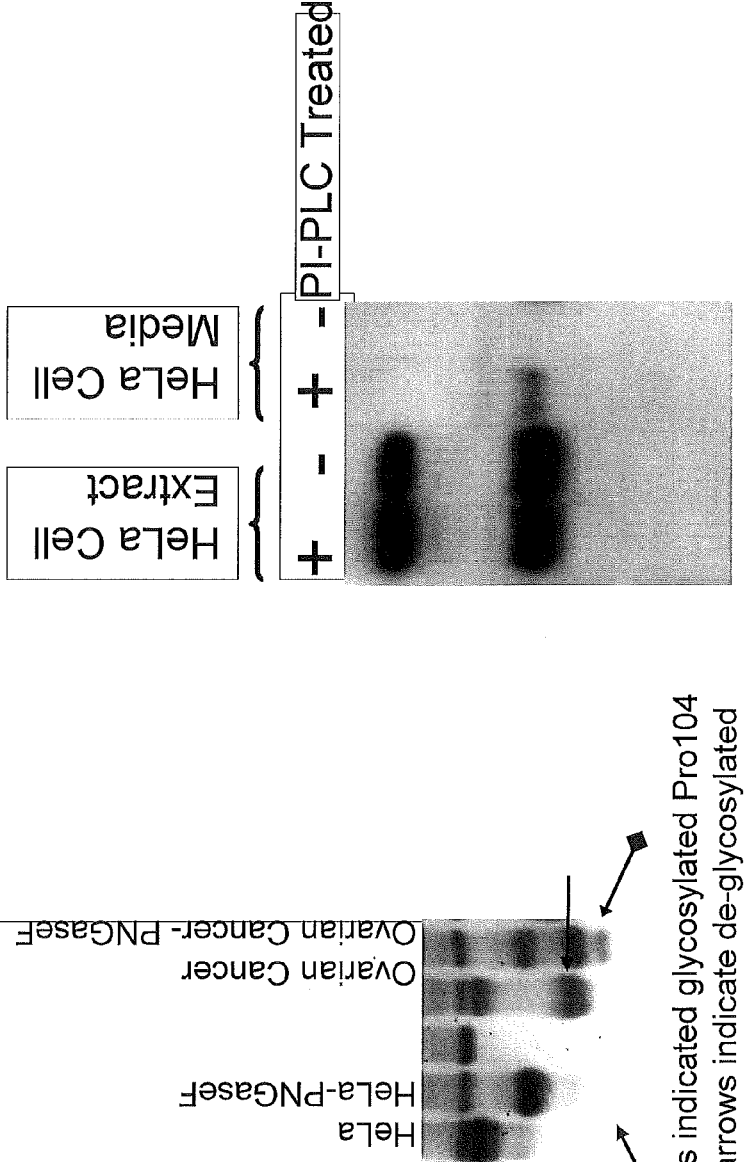

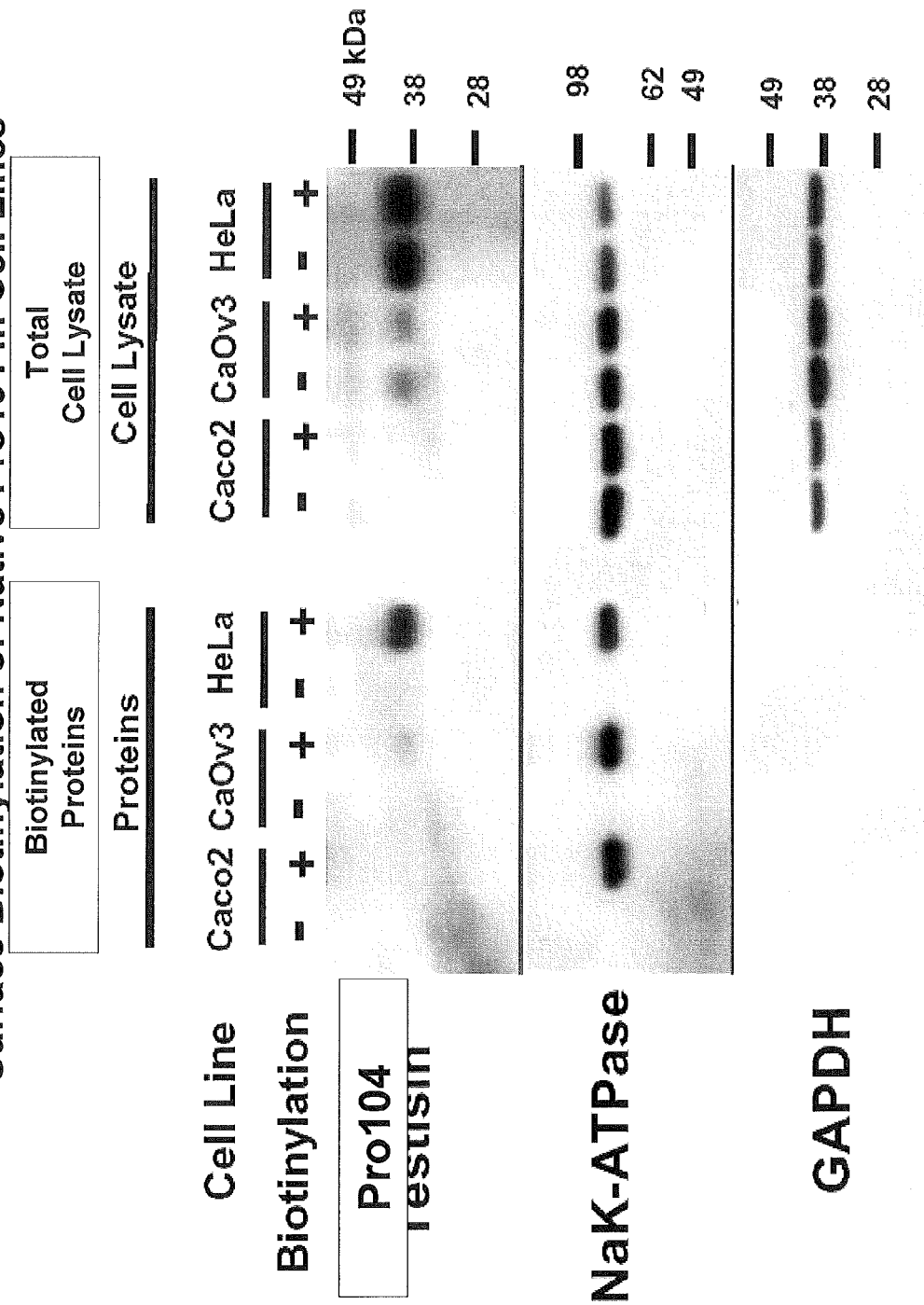

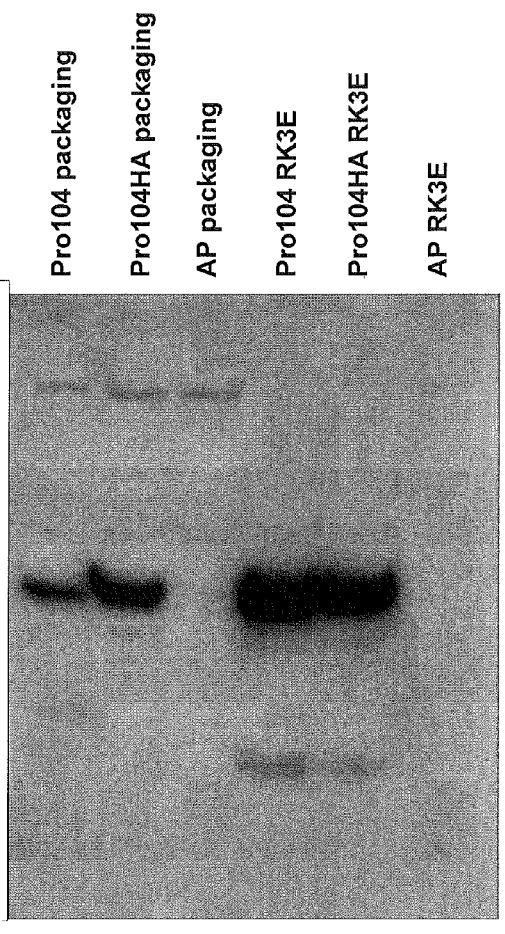

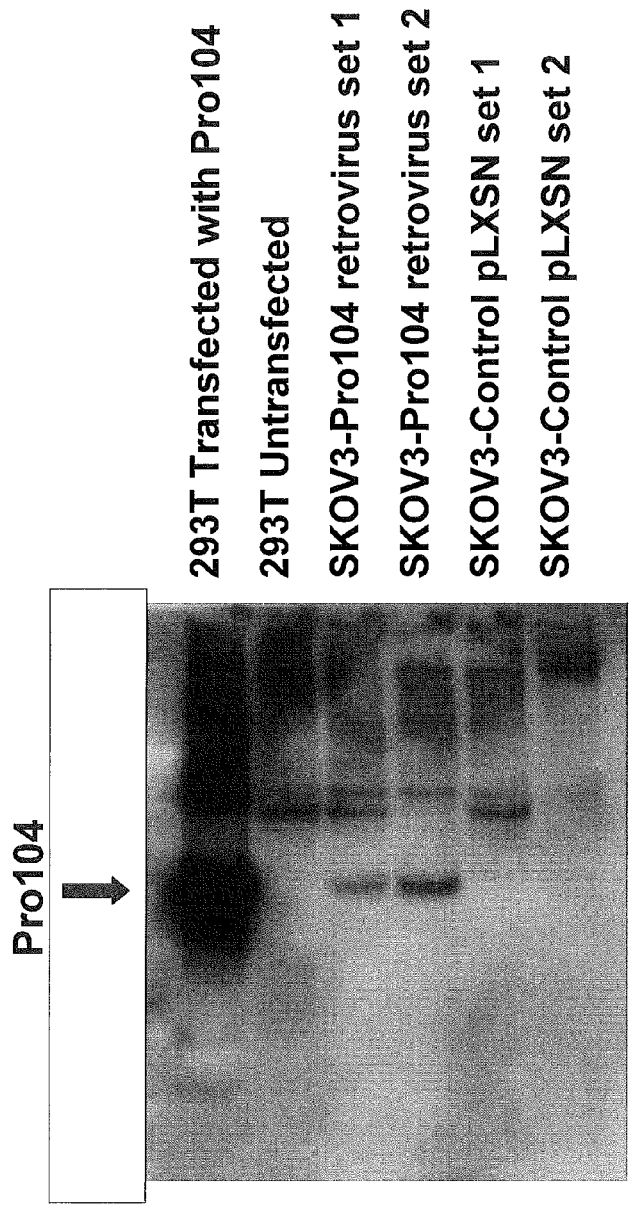

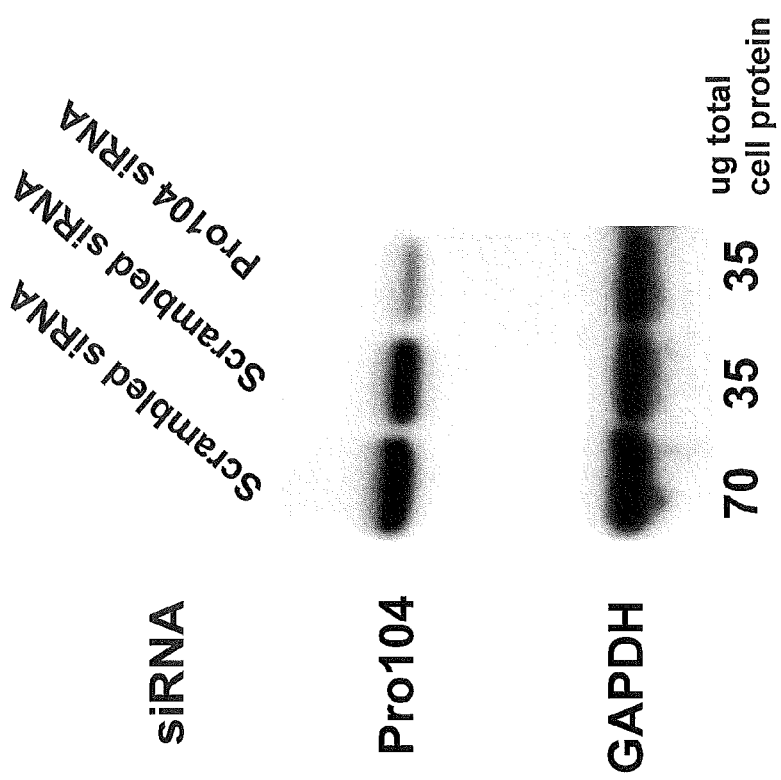

siRNA Mediates Down-Regulation of Pro104 Protein in CaOV3 Cells

FIGURE 23
Pro104 siRNA Specifically Knockdown Pro104 mRNA in CaOV3 Cells
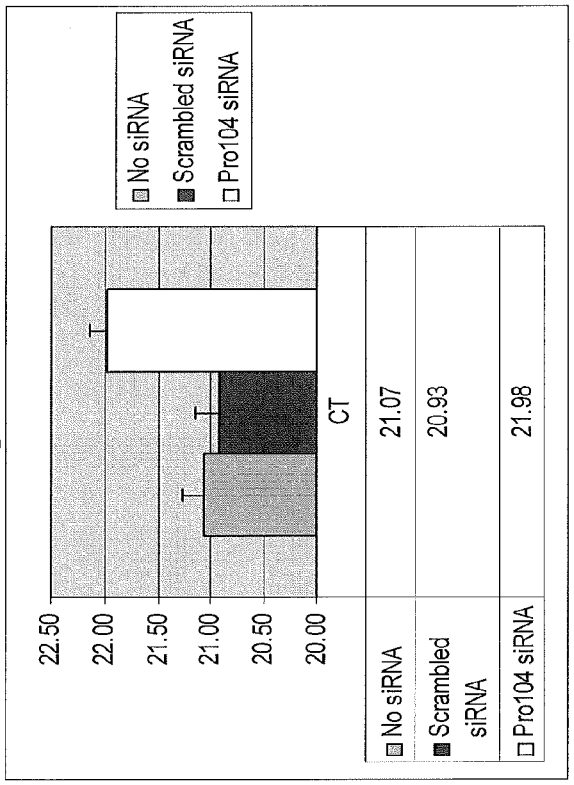
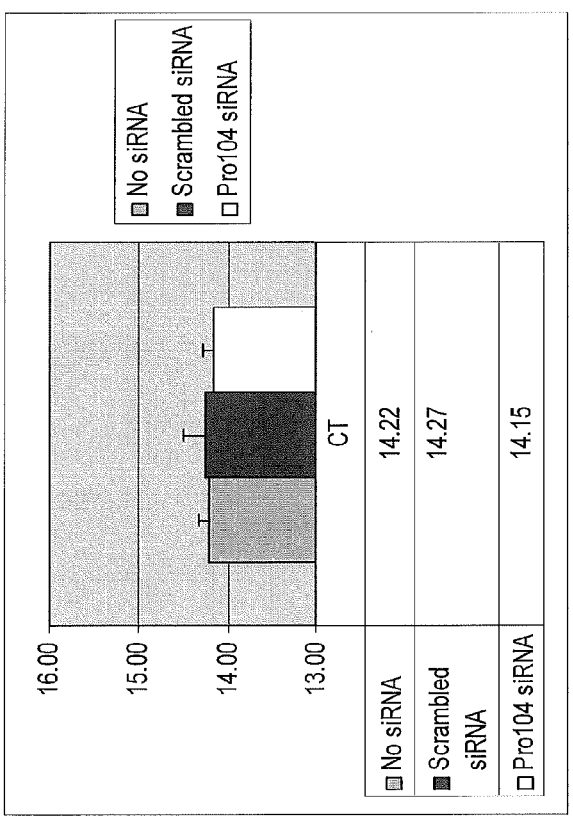
ΔCT =1 for Pro104 (Knockdown 50%)

FIGURE 24
Pro104 siRNA Specifically Knockdown Pro104 mRNA in HeLa Cells
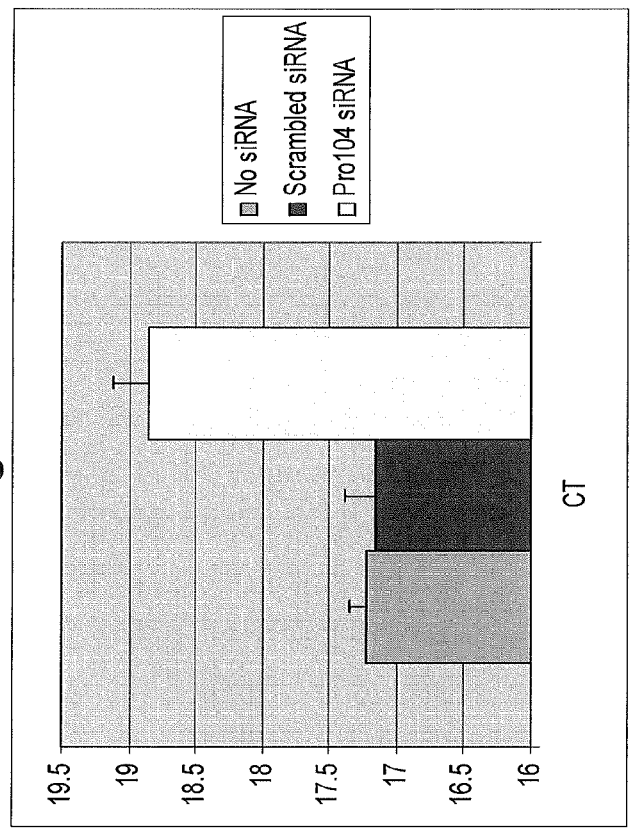
Fig. 24A
GAPDH Q-PCR Primers
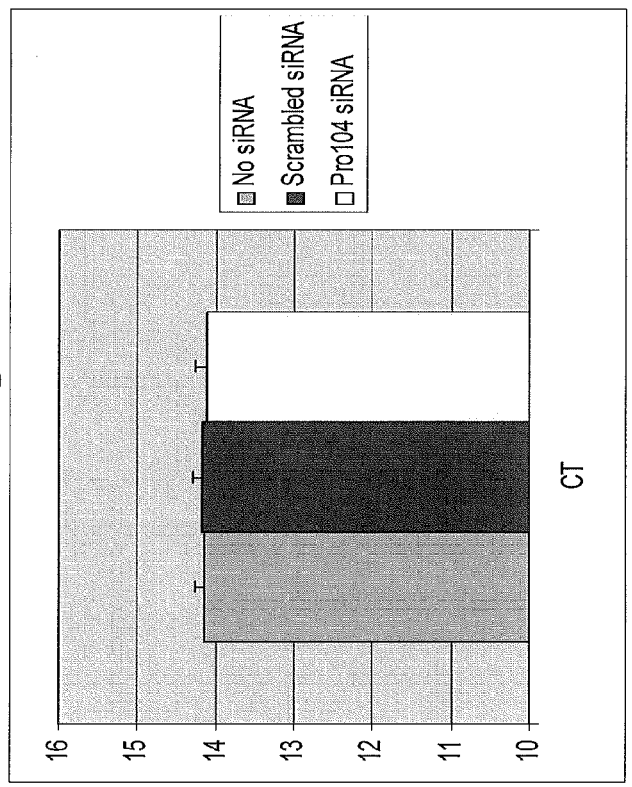
Fig. 24B
Pro104 Q-PCR Primers
$\Delta$ CT = 2 for Pro104 (Knockdown 75%)

FIGURE 26
Different Pro104 siRNAs Induce Specific mRNA Knockdown and Apoptosis in HeLa Cells
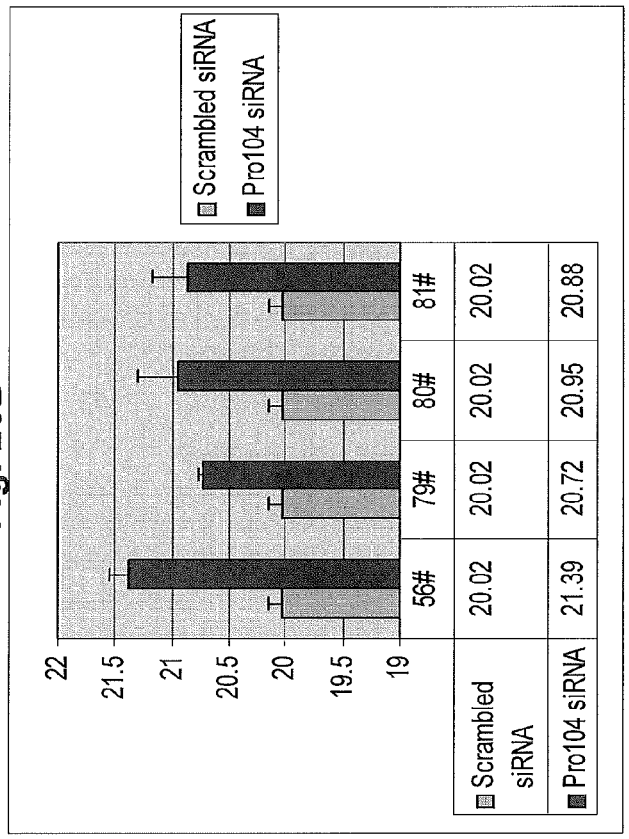
Fig. 26B
QPCR demonstrates Pro104 mRNA knockdown
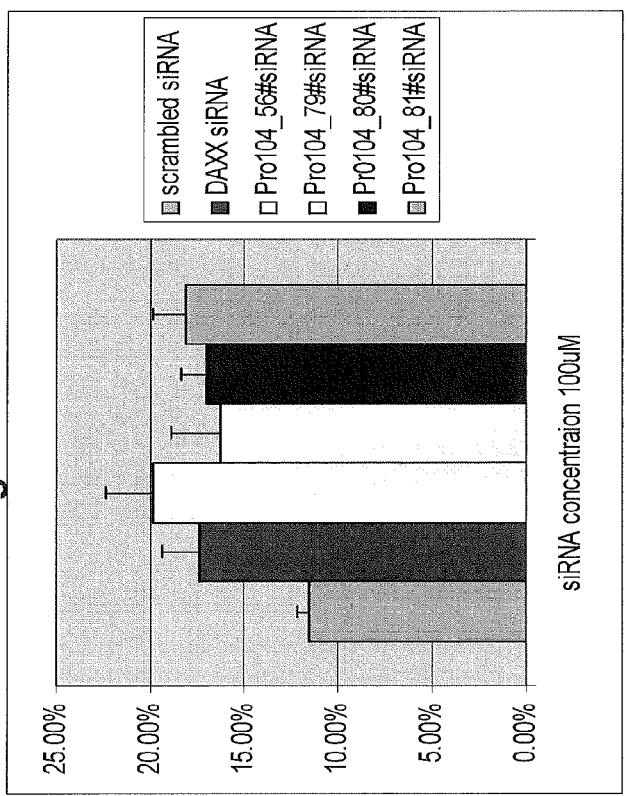
Fig. 26A
Annexin V assay for apoptosis
(DAXX positive control)

FIGURE 27
Specific Knockdown of Pro104 mRNA in HeLa Cells Induces Cell Death
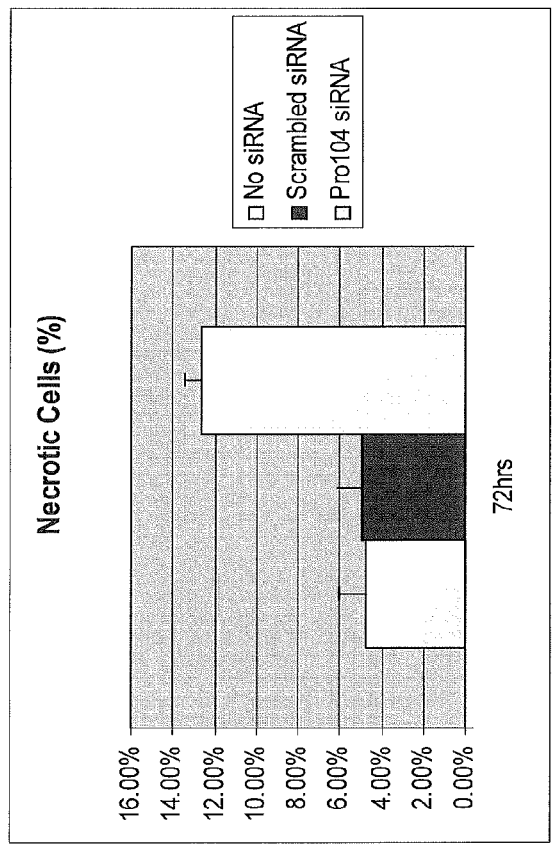
Fig. 27A
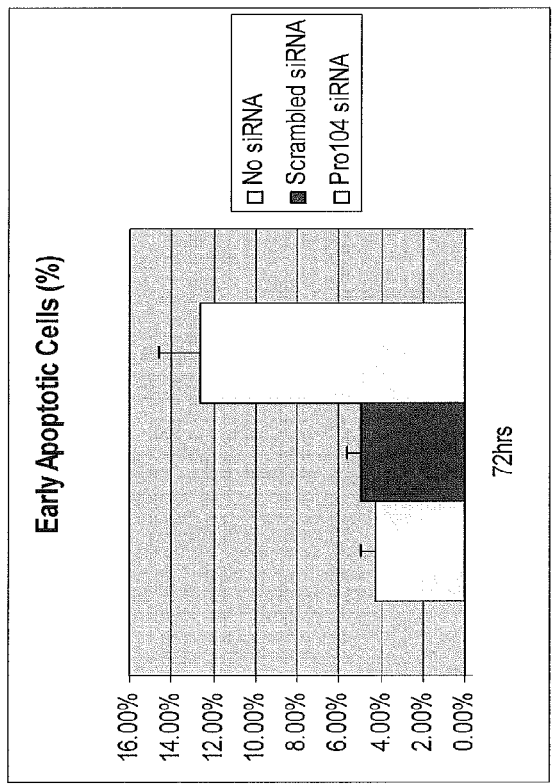
Fig. 27B
Annexin V Assay

FIGURE 28
Specific mRNA Knockdown by Pro104 siRNA Induces Apoptosis in HeLa Cells; Measured by Two Different Methods
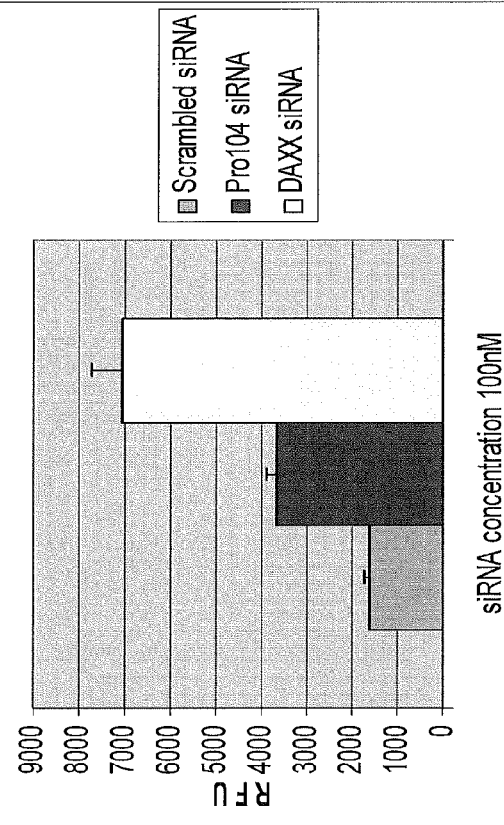
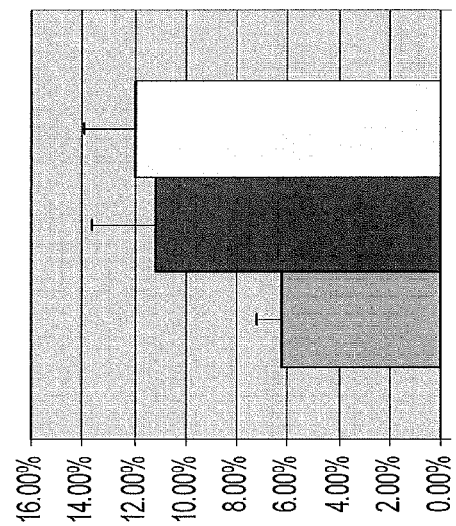
Apoptosis assays of cells treated with Pro104 siRNA

FIGURE 30
Pro104 siRNA Has no Effect on Apoptosis in Cells Without Pro104 mRNA
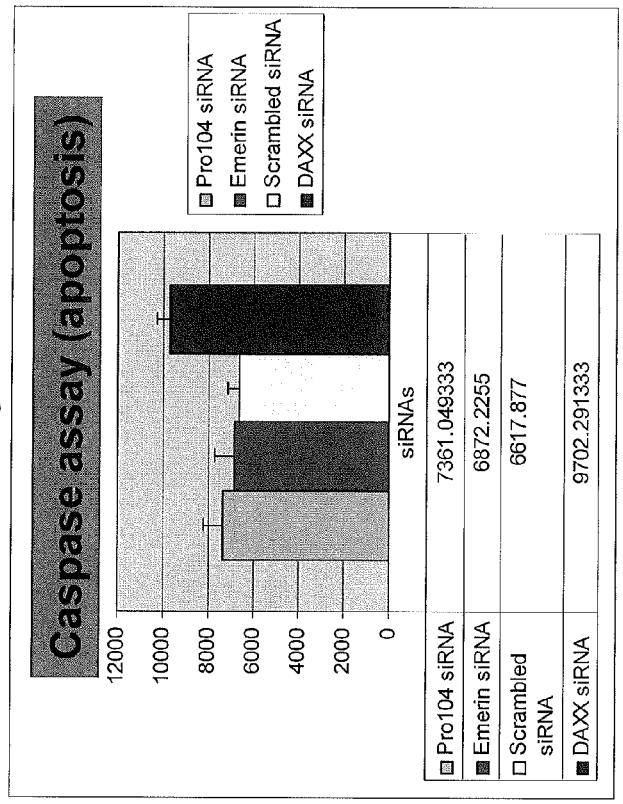
Fig. 30A
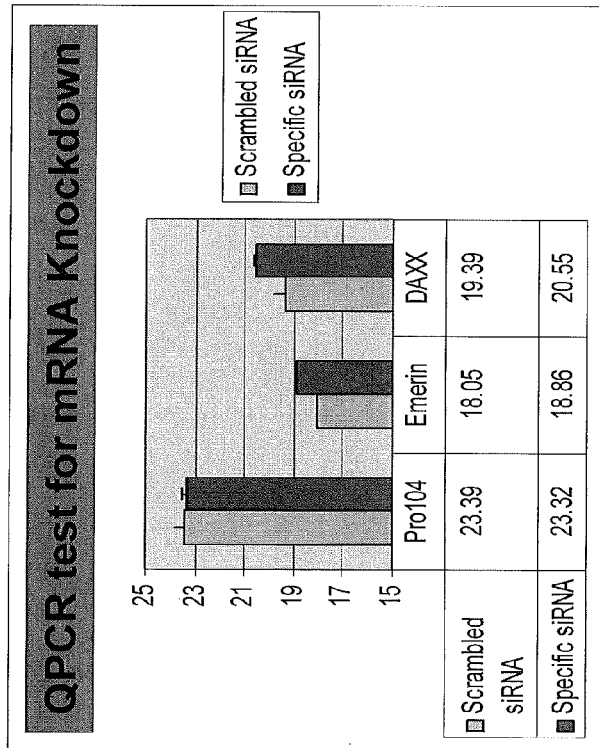
Fig. 30B
SKBR3 cells
Knockdown:
Pro104: none (no mRNA)
DAXX: 65% (positive control)
Emerin: 50% (mRNA +, non-essential)

FIGURE 31
Overexpression of Pro104 Induces Cell Growth in Soft Agar
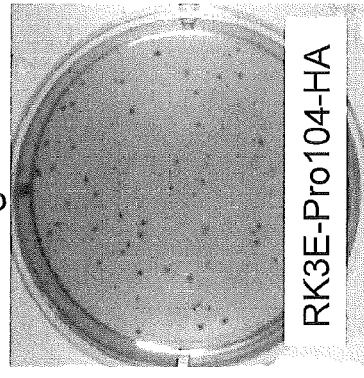
Fig. 31C RK3E-Pro104-HA
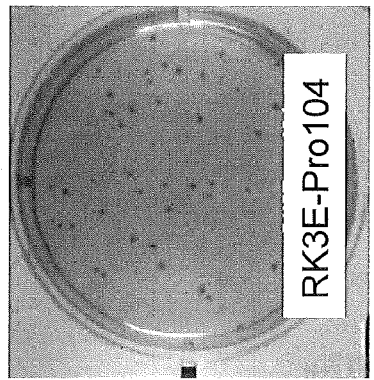
Fig. 31B RK3E-Pro104
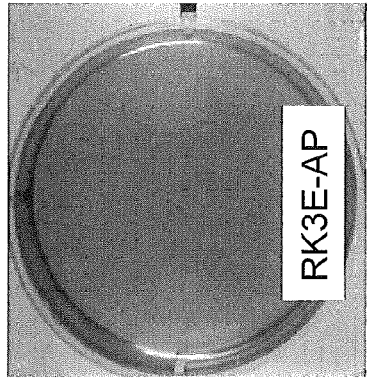
Fig. 31A RK3E-AP
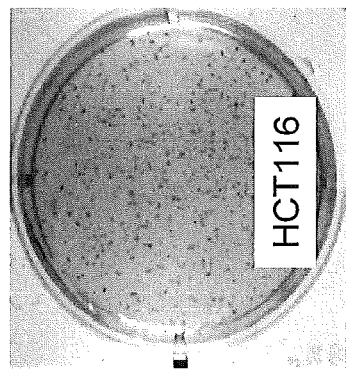
Fig. 31E HCT116
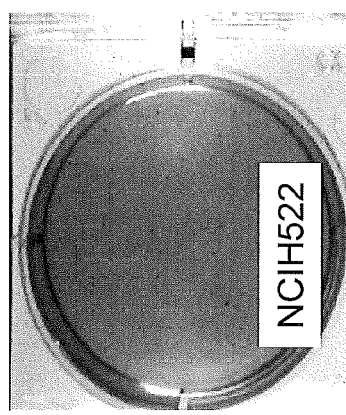
Fig. 31D NCIH522

FIGURE 32
Pro104 Protease Activity is Required for Cell Growth
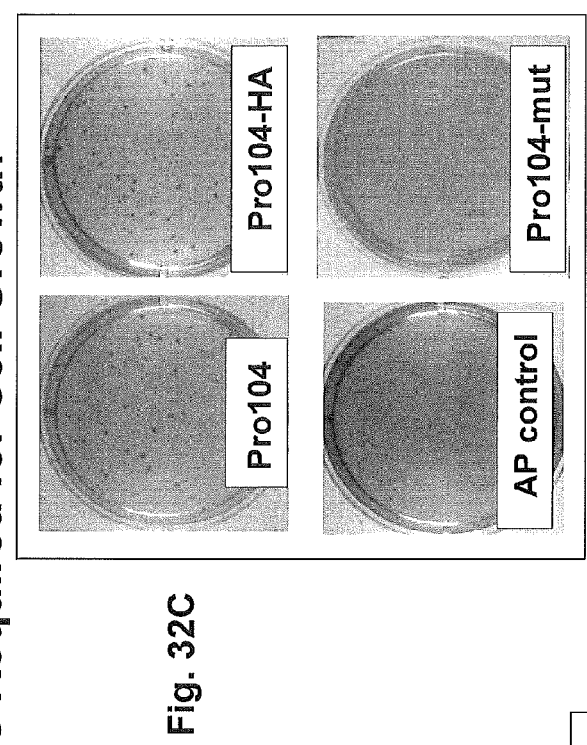
Fig. 32A
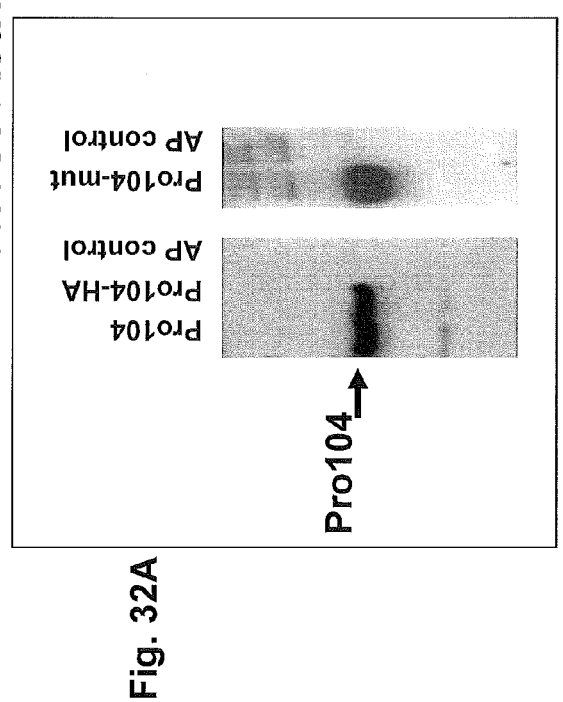
Fig. 32C
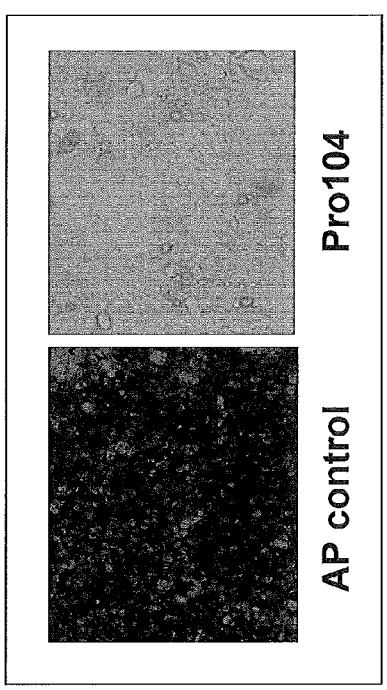
Fig. 32D
| Cell Type | # Colonies per field |
|---|---|
| AP control | 0 |
| Pro104 | 60 |
| Pro104-HA | 68 |
| Pro104-mut | 0 |
Fig. 32B
RK3E cells with Pro104-mut lack Pro104 protease activity Knockdown of Pro104 mRNA by siRNA Inhibits Growth of HeLa Cells in Soft Agar

FIGURE 34
Knockdown of Pro104 mRNA by siRNA Inhibits Growth of HeLa Cells in Soft Agar
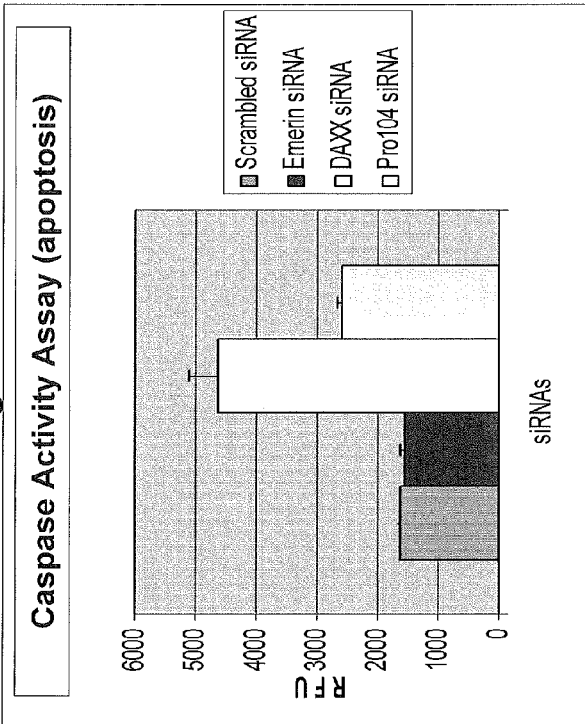
Fig. 34A
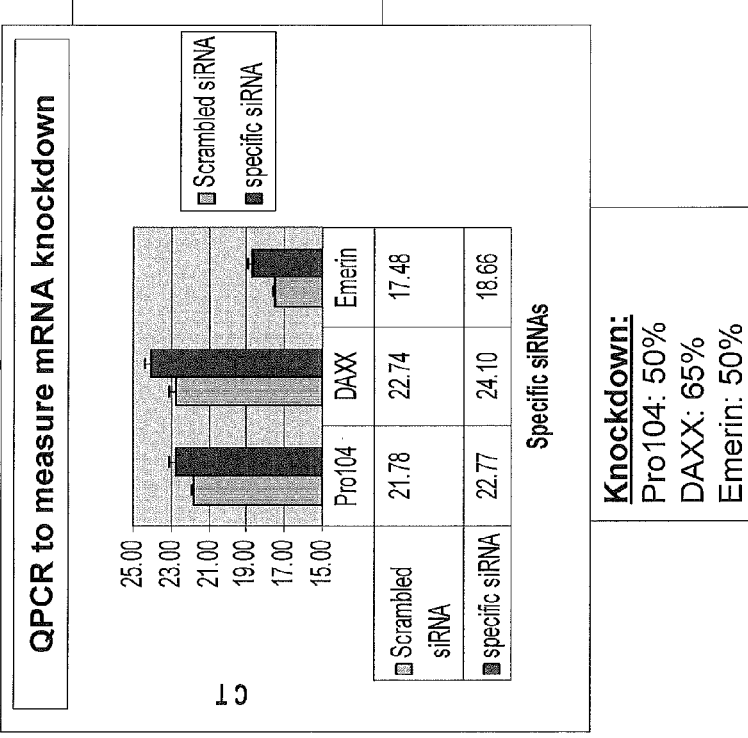
Fig. 34B

FIGURE 35
Increased Growth of Human Tumor Cells Over-Expressing Pro104
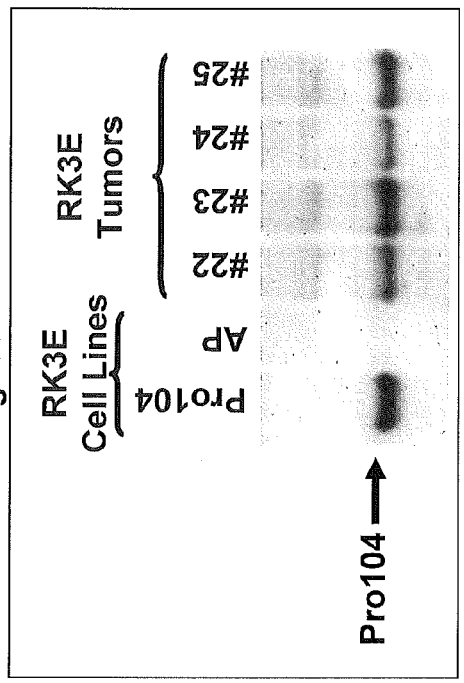
Fig. 35A
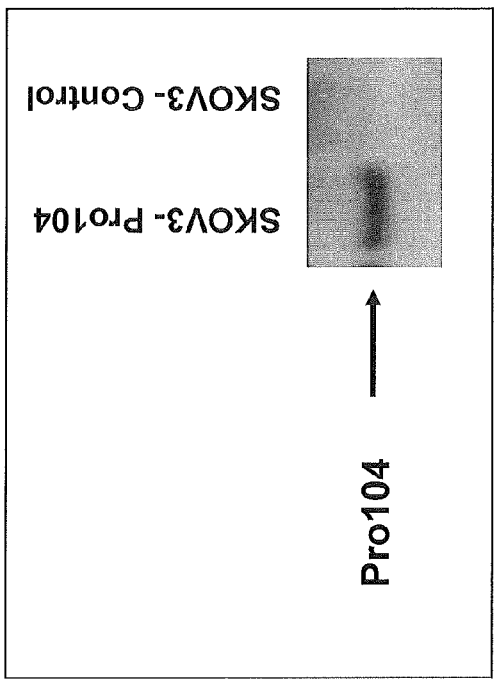
Fig. 35B
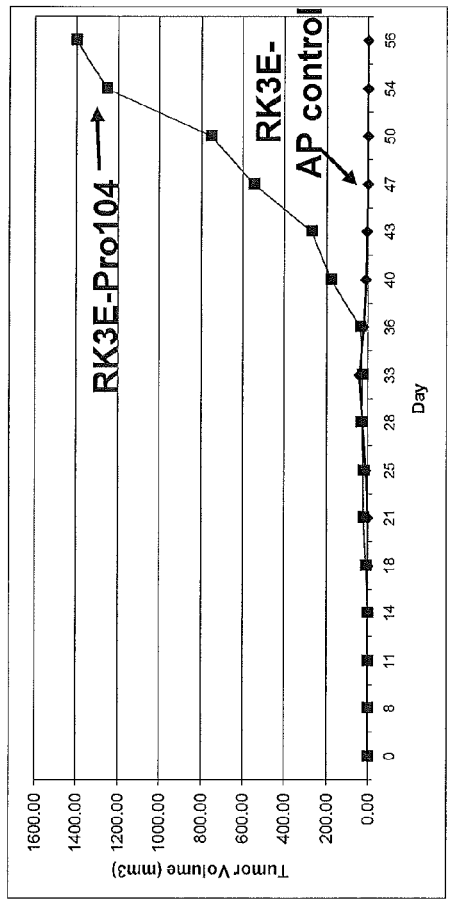
Fig. 35C
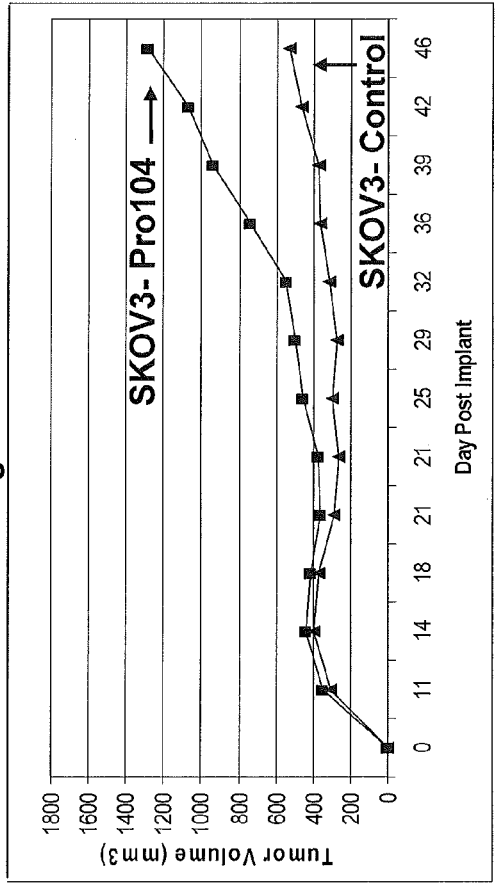
Fig. 35D

PRO104 ANTIBODY COMPOSITIONS AND METHODS OF USE

This patent application is a continuation of U.S. application Ser. No. 10/562,259, filed Dec. 21, 2005, now issued as U.S. Pat. No. 7,479,546, which is the U.S. National Stage of PCT Application number PCT/US2004/020741, filed Jun. 28, 2004, which claims the benefit of priority from U.S. Provisional Patent Application Ser. No. 60/523,271, filed Nov. 17, 2003 and U.S. Provisional Patent Application Ser. No. 60/485,346, filed Jun. 27, 2003, each of which are herein incorporated by reference in their entireties.

FIELD OF THE INVENTION

The present invention relates to anti-Pro104 antibody compositions and methods of detecting Pro104 expressing cancers and killing Pro104-expressing breast, ovarian pancreatic and lung cancers cells. In addition, this invention relates to methods of modulating or killing a Pro104 expressing cell by administering an effective amount of a compound capable of modulating Pro104 function.

BACKGROUND OF THE INVENTION

Breast Cancer

Breast cancer, also referred to as mammary tumor cancer, is the second most common cancer among women, accounting for a third of the cancers diagnosed in the United States. One in nine women will develop breast cancer in her lifetime and about 192,000 new cases of breast cancer are diagnosed annually with about 42,000 deaths. Bevers, *Primary Prevention of Breast Cancer*, in *Breast Cancer,* 20-54 (Kelly K Hunt et al., ed., 2001); Kochanek et al., 49 *Nat'l. Vital Statistics Reports* 1, 14 (2001). Breast cancer is extremely rare in women younger than 20 and is very rare in women under 30. The incidence of breast cancer rises with age and becomes significant by age 50. White Non-Hispanic women have the highest incidence rate for breast cancer and Korean women have the lowest. Increased prevalence of the genetic mutations BRCA1 and BRCA2 that promote breast and other cancers are found in Ashkenazi Jews. African American women have the highest mortality rate for breast cancer among these same groups (31 per 100,000), while Chinese women have the lowest at 11 per 100,000. Although men can get breast cancer, this is extremely rare. In the United States it is estimated there will be 217,440 new cases of breast cancer and 40,580 deaths due to breast cancer in 2004. (American Cancer Society Website: cancer with the extension .org of the world wide web). With the exception of those cases with associated genetic factors, precise causes of breast cancer are not known.

In the treatment of breast cancer, there is considerable emphasis on detection and risk assessment because early and accurate staging of breast cancer has a significant impact on survival. For example, breast cancer detected at an early stage (stage T0, discussed below) has a five-year survival rate of 92%. Conversely, if the cancer is not detected until a late stage (i.e., stage T4 (IV)), the five-year survival rate is reduced to 13%. *AJCC Cancer Staging Handbook* pp. 164-65 (Irvin D. Fleming et al. eds., 5$^{th}$ ed. 1998). Some detection techniques, such as mammography and biopsy, involve increased discomfort, expense, and/or radiation, and are only prescribed only to patients with an increased risk of breast cancer.

Current methods for predicting or detecting breast cancer risk are not optimal. One method for predicting the relative risk of breast cancer is by examining a patient's risk factors and pursuing aggressive diagnostic and treatment regiments for high risk patients. A patient's risk of breast cancer has been positively associated with increasing age, nulliparity, family history of breast cancer, personal history of breast cancer, early menarche, late menopause, late age of first full term pregnancy, prior proliferative breast disease, irradiation of the breast at an early age and a personal history of malignancy. Lifestyle factors such as fat consumption, alcohol consumption, education, and socioeconomic status have also been associated with an increased incidence of breast cancer although a direct cause and effect relationship has not been established. While these risk factors are statistically significant, their weak association with breast cancer limited their usefulness. Most women who develop breast cancer have none of the risk factors listed above, other than the risk that comes with growing older. NIH Publication No. 00-1556 (2000).

Current screening methods for detecting cancer, such as breast self-exam, ultrasound, and mammography have drawbacks that reduce their effectiveness or prevent their widespread adoption. Breast self-exams, while useful, are unreliable for the detection of breast cancer in the initial stages where the tumor is small and difficult to detect by palpation. Ultrasound measurements require skilled operators at an increased expense. Mammography, while sensitive, is subject to over diagnosis in the detection of lesions that have questionable malignant potential. There is also the fear of the radiation used in mammography because prior chest radiation is a factor associated with an increase incidence of breast cancer.

At this time, there are no adequate methods of breast cancer prevention. The current methods of breast cancer prevention involve prophylactic mastectomy (mastectomy performed before cancer diagnosis) and chemoprevention (chemotherapy before cancer diagnosis) which are drastic measures that limit their adoption even among women with increased risk of breast cancer. Bevers, supra.

A number of genetic markers have been associated with breast cancer. Examples of these markers include carcinoembryonic antigen (CEA) (Mughal et al., *JAMA* 249:1881 (1983)), MUC-1 (Frische and Liu, *J. Clin. Ligand* 22:320 (2000)), HER-2/neu (Haris et al., *Proc. Am. Soc. Clin. Oncology* 15:A96 (1996)), uPA, PAI-1, LPA, LPC, RAK and BRCA (Esteva and Fritsche, *Serum and Tissue Markers for Breast Cancer,* in *Breast Cancer,* 286-308 (2001)). These markers have problems with limited sensitivity, low correlation, and false negatives which limit their use for initial diagnosis. For example, while the BRCA1 gene mutation is useful as an indicator of an increased risk for breast cancer, it has limited use in cancer diagnosis because only 6.2% of breast cancers are BRCA1 positive. Malone et al., *JAMA* 279:922 (1998). See also, Mewman et al., *JAMA* 279:915 (1998) (correlation of only 3.3%).

There are four primary classifications of breast cancer varying by the site of origin and the extent of disease development.

I. Ductal carcinoma in situ (DCIS): Malignant transformation of ductal epithelial cells that remain in their normal position. DCIS is a purely localized disease, incapable of metastasis.

II. Invasive ductal carcinoma (IDC): Malignancy of the ductal epithelial cells breaking through the basal membrane and into the supporting tissue of the breast. IDC may eventually spread elsewhere in the body.

III. Lobular carcinoma in situ (LCIS): Malignancy arising in a single lobule of the breast that fails to extend through the lobule wall, it generally remains localized.

IV. Infiltrating lobular carcinoma (ILC): Malignancy arising in a single lobule of the breast and invading directly through the lobule wall into adjacent tissues. By virtue of its invasion beyond the lobule wall, ILC may penetrate lymphatics and blood vessels and spread to distant sites.

For purpose of determining prognosis and treatment, these four breast cancer types have been staged according to the size of the primary tumor (T), the involvement of lymph nodes (N), and the presence of metastasis (M). Although DCIS by definition represents localized stage I disease, the other forms of breast cancer may range from stage II to stage IV. There are additional prognostic factors that further serve to guide surgical and medical intervention. The most common ones are total number of lymph nodes involved, ER (estrogen receptor) status, Her2/neu receptor status and histologic grades.

Breast cancers are diagnosed into the appropriate stage categories recognizing that different treatments are more effective for different stages of cancer. Stage TX indicates that primary tumor cannot be assessed (i.e., tumor was removed or breast tissue was removed). Stage T0 is characterized by abnormalities such as hyperplasia but with no evidence of primary tumor. Stage Tis is characterized by carcinoma in situ, intraductal carcinoma, lobular carcinoma in situ, or Paget's disease of the nipple with no tumor. Stage T1 (I) is characterized as having a tumor of 2 cm or less in the greatest dimension. Within stage T1, Tmic indicates microinvasion of 0.1 cm or less, T1a indicates a tumor of between 0.1 to 0.5 cm, T1b indicates a tumor of between 0.5 to 1 cm, and T1c indicates tumors of between 1 cm to 2 cm. Stage T2 (II) is characterized by tumors from 2 cm to 5 cm in the greatest dimension. Tumors greater than 5 cm in size are classified as stage T3 (III). Stage T4 (IV) indicates a tumor of any size with extension to the chest wall or skin. Within stage T4, T4a indicates extension of the tumor to the chess wall, T4b indicates edema or ulceration of the skin of the breast or satellite skin nodules confined to the same breast, T4c indicates a combination of T4a and T4b, and T4d indicates inflammatory carcinoma. *AJCC Cancer Staging Handbook* pp. 159-70 (Irvin D. Fleming et al. eds., $5^{th}$ ed. 1998). In addition to standard staging, breast tumors may be classified according to their estrogen receptor and progesterone receptor protein status. Fisher et al., *Breast Cancer Research and Treatment* 7:147 (1986). Additional pathological status, such as HER2/neu status may also be useful. Thor et al., *J. Nat'l. Cancer Inst.* 90:1346 (1998); Paik et al., *J. Nat'l. Cancer Inst.* 90:1361 (1998); Hutchins et al., *Proc. Am. Soc. Clin. Oncology* 17:A2 (1998); and Simpson et al., *J. Clin. Oncology* 18:2059 (2000).

In addition to the staging of the primary tumor, breast cancer metastases to regional lymph nodes may be staged. Stage NX indicates that the lymph nodes cannot be assessed (e.g., previously removed). Stage N0 indicates no regional lymph node metastasis. Stage N1 indicates metastasis to movable ipsilateral axillary lymph nodes. Stage N2 indicates metastasis to ipsilateral axillary lymph nodes fixed to one another or to other structures. Stage N3 indicates metastasis to ipsilateral internal mammary lymph nodes. Id.

Stage determination has potential prognostic value and provides criteria for designing optimal therapy. Simpson et al., *J. Clin. Oncology* 18:2059 (2000). Generally, pathological staging of breast cancer is preferable to clinical staging because the former gives a more accurate prognosis. However, clinical staging would be preferred if it were as accurate as pathological staging because it does not depend on an invasive procedure to obtain tissue for pathological evaluation. Staging of breast cancer would be improved by detecting new markers in cells, tissues, or bodily fluids which could differentiate between different stages of invasion. Progress in this field will allow more rapid and reliable method for treating breast cancer patients.

Treatment of breast cancer is generally decided after an accurate staging of the primary tumor. Primary treatment options include breast conserving therapy (lumpectomy, breast irradiation, and surgical staging of the axilla), and modified radical mastectomy. Additional treatments include chemotherapy, regional irradiation, and, in extreme cases, terminating estrogen production by ovarian ablation.

Until recently, the customary treatment for all breast cancer was mastectomy. Fonseca et al., *Annals of Internal Medicine* 127:1013 (1997). However, recent data indicate that less radical procedures may be equally effective, in terms of survival, for early stage breast cancer. Fisher et al., *J. of Clinical Oncology* 16:441 (1998). The treatment options for a patient with early stage breast cancer (i.e., stage Tis) may be breast-sparing surgery followed by localized radiation therapy at the breast. Alternatively, mastectomy optionally coupled with radiation or breast reconstruction may be employed. These treatment methods are equally effective in the early stages of breast cancer.

Patients with stage I and stage II breast cancer requires surgery with chemotherapy and/or hormonal therapy. Surgery is of limited use in Stage III and stage IV patients. Thus, these patients are better candidates for chemotherapy and radiation therapy with surgery limited to biopsy to permit initial staging or subsequent restaging because cancer is rarely curative at this stage of the disease. *AJCC Cancer Staging Handbook* 84, 164-65 (Irvin D. Fleming et al. eds., $5^{th}$ ed. 1998).

In an effort to provide more treatment options to patients, efforts are underway to define an earlier stage of breast cancer with low recurrence which could be treated with lumpectomy without postoperative radiation treatment. While a number of attempts have been made to classify early stage breast cancer, no consensus recommendation on postoperative radiation treatment has been obtained from these studies. Page et al., *Cancer* 75:1219 (1995); Fisher et al., *Cancer* 75:1223 (1995); Silverstein et al., *Cancer* 77:2267 (1996).

Ovarian Cancer

Cancer of the ovaries is the fourth-most common cause of cancer death in women in the United States, with more than 23,000 new cases and roughly 14,000 deaths predicted for the year 2001. Shridhar, V. et al., *Cancer Res.* 61(15): 5895-904 (2001); Memarzadeh, S. & Berek, J. S., *J. Reprod. Med.* 46(7): 621-29 (2001). The American Cancer Society estimates that there will be about 25,580 new cases of ovarian cancer in 2004 in the United States alone. Ovarian cancer will cause about 16,090 deaths in the United States. ACS Website: cancer with the extension org of the world wide web. The incidence of ovarian cancer is of serious concern worldwide, with an estimated 191,000 new cases predicted annually. Runnebaum, I. B. & Stickeler, E., *J. Cancer Res. Clin. Oncol.* 127(2): 73-79 (2001). Unfortunately, women with ovarian cancer are typically asymptomatic until the disease has metastasized. Because effective screening for ovarian cancer is not available, roughly 70% of women diagnosed have an advanced stage of the cancer with a five-year survival rate of approximately 25-30%. Memarzadeh, S. & Berek, J. S., supra; Nunns, D. et al., *Obstet. Gynecol. Surv.* 55(12): 746-51. Conversely, women diagnosed with early stage ovarian cancer enjoy considerably higher survival rates. Werness, B. A. & Eltabbakh, G. H., *Int'l. J. Gynecol. Pathol.* 20(1): 48-63 (2001). Although our understanding of the etiology of ovarian cancer is incomplete, the results of extensive research in this area point to a combination of age, genetics, reproductive, and dietary/environmental factors. Age is a key risk factor in the development of ovarian cancer: while the risk for developing ovarian cancer before the age of 30 is slim, the incidence of ovarian cancer rises linearly between ages 30 to 50, increasing at a slower rate thereafter, with the highest incidence being among septagenarian women. Jeanne M. Schilder et al., *Hereditary Ovarian Cancer. Clinical Syndromes and Management*, in *Ovarian Cancer* 182 (Stephen C. Rubin & Gregory P. Sutton eds., 2d ed. 2001).

With respect to genetic factors, a family history of ovarian cancer is the most significant risk factor in the development of the disease, with that risk depending on the number of affected family members, the degree of their relationship to the woman, and which particular first degree relatives are affected by the disease. Id. Mutations in several genes have been associated with ovarian cancer, including BRCA1 and BRCA2, both of which play a key role in the development of breast cancer, as well as hMSH2 and hMLH1, both of which are associated with hereditary non-polyposis colon cancer. Katherine Y. Look, *Epidemiology, Etiology, and Screening of Ovarian Cancer*, in *Ovarian Cancer* 169, 171-73 (Stephen C. Rubin & Gregory P. Sutton eds., 2d ed. 2001). BRCA1, located on chromosome 17, and BRCA2, located on chromosome 13, are tumor suppressor genes implicated in DNA repair; mutations in these genes are linked to roughly 10% of ovarian cancers. Id. at 171-72; Schilder et al., supra at 185-86. hMSH2 and hMLH1 are associated with DNA mismatch repair, and are located on chromosomes 2 and 3, respectively; it has been reported that roughly 3% of hereditary ovarian carcinomas are due to mutations in these genes. Look, supra at 173; Schilder et al., supra at 184, 188-89.

Reproductive factors have also been associated with an increased or reduced risk of ovarian cancer. Late menopause, nulliparity, and early age at menarche have all been linked with an elevated risk of ovarian cancer. Schilder et al., supra at 182. One theory hypothesizes that these factors increase the number of ovulatory cycles over the course of a woman's life, leading to "incessant ovulation," which is thought to be the primary cause of mutations to the ovarian epithelium. Id.; Laura J. Havrilesky & Andrew Berchuck, *Molecular Alterations in Sporadic Ovarian Cancer*, in *Ovarian Cancer* 25 (Stephen C. Rubin & Gregory P. Sutton eds., 2d ed. 2001). The mutations may be explained by the fact that ovulation results in the destruction and repair of that epithelium, necessitating increased cell division, thereby increasing the possibility that an undetected mutation will occur. Id. Support for this theory may be found in the fact that pregnancy, lactation, and the use of oral contraceptives, all of which suppress ovulation, confer a protective effect with respect to developing ovarian cancer. Id.

Among dietary/environmental factors, there would appear to be an association between high intake of animal fat or red meat and ovarian cancer, while the antioxidant Vitamin A, which prevents free radical formation and also assists in maintaining normal cellular differentiation, may offer a protective effect. Look, supra at 169. Reports have also associated asbestos and hydrous magnesium trisilicate (talc), the latter of which may be present in diaphragms and sanitary napkins. Id. at 169-70.

Current screening procedures for ovarian cancer, while of some utility, are quite limited in their diagnostic ability, a problem that is particularly acute at early stages of cancer progression when the disease is typically asymptomatic yet is most readily treated. Walter J. Burdette, *Cancer: Etiology Diagnosis and Treatment* 166 (1998); Memarzadeh & Berek, supra; Runnebaum & Stickeler, supra; Werness & Eltabbakh, supra. Commonly used screening tests include biannual rectovaginal pelvic examination, radioimmunoassay to detect the CA-125 serum tumor marker, and transvaginal ultrasonography. Burdette, supra at 166.

Pelvic examination has failed to yield adequate numbers of early diagnoses, and the other methods are not sufficiently accurate. Id. One study reported that only 15% of patients who suffered from ovarian cancer were diagnosed with the disease at the time of their pelvic examination. Look, supra at 174. Moreover, the CA-125 test is prone to giving false positives in pre-menopausal women and has been reported to be of low predictive value in post-menopausal women. Id. at 174-75. Although transvaginal ultrasonography is now the preferred procedure for screening for ovarian cancer, it is unable to distinguish reliably between benign and malignant tumors, and also cannot locate primary peritoneal malignancies or ovarian cancer if the ovary size is normal. Schilder et al., supra at 194-95. While genetic testing for mutations of the BRCA1, BRCA2, hMSH2, and hMLH1 genes is now available, these tests may be too costly for some patients and may also yield false negative or indeterminate results. Schilder et al., supra at 191-94.

Other markers of interest are HE4 and mesothelin. See Urban et al. Ovarian cancer screening Hematol Oncol Clin North Am. 2003 August; 17(4):989-1005; Hellstrom et al. The HE4 (WFDC2) protein is a biomarker for ovarian carcinoma, Cancer Res. 2003 Jul. 1; 63(13):3695-700; Ordonez, Application of mesothelin immunostaining in tumor diagnosis, Am J Surg Pathol. 2003 November; 27(11): 1418-28.

The staging of ovarian cancer, which is accomplished through surgical exploration, is crucial in determining the course of treatment and management of the disease. *AJCC Cancer Staging Handbook* 187 (Irvin D. Fleming et al. eds., 5th ed. 1998); Burdette, supra at 170; Memarzadeh & Berek, supra; Shridhar et al., supra. Staging is performed by reference to the classification system developed by the International Federation of Gynecology and Obstetrics. David H. Moore, *Primary Surgical Management of Early Epithelial Ovarian Carcinoma*, in *Ovarian Cancer* 203 (Stephen C. Rubin & Gregory P. Sutton eds., 2d ed. 2001); Fleming et al. eds., supra at 188. Stage I ovarian cancer is characterized by tumor growth that is limited to the ovaries and is comprised of three substages. Id. In substage IA, tumor growth is limited to one ovary, there is no tumor on the external surface of the ovary, the ovarian capsule is intact, and no malignant cells are present in ascites or peritoneal washings. Id. Substage IB is identical to IA, except that tumor growth is limited to both ovaries. Id. Substage IC refers to the presence of tumor growth limited to one or both ovaries, and also includes one or more of the following characteristics: capsule rupture, tumor growth on the surface of one or both ovaries, and malignant cells present in ascites or peritoneal washings. Id.

Stage II ovarian cancer refers to tumor growth involving one or both ovaries, along with pelvic extension. Id. Substage IIA involves extension and/or implants on the uterus and/or fallopian tubes, with no malignant cells in the ascites or peritoneal washings, while substage IIB involves extension into other pelvic organs and tissues, again with no malignant cells in the ascites or peritoneal washings. Id. Substage IIC involves pelvic extension as in IIA or IIB, but with malignant cells in the ascites or peritoneal washings. Id.

Stage III ovarian cancer involves tumor growth in one or both ovaries, with peritoneal metastasis beyond the pelvis confirmed by microscope and/or metastasis in the regional lymph nodes. Id. Substage IIIA is characterized by microscopic peritoneal metastasis outside the pelvis, with substage IIIB involving macroscopic peritoneal metastasis outside the pelvis 2 cm or less in greatest dimension. Id. Substage IIIC is identical to IIIB, except that the metastasis is greater than 2 cm in greatest dimension and may include regional lymph node metastasis. Id. Lastly, Stage IV refers to the presence distant metastasis, excluding peritoneal metastasis. Id.

While surgical staging is currently the benchmark for assessing the management and treatment of ovarian cancer, it suffers from considerable drawbacks, including the invasiveness of the procedure, the potential for complications, as well as the potential for inaccuracy. Moore, supra at 206-208, 213. In view of these limitations, attention has turned to developing alternative staging methodologies through understanding differential gene expression in various stages of ovarian cancer and by obtaining various biomarkers to help better assess the progression of the disease. Vartainen, J. et al., *Int'l J. Cancer*, 95(5): 313-16 (2001); Shridhar et al. supra; Baekelandt, M. et al., *J. Clin. Oncol.* 18(22): 3775-81.

The treatment of ovarian cancer typically involves a multiprong attack, with surgical intervention serving as the foundation of treatment. Dennis S. Chi & William J. Hoskins, *Primary Surgical Management of Advanced Epithelial Ovarian Cancer*, in *Ovarian Cancer* 241 (Stephen C. Rubin & Gregory P. Sutton eds., 2d ed. 2001). For example, in the case of epithelial ovarian cancer, which accounts for approximately 90% of cases of ovarian cancer, treatment typically consists of: (1) cytoreductive surgery, including total abdominal hysterectomy, bilateral salpingo-oophorectomy, omentectomy, and lymphadenectomy, followed by (2) adjuvant chemotherapy with paclitaxel and either cisplatin or carboplatin. Eltabbakh, G. H. & Awtrey, C. S., *Expert Op. Pharmacother.* 2(10): 109-24. Despite a clinical response rate of 80% to the adjuvant therapy, most patients experience tumor recurrence within three years of treatment. Id. Certain patients may undergo a second cytoreductive surgery and/or second-line chemotherapy. Memarzadeh & Berek, supra.

From the foregoing, it is clear that procedures used for detecting, diagnosing, monitoring, staging, prognosticating, and preventing the recurrence of ovarian cancer are of critical importance to the outcome of the patient. Moreover, current procedures, while helpful in each of these analyses, are limited by their specificity, sensitivity, invasiveness, and/or their cost. As such, highly specific and sensitive procedures that would operate by way of detecting novel markers in cells, tissues, or bodily fluids, with minimal invasiveness and at a reasonable cost, would be highly desirable.

Accordingly, there is a great need for more sensitive and accurate methods for predicting whether a person is likely to develop ovarian cancer, for diagnosing ovarian cancer, for monitoring the progression of the disease, for staging the ovarian cancer, for determining whether the ovarian cancer has metastasized, and for imaging the ovarian cancer. There is also a need for better treatment of ovarian cancer.

Pancreatic Cancer

Pancreatic cancer is the thirteenth-most common cancer and eighth-most cause of cancer death worldwide. Donghui Li, *Molecular Epidemiology*, in *Pancreatic Cancer* 3 (Douglas B. Evans et al. eds., 2002). In the United States, cancer of the pancreas is the fourth-most common cancer in both males and females, accounting for five percent of cancer deaths and nearly 30,000 deaths overall. Id. The rates of pancreatic cancer are higher in men than women and higher in African-Americans as opposed to Caucasians. Id. at 9. The most significant predictor of pancreatic cancer is patient age; among Caucasians, the age-related incidence of pancreatic cancer increases continuously, even through the 85 and older category. Id. at 3. Approximately 80% of cases occur in the age range of 60 to 80, with those in their 80s experiencing a risk of acquiring the disease 40 times that of those in their 40s. Id. Furthermore, the American Cancer Society estimates that there will be about 31,800 new cases of pancreatic cancer in 2004 in the United States alone. Pancreatic cancer will cause about 31,200 deaths in the United States in the same year. ACS Website: cancer with the extension .org of the world wide web. Despite the efforts of researchers and physicians in devising treatments for pancreatic cancer, it remains almost universally fatal. James R. Howe, *Molecular Markers as a Tool for the Early Diagnosis of Pancreatic Cancer*, in *Pancreatic Cancer* 29 (Douglas B. Evans et al. eds., 2002).

Aside from age, a number of risk factors for pancreatic cancer have been identified, including smoking, diet, occupation, certain medical conditions, heredity, and molecular biologic. Smoking is the most important risk factor for acquiring the disease, with the link between smoking and pancreatic cancer being established in numerous studies. Li, supra at 3. The relative risk amounts to at least 1.5, increasing with the level of smoking to an outer risk ratio of 10-fold. Id. The next most important factor would appear to be diet, with increased risk associated with animal protein and fat intake, and decreased risk associated with intake of fruits and vegetables. Id. at 3-4. As for particular occupations, excessive rates of pancreatic cancer have been associated with workers in chemistry, coal and gas exploration, the metal industry, leather tanning, textiles, aluminum milling, and transportation. Id. at 4. A number of medical conditions have also been associated with an increased incidence of pancreatic cancer, including diabetes, chronic pancreatitis, gastrectomy, and cholecystectomy, although the cause and effect relationship between these conditions and pancreatic cancer has not been established. Id.

Hereditary genetic factors comprise less than 10% of the pancreatic cancer burden, with associations documented with hereditary pancreatitis, as well as germline mutations in familial cancer syndrome genes such as hMSH2 and hMLH1 (hereditary nonpolyposis colon cancer), p16 (familial atypical multiple mole-melanoma) and BRCA1/BRCA2 (breast and ovarian cancer). Id. at 3. While no other organ has a higher inherited basis for cancer than the pancreas, researchers have been unable to pinpoint the particular genetic defect(s) that contribute to one's susceptibility to pancreatic cancer. David H. Berger & William E. Fisher, *Inherited Pancreatic Cancer Syndromes*, in *Pancreatic Cancer* 73 (Douglas B. Evans et al. eds., 2002).

From the standpoint of molecular biology, research has revealed an association between pancreatic cancer and a number of genetic mutations, including the activation of the proto-oncogene K-ras and the inactivation of the tumor suppressor genes p53, p16, and DPC4. Marina E. Jean et al., *The Molecular Biology of Pancreatic Cancer*, in *Pancreatic Cancer* 15 (Douglas B. Evans et al. eds., 2002).

In one study of pancreatic adenocarcinomas, 83% possessed K-ras activation along with inactivation of p16 and p53. Id. K-ras mutations are found in 80 to 95% of pancreatic adenocarcinomas, with p53, p16, and DPC4 genes being the must frequently deleted tumor suppressor genes in cancer of the pancreas. Howe, supra at 29. Homozygous deletions, hypermethylation, and mutations of the p16 gene have been discovered in 85 to 98% of adenocarcinomas of the pancreas. Id. As might be expected by the role of alterations in the K-ras, p53, p16, and DPC4 genes, loss of regulation of the cell cycle would appear to be key to tumorigenesis in the pancreas, and may explain why this cancer is so aggressive. Jean, supra at 15. Research has also revealed a link between this cancer and abnormal regulation of certain growth factors and growth factor receptors, as well as an upregulation of matrix metalloproteinases and tumor angiogenesis regulators. Id. Epidermal growth factor, fibroblast growth factor, transforming growth factor-β, insulin-like growth factor, hepatocyte growth factor, and vascular endothelial growth factor may play various roles in pancreatic cancer, although such roles have not been elucidated. Id. at 18-22.

The development of screening techniques to detect the presence of pancreatic cancer is particularly essential for this deadly cancer, as most patients fail to present until their pancreatic tumors obstruct the bile duct or induce pain, at which point the tumors have invaded the capillary and lymphatic vessels that surround the pancreas, Howe, supra at 29; unfortunately, patients with the metastatic form of the disease typically survive less than one year after diagnosis, Jean et al., supra at 15. While computed tomography (CT) and endoscopic retrograde cholangiopancreatography (ERCP) may assist in the diagnosis of symptomatic patients, there is presently no tool for screening for pancreatic tumors that would permit their early discovery, at which point they might be curable. Howe, supra at 29. Markers such as carcinoembryonic antigen, and antibodies generated against cell lines of human colonic cancer (CA 19-9 and CA 195), human ovarian cancer (CA 125), and human pancreatic cancer (SPAN-1 and DUPAN-2) may be elevated in the serum of patients with pancreatic cancer, but these markers are not sufficiently reliable to serve as screening tools due to their lack of specificity and appearance late in the disease. Walter J. Burdette, *Cancer: Etiology, Diagnosis, and Treatment* 99 (1998); Hasholzner, U. et al., *Anticancer Res.* 19(4A): 2477-80 (1999).

Due to the present lack of adequate screening methods, physicians are increasingly turning to techniques which employ methods of molecular biology as the most promising means for early diagnosis of the disease. Howe, supra at 30. At present, there is no high sensitivity, high specificity marker that enables the detection of pancreatic cancer in asymptomatic individuals, but several biological markers are under investigation. Id. Considerable efforts are currently focusing on K-ras, with researchers devising techniques to screen samples of pancreatic juice, bile, duodenal juice, or ERCP brushings to detect K-ras mutations. Id. Because the collection of these samples is invasive and not particularly helpful in screening those who are asymptomatic, researchers have also turned to serum and stool analysis for K-ras mutations, with the former being the most promising, as the latter is hindered by the complexity of the source material. Id. at 35-38, 42. Moreover, because serum levels of the transcription factor protein p53 may parallel cancer progression, p53 is likewise being studied as possible tumor marker. Id. at 37; Jean et al., supra at 17.

Once pancreatic cancer has been diagnosed, treatment decisions are made in reference to the stage of cancer progression. A number of imaging techniques are employed to stage pancreatic cancer, with computed tomography (CT) being the present method of choice, Harmeet Kaur et al., *Pancreatic Cancer: Radiologic Staging*, in *Pancreatic Cancer* 86 (Douglas B. Evans et al. eds., 2002); Ishiguchi, T. et al., *Hepatogastroenterology* 48(40): 923-27 (2001), despite the fact that it frequently underestimates the extent of the cancer, as small-volume metastases are often beyond the resolution of CT, H. J. Kim & K. C. Conlon, *Laparascopic Staging*, in *Pancreatic Cancer* 15 (Douglas B. Evans et al. eds., 2002). MRI may at some point supplant CT in view of, inter alia, its ability to (1) contrast among various tissue, (2) modify pulse sequences to improve visualization of lesions and minimize artifacts, (3) perform imaging while limiting a patient's exposure to ionizing radiation, and (4) visualize vessels without using IV iodinated contrast reagents. Kaur et al., supra at 87. At present, however, MRI has not demonstrated a clear advantage over CT. Kim & Conlon, supra at 116.

A variety of ultrasonic techniques are also currently employed in staging, including transabdominal ultrasound (TUS), endoscopic ultrasound (EUS), and intraoperative ultrasound (JUS), with EUS being one of the most promising. Kaur et al., supra at 86; Richard A. Erickson, *Endoscopic Diagnosis and Staging: Endoscopic Ultrasound, Endoscopic Retrograde Cholangiopancreatography*, in *Pancreatic Cancer* 97-106 (Douglas B. Evans et al. eds., 2002). These techniques, however, are each limited by a variety of factors: TUS is hindered by gas in the gastrointestinal tract and fat in the peritoneum, EUS requires considerable experience in ultrasonography and endoscopy and may not be widely available, and IUS can only be used intraoperatively. Kaur et al., supra at 86.

Although in its nascent stages, the search for markers that will assist in staging pancreatic cancer has found some possible leads. For example, research has revealed that two metastasis-suppressing genes, nm23-H1 and KAI1, are differentially expressed depending on the stage of pancreatic cancer, with their expression being upregulated at early stages and down regulated at later stages of the disease. Friess, H. et al., *J. Clin. Oncol.* 19(9): 2422-32 (2001). Researchers have also focused on genetic lymph node staging, particularly searching for mutations in the K-ras proto-oncogene. Yamada, T. et al., *Int'l J. Oncol.* 16(6): 1165-71 (2000). Likewise, research has identified that the presence of mutated K-ras sequences in plasma/serum is associated with late stage pancreatic cancer, although the presence of early stage pancreatic cancer can be detected this way as well. Sorenson, G. D., *Clin. Cancer Res.* 6(6): 2129-37 (2000). A promising staging technique using a multimarker reverse transcriptase-polymerase chain reaction assay has successfully distinguished pancreatic cancer stages by assaying blood and tissue samples for mRNA expression of the following tumor markers: the β-human chorionic gonadotropin gene, the hepatocyte growth factor receptor gene c-met, and the β-1,4-N-acetyl-galactosaminyl-transferase gene. Bilchik, A. et al., *Cancer* 88(5): 1037-44 (2000).

One classification system commonly used to stage pancreatic cancer is the TNM system devised by the Union Internationale Contre le Cancer. *AJCC Cancer Staging Handbook* 3 (Irvin D. Fleming et al. eds., 5$^{th}$ ed. 1998). This system is divided into several stages, each of which evaluates the extent of cancer growth with respect to primary tumor (T), regional lymph nodes (N), and distant metastasis (M). Id.

Stage 0 is characterized by carcinoma in situ (Tis), with no regional lymph node metastasis (N0) and no distant metastasis (M0). Id. at 113. Stages I and II differ from stage 0 only in terms of tumor category: stage I involves a tumor limited only to the pancreas that is either (1) 2 cm or less in greatest dimension (T1) or (2) more than 2 cm in greatest dimension (T2), while stage II involves a tumor that extends directly into the duodenum, bile duct, or peripancreatic tissues (T3). Id. Stage III involves tumor category T1, T2, or T3; regional lymph node metastasis (N1), which involves either a single lymph node (pN1a) or multiple lymph nodes (pN1b); and no distant metastasis (M0). Stage IVA is characterized by tumor extension directly into the stomach, spleen, colon, or adjacent large vessels (T4); any N category; and no distant metastasis (M0). Lastly, stage IVB is characterized by any T category, any N category, and distant metastasis (M1). Id.

Once the cancer has been staged, the only consistently effective treatment for the disease is surgery, and with only ten to fifteen percent of patients being able to undergo potentially curative resection. Jean et al., supra at 15; Fleming et al. eds., supra at 111; William F. Regine, *Postoperative Adjuvant Therapy: Past, Present, and Future Trial Development*, in *Pancreatic Cancer* 235 (Douglas B. Evans et al. eds., 2002). Moreover, the five-year survival of those patients undergoing resection is below twenty percent. Regine, supra at 235. While chemotherapeutic agents such as gemcitabine and 5-fluorouracil have shown some effectiveness against pancreatic carcinomas, the reality is that chemotherapy has shown little impact on survival from pancreatic cancer. Burdette, supra at 101. Radiation therapy has provided conflicting results with respect to its efficacy, id., although radiation in combination with 5-fluorouracil has shown some promise, Regine, supra at 235.

In view of the failure of conventional techniques at treating pancreatic cancer, a number of novel approaches employing the techniques of molecular biology have been investigated. Considerable research has been performed in the area of gene therapy, including antisense technology, gene-directed prodrug activation strategies, promoter gene strategies, and oncolytic viral therapies. Eugene A. Choi & Francis R. Spitz, *Strategies for Gene Therapy*, in *Pancreatic Cancer* 331 (Douglas B. Evans et al. eds., 2002); Kasuya, H. et al., *Hepatogastroenterology* 48(40): 957-61 (2001). Other recent approaches have focused on the inhibition of matrix metalloproteinases, enzymes which facilitate the metastasis and invasion of tumor cells through their degradation of basement membranes, and their role in peritumoral stromal degradation and angiogenesis. Alexander S. Rosemurgy, II & Mahmudul Haq, *Role of Matrix Metalloproteinase Inhibition in the Treatment of Pancreatic Cancer*, in *Pancreatic Cancer* 369 (Douglas B. Evans et al. eds., 2002).

From the foregoing, it is clear that procedures used for detecting, diagnosing, monitoring, staging, prognosticating, and preventing the recurrence of pancreatic cancer are of critical importance to the outcome of the patient. Moreover, current procedures, while helpful in each of these analyses, are limited by their specificity, sensitivity, invasiveness, and/or their cost. As such, highly specific and sensitive procedures that would operate by way of detecting novel markers in cells, tissues, or bodily fluids, with minimal invasiveness and at a reasonable cost, would be highly desirable.

Lung Cancer

Throughout the last hundred years, the incidence of lung cancer has steadily increased, so much so that now in many countries, it is the most common cancer. In fact, lung cancer is the second most prevalent type of cancer for both men and women in the United States and is the most common cause of cancer death in both sexes. Lung cancer deaths have increased ten-fold in both men and women since 1930, primarily due to an increase in cigarette smoking, but also due to an increased exposure to arsenic, asbestos, chromates, chloromethyl ethers, nickel, polycyclic aromatic hydrocarbons and other agents. See Scott, *Lung Cancer: A Guide to Diagnosis and Treatment*, Addicus Books (2000) and Alberg et al., in Kane et al. (eds.) *Biology of Lung Cancer*, pp. 11-52, Marcel Dekker, Inc. (1998). The American Cancer Society estimates there will be over 173,550 new cases of lung cancer in 2004. Additionally, there will be an estimated 160,440 deaths from lung cancer in 2004. ACS Website: cancer with the extension .org of the world wide web.

Lung cancer may result from a primary tumor originating in the lung or a secondary tumor which has spread from another organ such as the bowel or breast. Although there are over a dozen types of lung cancer, over 90% fall into two categories: small cell lung cancer (SCLC) and non-small cell lung cancer (NSCLC). See Scott, supra. About 20-25% of all lung cancers are characterized as SCLC, while 70-80% are diagnosed as NSCLC. Id. A rare type of lung cancer is mesothelioma, which is generally caused by exposure to asbestos, and which affects the pleura of the lung. Lung cancer is usually diagnosed or screened for by chest x-ray, CAT scans, PET scans, or by sputum cytology. A diagnosis of lung cancer is usually confirmed by biopsy of the tissue. Id.

SCLC tumors are highly metastatic and grow quickly. By the time a patient has been diagnosed with SCLC, the cancer has usually already spread to other parts of the body, including lymph nodes, adrenals, liver, bone, brain and bone marrow. See Scott, supra; Van Houtte et al. (eds.), *Progress and Perspective in the Treatment of Lung Cancer*, Springer-Verlag (1999). Because the disease has usually spread to such an extent that surgery is not an option, the current treatment of choice is chemotherapy plus chest irradiation. See Van Houtte, supra. The stage of disease is a principal predictor of long-term survival. Less than 5% of patients with extensive disease that has spread beyond one lung and surrounding lymph nodes, live longer than two years. Id. However, the probability of five-year survival is three to four times higher if the disease is diagnosed and treated when it is still in a limited stage, i.e., not having spread beyond one lung. Id.

NSCLC is generally divided into three types: squamous cell carcinoma, adenocarcinoma and large cell carcinoma. Both squamous cell cancer and adenocarcinoma develop from the cells that line the airways; however, adenocarcinoma develops from the goblet cells that produce mucus. Large cell lung cancer has been thus named because the cells look large and rounded when viewed microscopically, and generally are considered relatively undifferentiated. See Yesner, *Atlas of Lung Cancer*, Lippincott-Raven (1998).

Secondary lung cancer is a cancer initiated elsewhere in the body that has spread to the lungs. Cancers that metastasize to the lung include, but are not limited to, breast cancer, melanoma, colon cancer and Hodgkin's lymphoma. Treatment for secondary lung cancer may depend upon the source of the original cancer. In other words, a lung cancer that originated from breast cancer may be more responsive to breast cancer treatments and a lung cancer that originated from the colon cancer may be more responsive to colon cancer treatments.

The stage of a cancer indicates how far it has spread and is an important indicator of the prognosis. In addition, staging is important because treatment is often decided according to the stage of a cancer. SCLC is divided into two stages: limited disease, i.e., cancer that can only be seen in one lung and in nearby lymph nodes; and extensive disease, i.e., cancer that has spread outside the lung to the chest or to other parts of the body. For most patients with SCLC, the disease has already progressed to lymph nodes or elsewhere in the body at the time of diagnosis. See Scott, supra. Even if spreading is not apparent on the scans, it is likely that some cancer cells may have spread away and traveled through the bloodstream or lymph system. In general, chemotherapy with or without radiotherapy is often the preferred treatment. The initial scans and tests done at first will be used later to see how well a patient is responding to treatment.

In contrast, non-small cell cancer may be divided into four stages. Stage I is highly localized cancer with no cancer in the lymph nodes. Stage II cancer has spread to the lymph nodes at the top of the affected lung. Stage III cancer has spread near to where the cancer started. This can be to the chest wall, the covering of the lung (pleura), the middle of the chest (mediastinum) or other lymph nodes. Stage IV cancer has spread to another part of the body. Stage I-III cancer is usually treated with surgery, with or without chemotherapy. Stage IV cancer is usually treated with chemotherapy and/or palliative care.

A number of chromosomal and genetic abnormalities have been observed in lung cancer. In NSCLC, chromosomal aberrations have been described on 3p, 9p, 11p, 15p and 17p, and chromosomal deletions have been seen on chromosomes 7, 11, 13 and 19. See Skarin (ed.), *Multimodality Treatment of Lung Cancer*, Marcel Dekker, Inc. (2000); Gemmill et al., pp. 465-502, in Kane, supra; Bailey-Wilson et al., pp. 53-98, in Kane, supra. Chromosomal abnormalities have been described on 1p, 3p, 5q, 6q, 8q, 13q and 17p in SCLC. Id. In addition, the loss of the short arm of chromosome 3p has also been seen in greater than 90% of SCLC tumors and approximately 50% of NSCLC tumors. Id.

A number of oncogenes and tumor suppressor genes have been implicated in lung cancer. See Mabry, pp. 391-412, in Kane, supra and Sclafani et al., pp. 295-316, in Kane, supra. In both SCLC and NSCLC, the p53 tumor suppressor gene is mutated in over 50% of lung cancers. See Yesner, supra. Another tumor suppressor gene, FHIT, which is found on chromosome 3p, is mutated by tobacco smoke. Id.; Skarin, supra. In addition, more than 95% of SCLCs and approximately 20-60% of NSCLCs have an absent or abnormal retinoblastoma (Rb) protein, another tumor suppressor gene. The ras oncogene (particularly K-ras) is mutated in 20-30% of NSCLC specimens and the c-erbB2 oncogene is expressed in 18% of stage 2 NSCLC and 60% of stage 4 NSCLC specimens. See Van Houtte, supra. Other tumor suppressor genes that are found in a region of chromosome 9, specifically in the region of 9p21, are deleted in many cancer cells, including $p16^{INK4A}$ and $p15^{INK4B}$. See Bailey-Wilson, supra; Sclafani et al., supra. These tumor suppressor genes may also be implicated in lung cancer pathogenesis.

In addition, many lung cancer cells produce growth factors that may act in an autocrine or paracrine fashion on lung cancer cells. See Siegfried et al., pp. 317-336, in Kane, supra; Moody, pp. 337-370, in Kane, supra and Heasley et al., 371-390, in Kane, supra. In SCLC, many tumor cells produce gastrin-releasing peptide (GRP), which is a proliferative growth factor for these cells. See Skarin, supra. Many NSCLC tumors express epidermal growth factor (EGF) receptors, allowing NSCLC cells to proliferate in response to EGF. Insulin-like growth factor (IGF-I) is elevated in greater than 95% of SCLC and greater than 80% of NSCLC tumors; it is thought to function as an autocrine growth factor. Id. Finally, stem cell factor (SCF, also known as steel factor or kit ligand) and c-Kit (a proto-oncoprotein tyrosine kinase receptor for SCF) are both expressed at high levels in SCLC, and thus may form an autocrine loop that increases proliferation. Id.

Although the majority of lung cancer cases are attributable to cigarette smoking, most smokers do not develop lung cancer. Epidemiological evidence has suggested that susceptibility to lung cancer may be inherited in a Mendelian fashion, and thus have an inherited genetic component. Bailey-Wilson, supra. Thus, it is thought that certain allelic variants at some genetic loci may affect susceptibility to lung cancer. Id. One way to identify which allelic variants are likely to be involved in lung cancer susceptibility, as well as susceptibility to other diseases, is to look at allelic variants of genes that are highly expressed in lung.

The lung is susceptible to a number of other debilitating diseases as well, including, without limitation, emphysema, pneumonia, cystic fibrosis and asthma. See Stockley (ed.), *Molecular Biology of the Lung, Volume I: Emphysema and Infection*, Birkhauser Verlag (1999), hereafter Stockley I, and Stockley (ed.), *Molecular Biology of the Lung, Volume II: Asthma and Cancer*, Birkhauser Verlag (1999), hereafter Stockley II. The cause of many these disorders is still not well understood and there are few, if any, good treatment options for many of these noncancerous lung disorders. Thus, there remains a need to understand various noncancerous lung disorders and to identify treatments for these diseases.

The development and differentiation of lung tissue during embryonic development is also very important. All of the epithelial cells of the respiratory tract, including those of the lung and bronchi, are derived from the primitive endodermal cells that line the embryonic outpouching. See Yesner, supra. During embryonic development, multipotent endodermal stem cells differentiate into many different types of specialized cells, which include ciliated cells for moving inhaled particles, goblet cells for producing mucus, Kulchitsky's cells for endocrine function, and Clara cells and type II pneumocytes for secreting surfactant protein. Id. Improper development and differentiation may cause respiratory disorders and distress in infants, particularly in premature infants, whose lungs cannot produce sufficient surfactant when they are born. Further, some lung cancer cells, particularly small cell carcinomas, are plastic and can alter their phenotype into a number of cell types, including large cell carcinoma, adenocarcinoma and squamous cell carcinoma. Id. Thus, a better understanding of lung development and differentiation may help facilitate understanding of lung cancer initiation and progression.

The most common screening tests for lung cancer are chest x-ray and sputum cytology. Randomized controlled trials have not demonstrated a reduction in lung cancer mortality resulting from screening with chest x-ray and/or sputum cytology. Additionally, sputum cytology has not been shown to be effective when used as an adjunct to annual chest x-ray. Screening with chest x-ray plus sputum cytology appears to detect lung cancer at an earlier stage, but this would be expected in a screening test whether or not it was effective at reducing mortality. Since early detection by current screening methods fails to reduce mortality in lung cancer patients, current lung cancer screening methods are inadequate.

There are two important potential hazards associated with chest radiography screening. First, false positive test results can lead to an unnecessary invasive procedure, such as percutaneous needle biopsy or thoracotomy. These procedures are costly and due to their invasive nature carry risks of their own. The second hazard with chest radiography screening is overdiagnosis. Overdiagnosis is the diagnosis of a small or slowly growing tumor that would not have become clinically significant had it not been detected by screening. Although overdiagnosis is almost impossible to document in a living individual, autopsy studies suggest that many individuals die with lung cancer rather than from it.

Additionally, the spectrum of lung cancer type has shifted over the last two decades. Whereas the most common type used to be squamous cell cancer (usually centrally located), the most common type now is adenocarcinoma (usually peripherally located). The latter may be more amenable to early detection by chest x-ray, the limitations of which are described above. In contrast, sputum cytology, is more sensitive in the detection of squamous cell cancer than in detecting adenocarcinoma, and therefore lacks usefulness in detecting the more common adenocarcinomas. Clearly, new highly sensitive non-invasive methods of detecting lung cancer are needed.

There are intensive efforts to improve lung cancer screening with newer technologies, including low-dose helical computed tomography (LDCT) and molecular techniques. LDCT is far more sensitive than chest radiography. In a recent screening study, CT detected almost 6 times as many stage I lung cancers as chest radiography and most of these tumors were 1 cm or less in diameter. However, the effectiveness of screening with LDCT has not yet been evaluated in a controlled clinical trial.

There are two potential hazards that must be considered against any potential benefit of screening with LDCT. The more common and familiar hazard is the false positive test result, which may lead to anxiety and invasive diagnostic procedures. A less familiar hazard is overdiagnosis, the diagnosis of a condition that would not have become clinically significant had it not been detected by screening. In the case of screening with LDCT, overdiagnosis could lead to unnecessary diagnosis of lung cancer requiring some combination of surgery, e.g., lobectomy, chemotherapy and radiation therapy. As stated above, overdiagnosis is almost impossible to document in a living individual. In one large study, about one-sixth of all lung cancers found at autopsy had not been clinically recognized before death. Furthermore, autopsy probably fails to detect many small lung cancers that are detectable by CT.

Current therapies for lung cancer are quite limited. Generally, patient options comprise surgery, radiation therapy, and chemotherapy.

Depending on the type and stage of a lung cancer, surgery may be used to remove the tumor along with some surrounding lung tissue. A lobectomy refers to a lobe (section) of the lung being removed. If the entire lung is removed, the surgery is called a pneumonectomy. Removing only part of a lobe is known as a segmentectomy or wedge resection.

If the cancer has spread to the brain, benefit may be gained from removal of the brain metastasis. This involves a craniotomy (surgery through a hole in the skull).

For radiation therapy several methods exist. External beam radiation therapy uses radiation delivered from outside the body that is focused on the cancer. This type of radiation therapy is most often used to treat a primary lung cancer or its metastases to other organs.

Brachytherapy uses a small pellet of radioactive material placed directly into the cancerous tissue or into the airway next to the cancer. Radiation therapy is sometimes used as the main (primary) treatment of lung cancer, especially if the general health of the patient is too poor to undergo surgery. Brachytherapy can also be used to help relieve blockage of large airways by cancer.

Additionally, radiation therapy can be used as a post surgical treatment to kill very small deposits of cancer that cannot be seen or removed during surgery. Radiation therapy can also be used to palliate (relieve) symptoms of lung cancer such as pain, bleeding, difficulty swallowing, and problems caused by brain metastases.

For chemotherapy, cisplatin or a related drug, carboplatin, are the chemotherapy agents most often used in treating NSCLC. Recent studies found that combining either of these with drugs such as gemcitabine, paclitaxel, docetaxel, etoposide, or vinorelbine appear to be more effective in treating NSCLC.

Recently, the National Comprehensive Cancer Network (NCCN; nccn with the extension .org of the world wide web), an alliance of nineteen of the world's leading cancer centers, announces a major update of the NCCN Non-Small Cell Lung Cancer Clinical Practice Guidelines. The NCCN is widely recognized as a standard for clinical policy in oncology.

Recently approved targeted therapy, gefitinib (IRESSA®, AstraZeneca Pharmaceuticals LP) is now recommended as third-line therapy and as second-line only if the platinum/docetaxel combination was used as first-line therapy.

The NCCN's Non-Small Cell Lung Cancer (NSCLC) guidelines contain recommendations for administration of chemotherapy to patients with this disease including patient selection criteria and definition of first-, second-, and third-line agents and combinations.

Chemotherapeutic agents are specified as two-agent regimens for first-line therapy, two agent regimens or single agents for second-line therapy, and one single agent for third-line therapy. Agents used in first- and second-line therapy are: cisplatin (PLATINOL®, Bristol-Myers Squibb Company), carboplatin (PARAPLATIN®, Bristol-Myers Squibb Company), paclitaxel (TAXOL®, Bristol-Myers Squibb Company), docetaxel (TAXOTERE®, Aventis Pharmaceuticals Inc.), vinorelbine (NAVELBINE®, GlaxoSmithKline), gemcitabine (GEMZAR®, Eli Lilly and Company), etoposide (TOPOSAR®, Pfizer, Inc.; VEPESID®, Bristol-Myers Squibb Company; ETOPOPHOS®, Bristol-Myers Squibb Company), irinotecan (CAMPTOSAR®, Pfizer, Inc.), vinblastine (VELBAN®, Eli Lilly and Company), mitomycin (MUTAMYCIN®, Bristol-Myers Squibb Company), and ifosfamide (IFEX®, Bristol-Myers Squibb Company).

Some of the usual chemotherapy combinations used for patients with SCLC include: EP (etoposide and cisplatin); ET (etoposide and carboplatin); ICE (ifosfamide, carboplatin, and etoposide); and CAV (cyclophosphamide, doxorubicin, and vincristine).

New drugs such as gemcitabine, paclitaxel, vinorelbine, topotecan, and teniposide have shown promising results in some SCLC studies. Growth factors may be given in conjunction to chemotherapy agents if patient health is good. The administration of growth factors help prevent bone marrow side effects.

Ongoing or recently completed therapeutic trials for various compounds to treat lung cancer include alitretinoin (PANRETIN®, Ligand Pharmaceuticals), topotecan HCl (HYCAMTIN®, GlaxoSmithKline), liposomal ether lipid (Elan Pharmaceutical), cantuzumab mertansine (ImmunoGen), oncolytic virus therapy (GAVAX®, Cell Genesys), vincristine (ONCO TCS®, Inex Pharmaceuticals), a concentrate of shark cartilage (NEOVASTAT®, AEterna Laboratories), squalamine (Genaera), mirostipen (Human Genome Sciences Inc.), p53 tumor suppressor therapy (ADVEXINN®, Introgen Therapeutics), biricodar dicitrate (INCEL®, Vertex Pharmaceuticals), flavopiridol (Aventis), pemetrexed (AL-IMTA®, Eli Lilly and Company), pivaloyloxymethylbutyrate (PIVANEX®, Titan Pharmaceuticals), tirapazamine (TIRAZONE®, Sanofi-Synthelabo Pharmaceuticals), irinotecan (CAMPTOSAR®, Pharmacia), tezacitabine (Chiron), cisplatin/vinblastine/amifostine (MedImmune), paclitaxel/carboplatin/amifostine (MedImmune), antisense agent (ONCO-MYC-NG®, AVI BioPharma), exisulind/vinorelbine (APTOSYN®/NAVELBINE®, Cell Pathways), tariquidar (QLT), paclitaxel poliglumex (XYOTAX®, Cell Therapeutics), PEG-camptothecin (PROTHECAN®, Enzon), decitabine (SuperGen), erlotinib (TARCEVA®, OSI Pharmaceuticals), ABX-EGF (Abgenix), vitamin E-based emulsion formulation of paclitaxel (TOCOSOL PACLITAXEL®, Sonus Pharmaceuticals), a fragment of the mouse antibody HMFG-1 labeled with yttrium 90 (THERAFAB®, Antisoma), minodronate (Yamanouchi Pharmaceutical), exisulind/docetaxel/carboplatin (APTOSYN®/TAXOTERE®V/PARAPLATIN®, Cell Pathways), exisulind/gemcitabine HCl (APTOSYN®/GEMZAR®), Cell Pathways), IMC-C225/carboplatin/paclitaxel (ERBITUX®/CARBOPLATIN®/PACLITAXEL®, ImClone Systems), and vinorelbine (NAVELBINE®, GlaxoSmithKline).

As indicated above, many therapeutics are recommended for use in combination as a first-line therapy or only if other therapeutics have failed as second-, and third-line agents. While there are many compounds in ongoing or recently completed therapeutic trials, there is great need for additional therapeutic compounds capable of treating early stage and advanced or metastasized lung cancer.

Accordingly, there is a great need for more sensitive and accurate methods for predicting whether a person is likely to develop lung cancer, for diagnosing lung cancer, for monitoring the progression of the disease, for staging the lung cancer, for determining whether the lung cancer has metastasized and for imaging the lung cancer. There is also a need for better treatment of lung cancer. Further, there is a great need for diagnosing and treating noncancerous lung disorders such as emphysema, pneumonia, lung infection, pulmonary fibrosis, cystic fibrosis and asthma. There is also a need for compositions and methods of using these compositions to identify lung tissue for forensic purposes and for determining whether a particular cell or tissue exhibits lung-specific characteristics.

As discussed above, each of the methods for diagnosing and staging breast, ovarian pancreatic, and lung cancer is limited by the technology employed. Accordingly, there is need for sensitive molecular and cellular markers and reagents for the detection of breast, ovarian, pancreatic and lung cancer including metastatic cancer. There is a need for molecular markers and reagents for the accurate staging, including clinical and pathological staging, of breast, ovarian, pancreatic and lung cancers to optimize treatment methods. Finally, there is a need for sensitive molecular and cellular markers and reagents to monitor the progress of cancer treatments, including markers that can detect recurrence of breast, ovarian, pancreatic and lung cancers following remission.

The present invention provides alternative reagents and methods for treating breast, ovarian, pancreatic and lung cancer that overcome the limitations of conventional therapeutic methods as well as offer additional advantages that will be apparent from the detailed description below.

Angiogenesis in Cancer

Growth and metastasis of solid tumors are also dependent on angiogenesis. Folkman, J., 1986, *Cancer Research*, 46, 467-473; Folkman, J., 1989, *Journal of the National Cancer Institute*, 82, 4-6. It has been shown, for example, that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites such as liver, lung or bone. Weidner, N., et al., 1991, *The New England Journal of Medicine*, 324(1), 1-8.

Angiogenesis, defined as the growth or sprouting of new blood vessels from existing vessels, is a complex process that primarily occurs during embryonic development. The process is distinct from vasculogenesis, in that the new endothelial cells lining the vessel arise from proliferation of existing cells, rather than differentiating from stem cells. The process is invasive and dependent upon proteolysis of the extracellular matrix (ECM), migration of new endothelial cells, and synthesis of new matrix components. Angiogenesis occurs during embryogenic development of the circulatory system; however, in adult humans, angiogenesis only occurs as a response to a pathological condition (except during the reproductive cycle in women).

Under normal physiological conditions in adults, angiogenesis takes place only in very restricted situations such as hair growth and wounding healing. Auerbach, W. and Auerbach, R., 1994, *Pharmacol Ther.* 63(3):265-3 11; Ribatti et al., 1991, *Haematologica* 76(4):3 11-20; Risau, 1997, *Nature* 386(6626):67 1-4. Angiogenesis progresses by a stimulus which results in the formation of a migrating column of endothelial cells. Proteolytic activity is focused at the advancing tip of this "vascular sprout", which breaks down the ECM sufficiently to permit the column of cells to infiltrate and migrate. Behind the advancing front, the endothelial cells differentiate and begin to adhere to each other, thus forming a new basement membrane. The cells then cease proliferation and finally define a lumen for the new arteriole or capillary.

Unregulated angiogenesis has gradually been recognized to be responsible for a wide range of disorders, including, but not limited to, cancer, cardiovascular disease, rheumatoid arthritis, psoriasis and diabetic retinopathy. Folkman, 1995, *Nat Med* 1(1):27-31; Isner, 1999, *Circulation* 99(13): 1653-5; Koch, 1998, *Arthritis Rheum* 41(6):951-62; Walsh, 1999, *Rheumatology* (Oxford) 38(2):103-12; Ware and Simons, 1997, *Nat Med* 3(2): 158-64.

Of particular interest is the observation that angiogenesis is required by solid tumors for their growth and metastases. Folkman, 1986 supra; Folkman 1990, *J Natl. Cancer Inst.*, 82(1) 4-6; Folkman, 1992, *Semin Cancer Biol* 3(2):65-71; Zetter, 1998, *Annu Rev Med* 49:407-24. A tumor usually begins as a single aberrant cell which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. The precise mechanisms that control the angiogenic switch is not well understood, but it is believed that neovascularization of tumor mass results from the net balance of a multitude of angiogenesis stimulators and inhibitors Folkman, 1995, supra.

One of the most potent angiogenesis inhibitors is endostatin identified by O'Reilly and Folkman. O'Reilly et al., 1997, *Cell* 88(2):277-85; O'Reilly et al., 1994, *Cell* 79(2):3 15-28. Its discovery was based on the phenomenon that certain primary tumors can inhibit the growth of distant metastases. O'Reilly and Folkman hypothesized that a primary tumor initiates angiogenesis by generating angiogenic stimulators in excess of inhibitors. However, angiogenic inhibitors, by virtue of their longer half-life in the circulation, reach the site of a secondary tumor in excess of the stimulators. The net result is the growth of primary tumor and inhibition of secondary tumor. Endostatin is one of a growing list of such angiogenesis inhibitors produced by primary tumors. It is a proteolytic fragment of a larger protein: endostatin is a 20 kDa fragment of collagen XVIII (amino acid H1132-K1315 in murine collagen XVIII). Endostatin has been shown to specifically inhibit endothelial cell proliferation in vitro and block angiogenesis in vivo. More importantly, administration of endostatin to tumor-bearing mice leads to significant tumor regression, and no toxicity or drug resistance has been observed even after multiple treatment cycles. Boehm et al., 1997, Nature 390(6658):404-407. The fact that endostatin targets genetically stable endothelial cells and inhibits a variety of solid tumors makes it a very attractive candidate for anticancer therapy. Fidler and Ellis, 1994, Cell 79(2): 185-8; Gastl et al., 1997, Oncology 54(3):177-84; Hinsbergh et al., 1999, Ann Oncol 10 Suppl 4:60-3. In addition, angiogenesis inhibitors have been shown to be more effective when combined with radiation and chemotherapeutic agents. Klement, 2000, J. Clin Invest, 105(8) R15-24. Browder, 2000, Cancer Res. 6-(7) 1878-86, Arap et al., 1998, Science 279(5349): 377-80; Mauceri et al., 1998, Nature 394(6690):287-91.

The present invention provides alternative methods of treating breast, ovarian, pancreatic and lung cancer that overcome the limitations of conventional therapeutic methods as well as offer additional advantages that will be apparent from the detailed description below.

SUMMARY OF THE INVENTION

This invention is directed to an isolated Pro104 antibody that binds to Pro104 on a mammalian cell in vivo. The invention is further directed to an isolated Pro104 antibody that internalizes upon binding to Pro104 on a mammalian cell in vivo. The antibody may be a monoclonal antibody. Alternatively, the antibody is an antibody fragment or a chimeric or a humanized antibody. The monoclonal antibody may be produced by a hybridoma selected from the group of hybridomas deposited under American Type Culture Collection accession number PTA-5277, 6076, 6077 and 6078.

The antibody may compete for binding to the same epitope as the epitope bound by the monoclonal antibody produced by a hybridoma selected from the group of hybridomas deposited under the American Type Culture Collection accession number PTA-5277, 6076, 6077 and 6078.

The invention is also directed to conjugated antibodies. They may be conjugated to a growth inhibitory agent or a cytotoxic agent. The cytotoxic agent may be selected from the group consisting of toxins, antibiotics, radioactive isotopes and nucleolytic enzymes and toxins. Examples of toxins include, but are not limited to, maytansin, maytansinoids, saporin, gelonin, ricin or calicheamicin.

The mammalian cell may be a cancer cell. Preferably, the anti-Pro104 monoclonal antibody inhibits the growth of Pro104-expressing cancer cells in vivo.

The antibody may be produced in bacteria. Alternatively, the antibody may be a humanized form of an anti-Pro104 antibody produced by a hybridoma selected from the group of hybridomas having ATCC accession number PTA-5277, 6076, 6077 and 6078.

Preferably, the cancer is selected from the group consisting of breast, ovarian, pancreatic and lung cancer. The invention is also directed to a method of producing the antibodies comprising culturing an appropriate cell and recovering the antibody from the cell culture.

The invention is also directed to compositions comprising the antibodies and a carrier. The antibody may be conjugated to a cytotoxic agent. The cytotoxic agent may be a radioactive isotope or other chemotherapeutic agent.

The invention is also directed to a method of killing a Pro104-expressing cancer cell, comprising contacting the cancer cell with the antibodies of this invention, thereby killing the cancer cell. The cancer cell may be selected from the group consisting of breast, ovarian, pancreatic and lung cancer cells.

The ovarian cancer may be ovarian serous adenocarcinoma.

The breast cancer may be breast infiltrating ductal carcinoma.

The breast, ovarian, pancreatic or lung cancer may also be metastatic.

The invention is also directed to a method of alleviating a Pro104-expressing cancer in a mammal, comprising administering a therapeutically effective amount of the antibodies to the mammal.

In addition, the invention is directed to an article of manufacture comprising a container and a composition contained therein, wherein the composition comprises an antibody as described herein. The article of manufacture may also comprise an additional component, e.g., a package insert indicating that the composition can be used to treat ovarian or pancreatic cancer.

BRIEF DESCRIPTION OF THE FIGURES

FIG. 3 shows that Pro104.C19.1 binds to live HeLa cancer cells expressing Pro104 (FIG. 3A) and does not bind to live cancer cells which do not express Pro104 (FIG. 3B).

FIG. 4 shows that Cy3-Pro104.C25.1 binds to live HeLa cancer cells expressing Pro104 (FIG. 4A) and does not bind to live cancer cells which do not express Pro104 (FIG. 4B).

FIG. 5 shows that Cy3-Pro104.C25.1 binds to and is internalized in live HeLa cancer cells expressing Pro104.

FIG. 6 shows that Cy3-Pro104.C19.1 binds to and is internalized in pancreatic cancer cells expressing Pro104 (FIG. 6A) and does not bind to and is not internalized in cancer cells which do not express Pro104 (FIG. 6B).

FIG. 7 shows that Cy3-Pro104.C55.1 binds to and is internalized in pancreatic cancer cells expressing Pro104 (FIG. 7A) and does not bind to and is not internalized in cancer cells which do not express Pro104 (FIG. 7B).

FIG. 8 shows that Pro104.C25.1 binds to Pro104 on cancer cells in ovarian tumors (FIG. 8A and FIG. 8C) and does not bind to normal ovarian cells (FIG. 8B and FIG. 8D).

FIG. 9 shows that Pro104.C25.1 binds to Pro104 on the cell membrane of ovarian cancer cells.

FIG. 10 shows that Pro104.D9 binds to Pro104 on the cell membrane of ovarian cancer cells.

FIG. 11 shows that Pro104.D133 binds to Pro104 on the cell membrane of serous ovarian cancer cells.

FIG. 12 shows that Pro104.C25.1 binds to Pro104 on cancer cells in pancreatic tumors (FIG. 12A and FIG. 12C) and does not bind to normal pancreatic cells (FIG. 12B and FIG. 12D).

FIG. 13 shows controls demonstrating Pro104 MAb immunolabeling specificity in mouse IgG (FIG. 13A) and absorption with Pro104 antigen (FIG. 13B).

FIG. 14 shows an epitope map of Pro104 MAbs.

FIG. 15 shows a western blot showing detection of Pro104 protein in mRNA+ cell lines (FIG. 15A) and ovarian tumor tissue (T) but not normal adjacent tissue (N) (FIG. 15B).

FIG. 16 shows that overexpression of Pro104 leads to phosphorylation of EGF Receptor.

FIG. 17 shows that the Pro104 protein is glycosylated (FIG. 17A) and GPI-Linked (FIG. 17B).

FIG. 18 shows the surface biotinylation of native Pro104 in cell lines.

FIG. 19 shows retroviral-mediated overexpression of Pro104 protein in RK3E cells.

FIG. 20 shows retroviral-mediated overexpression of Pro104 protein in SKOV3 Cells.

FIG. 21 shows siRNA mediates specific down-regulation of Pro104 protein in HeLa cells.

FIG. 23 shows Pro104 siRNA specific knockdown of Pro104 mRNA (FIG. 23B) and not knock down of GAPDH mRNA (FIG. 23A) in CaOV3 cells.

FIG. 24 shows Pro104 siRNA specific knockdown of Pro104 mRNA (FIG. 24A) and not knock down GAPDH mRNA (FIG. 24B)in HeLa cells.

FIG. 26 shows different Pro104 siRNAs inducing specific mRNA knockdown (FIG. 26B) and apoptosis (FIG. 26A) in HeLa cells.

FIG. 27 shows specific knockdown of Pro104 mRNA in HeLa Cells inducing cell death as determined by apoptotic cells (FIG. 27A) and necrotic cells (FIG. 27B).

FIG. 28 shows specific mRNA knockdown by Pro104 siRNA inducing apoptosis in HeLa cells measured by Annexin V assay (FIG. 28A) and Caspase Activity Assay (FIG. 28B).

FIG. 30 shows Pro104 siRNA having no knockdown effect (FIG. 30A) and no effect on apoptosis (FIG. 30B) in cells without Pro104 mRNA.

FIG. 31 shows overexpression of Pro104 inducing cell growth in soft agar. Alkaline Phosphatase (AP) does not induce cell growth in soft agar (FIG. 31A) while expression and overexpression of Pro104 (FIG. 31E and B versus FIG. 31D) and overexpression of Pro104-HA (FIG. 31C) induces cell growth in soft agar.

FIG. 32 shows Pro104 protease activity is required for cell growth with FIG. 32A showing Pro104, Pro104-HA and protease inactive mutant Pro104-mut proteins being expressed in retrovirally infected cells, FIG. 32B showing stains for AP activity, demonstrating that selected cells were producing the gene of interest and FIG. 32C showing soft agar assays demonstrating Pro104 protease activity is required for cell growth, and FIG. 32D shows number of Colonies formed in Soft Agar assays demonstrating Pro104 Protease Activity is Required for Cell Growth.

FIG. 34 shows knockdown of Pro104 mRNA by siRNA inhibiting growth of HeLa cells in soft agar as measured by QPCR (FIG. 34A) and caspase activity assay (FIG. 34B).

FIG. 35 shows increased growth of human tumor cells over-expressing Pro104 (FIG. 35A and FIG. 35B) and SKOV3 cells transfected with Pro104 (FIG. 35C and FIG. 35D).

DETAILED DESCRIPTION OF THE INVENTION

Definitions and General Techniques

Figure 1B:
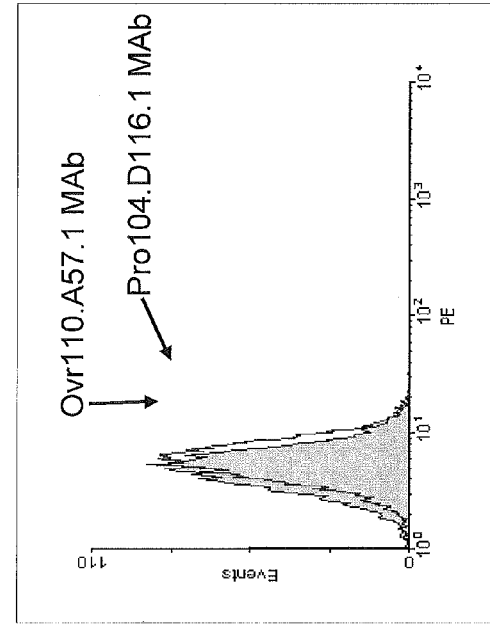
FIG. 1 shows that Pro104.D116.1 MAb binds to 293F cells transiently transfected with Pro104 (FIG. 1A) and does not bind to 293F cells that do not express Pro104 (FIG. 1B).

Human "Pro104" as used herein, refers to a protein of 314 amino acids that is expressed on the cell surface as a glycoprotein. The nucleotide and amino acid sequences of Pro104 have been disclosed, e.g., WO200016805-A1 PA (DIAD-) DIADEXUS Human cancer-specific gene, Pro104; WO9836054-A1 PA (AMRA-) AMRAD Nucleotide sequence of short isoform of HELA2; and J. D. Hooper et al. Testisin, a new human serine protease expressed by premeiotic testicular germ cells and lost in testicular germ cell tumors. *Cancer Research* 59:3199-3205 (1999)). Pro104 has also been disclosed in the REFSEQ database as: NM_006799.2 (GI: 21614534) *Homo sapiens* protease, serine, 21 (testisin) (PRSS21), transcript variant 1, mRNA. RefSeq gives the following summary of PRSS21 (Pro104):

> This gene encodes a cell-surface anchored serine protease, which is a member of the trypsin family of serine proteases. It is predicted to be active on peptide linkages involving the carboxyl group of lysine or arginine. The protein localizes to the cytoplasm and the plasma membrane of premeiotic testicular germ cells and it may be involved in progression of testicular tumors of germ cell origin. Alternative splicing of this gene results in three transcript variants encoding three different isoforms.

The amino acids of Pro104 are presumably located on the cell surface. Pro104 as used herein include allelic variants and conservative substitution mutants of the protein which have Pro104 biological activity. Additionally, splice variants may have Pro104 biological activity. The RefSeq accessions for the splice variants referenced above include: NM_144956.1 (GI: 21614530) *Homo sapiens* protease, serine, 21 (testisin) (PRSS21), transcript variant 2, mRNA; and NM_144957 (GI: 21614532) *Homo sapiens* protease, serine, 21 (testisin) (PRSS21), transcript variant 3, mRNA.

Our findings that Pro104 is apparently associated with the more aggressive breast, ovarian, pancreatic and lung cancers makes this cell surface antigen an attractive target for immunotherapy of these and possibly other tumor types.

The term "antibody" (Ab) as used herein includes monoclonal antibodies, polyclonal antibodies, multispecific antibodies (e.g. bispecific antibodies), and antibody fragments, so long as they exhibit the desired biological activity. The term "immunoglobulin" (Ig) is used interchangeably with "antibody" herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. Preferably, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the a, δ and γ chains and four CH domains for μ and ε isotypes. Each L chain has at the N-terminus, a variable domain (VL) followed by a constant domain (CL) at its other end.

The VL is aligned with the VH and the CL is aligned with the first constant domain of the heavy chain (CHI). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Teff and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated $\alpha$, $\delta$, $\epsilon$, $\gamma$ and $\mu$, respectively. The $\gamma$ and $\alpha$ classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of a particular antibody for its particular antigen. However, the variability is not evenly distributed across the 1-10-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a P-sheet configuration, connected by three hypervariable regions, which form loops connecting, and in some cases forming part of, the P-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (LI), 5056 (L2) and 89-97 (L3) in the VL, and around about 1-35 (HI), 50-65 (H2) and 95-102 (113) in the VH; Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (LI), 50-52 (L2) and 91-96 (U) in the VL, and 26-32 (HI), 53-55 (1-12) and 96-101 (H3) in the VH; Chothia and Lesk J. Mol. Biol. 196: 901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a CL and at least heavy chain constant domains, CHI, CH2 and CH3. The constant domains may be native sequence constant domains (e.g. human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CHI). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CHI domain including one or more cysteines from the antibody hinge region. Fab'-SH is the designation herein for Fab' in which the cysteine residue(s) of the constant domains bear a free thiol group. F(ab')2 antibody fragments originally were produced as pairs of 8 Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

A "native sequence" polypeptide is one which has the same amino acid sequence as a polypeptide (e.g., antibody) derived from nature. Such native sequence polypeptides can be isolated from nature or can be produced by recombinant or synthetic means. Thus, a native sequence polypeptide can have the amino acid sequence of a naturally occurring human polypeptide, murine polypeptide, or polypeptide from any other mammalian species.

The term "amino acid sequence variant" refers to a polypeptide that has amino acid sequences that differ to some extent from a native sequence polypeptide. Ordinarily, amino acid sequence variants of Pro104 will possess at least about 70% homology with the native sequence Pro104, preferably, at least about 80%, more preferably at least about 85%, even more preferably at least about 90% homology, and most preferably at least 95%. The amino acid sequence variants can possess substitutions, deletions, and/or insertions at certain positions within the amino acid sequence of the native amino acid sequence.

The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such molecule from having the ability to bind to the high affinity receptor, FcεRI.

"Homology" is defined as the percentage of residues in the amino acid sequence variant that are identical after aligning the sequences and introducing gaps, if necessary, to achieve the maximum percent homology. Methods and computer programs for the alignment are well known in the art. Sequence similarity may be measured by any common sequence analysis algorithm, such as GAP or BESTFIT or other variation Smith-Waterman alignment. See, T. F. Smith and M. S. Waterman, J. Mol. Biol. 147:195-197 (1981) and W. R. Pearson, Genomics 11:635-650 (1991).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

As used herein, an anti-Pro104 antibody that "internalizes" is one that is taken up by (i.e., enters) the cell upon binding to Pro104 on a mammalian cell (i.e. cell surface Pro104). The internalizing antibody will of course include antibody fragments, human or humanized antibody and antibody conjugate. For therapeutic applications, internalization in vivo is contemplated. The number of antibody molecules internalized will be sufficient or adequate to kill a Pro104-expressing cell, especially a Pro104-expressing cancer cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the tumor cell.

Whether an anti-Pro104 antibody internalizes upon binding Pro104 on a mammalian cell can be determined by various assays including those described in the experimental examples below. For example, to test internalization in vivo, the test antibody is labeled and introduced into an animal known to have Pro104 expressed on the surface of certain cells. The antibody can be radiolabeled or labeled with fluorescent or gold particles, for instance. Animals suitable for this assay include a mammal such as a NCR nude mouse that contains a human Pro104-expressing tumor transplant or xenograft, or a mouse into which cells transfected with human Pro104 have been introduced, or a transgenic mouse expressing the human Pro104 transgene. Appropriate controls include animals that did not receive the test antibody or that received an unrelated antibody, and animals that received an antibody to another antigen on the cells of interest, which antibody is known to be internalized upon binding to the antigen. The antibody can be administered to the animal, e.g., by intravenous injection. At suitable time intervals, tissue sections of the animal can be prepared using known methods or as described in the experimental examples below, and analyzed by light microscopy or electron microscopy, for internalization as well as the location of the internalized antibody in the cell. For internalization in vitro, the cells can be incubated in tissue culture dishes in the presence or absence of the relevant antibodies added to the culture media and processed for microscopic analysis at desired time points. The presence of an internalized, labeled antibody in the cells can be directly visualized by microscopy or by autoradiography if radiolabeled antibody is used. Alternatively, in a quantitative biochemical assay, a population of cells comprising Pro104-expressing cells are contacted in vitro or in vivo with a radiolabeled test antibody and the cells (if contacted in vivo, cells are then isolated after a suitable amount of time) are treated with a protease or subjected to an acid wash to remove uninternalized antibody on the cell surface. The cells are ground up and the amount of protease resistant, radioactive counts per minute (cpm) associated with each batch of cells is measured by passing the homogenate through a scintillation counter. Based on the known specific activity of the radiolabeled antibody, the number of antibody molecules internalized per cell can be deduced from the scintillation counts of the ground-up cells. Cells are "contacted" with antibody in vitro preferably in solution form such as by adding the cells to the cell culture media in the culture dish or flask and mixing the antibody well with the media to ensure uniform exposure of the cells to the antibody. Instead of adding to the culture media, the cells can be contacted with the test antibody in an isotonic solution such as PBS in a test tube for the desired time period. In vivo, the cells are contacted with antibody by any suitable method of administering the test antibody such as the methods of administration described below when administered to a patient.

The faster the rate of internalization of the antibody upon binding to the Pro104-expressing cell in vivo, the faster the desired killing or growth inhibitory effect on the target Pro104-expressing cell can be achieved, e.g., by a cytotoxic immunoconjugate. Preferably, the kinetics of internalization of the anti-Pro104 antibodies are such that they favor rapid killing of the Pro104-expressing target cell. Therefore, it is desirable that the anti-Pro104 antibody exhibit a rapid rate of internalization preferably, within 24 hours from administration of the antibody in vivo, more preferably within about 12 hours, even more preferably within about 30 minutes to 1 hour, and most preferably, within about 30 minutes. The present invention provides antibodies that internalize as fast as about 15 minutes from the time of introducing the anti-Pro104 antibody in vivo. The antibody will preferably be internalized into the cell within a few hours upon binding to Pro104 on the cell surface, preferably within 1 hour, even more preferably within 15-30 minutes.

To determine if a test antibody can compete for binding to the same epitope as the epitope bound by the anti-Pro104 antibodies of the present invention including the antibodies produced by the hybridomas deposited with the ATCC, a cross-blocking assay e.g., a competitive ELISA assay can be performed. In an exemplary competitive ELISA assay, Pro104-coated wells of a microtiter plate, or Pro104-coated sepharose beads, are pre-incubated with or without candidate competing antibody and then a biotin-labeled anti-Pro104 antibody of the invention is added. The amount of labeled anti-Pro104 antibody bound to the Pro104 antigen in the wells or on the beads is measured using avidin-peroxidase conjugate and appropriate substrate.

Alternatively, the anti-Pro104 antibody can be labeled, e.g., with a radioactive or fluorescent label or some other detectable and measurable label. The amount of labeled anti-Pro104 antibody that binds to the antigen will have an inverse correlation to the ability of the candidate competing antibody (test antibody) to compete for binding to the same epitope on the antigen, i.e., the greater the affinity of the test antibody for the same epitope, the less labeled anti-Pro104 antibody will be bound to the antigen-coated wells. A candidate competing antibody is considered an antibody that binds substantially to the same epitope or that competes for binding to the same epitope as an anti-Pro104 antibody of the invention if the candidate competing antibody can block binding of the anti-Pro104 antibody by at least 20%, preferably by at least 20-50%, even more preferably, by at least 50% as compared to a control performed in parallel in the absence of the candidate competing antibody (but may be in the presence of a known noncompeting antibody). It will be understood that variations of this assay can be performed to arrive at the same quantitative value.

An antibody having a "biological characteristic" of a designated antibody, such as any of the monoclonal antibodies Pro104.C1, Pro104.C4, Pro104.C13, Pro104.C17, Pro104.C18, Pro104.C19, Pro104.C24, Pro104.C25, Pro104.C27, Pro104.C34, Pro104.C37, Pro104.C46, Pro104.C48, Pro104.C49, Pro104.C50, Pro104.C53, Pro104.C54, Pro104.C55, Pro104.C57, Pro104.C60, Pro104.C66, Pro104.C75, Pro104.C84, Pro104.D4, Pro104.D6, Pro104.D9, Pro104.D12, Pro104.D14, Pro104.D18, Pro104.D19, Pro104.D20, Pro104.D21, Pro104.D26, Pro104.D29, Pro104.D31, Pro104.D43, Pro104.D47, Pro104.D51, Pro104.D55, Pro104.D56, Pro104.D58, Pro104.D62, Pro104.D63, Pro104.D64, Pro104.D68, Pro104.D69, Pro104.D75, Pro104.D81, Pro104.D85, Pro104.D88, Pro104.D91, Pro104.D94, Pro104.D102, Pro104.D106, Pro104.D111, Pro104.D112, Pro104.D113, Pro104.D114, Pro104.D115, Pro104.D116, Pro104.D117, Pro104.D118, Pro104.D119, Pro104.D120, Pro104.D121, Pro104.D122, Pro104.D123, Pro104.D, Pro104.D124, Pro104.D125, Pro104.D126, Pro104.D127, Pro104.D, Pro104.D128, Pro104.D129, Pro104.D130, Pro104.D131, Pro104.D132, Pro104.D133, Pro104.D134, Pro104.D135, Pro104.D136, Pro104.D137, Pro104.D138, Pro104.D139, Pro104.K14, Pro104.K15, Pro104.K16, Pro104.K47, Pro104.K71, Pro104.K72, Pro104.K74, Pro104.K75, Pro104.K76, Pro104.K78, Pro104.K81, Pro104.K87, Pro104.K88, Pro104.K89, Pro104.K155, Pro104.K156, Pro104.K157, Pro104.K158, Pro104.K159, Pro104.K160, Pro104.K163, Pro104.K164, Pro104.K176, Pro104.K217, Pro104.K226, Pro104.K227, Pro104.K240, Pro104.K274, Pro104.K264, Pro104.K281, Pro104.K358 or Pro104.K362, is one which possesses one or more of the biological characteristics of that antibody which distinguish it from other antibodies that bind to the same antigen, Pro104.C1, Pro104.C4, Pro104.C13, Pro104.C17, Pro104.C18, Pro104.C19, Pro104.C24, Pro104.C25, Pro104.C27, Pro104.C34, Pro104.C37, Pro104.C46, Pro104.C48, Pro104.C49, Pro104.C50, Pro104.C53, Pro104.C54, Pro104.C55, Pro104.C57, Pro104.C60, Pro104.C66, Pro104.C75, Pro104.C84, Pro104.D4, Pro104.D6, Pro104.D9, Pro104.D12, Pro104.D14, Pro104.D18, Pro104.D19, Pro104.D20, Pro104.D21, Pro104.D26, Pro104.D29, Pro104.D31, Pro104.D43, Pro104.D47, Pro104.D51, Pro104.D55, Pro104.D56, Pro104.D58, Pro104.D62, Pro104.D63, Pro104.D64, Pro104.D68, Pro104.D69, Pro104.D75, Pro104.D81, Pro104.D85, Pro104.D88, Pro104.D91, Pro104.D94, Pro104.D102, Pro104.D106, Pro104.D111, Pro104.D112, Pro104.D113, Pro104.D114, Pro104.D115, Pro104.D116, Pro104.D117, Pro104.D118, Pro104.D119, Pro104.D120, Pro104.D121, Pro104.D122, Pro104.D123, Pro104.D, Pro104.D124, Pro104.D125, Pro104.D126, Pro104.D127, Pro104.D, Pro104.D128, Pro104.D129, Pro104.D130, Pro104.D131, Pro104.D132, Pro104.D133, Pro104.D134, Pro104.D135, Pro104.D136, Pro104.D137, Pro104.D138, Pro104.D139, Pro104.K14, Pro104.K15, Pro104.K16, Pro104.K47, Pro104.K71, Pro104.K72, Pro104.K74, Pro104.K75, Pro104.K76, Pro104.K78, Pro104.K81, Pro104.K87, Pro104.K88, Pro104.K89, Pro104.K155, Pro104.K156, Pro104.K157, Pro104.K158, Pro104.K159, Pro104.K160, Pro104.K163, Pro104.K164, Pro104.K176, Pro104.K217, Pro104.K226, Pro104.K227, Pro104.K240, Pro104.K274, Pro104.K264, Pro104.K281, Pro104.K358 or Pro104.K362 will bind the same epitope as that bound by Pro104.C1, Pro104.C4, Pro104.C13, Pro104.C17, Pro104.C18, Pro104.C19, Pro104.C24, Pro104.C25, Pro104.C27, Pro104.C34, Pro104.C37, Pro104.C46, Pro104.C48, Pro104.C49, Pro104.C50, Pro104.C53, Pro104.C54, Pro104.C55, Pro104.C57, Pro104.C60, Pro104.C66, Pro104.C75, Pro104.C84, Pro104.D4, Pro104.D6, Pro104.D9, Pro104.D12, Pro104.D14, Pro104.D18, Pro104.D19, Pro104.D20, Pro104.D21, Pro104.D26, Pro104.D29, Pro104.D31, Pro104.D43, Pro104.D47, Pro104.D51, Pro104.D55, Pro104.D56, Pro104.D58, Pro104.D62, Pro104.D63, Pro104.D64, Pro104.D68, Pro104.D69, Pro104.D75, Pro104.D81, Pro104.D85, Pro104.D88, Pro104.D91, Pro104.D94, Pro104.D102, Pro104.D106, Pro104.D111, Pro104.D112, Pro104.D113, Pro104.D114, Pro104.D115, Pro104.D116, Pro104.D117, Pro104.D118, Pro104.D19, Pro104.D120, Pro104.D121, Pro104.D122, Pro104.D123, Pro104.D, Pro104.D124, Pro104.D125, Pro104.D126, Pro104.D127, Pro104.D, Pro104.D128, Pro104.D129, Pro104.D130, Pro104.D131, Pro104.D132, Pro104.D133, Pro104.D134, Pro104.D135, Pro104.D136, Pro104.D137, Pro104.D138, Pro104.D139, Pro104.K14, Pro104.K15, Pro104.K16, Pro104.K47, Pro104.K71, Pro104.K72, Pro104.K74, Pro104.K75, Pro104.K76, Pro104.K78, Pro104.K81, Pro104.K87, Pro104.K88, Pro104.K89, Pro104.K155, Pro104.K156, Pro104.K157, Pro104.K158, Pro104.K159, Pro104.K160, Pro104.K163, Pro104.K164, Pro104.K176, Pro104.K217, Pro104.K226, Pro104.K227, Pro104.K240, Pro104.K274, Pro104.K264, Pro104.K281, Pro104.K358 or Pro104.K362 (e.g. which competes for binding or blocks binding of monoclonal antibody Pro104.C1, Pro104.C4, Pro104.C13, Pro104.C17, Pro104.C18, Pro104.C19, Pro104.C24, Pro104.C25, Pro104.C27, Pro104.C34, Pro104.C37, Pro104.C46, Pro104.C48, Pro104.C49, Pro104.C50, Pro104.C53, Pro104.C54, Pro104.C55, Pro104.C57, Pro104.C60, Pro104.C66, Pro104.C75, Pro104.C84, Pro104.D4, Pro104.D6, Pro104.D9, Pro104.D12, Pro104.D14, Pro104.D18, Pro104.D19, Pro104.D20, Pro104.D21, Pro104.D26, Pro104.D29, Pro104.D31, Pro104.D43, Pro104.D47, Pro104.D51, Pro104.D55, Pro104.D56, Pro104.D58, Pro104.D62, Pro104.D63, Pro104.D64, Pro104.D68, Pro104.D69, Pro104.D75, Pro104.D81, Pro104.D85, Pro104.D88, Pro104.D91, Pro104.D94, Pro104.D102, Pro104.D106, Pro104.D111, Pro104.D112, Pro104.D113, Pro104.D114, Pro104.D115, Pro104.D116, Pro104.D117, Pro104.D118, Pro104.D119, Pro104.D120, Pro104.D121, Pro104.D122, Pro104.D123, Pro104.D, Pro104.D124, Pro104.D125, Pro104.D126, Pro104.D127, Pro104.D, Pro104.D128, Pro104.D129, Pro104.D130, Pro104.D131, Pro104.D132, Pro104.D133, Pro104.D134, Pro104.D135, Pro104.D136, Pro104.D137, Pro104.D138, Pro104.D139, Pro104.K14, Pro104.K15, Pro104.K16, Pro104.K47, Pro104.K71, Pro104.K72, Pro104.K74, Pro104.K75, Pro104.K76, Pro104.K78, Pro104.K81, Pro104.K87, Pro104.K88, Pro104.K89, Pro104.K155, Pro104.K156, Pro104.K157, Pro104.K158, Pro104.K159, Pro104.K160, Pro104.K163, Pro104.K164, Pro104.K176, Pro104.K217, Pro104.K226, Pro104.K227, Pro104.K240, Pro104.K274, Pro104.K264, Pro104.K281, Pro104.K358 or Pro104.K362 to Pro104), be able to target a Pro104-expressing tumor cell in vivo and will bind to Pro104 on a mammalian cell in vivo.

Furthermore, an antibody with the biological characteristic of the Pro104.C1, Pro104.C4, Pro104.C13, Pro104.C17, Pro104.C18, Pro104.C19, Pro104.C24, Pro104.C25, Pro104.C27, Pro104.C34, Pro104.C37, Pro104.C46, Pro104.C48, Pro104.C49, Pro104.C50, Pro104.C53, Pro104.C54, Pro104.C55, Pro104.C57, Pro104.C60, Pro104.C66, Pro104.C75, Pro104.C84, Pro104.D4, Pro104.D6, Pro104.D9, Pro104.D12, Pro104.D14, Pro104.D18, Pro104.D 19, Pro104.D20, Pro104.D21, Pro104.D26, Pro104.D29, Pro104.D31, Pro104.D43, Pro104.D47, Pro104.D51, Pro104.D55, Pro104.D56, Pro104.D58, Pro104.D62, Pro104.D63, Pro104.D64, Pro104.D68, Pro104.D69, Pro104.D75, Pro104.D81, Pro104.D85, Pro104.D88, Pro104.D91, Pro104.D94, Pro104.D102, Pro104.D106, Pro104.D111, Pro104.D112, Pro104.D113, Pro104.D114, Pro104.D115, Pro104.D116, Pro104.D117, Pro104.D118, Pro104.D119, Pro104.D120, Pro104.D121, Pro104.D122, Pro104.D123, Pro104.D, Pro104.D124, Pro104.D125, Pro104.D126, Pro104.D127, Pro104.D, Pro104.D128, Pro104.D129, Pro104.D130, Pro104.D131, Pro104.D132, Pro104.D133, Pro104.D134, Pro104.D135, Pro104.D136, Pro104.D137, Pro104.D138, Pro104.D139, Pro104.K14, Pro104.K15, Pro104.K16, Pro104.K47, Pro104.K71, Pro104.K72, Pro104.K74, Pro104.K75, Pro104.K76, Pro104.K78, Pro104.K81, Pro104.K87, Pro104.K88, Pro104.K89, Pro104.K155, Pro104.K156, Pro104.K157, Pro104.K158, Pro104.K159, Pro104.K160, Pro104.K163, Pro104.K164, Pro104.K176, Pro104.K217, Pro104.K226, Pro104.K227, Pro104.K240, Pro104.K274, Pro104.K264, Pro104.K281, Pro104.K358 or Pro104.K362 antibody will internalize upon binding to Pro104 on a mammalian cell in vivo.

Likewise, an antibody with the biological characteristic of the Pro104.C1, Pro104.C4, Pro104.C13, Pro104.C17, Pro104.C18, Pro104.C19, Pro104.C24, Pro104.C25, Pro104.C27, Pro104.C34, Pro104.C37, Pro104.C46, Pro104.C48, Pro104.C49, Pro104.C50, Pro104.C53, Pro104.C54, Pro104.C55, Pro104.C57, Pro104.C60, Pro104.C66, Pro104.C75, Pro104.C84, Pro104.D4, Pro104.D6, Pro104.D9, Pro104.D12, Pro104.D14, Pro104.D18, Pro104.D19, Pro104.D20, Pro104.D21, Pro104.D26, Pro104.D29, Pro104.D31, Pro104.D43, Pro104.D47, Pro104.D51, Pro104.D55, Pro104.D56, Pro104.D58, Pro104.D62, Pro104.D63, Pro104.D64, Pro104.D68, Pro104.D69, Pro104.D75, Pro104.D81, Pro104.D85, Pro104.D88, Pro104.D91, Pro104.D94, Pro104.D102, Pro104.D106, Pro104.D111, Pro104.D112, Pro104.D113, Pro104.D114, Pro104.D115, Pro104.D116, Pro104.D117, Pro104.D118, Pro104.D19, Pro104.D120, Pro104.D121, Pro104.D122, Pro104.D123, Pro104.D, Pro104.D124, Pro104.D125, Pro104.D126, Pro104.D127, Pro104.D, Pro104.D128, Pro104.D129, Pro104.D130, Pro104.D131, Pro104.D132, Pro104.D133, Pro104.D134, Pro104.D135, Pro104.D136, Pro104.D137, Pro104.D138, Pro104.D139, Pro104.K14, Pro104.K15, Pro104.K16, Pro104.K47, Pro104.K71, Pro104.K72, Pro104.K74, Pro104.K75, Pro104.K76, Pro104.K78, Pro104.K81, Pro104.K87, Pro104.K88, Pro104.K89, Pro104.K155, Pro104.K156, Pro104.K157, Pro104.K158, Pro104.K159, Pro104.K160, Pro104.K163, Pro104.K164, Pro104.K176, Pro104.K217, Pro104.K226, Pro104.K227, Pro104.K240, Pro104.K274, Pro104.K264, Pro104.K281, Pro104.K358 or Pro104.K362 antibody will have the same epitope binding, targeting, internalizing, tumor growth inhibitory and cytotoxic properties of the antibody.

The term "antagonist" antibody is used in the broadest sense, and includes an antibody that partially or fully blocks, inhibits, or neutralizes a biological activity of a native Pro104 protein disclosed herein. Methods for identifying antagonists of a Pro104 polypeptide may comprise contacting a Pro104 polypeptide or a cell expressing Pro104 on the cell surface, with a candidate antagonist antibody and measuring a detectable change in one or more biological activities normally associated with the Pro104 polypeptide.

An "antibody that inhibits the growth of tumor cells expressing Pro104" or a "growth inhibitory" antibody is one which binds to and results in measurable growth inhibition of cancer cells expressing or overexpressing Pro104. Preferred growth inhibitory anti-Pro104 antibodies inhibit growth of Pro104-expressing tumor cells e.g., breast, ovarian, pancreatic and lung cancer cells) by greater than 20%, preferably from about 20% to about 50%, and even more preferably, by greater than 50% (e.g. from about 50% to about 100%) as compared to the appropriate control, the control typically being tumor cells not treated with the antibody being tested. Growth inhibition can be measured at an antibody concentration of about 0.1 to 30 pg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-Pro104 antibody at about 1 pg/kg to about 100 mg/kg body weight results in reduction in tumor size or tumor cell proliferation within about 5 days to 3 months from the first administration of the antibody, preferably within about 5 to 30 days.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses Pro104. Preferably the cell is a tumor cell, e.g. an breast, ovarian, pancreatic and lung cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cells in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRI1B contains an immunoreceptor tyro sine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126.330-41 (1995). Other FcRs, including those to be identified in the future, are encompassed by the term "FcR" herein. The term also includes the neonatal receptor, FcRn, which is responsible for the transfer, of maternal IgGs to the fetus (Guyer et al., J. Immunol. 117:587 (1976) and Kim et al., J. Immunol. 24:249 (1994)).

"Human effector cells" are leukocytes which express one or more FeRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g. from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., J. Immunol. Methods 202:163 (1996) may be performed.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

A "Pro104-expressing cell" is a cell which expresses endogenous or transfected Pro104 on the cell surface. A "Pro104-expressing cancer" is a cancer comprising cells that have Pro104 protein present on the cell surface. A "Pro104-expressing cancer" produces sufficient levels of Pro104 on the surface of cells thereof, such that an anti-Pro104 antibody can bind thereto and have a therapeutic effect with respect to the cancer. A cancer which "overexpresses" Pro104 is one which has significantly higher levels of Pro104 at the cell surface thereof, compared to a noncancerous cell of the same tissue type. Such overexpression may be caused by gene amplification or by increased transcription or translation. Pro104 overexpression may be determined in a diagnostic or prognostic assay by evaluating increased levels of the Pro104 protein present on the surface of a cell (e.g. via an immunohistochemistry assay; FACS analysis). Alternatively, or additionally, one may measure levels of Pro104-encoding nucleic acid or mRNA in the cell, e.g. via fluorescent in situ hybridization; (FISH; see WO98/45479 published October, 1998), Southern blotting, Northern blotting, or polymerase chain reaction (PCR) techniques, such as real time quantitative PCR(RT-PCR). One may also study Pro104 overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. J. Immunol. Methods 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody. A Pro104-expressing cancer includes ovarian, pancreatic, lung or breast cancer.

A "mammal" for purposes of treating a cancer or alleviating the symptoms of cancer, refers to any mammal, including—humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a Pro104-expressing cancer if, after receiving a therapeutic amount of an anti-Pro104 antibody according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-Pro104 antibody may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR).

The term "therapeutically effective amount" refers to an amount of an antibody or a drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See preceding definition of "treating". To the extent the drug may prevent growth and/or kill existing cancer cells, it may be cytostatic and/or cytotoxic.

"Chronic" administration refers to administration of the agent(s) in a continuous mode as opposed to an acute mode, so as to maintain the initial therapeutic effect (activity) for an extended period of time.

"Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed.

Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, e.g., gelonin, ricin, saporin, and the various antitumor or anticancer agents disclosed below. Other cytotoxic agents are described below. A tumoricidal agent causes destruction of tumor cells.

A "growth inhibitory agent" when used herein refers to a compound or composition which inhibits growth of a cell, especially a Pro104-expressing cancer cell, either in vitro or in vivo. Thus, the growth inhibitory agent may be one which significantly reduces the percentage of Pro104-expressing cells in S phase. Examples of growth inhibitory agents include agents that block cell cycle progression (at a place other than S phase), such as agents that induce GI arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest GI also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semi synthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" as used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

The term "epitope tagged" used herein refers to a chimeric polypeptide comprising an anti-Pro104 antibody polypeptide fused to a "tag polypeptide". The tag polypeptide has enough residues to provide an epitope against which an antibody can be made, yet is short enough such that it does not interfere with activity of the Ig polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The term "package insert" is used to refer to instructions customarily included in commercial packages of therapeutic products, that contain information about the indications, usage, dosage, administration, contraindications and/or warnings concerning the use of such therapeutic products.

An "isolated nucleic acid molecule" is a nucleic acid molecule, e.g., an RNA, DNA, or a mixed polymer, which is substantially separated from other genome DNA sequences as well as proteins or complexes such as ribosomes and polymerases, which naturally accompany a native sequence. The term embraces a nucleic acid molecule which has been removed from its naturally occurring environment, and includes recombinant or cloned DNA isolates and chemically synthesized analogues or analogues biologically synthesized by heterologous systems. A substantially pure nucleic acid molecule includes isolated forms of the nucleic acid molecule.

"Vector" includes shuttle and expression vectors and includes, e.g., a plasmid, cosmid, or phagemid. Typically, a plasmid construct will also include an origin of replication (e.g., the ColEl origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in prokaryotic, e.g., bacterial, or eukaryotic cells. Suitable vectors are disclosed below.

The cell that produces an anti-Pro104 antibody of the invention will include the parent hybridoma cell e.g., the hybridomas that are deposited with the ATCC, as well as bacterial and eukaryotic host cells into which nucleic acid encoding the antibodies have been introduced. Suitable host cells are disclosed below.

RNA interference refers to the process of sequence-specific post transcriptional gene silencing in animals mediated by short interfering RNAs (siRNA) (Fire et al., 1998, Nature, 391, 806). The corresponding process in plants is commonly referred to as post transcriptional gene silencing or RNA silencing and is also referred to as quelling in fungi. The process of post transcriptional gene silencing is thought to be an evolutionarily conserved cellular defense mechanism used to prevent the expression of foreign genes which is commonly shared by diverse flora and phyla (Fire et al., 1999, Trends Genet., 15, 358). Such protection from foreign gene expression may have evolved in response to the production of double stranded RNAs (dsRNA) derived from viral infection or the random integration of transposon elements into a host genome via a cellular response that specifically destroys homologous single stranded RNA or viral genomic RNA. The presence of dsRNA in cells triggers the RNAi response though a mechanism that has yet to be fully characterized. This mechanism appears to be different from the interferon response that results from dsRNA mediated activation of protein kinase PKR and 2',5'-oligoadenylate synthetase resulting in non-specific cleavage of mRNA by ribonuclease L.

The presence of long dsRNAs in cells stimulates the activity of a ribonuclease III enzyme referred to as dicer. Dicer is involved in the processing of the dsRNA into short pieces of dsRNA known as short interfering RNAs (siRNA) (Berstein et al., 2001, Nature, 409, 363). Short interfering RNAs derived from dicer activity are typically about 21-23 nucleotides in length and comprise about 19 base pair duplexes. Dicer has also been implicated in the excision of 21 and 22 nucleotide small temporal RNAs (stRNA) from precursor RNA of conserved structure that are implicated in translational control (Hutvagner et al., 2001, Science, 293, 834). The RNAi response also features an endonuclease complex containing a siRNA, commonly referred to as an RNA-induced silencing complex (RISC), which mediates cleavage of single stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

Short interfering RNA mediated RNAi has been studied in a variety of systems. Fire et al., 1998, Nature, 391, 806, were the first to observe RNAi in *C. Elegans*. Wianny and Goetz, 1999, Nature Cell Biol., 2, 70, describe RNAi mediated by dsRNA in mouse embryos. Hammond et al., 2000, Nature, 404, 293, describe RNAi in *Drosophila* cells transfected with dsRNA. Elbashir et al., 2001, Nature, 411, 494, describe RNAi induced by introduction of duplexes of synthetic 21-nucleotide RNAs in cultured mammalian cells including human embryonic kidney and HeLa cells. Recent work in *Drosophila* embryonic lysates (Elbashir et al., 2001, EMBO J., 20, 6877) has revealed certain requirements for siRNA length, structure, chemical composition, and sequence that are essential to mediate efficient RNAi activity. These studies have shown that 21 nucleotide siRNA duplexes are most active when containing two nucleotide 3'-overhangs. Furthermore, complete substitution of one or both siRNA strands with 2'-deoxy (2'-H) or 2'-O-methyl nucleotides abolishes RNAi activity, whereas substitution of the 3'-terminal siRNA overhang nucleotides with deoxy nucleotides (2'-H) was shown to be tolerated. Single mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, EMBO J., 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, Cell, 107, 309).

Studies have shown that replacing the 3'-overhanging segments of a 21-mer siRNA duplex having 2 nucleotide 3' overhangs with deoxyribonucleotides does not have an adverse effect on RNAi activity. Replacing up to 4 nucleotides on each end of the siRNA with deoxyribonucleotides has been reported to be well tolerated whereas complete substitution with deoxyribonucleotides results in no RNAi activity (Elbashir et al., 2001, EMBO J., 20, 6877). In addition, Elbashir et al., supra, also report that substitution of siRNA with 2'-O-methyl nucleotides completely abolishes RNAi activity. Li et al., International PCT Publication No. WO 00/44914, and Beach et al., International PCT Publication No. WO 01/68836 both suggest that siRNA "may include modifications to either the phosphate-sugar back bone or the nucleoside to include at least one of a nitrogen or sulfur heteroatom", however neither application teaches to what extent these modifications are tolerated in siRNA molecules nor provide any examples of such modified siRNA. Kreutzer and Limmer, Canadian Patent Application No. 2,359,180, also describe certain chemical modifications for use in dsRNA constructs in order to counteract activation of double stranded-RNA-dependent protein kinase PKR, specifically 2'-amino or 2'-O-methyl nucleotides, and nucleotides containing a 2'-O or 4'-C methylene bridge. However, Kreutzer and Limmer similarly fail to show to what extent these modifications are tolerated in siRNA molecules nor do they provide any examples of such modified siRNA.

Parrish et al., 2000, Molecular Cell, 6, 1977-1087, tested certain chemical modifications targeting the unc-22 gene in *C. elegans* using long (>25 nt) siRNA transcripts. The authors describe the introduction of thiophosphate residues into these siRNA transcripts by incorporating thiophosphate nucleotide analogs with T7 and T3 RNA polymerase and observed that "RNAs with two (phosphorothioate) modified bases also had substantial decreases in effectiveness as RNAi triggers (data not shown); (phosphorothioate) modification of more than two residues greatly destabilized the RNAs in vitro and we were not able to assay interference activities." Id. at 1081. The authors also tested certain modifications at the 2'-position of the nucleotide sugar in the long siRNA transcripts and observed that substituting deoxynucleotides for ribonucleotides "produced a substantial decrease in interference activity", especially in the case of Uridine to Thymidine and/or Cytidine to deoxy-Cytidine substitutions. Id. In addition, the authors tested certain base modifications, including substituting 4-thiouracil, 5-bromouracil, 5-iodouracil, 3-(aminoallyl) uracil for uracil, and inosine for guanosine in sense and antisense strands of the siRNA, and found that whereas 4-thiouracil and 5-bromouracil were all well tolerated, inosine "produced a substantial decrease in interference activity" when incorporated in either strand. Incorporation of 5-iodouracil and 3-(aminoallyl)uracil in the antisense strand resulted in substantial decrease in RNAi activity as well.

Beach et al., International PCT Publication No. WO 01/68836, describes specific methods for attenuating gene expression using endogenously derived dsRNA. Tuschl et al., International PCT Publication No. WO 01/75164, describes a *Drosophila* in vitro RNAi system and the use of specific siRNA molecules for certain functional genomic and certain therapeutic applications; although Tuschl, 2001, Chem. Biochem., 2, 239-245, doubts that RNAi can be used to cure genetic diseases or viral infection due "to the danger of activating interferon response". Li et al., International PCT Publication No. WO 00/44914, describes the use of specific dsRNAs for use in attenuating the expression of certain target genes. Zernicka-Goetz et al., International PCT Publication No. WO 01/36646, describes certain methods for inhibiting the expression of particular genes in mammalian cells using certain dsRNA molecules. Fire et al., International PCT Publication No. WO 99/32619, describes particular methods for introducing certain dsRNA molecules into cells for use in inhibiting gene expression. Plaetinck et al., International PCT Publication No. WO 00/01846, describes certain methods for identifying specific genes responsible for conferring a particular phenotype in a cell using specific dsRNA molecules. Mello et al., International PCT Publication No. WO 01/29058, describes the identification of specific genes involved in dsRNA mediated RNAi. Deschamps Depaillette et al., International PCT Publication No. WO 99/07409, describes specific compositions consisting of particular dsRNA molecules combined with certain anti-viral agents. Driscoll et al., International PCT Publication No. WO 01/49844, describes specific DNA constructs for use in facilitating gene silencing in targeted organisms. Parrish et al., 2000, Molecular Cell, 6, 1977-1087, describes specific chemically modified siRNA constructs targeting the unc-22 gene of *C. elegans*. Tuschl et al., International PCT Publication No. WO 02/44321, describe certain synthetic siRNA constructs.

Compositions and Methods of the Invention

The invention provides anti-Pro104 antibodies. Preferably, the anti-Pro104 antibodies internalize upon binding to cell surface Pro104 on a mammalian cell. The anti-Pro104 antibodies may also destroy or lead to the destruction of tumor cells bearing Pro104.

It was not apparent that Pro104 was internalization-competent. In addition the ability of an antibody to internalize depends on several factors including the affinity, avidity, and isotype of the antibody, and the epitope that it binds. We have demonstrated herein that the cell surface Pro104 is internalization competent upon binding by the anti-Pro104 antibodies of the invention. Additionally, it was demonstrated that the anti-Pro104 antibodies of the present invention can specifically target Pro104-expressing tumor cells in vivo and inhibit or kill these cells. These in vivo tumor targeting, internalization and growth inhibitory properties of the anti-Pro104 antibodies make these antibodies very suitable for therapeutic uses, e.g., in the treatment of various cancers including breast, ovarian, pancreatic and lung cancer. Internalization of the anti-Pro104 antibody is preferred, e.g., if the antibody or antibody conjugate has an intracellular site of action and if the cytotoxic agent conjugated to the antibody does not readily cross the plasma membrane (e.g., the toxin calicheamicin). Internalization is not necessary if the antibodies or the agent conjugated to the antibodies do not have intracellular sites of action, e.g., if the antibody can kill the tumor cell by ADCC or some other mechanism.

The anti-Pro104 antibodies of the invention also have various non-therapeutic applications. The anti-Pro104 antibodies of the present invention can be useful for diagnosis and staging of Pro104-expressing cancers (e.g., in radioimaging). They may be used alone or in combination with other ovarian cancer markers, including, but not limited to, CA125, HE4 and mesothelin. The antibodies are also useful for purification or immunoprecipitation of Pro104 from cells, for detection and quantitation of Pro104 in vitro, e.g. in an ELISA or a Western blot, to kill and eliminate Pro104-expressing cells from a population of mixed cells as a step in the purification of other cells. The internalizing anti-Pro104 antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies, an antibody sequence is fused to a heterologous polypeptide sequence. The antibodies can be modified in the Fc region to provide desired effector functions. As discussed in more detail in the sections below, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

The antibody may compete for binding, or binds substantially to, the same epitope bound by the antibodies of the invention. Antibodies having the biological characteristics of the present anti-Pro104 antibodies of the invention are also contemplated, e.g., an anti-Pro104 antibody which has the biological characteristics of a monoclonal antibody produced by the hybridomas accorded ATCC accession numbers PTA-5277, 6076, 6077 and 6078, specifically including the in vivo tumor targeting, internalization and any cell proliferation inhibition or cytotoxic characteristics. Specifically provided are anti-Pro104 antibodies that bind to an epitope present in amino acids 1-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, 290-300, 300-310, 310-314 of human Pro104.

Methods of producing the above antibodies are described in detail below.

The present anti-Pro104 antibodies are useful for treating a Pro104-expressing cancer or alleviating one or more symptoms of the cancer in a mammal. Such cancers include ovarian and pancreatic cancer, cancer of the urinary tract, prostate cancer, breast cancer, colon cancer, and lung cancer. Such a cancer includes more specifically, ovarian serous adenocarcinoma, breast infiltrating ductal carcinoma, prostate adenocarcinoma, renal cell carcinomas, colorectal adenocarcinomas, lung adenocarcinomas, lung squamous cell carcinomas, and pleural mesothelioma. The breast cancer may be HER-2 negative or positive breast cancer. The cancers encompass metastatic cancers of any of the preceding, e.g., breast, ovarian, pancreatic and lung cancer metastases. The antibody is able to bind to at least a portion of the cancer cells that express Pro104 in the mammal and preferably is one that does not induce or that minimizes HAMA response. Preferably, the antibody is effective to destroy or kill Pro104-expressing tumor cells or inhibit the growth of such tumor cells, in vitro or in vivo, upon binding to Pro104 on the cell. Such an antibody includes a naked anti-Pro104 antibody (not conjugated to any agent). Naked anti-Pro104 antibodies having tumor growth inhibition properties in vivo include the antibodies described in the Experimental Examples below. Naked antibodies that have cytotoxic or cell growth inhibition properties can be further conjugated with a cytotoxic agent to render them even more potent in tumor cell destruction. Cytotoxic properties can be conferred to an anti-Pro104 antibody by, e.g., conjugating the antibody with a cytotoxic agent, to form an immunoconjugate as described below. The cytotoxic agent or a growth inhibitory agent is preferably a small molecule. Toxins such as maytansin, maytansinoids, saporin, gelonin, ricin or calicheamicin and analogs or derivatives thereof, are preferable.

The invention provides a composition comprising an anti-Pro104 antibody of the invention, and a carrier. For the purposes of treating cancer, compositions can be administered to the patient in need of such treatment, wherein the composition can comprise one or more anti-Pro104 antibodies present as an immunoconjugate or as the naked antibody. Further, the compositions can comprise these antibodies in combination with other therapeutic agents such as cytotoxic or growth inhibitory agents, including chemotherapeutic agents. The invention also provides formulations comprising an anti-Pro104 antibody of the invention, and a carrier. The formulation may be a therapeutic formulation comprising a pharmaceutically acceptable carrier.

Another aspect of the invention is isolated nucleic acids encoding the internalizing anti-Pro104 antibodies. Nucleic acids encoding both the H and L chains and especially the hypervariable region residues, chains which encode the native sequence antibody as well as variants, modifications and humanized versions of the antibody, are encompassed.

The invention also provides methods useful for treating a Pro104-expressing cancer or alleviating one or more symptoms of the cancer in a mammal, comprising administering a therapeutically effective amount of an internalizing anti-Pro104 antibody to the mammal. The antibody therapeutic compositions can be administered short term (acute) or chronic, or intermittent as directed by physician. Also provided are methods of inhibiting the growth of, and killing a Pro104 expressing cell. Finally, the invention also provides kits and articles of manufacture comprising at least one antibody of this invention, preferably at least one anti-Pro104 antibody of this invention that binds to Pro104 on a mammalian cell in vivo or at least one internalizing anti-Pro104 antibody of this invention. Kits containing anti-Pro104 antibodies find use in detecting Pro104 expression, or in therapeutic or diagnostic assays, e.g., for Pro104 cell killing assays or for purification and/or immunoprecipitation of Pro104 from cells. For example, for isolation and purification of Pro104, the kit can contain an anti-Pro104 antibody coupled to a solid support, e.g., a tissue culture plate or beads (e.g., sepharose beads). Kits can be provided which contain antibodies for detection and quantitation of Pro104 in vitro, e.g. in an ELISA or a Western blot. Such antibody useful for detection may be provided with a label such as a fluorescent or radiolabel.

Production of Anti-Pro104 Antibodies

The following describes exemplary techniques for the production of the antibodies useful in the present invention. Some of these techniques are described further in Example 1. The Pro104 antigen to be used for production of antibodies may be, e.g., the full length polypeptide or a portion thereof, including a soluble form of Pro104 lacking the membrane spanning sequence, or synthetic peptides to selected portions of the protein.

Alternatively, cells expressing Pro104 at their cell surface (e.g. CHO or NIH-3T3 cells transformed to overexpress Pro104; ovarian, pancreatic, lung, breast or other Pro104-expressing tumor cell line), or membranes prepared from such cells can be used to generate antibodies. The nucleotide and amino acid sequences of human and murine Pro104 are available as provided above. Pro104 can be produced recombinantly in and isolated from, prokaryotic cells, e.g., bacterial cells, or eukaryotic cells using standard recombinant DNA methodology. Pro104 can be expressed as a tagged (e.g., epitope tag) or other fusion protein to facilitate its isolation as well as its identification in various assays.

Antibodies or binding proteins that bind to various tags and fusion sequences are available as elaborated below. Other forms of Pro104 useful for generating antibodies will be apparent to those skilled in the art.

Tags

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering, 3(6):547-553 (1990)). The FLAG-peptide (Hopp et al., BioTechnology, 6:1204-1210 (1988)) is recognized by an anti-FLAG M2 monoclonal antibody (Eastman Kodak Co., New Haven, Conn.). Purification of a protein containing the FLAG peptide can be performed by immunoaffinity chromatography using an affinity matrix comprising the anti-FLAG M2 monoclonal antibody covalently attached to agarose (Eastman Kodak Co., New Haven, Conn.). Other tag polypeptides include the KT3 epitope peptide [Martin et al., Science, 255:192-194 (1992)]; an α-tubulin epitope peptide (Skinner et al., J. Biol. Chenz., 266:15163-15166 (1991)); and the T7 gene protein peptide tag (Lutz-Freyermuth et al., Proc. Natl. Acad. Sci. USA, 87:6393-6397 (1990)).

Polyclonal Antibodies

Polyclonal antibodies are preferably raised in animals, preferably non-human animals, by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups. Conjugates also can be made in recombinant cell culture as protein fusions.

Animals are immunized against the antigen, immunogenic conjugates, or derivatives by combining, e.g., 5-100 pg of the protein or conjugate (for rabbits or mice, respectively) with 3 volumes of Freund's complete adjuvant and injecting the solution intradermally at multiple sites. One month later, the animals are boosted with ⅕ to ¹⁄₁₀ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Also, aggregating agents such as alum are suitably used to enhance the immune response.

Monoclonal Antibodies

Monoclonal antibodies may be made using the hybridoma method first described by Kohler et al., Nature, 256:495 (1975), or may be made by recombinant DNA methods (U.S. Pat. No. 4,816,567). In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a "fusion partner", e.g., a myeloma cell line using a suitable fusing agent, such as polyethylene glycol, to form a hybridoma cell (Goding, Monoclonal Antibodies. Principles and Practice, pp 103 (Academic Press, 1986)).

The hybridoma cells thus prepared are seeded and grown in a suitable culture medium which medium preferably contains one or more substances that inhibit the growth or survival of the unfused, fusion partner, e.g., the parental myeloma cells. For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-II mouse tumors available from the Salk Institute Cell Distribution Center, San Diego, Calif. USA, and SP-2 and derivatives e.g., X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Deldker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980). Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp 103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transformed or transfected into prokaryotic or eukaryotic host cells such as, e.g., *E coli* cells, simian COS cells, Chinese Hamster Ovary (CHO) cells, or myeloma cells, that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Phickthun, Immunol. Revs., 130:151-188 (1992).

Further, the monoclonal antibodies or antibody fragments can be isolated from antibody phage libraries generated using the techniques described in McCafferty et al., Nature, 348: 552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CL) sequences for the homologous murine sequences (U.S. Pat. No. 4,816,567; and Morrison, et al., Proc. Natl. Acad. Sci. USA, 81:6851 (1984)), or by fusing the immunoglobulin coding sequence with all or part of the coding sequence for a non-immunoglobulin polypeptide (heterologous polypeptide). The nonimmunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized Antibodies

Methods for humanizing non-human antibodies have been described in the art. Preferably, a humanized antibody has one or more amino acid residues introduced into it from a source which is nonhuman. These non-human amino acid residues are often referred to as "import" residues, which are typically taken from an "import" variable domain. Humanization can be essentially performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol., 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art.

Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-Pro104 antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); 5,545,807; and Alternatively, phage display technology (McCafferty et al., Nature 348: 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905. As discussed above, human antibodies may also be generated by in vitro activated B cells (see U.S. Pat. Nos. 5,567,610 and 5,229,275).

Antibody Fragments

In certain circumstances there are advantages of using antibody fragments, rather than whole antibodies. The smaller size of the fragments allows for rapid clearance, and may lead to improved access to solid tumors. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab)2 fragments (Carter et al., Bio/Technology 10: 163-167 (1992)). According to another approach, F(ab)2 fragments can be isolated directly from recombinant host cell culture. Fab and F(ab)2 fragment with increased in vivo half-life comprising a salvage receptor binding epitope residues are described in U.S. Pat. No. 5,869,046. Other techniques for the production of antibody fragments will be apparent to the skilled practitioner. The antibody of choice may also be a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Bispecific Antibodies

Bispecific antibodies are antibodies that have binding specificities for at least two different epitopes. Exemplary bispecific antibodies may bind to two different epitopes of the Pro104 protein. Other such antibodies may combine a Pro104 binding site with a binding site for another protein. Alternatively, an anti-Pro104.Arm may be combined with an arm which binds to a triggering molecule on a leukocyte such as a Tcell receptor molecule (e.g. C133), or Fc receptors for IgG (FcγR), such as FcγRI (CD64), FcγRII (CD32) and FcγRIII (CD16), so as to focus and localize cellular defense mechanisms to the Pro104-expressing cell. Bispecific antibodies may also be used to localize cytotoxic agents to cells which express Pro104. These antibodies possess a Pro104-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab)2 bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J, 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region (CHI) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Preferably, the bispecific antibodies in this approach are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

The "diabody" technology described by Hollinger et al., Proc. Natl. Acad. Sci. USA, 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1(X1n-VD2-(X2)n-Fc, wherein VDI is a first variable domain, VD2 is a second variable domain, Fc is one polypeptide chain of an Fc region, XI and X2 represent an amino acid or polypeptide, and n is 0 or 1. For instance, the polypeptide chain(s) may comprise: VH-CHI-flexible linker-VH-CHI-Fc region chain; or VH-CHI-VH-CHI-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Other Amino Acid Sequence Modifications

Amino acid sequence modification(s) of the anti-Pro104 antibodies described herein are contemplated. For example, it may be desirable to improve the binding affinity and/or other biological properties of the antibody. Amino acid sequence variants of the anti-Pro104 antibody are prepared by introducing appropriate nucleotide changes into the anti-Pro104 antibody nucleic acid, or by peptide synthesis.

Such modifications include, for example, deletions from, and/or insertions into, and/or substitutions of, residues within the amino acid sequences of the anti-Pro104 antibody. Any combination of deletion, insertion, and substitution is made to arrive at the final construct, provided that the final construct possesses the desired characteristics. The amino acid changes also may alter post-translational processes of the anti-Pro104 antibody, such as changing the number or position of glycosylation sites.

A useful method for identification of certain residues or regions of the anti-Pro104 antibody that are preferred locations for mutagenesis is called "alanine scanning mutagenesis" as described by Cunningham and Wells in Science, 244:1081-1085 (1989). Here, a residue or group of target residues within the anti-Pro104 antibody are identified (e.g., charged residues such as arg, asp, his, lys, and glu) and replaced by a neutral or negatively charged amino acid (most preferably alanine or polyalanine) to affect the interaction of the amino acids with Pro104 antigen.

Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at a target codon or region and the expressed anti-Pro104 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-Pro104 antibody with an N-terminal methionyl residue or the antibody fused to a cytotoxic polypeptide. Other insertional variants of the anti-Pro104 antibody molecule include the fusion to the N- or C-terminus of the anti-Pro104 antibody to an enzyme (e.g. for ADEPT) or a fusion to a polypeptide which increases the serum half-life of the antibody.

Another type of variant is an amino acid substitution variant. These variants have at least one amino acid residue in the anti-Pro104 antibody molecule replaced by a different residue. The sites of greatest interest for substitutional mutagenesis include the hypervariable regions, but FR alterations are also contemplated. Conservative substitutions are shown in Table I under the heading of "preferred substitutions". If such substitutions result in a change in biological activity, then more substantial changes, denominated "exemplary substitutions" in Table 1, or as further described below in reference to amino acid classes, may be introduced and the products screened for a desired characteristic.

TABLE I

Amino Acid Substitutions

| Original | Exemplary Substitutions | Preferred Substitutions |
|---|---|---|
| Ala (A) | val; leu; ile | Val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; | leu |
| Leu (L) | norleucine; ile; val; met; ala; | ile |
| Lys (K) | arg; gin; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | Phe |
| Val (V) | ile; leu; met; phe; ala; | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gin, his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the anti-Pro104 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibody variants thus generated are displayed in a monovalent fashion from filamentous phage particles as fusions to the gene III product of Ml3 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human Pro104. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-Pro104 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared nucleic acid molecule encoding a variant or a non-variant version of the anti-Pro104 antibody.

It may be desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of the antibody.

Screening for Antibodies with the Desired Properties

Techniques for generating antibodies have been described above. One may further select antibodies with certain biological characteristics, as desired.

The growth inhibitory effects of an anti-Pro104 antibody of the invention may be assessed by methods known in the art, e.g., using cells which express Pro104 either endogenously or following transfection with the Pro104 gene. For example, the tumor cell lines and Pro104-transfected cells provided in Example 1 below may be treated with an anti-Pro104 monoclonal antibody of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-Pro104 antibody of the invention. After antibody treatment, the cells are harvested and the amount of radioactivity incorporated into the DNA quantitated in a scintillation counter. Appropriated positive controls include treatment of a selected cell line with a growth inhibitory antibody known to inhibit growth of that cell line. Growth inhibition of tumor cells in vivo can be determined in various ways such as is described in the Experimental Examples section below. Preferably, the tumor cell is one that over-expresses Pro104. Preferably, the anti-Pro104 antibody will inhibit cell proliferation of a Pro104-expressing tumor cell in vitro or in vivo by about 25-100% compared to the untreated tumor cell, more preferably, by about 30-100%, and even more preferably by about 50-100% or 70-100%, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-Pro104 antibody at about 1 µg/kg to about 100 mg/kg body weight results in reduction in tumor size or tumor cell proliferation within about 5 days to 3 months from the first administration of the antibody, preferably within about 5 to 30 days.

To select for antibodies which induce cell death, loss of membrane integrity as indicated by, e.g., propidium iodide (PI), trypan blue or 7AAD uptake may be assessed relative to a control. A PI uptake assay can be performed in the absence of complement and immune effector cells. Pro104-expressing tumor cells are incubated with medium alone or medium containing of the appropriate monoclonal antibody at e.g., about 10 µg/ml. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those antibodies which induce statistically significant levels of cell death as determined by PI uptake may be selected as cell death-inducing antibodies.

To screen for antibodies which bind to an epitope on Pro104 bound by an antibody of interest, e.g., the Pro104 antibodies of this invention, a routine cross-blocking assay such as that describe in *Antibodies, A Laboratory Manual*, Cold Spring Harbor Laboratory, Ed Harlow and David Lane (1988), can be performed. This assay can be used to determine if a test antibody binds the same site or epitope as an anti-Pro104 antibody of the invention. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of Pro104 can be used in competition assays with the test antibodies or with a test antibody and an antibody with a characterized or known epitope.

For example, a method to screen for antibodies that bind to an epitope which is bound by an antibody this invention may comprise combining a Pro104-containing sample with a test antibody and an antibody of this invention to form a mixture, the level of Pro104 antibody bound to Pro104 in the mixture is then determined and compared to the level of Pro104 antibody bound in the mixture to a control mixture, wherein the level of Pro104 antibody binding to Pro104 in the mixture as compared to the control is indicative of the test antibody's binding to an epitope that is bound by the anti-Pro104 antibody of this invention. The level of Pro104 antibody bound to Pro104 is determined by ELISA. The control may be a positive or negative control or both. For example, the control may be a mixture of Pro104, Pro104 antibody of this invention and an antibody known to bind the epitope bound by the Pro104 antibody of this invention. The anti-Pro104 antibody labeled with a label such as those disclosed herein. The Pro104 may be bound to a solid support, e.g., a tissue culture plate or to beads, e.g., sepharose beads.

Immunoconjugates

The invention also pertains to therapy with immunoconjugates comprising an antibody conjugated to an anti-cancer agent such as a cytotoxic agent or a growth inhibitory agent.

Chemotherapeutic agents useful in the generation of such immunoconjugates have been described above. Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

Preferably, an anti-Pro104 antibody (full length or fragments) of the invention is conjugated to one or more maytansinoid molecules.

Maytansinoids are mitototic inhibitors which act by inhibiting tubulin polymerization. Maytansine was first isolated from the cast African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al. Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×10 5 HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-Pro104 Antibody-Maytansinoid Conjugates (Immunoconjugates)

Anti-Pro104 antibody-maytansinoid conjugates are prepared by chemically linking an anti-Pro104 antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B 1, and Chari et al. Cancer Research 52: 127-131 (1992). The linking groups include disulfide groups, thioether groups, acid labile groups, photolabile groups, peptidase labile groups, or esterase labile groups, as disclosed in the above-identified patents, disulfide and thioether groups being preferred. Conjugates of the antibody and maytansinoid may be made using a variety of bifunctional protein coupling agents such as N-succinimidyl (2-pyridyldithio) propionate (SPDP), succinimidyl-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as his (p-azidobenzoyl) hexanediamine), bis-diazonium derivatives (such as bis-(p-diazoniumbenzoyl)-ethylenediamine), diisocyanates (such as toluene 2,6diisocyanate), and bis-active fluorine compounds (such as 1,5-difluoro-2,4-dinitrobenzene). Particularly preferred coupling agents include N-succinimidyl (2-pyridyldithio) propionate (SPDP) (Carlsson et al., Biochem. J. 173:723-737 [1978]) and N-succinimidyl (2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. Preferably, the linkage is formed at the C-3 position of maytansinol or a maytansinol analogue.

Calicheamicin

Another immunoconjugate of interest comprises an anti-Pro104 antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$, (Hinman et al. Cancer Research 53: 3336 (1993), Lode et al. Cancer Research 5 8: 2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-Pro104 antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296). Enzymatically active toxins and fragments thereof which can be used include diphtheria A chain, 1 5 nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993. The present invention further contemplates an immunoconjugate formed between an antibody and a compound with nucleolytic activity (e.g. a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-Pro104 antibodies. Examples include $At^{211}$, $I^{131}$, $I^{125}$, $In^{111}$, $Y^{90}$, $Re^{186}$, $Re^{188}$, $Sm^{153}$, $Bi^{212}$, $P^{32}$, and radioactive isotopes of Lu. When the conjugate is used for diagnosis, it may comprise a radioactive atom for scintigraphic studies, for example $Tc^{99M}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $Tc^{99M}$, $I^{123}$, $In^{111}$, $Re^{186}$, $Re^{188}$, can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon labeled 1-isothiocyanatobenzyl methyldiethylene triaminepentaacetic acid (MX-DTPA) is an exemplary chelating agent for conjugation of radionucleotide to the antibody. See WO 94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al. Cancer Research 52: 127-131 (1992); U.S. Pat. No. 5,208,020) may be used.

Alternatively, a fusion protein comprising the anti-Pro104 antibody and cytotoxic agent may be made, e.g. by recombinant techniques or peptide synthesis. The length of DNA may comprise respective regions encoding the two portions of the conjugate either adjacent one another or separated by a region encoding a linker peptide which does not destroy the desired properties of the conjugate.

In addition, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as O-galactosidase and neuraminidase useful for converting glycosylated prodrugs into free drugs; P-lactamase useful for converting drugs derivatized with P-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a tumor cell population. The enzymes of this invention can be covalently bound to the anti-Pro104 antibodies by techniques well known in the art such as the use of the heterobifunctional crosslinking reagents discussed above.

Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The anti-Pro104 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); U.S. Pat. Nos. 4,485,045 and 4,544,545; and W097/38731 published Oct. 23, 1997. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81(19)1484 (1989).

Vectors, Host Cells, and Recombinant Methods

The invention also provides isolated nucleic acid molecule encoding the humanized anti-Pro104 antibody, vectors and host cells comprising the nucleic acid, and recombinant techniques for the production of the antibody. For recombinant production of the antibody, the nucleic acid molecule encoding it is isolated and inserted into a replicable vector for further cloning (amplification of the DNA) or inserted into a vector in operable linkage with a promoter for expression. DNA encoding the monoclonal antibody is readily isolated and sequenced using conventional procedures (e.g., by using oligonucleotide probes that are capable of binding specifically to nucleic acid molecules encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

Signal Sequence Component

The anti-Pro104 antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native anti-Pro104 antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, oc factor leader (including *Saccharomyces* and *Kluyveromyces* cc-factor leaders), or acid phosphatase leader, the *C albicans* glucoamylase leader, or the signal described in WO 90/13646. In mammalian cell expression, mammalian signal sequences as well as viral secretory leaders, for example, the herpes simplex gD signal, are available. The DNA for such precursor region is ligated in reading frame to DNA encoding the anti-Pro104 antibody.

Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the anti-Pro104 antibody nucleic acid, such as DHFR, thymidine kinase, metallothionein-I and -11, preferably primate metallothionein genes, adenosine deaminase, ornithine decarboxylase, etc. For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding anti-Pro104 antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4 Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 pm circular plasmid pKDI can be used for transformation of *Kluyveromyces* yeasts. Alternatively, an expression system for large-scale production of recombinant calf chymosin was reported for *K. lactis*. Van den Berg, Bio/Technology, 8:135 (1990). Stable multi-copy expression vectors for secretion of mature recombinant human serum albumin by industrial strains of *Kluyveromyces* have also been disclosed. Fleer et al., Bio/Technology, 9:968-975 (1991).

Promoter Component

Expression and cloning vectors usually contain a promoter that is recognized by the host organism and is operably linked to the anti-Pro104 antibody nucleic acid. Promoters suitable for use with prokaryotic hosts include the phoA promoter, P-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-Pro104 antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors. Examples of suitable promoter sequences for use with yeast hosts include the promoters for 3-phosphoglycerate kinase or other glycolytic enzymes, such as enolase, glyceraldehyde phosphate dehydrogenase, hexokinase, pyruvate decarboxylase, phosphofructokinase, glucose phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-Pro104 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human P-interferon cDNA in mouse cells under the control of a thymidine kinase promoter from herpes simplex virus. Alternatively, the Rous Sarcoma Virus long terminal repeat can be used as the promoter.

Enhancer Element Component

Transcription of a DNA encoding the anti-Pro104 antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the anti-Pro104 antibody-encoding sequence, but is preferably located at a site 5' from the promoter.

Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding anti-Pro104 antibody. One useful transcription termination component is the bovine growth hormone polyadenylation region. See WO 94/11026 and the expression vector disclosed therein.

Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *SerTatia*, e.g., *Serratia marcescans*, and *Shigella*, as well as Bacilli such as

*B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W31 10 (ATCC 27,325) are suitable. These examples are illustrative rather than limiting.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789, 199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for anti-Pro104 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183, 070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-Pro104 antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, *Arabidopsis* and tobacco can also be utilized as hosts. Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CVI ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, 1413 8065); mouse mammary tumor (MMT 060562, ATCC CCL5 1); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-Pro104 antibody production and cultured in conventional nutrient media modified as appropriate for inducing promoters, selecting transformants, or amplifying the genes encoding the desired sequences.

Culturing Host Cells

The host cells used to produce the anti-Pro104 antibody of this invention may be cultured in a variety of media. Commercially available media such as Ham's FIO (Sigma), Minimal Essential Medium (MEM)(Sigma), RPMI-1640 (Sigma), and Dulbecco's Modified Eagle's Medium (DMEM)(Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Purification of Anti-Pro104 Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma 1$, $\gamma 2$, or $\gamma 4$ heavy chains (Lindmark et al., J. Immunol. Meth. 62:1-13 (1983)). Protein G is recommended for all mouse isotypes and for human $\gamma 3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SIDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulations

Pharmaceutical formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol, and mcresol); low molecular weight (less than about 10 residues) polypeptides; proteins, such as serum albumin, gelatin, or immunoglobulins; hydrophilic polymers such as polyvinylpyllolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). The antibody preferably comprises the antibody at a concentration of between 5-200 mg/ml, preferably between 10-100 mg/ml.

The formulation herein may also contain more than one active compound as necessary for the particular indication being treated, preferably those with complementary activities that do not adversely affect each other. For example, in addition to the anti-Pro104 antibody which internalizes, it may be desirable to include in the one formulation, an additional antibody, e.g. a second anti-Pro104 antibody which binds a different epitope on Pro104, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and $\gamma$ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−) hydroxybutyric acid.

The formulations to be used for in vivo administration must be sterile. This is readily accomplished by filtration through sterile filtration membranes.

Methods and Treatment Using Anti-Pro104 Antibodies

According to the present invention, the anti-Pro104 antibody that internalizes upon binding Pro104 on a cell surface is used to treat a subject in need thereof having a cancer characterized by Pro104-expressing cancer cells, in particular, ovarian, pancreatic, lung or breast cancer, such as ovarian serous adenocarcinoma or breast infiltrating ductal carcinoma cancer, and associated metastases.

The cancer will generally comprise Pro104-expressing cells, such that the anti-Pro104 antibody is able to bind thereto. While the cancer may be characterized by overexpression of the Pro104 molecule, the present application further provides a method for treating cancer which is not considered to be a Pro104-overexpressing cancer.

This invention also relates to methods for detecting cells which overexpress Pro104 and to diagnostic kits useful in detecting cells expressing Pro104 or in detecting Pro104 in serum from a patient. The methods may comprise combining a cell-containing test sample with an antibody of this invention, assaying the test sample for antibody binding to cells in the test sample and comparing the level of antibody binding in the test sample to the level of antibody binding in a control sample of cells. A suitable control is, e.g., a sample of normal cells of the same type as the test sample or a cell sample known to be free of Pro104 overexpressing cells. A level of Pro104 binding higher than that of such a control sample would be indicative of the test sample containing cells that overexpress Pro104. Alternatively the control may be a sample of cells known to contain cells that overexpress Pro104. In such a case, a level of Pro104 antibody binding in the test sample that is similar to, or in excess of, that of the control sample would be indicative of the test sample containing cells that overexpress Pro104.

Pro104 overexpression may be detected with a various diagnostic assays. For example, over expression of Pro104 may be assayed by immunohistochemistry (IHC). Parrafin embedded tissue sections from a tumor biopsy may be subjected to the IHC assay and accorded a Pro104 protein staining intensity criteria as follows.

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for Pro104 expression may be characterized as not overexpressing Pro104, whereas those tumors with 2+ or 3+ scores may be characterized as overexpressing Pro104.

Alternatively, or additionally, FISH assays such as the INFORM™ (sold by Ventana, Ariz.) or PATHVISION™ (VySiS, Ill.) may be carried out on formalin-fixed, paraffin-embedded tumor tissue to determine the extent (if any) of Pro104 overexpression in the tumor. Pro104 overexpression or amplification may be evaluated using an in vivo diagnostic assay, e.g. by administering a molecule (such as an antibody of this invention) which binds Pro104 and which is labeled with a detectable label (e.g. a radioactive isotope or a fluorescent label) and externally scanning the patient for localization of the label.

A sample suspected of containing cells expressing or overexpressing Pro104 is combined with the antibodies of this invention under conditions suitable for the specific binding of the antibodies to Pro104. Binding and/or internalizing the Pro104 antibodies of this invention is indicative of the cells expressing Pro104. The level of binding may be determined and compared to a suitable control, wherein an elevated level of bound Pro104 as compared to the control is indicative of Pro104 overexpression. The sample suspected of containing cells overexpressing Pro104 may be a cancer cell sample, particularly a sample of an ovarian cancer, e.g. ovarian serous adenocarcinoma, or a breast cancer, e.g., a breast infiltrating ductal carcinoma. A serum sample from a subject may also be assayed for levels of Pro104 by combining a serum sample from a subject with a Pro104 antibody of this invention, determining the level of Pro104 bound to the antibody and comparing the level to a control, wherein an elevated level of Pro104 in the serum of the patient as compared to a control is indicative of overexpression of Pro104 by cells in the patient. The subject may have a cancer such as e.g., an ovarian cancer, e.g. ovarian serous adenocarcinoma, or a breast cancer, e.g., a breast infiltrating ductal carcinoma.

Currently, depending on the stage of the cancer, ovarian, pancreatic, lung or breast cancer treatment involves one or a combination of the following therapies: surgery to remove the cancerous tissue, radiation therapy, androgen deprivation (e.g., hormonal therapy), and chemotherapy. Anti-Pro104 antibody therapy may be especially desirable in elderly patients who do not tolerate the toxicity and side effects of chemotherapy well, in metastatic disease where radiation therapy has limited usefulness, and for the management of prostatic carcinoma that is resistant to androgen deprivation treatment. The tumor targeting and internalizing anti-Pro104 antibodies of the invention are useful to alleviate Pro104-expressing cancers, e.g., ovarian, pancreatic, lung or breast cancers upon initial diagnosis of the disease or during relapse. For therapeutic applications, the anti-Pro104 antibody can be used alone, or in combination therapy with, e.g., hormones, antiangiogens, or radiolabelled compounds, or with surgery, cryotherapy, and/or radiotherapy, notably for ovarian, pancreatic, lung or breast cancers, also particularly where shed cells cannot be reached. Anti-Pro104 antibody treatment can be administered in conjunction with other forms of conventional therapy, either consecutively with, pre- or post-conventional therapy, Chemotherapeutic drugs such as Taxotere® (docetaxel), Taxol® (paclitaxel), estramustine and mitoxantrone are used in treating metastatic and hormone refractory ovarian, pancreatic, lung or breast cancer, in particular, in good risk patients. In the present method of the invention for treating or alleviating cancer, in particular, androgen independent and/or metastatic ovarian, pancreatic, lung or breast cancer, the cancer patient can be administered anti-Pro104 antibody in conjunction with treatment with the one or more of the preceding chemotherapeutic agents. In particular, combination therapy with palictaxel and modified derivatives (see, e.g., EP0600517) is contemplated. The anti-Pro104 antibody will be administered with a therapeutically effective dose of the chemotherapeutic agent. The anti-Pro104 antibody may also be administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

Particularly, an immunoconjugate comprising the anti-Pro104 antibody conjugated with a cytotoxic agent may be administered to the patient. Preferably, the immunoconjugate bound to the Pro104 protein is internalized by the cell, resulting in increased therapeutic efficacy of the immunoconjugate in killing the cancer cell to which it binds. Preferably, the cytotoxic agent targets or interferes with the nucleic acid in the cancer cell. Examples of such cytotoxic agents are described above and include maytansin, maytansinoids, saporin, gelonin, ricin, calicheamicin, ribonucleases and DNA endonucleases.

The anti-Pro104 antibodies or immunoconjugates are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The antibodies or immunoconjugates may be injected directly into the tumor mass. Intravenous or subcutaneous administration of the antibody is preferred. Other therapeutic regimens may be combined with the administration of the anti-Pro104 antibody.

The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-Pro104 antibody or antibodies, with administration of an antibody directed against another tumor antigen associated with the particular cancer. As such, this invention is also directed to an antibody "cocktail" comprising one or more antibodies of this invention and at least one other antibody which binds another tumor antigen associated with the Pro104-expressing tumor cells. The cocktail may also comprise antibodies that are directed to other epitopes of Pro104. Preferably the other antibodies do not interfere with the binding and or internalization of the antibodies of this invention.

The antibody therapeutic treatment method of the present invention may involve the combined administration of an anti-Pro104 antibody (or antibodies) and one or more chemotherapeutic agents or growth inhibitory agents, including co-administration of cocktails of different chemotherapeutic agents. Chemotherapeutic agents include, e.g., estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M.C. Perry, Williams & Wilkins, Baltimore, Md. (1992).

The antibody may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-Pro104 antibody (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody therapy. Suitable dosages for any of the above co-administered agents are those presently used and may be lowered due to the combined action (synergy) of the agent and anti-Pro104 antibody.

For the prevention or treatment of disease, the dosage and mode of administration will be chosen by the physician according to known criteria. The appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 pg/kg to about 50 mg/kg body weight (e.g. about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-Pro104 antibody. However, other dosage regimens may be useful. A typical daily dosage might range from about 1 pg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of a nucleic acid molecule encoding the antibody is encompassed by the expression "administering a therapeutically effective amount of an antibody". See, for example, WO 96/07321 published Mar. 14, 1996 concerning the use of gene therapy to generate intracellular antibodies.

There are two major approaches to introducing the nucleic acid molecule (optionally contained in a vector) into the patient's cells; in vivo and ex vivo. For in vivo delivery the nucleic acid molecule is injected directly into the patient, usually at the site where the antibody is required. For ex vivo treatment, the patient's cells are removed, the nucleic acid molecule is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acid molecules into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid molecule transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et at., Science 256:808-813 (1992). See also WO 93/25673 and the references cited therein.

Articles of Manufacture and Kits

The invention also relates to an article of manufacture containing materials useful for the detection for Pro104 over-expressing cells and/or the treatment of Pro104 expressing cancer, in particular breast, ovarian, pancreatic and lung cancer. The article of manufacture comprises a container and a composition contained therein comprising an antibody of this invention. The composition may further comprise a carrier. The article of manufacture may also comprise a label or package insert on or associated with the container. Suitable containers include, for example, bottles, vials, syringes, etc. The containers may be formed from a variety of materials such as glass or plastic. The container holds a composition which is effective for detecting Pro104 expressing cells and/or treating a cancer condition and may have a sterile access port (for example the container may be an intravenous solution bag or a vial having a stopper pierceable by a hypodermic injection needle). At least one active agent in the composition is an anti-Pro104 antibody of the invention. The label or package insert indicates that the composition is used for detecting Pro104 expressing cells and/or for treating breast, ovarian, pancreatic and lung cancer, or more specifically ovarian serous adenocarcinoma, breast infiltrating ductal carcinoma, prostate adenocarcinoma, renal cell carcinomas, colorectal adenocarcinomas, lung adenocarcinomas, lung squamous cell carcinomas, and pleural mesothelioma, in a patient in need thereof. The breast cancer may be HER-2 negative or positive breast cancer. The cancers encompass metastatic cancers of any of the preceding, e.g., breast, ovarian, pancreatic and lung cancer metastases. The label or package insert may further comprise instructions for administering the antibody composition to a cancer patient. Additionally, the article of manufacture may further comprise a second container comprising a substance which detects the antibody of this invention, e.g., a second antibody which binds to the antibodies of this invention. The substance may be labeled with a detectable label such as those disclosed herein. The second container may contain e.g., a pharmaceutically-acceptable buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

Kits are also provided that are useful for various purposes, e.g., for Pro104 cell killing assays, for purification or immunoprecipitation of Pro104 from cells or for detecting the presence of Pro104 in a serum sample or detecting the presence of Pro104-expressing cells in a cell sample. For isolation and purification of Pro104, the kit can contain an anti-Pro104 antibody coupled to a solid support, e.g., a tissue culture plate or beads (e.g., sepharose beads). Kits can be provided which contain the antibodies for detection and quantitation of Pro104 in vitro, e.g. in an ELISA or a Western blot. As with the article of manufacture, the kit comprises a container and a composition contained therein comprising an antibody of this invention. The kit may further comprise a label or package insert on or associated with the container. The kits may comprise additional components, e.g., diluents and buffers, substances which bind to the antibodies of this invention, e.g., a second antibody which may comprise a label such as those disclosed herein, e.g., a radiolabel, fluorescent label, or enzyme, or the kit may also comprise control antibodies. The additional components may be within separate containers within the kit. The label or package insert may provide a description of the composition as well as instructions for the intended in vitro or diagnostic use.

EXAMPLES

Example 1

Production and Isolation of Monoclonal Antibody Producing Hybridomas

The following MAb/hybridomas of the present invention are described below: Pro104.C1, Pro104.C4, Pro104.C13, Pro104.C17, Pro104.C18, Pro104.C19, Pro104.C24, Pro104.C25, Pro104.C27, Pro104.C34, Pro104.C37, Pro104.C46, Pro104.C48, Pro104.C49, Pro104.C50, Pro104.C53, Pro104.C54, Pro104.C55, Pro104.C57, Pro104.C60, Pro104.C66, Pro104.C75, Pro104.C84, Pro104.D4, Pro104.D6, Pro104.D9, Pro104.D12, Pro104.D14, Pro104.D18, Pro104.D19, Pro104.D20, Pro104.D21, Pro104.D26, Pro104.D29, Pro104.D31, Pro104.D43, Pro104.D47, Pro104.D51, Pro104.D55, Pro104.D56, Pro104.D58, Pro104.D62, Pro104.D63, Pro104.D64, Pro104.D68, Pro104.D69, Pro104.D75, Pro104.D81, Pro104.D85, Pro104.D88, Pro104.D91, Pro104.D94, Pro104.D102, Pro104.D106, Pro104.D111, Pro104.D112, Pro104.D113, Pro104.D114, Pro104.D115, Pro104.D116, Pro104.D117, Pro104.D118, Pro104.D119, Pro104.D120, Pro104.D121, Pro104.D122, Pro104.D123, Pro104.D, Pro104.D124, Pro104.D125, Pro104.D126, Pro104.D127, Pro104.D, Pro104.D128, Pro104.D129, Pro104.D130, Pro104.D131, Pro104.D132, Pro104.D133, Pro104.D134, Pro104.D135, Pro104.D136, Pro104.D137, Pro104.D138, Pro104.D139, Pro104.K14, Pro104.K15, Pro104.K16, Pro104.K47, Pro104.K71, Pro104.K72, Pro104.K74, Pro104.K75, Pro104.K76, Pro104.K78, Pro104.K81, Pro104.K87, Pro104.K88, Pro104.K89, Pro104.K155, Pro104.K156, Pro104.K157, Pro104.K158, Pro104.K159, Pro104.K160, Pro104.K163, Pro104.K164, Pro104.K176, Pro104.K217, Pro104.K226, Pro104.K227, Pro104.K240, Pro104.K274, Pro104.K264, Pro104.K281, Pro104.K358 or Pro104.K362.

If the MAb has been cloned, it will get the nomenclature "X.1," e.g., the first clone of A7 will be referred to as A7.1, the second clone of A7 will be referred to as A7.2, etc. For the purposes of this invention, a reference to A7 will include all clones, e.g., A7.1, A7.2, etc.

Immunogens and Antigens (Recombinant Proteins, HA & His Tags & Transfected Cells)

Pro104 (Testisin) Full Length, Fragment *E. coli* Expressed Sequence & Protein Production For immunization of mice and production of the C series of MAbs, a Pro104 construct encoding a region of Pro104 from Lys20 to Trp297 was introduced into a standard *E. coli* expression vector via restriction enzyme sites. The construct was cloned in-frame to the C-terminus of a six-histidine tag so that the Pro104 construct would be expressed as a six-histidine tagged protein of 288 amino acids. The recombinant plasmid was used to transform competent *E. coli* cells and Pro104 expression was performed in shaker flasks. The bacterial paste, collected after induction with IPTG, was used for Pro104 purification via Ni-NTA column chromatography.

Pro104 (Lys20 (underlined)-Trp297) expressed amino acid sequence (the bold type represents the hexa histidine tag)

(SEQ ID NO. 1)

MAKPESQEAAPLSGPCGRRVITSRIVGGEDAELGRWPWQGSLRLWDSHVC

GVSLLSHRWALTAAHCFETYSDLSDPSGWMVQFGQLTSMPSFWSLQAYYT

RYFVSNIYLSPRYLGNSPYDIALVKLSAPVTYTKHIQPICLQASTFEFEN

RTDCWVTGWGYIKEDEALPSPHTLQEVQVAIINNSMCNHLFLKYSFRKDI

FGDMVCAGNAQGGKDACFGDSGGPLACNKNGLWYQIGVVSWGVGCGRPNR

PGVYTNISHHFEWIQKLMAQSGMSQPDPSWLEHHHHHH

Pro104 (Testisin) Insect Cell Expressed Sequence & Protein Production

For immunization of mice and production of the D series of MAbs, a Pro104 construct encoding a honey bee melletin secretion signal, a region of Pro104 from Ile42 to Trp297 and a six histidine tag was cloned and expressed using standard techniques. Pro104 was purified using Ni-NTA resin.

Pro104 (Ile42-Trp297) expressed amino acid sequence (underlined portion represents the honey bee melletin secretion signal and the bold type represents the hexa histidine tag)
(SEQ ID NO. 2)
<u>MKFLVNVALVFMVVYISYIYADPMA</u>IVGGEDAELGRWPWQGSLRLWDSHV

CGVSLLSHRWALTAAHCFETYSDLSDPSGWMVQFGQLTSMPSFWSLQAYY

TRYFVSNIYLSPRYLGNSPYDIALVKLSAPVTYTKHIQPICLQASTFEFE

NRTDCWVTGWGYIKEDEALPSPHTLQEVQVAIINNSMCNHLFLKYSFRKD

IFGDMVCAGNAQGGKDACFGDSGGPLACNKNGLWYQIGVVSWGVGCRPN

RPGVYTNISHHFEWIQKLMAQSGMSQPDPSWHHHHHH

Pro104 (Testisin) 293T & LMTK Cell Expressed Sequences & Protein Production

For screening of both C and D series Pro104 MAbs, full length Pro104 protein (Met1-Val314) was expressed both with and without an HA tag (bold) and spacer (underlined) located at the C-terminus, downstream from the recombination site (*italics*), using standard mammalian expression techniques.

Pro104 transfected human 293T and mouse LMTK cell amino acid sequence
(SEQ ID NO. 3)
MGARGALLLALLLARAGLRKPESQEAAPLSGPCGRRVITSRIVGGEDAEL

GRWPWQGSLRLWDSHVCGVSLLSHRWALTAAHCFETYSDLSDPSGWMVQF

GQLTSMPSFWSLQAYYTRYFVSNIYLSPRYLGNSPYDIALVKLSAPVTYT

KHIQPICLQASTFEFENRTDCWVTGWGYIKEDEALPSPHTLQEVQVAIIN

NSMCNHLFLKYSFRKDIFGDMVCAGNAQGGKDACFGDSGGPLACNKNGLW

YQIGVVSWGVGCGRPNRPGVYTNISHHFEWIQKLMAQSGMSQPDPSWPLL

FFPLLWALPLLGPV*DPAFLYKVVR*<u>SRMAS</u>YPYDVPDYASL

Pro104 (Testisin) CHO Cell Expressed Sequences & Protein Production

For immunization of mice and production of the K-series Pro104 MAbs, full length Pro104 protein (Met1-Val314) was expressed without a tag using standard mammalian expression techniques.

Hamster CHO cells were stably transfected with Tetracycline Receptor (TR) using standard recombinant techniques. Prior to Pro104 transfection, CHO-TR cells were cultured in HAM F12 medium with 10% fetal bovine serum (FBS). A vector encoding full length Pro104 protein (Met1-Val314) was transfected into the CHO cells. Stable transfectants were selected in HAM F12 medium with 10% FBS with Hydromycin B at 300 ug/ml, for 15 days. Hydromycin B-resistant cells were checked for expression of Pro104 by western blot using diaDexus Pro104.C25.1 monoclonal antibody after 16-20 hour stimulation with 1 ug/ml Tetracycline. Cells were expanded, scaled-up and cryopreserved in FBS with 10% DMSO and stored in liquid nitrogen at −196° C. to assure maintenance of viable clone cultures.

Pro104 transfected hamster CHO cell amino acid sequence
(SEQ ID NO. 4)
MGARGALLLALLLARAGLRKPESQEAAPLSGPCGRRVITSRIVGGEDAEL

GRWPWQGSLRLWDSHVCGVSLLSHRWALTAAHCFETYSDLSDPSGWMVQF

-continued
GQLTSMPSFWSLQAYYTRYFVSNIYLSPRYLGNSPYDIALVKLSAPVTYT

KHIQPICLQASTFEFENRTDCWVTGWGYIKEDEALPSPHTLQEVQVAIIN

NSMCNHLFLKYSFRKDIFGDMVCAGNAQGGKDACFGDSGGPLACNKNGLW

YQIGVVSWGVGCGRPNRPGVYTNISHHFEWIQKLMAQSGMSQPDPSWPLL

FFPLLWALPLLGPV

Ovr115 Serine Protease Domain Sequence & Protein Production

Ovr115 (TMPRSS4) was used to screen out cross reactive hybridoma clones, since this antigen was also upregulated in ovarian and pancreatic cancers and since it also contained a potentially cross-reactive serine protease domain.

An Ovr115 construct encoding a tobacco etch virus protease (TEV) recognition site and the serine protease domain of Ovr115 from Val203 to Leu435 was cloned in-frame to the C-terminus of glutathione S-transferase (GST) so that the Ovr115 construct was expressed as a GST-fusion protein of 486 amino acids using standard techniques. Purification of Ovr115 was completed via glutathione sepharose column.

Ovr115 serine protease domain construct amino acid sequence (GST sequence is underlined, TEV sequence is in italics and tag sequence is in bold type)
(SEQ ID NO. 5)
<u>MAPILGYWKIKGLVQPTRLLLEYLEEKYEEHLYERDEGDKWRNKKFELGL</u>

<u>EFPNLPYYIDGDVKLTQSMAIIRYIADKHNMLGGCPKERAEISMLEGAVL</u>

<u>DIRYGVSRIAYSKDFETLKVDFLSKLPEMLKMFEDRLCHKTYLNGDHVTH</u>

<u>PDFMLYDALDVVLYMDPMCLDAFPKLVCFKKRIEAIPQIDKYLKSSKYIA</u>

<u>WPLQGWQATFGGGDHPPKSDLVPRHNQTSLYKKAGF</u>*ENLYFQG*VVGGEEA

SVDSWPWQVSIQYDKQHVCGGSILDPHWVLTAAHCFRKHTDVFNWKVRAG

SDKLGSFPSLAVAKIIIEFNPMYPKDNDIALMKLQFPLTFSGTVRPICL

PFFDEELTPATPLWIIGWGFTKQNGGKMSDILLQASVQVIDSTRCNADDA

YQGEVTEKMMCAGIPEGGVDTCQGDSGGPLMYQSDQWHVVGIVSWGYGCG

GPSTPGVYTKVSAYLNWIYNVWKAELSNWSHPQFEK

Ovr115 Extracellular Fragment Sequence & Protein Production

An Ovr115 (TMPRSS4) construct encoding a region of Ovr115 from Lys52 to Leu435, which constituted only the predicted extracellular portion of the molecule, was cloned with a six-histidine tag immediately downstream of codon Leu435. Ovr115 was purified using Ni-NTA resin.

Ovr115 extracellular construct (Ovr115 Lys52 (underlined)-Leu435) amino acid sequence (6 His tag sequence is in bold type)
(SEQ ID NO. 6)
M<u>K</u>VILDKYYFLCGQPLHFIPRKQLCDGELDCPLGEDEEHCVKSFPEGPAV

AVRLSKDRSTLQVLDSATGNWFSACFDNFTEALAETACRQMGYSSKPTFR

AVEIGPDQDLDVVEITENSQELRMRNSSGPCLSGSLVSLHCLACGKSLKT

PRVVGGEEASVDSWPWQVSIQYDKQHVCGGSILDPHWVLTAAHCFRKHTD

VFNWKVRAGSDKLGSFPSLAVAKIIIEFNPMYPKDNDIALMKLQFPLTF

-continued
SGTVRPICLPFFDEELTPATPLWIIGWGFTKQNGGKMSDILLQASVQVID

STRCNADDAYQGEVTEKMMCAGIPEGGVDTCQGDSGGPLMYQSDQWHVVG

IVSWGYGCGGPSTPGVYTKVSAYLNWIYNVWKAELHHHHHH

Generation of Stable Ovr115 LMTK Mouse Cell Lines

Full length HA-tagged Ovr115 (Met1-Leu435) (underlined) was transfected into mouse LMTK cells after cloning into a mammalian expression vector with an HA tag. Individual clones were checked for expression of Ovr115 by western blot using anti-HA antibody (Covance, Richmond, Calif.), after 1 week in culture.

Ovr115 transfected LMTK amino acid sequence
(SEQ ID NO. 7)
MDPDSDQPLNSLDVKPLRKPRIPMETFRKVGIPIIIALLSLASIIIVVVL

IKVILDKYYFLCGQPLHFIPRKQLCDGELDCPLGEDEEHCVKSFPEGPAV

AVRLSKDRSTLQVLDSATGNWFSACFDNFTEALAETACRQMGYSSKPTFR

AVEIGPDQDLDVVEITENSQELRMRNSSGPCLSGSLVSLHCLACGKSLKT

PRVVGGEEASVDSWPWQVSIQYDKQHVCGGSILDPHWVLTAAHCFRKHTD

VFNWKVRAGSDKLGSFPSLAVAKIIIIEFNPMYPKDNDIALMKLQFPLTF

SGTVRPICLPFFDEELTPATPLWIIGWGFTKQNGGKMSDILLQASVQVID

STRCNADDAYQGEVTEKMMCAGIPEGGVDTCQGDSGGPLMYQSDQWHVVG

IVSWGYGCGGPSTPGVYTKVSAYLNWIYNVWKAELDPAFLYKVVRSRMAS

YPYDVPDYASL

Immunizations

For generation of the C series MAbs mice were immunized with soluble *E. coli* expressed Pro104 recombinant protein, encoding a region of Pro104 from Lys20 to Trp297 of the full length protein. Groups of 8 BALB/c mice were immunized intradermally in both rear footpads. All injections were 25 uL per foot. The first injection (day 1) of 10 ug of antigen per mouse was in Dulbecco's phosphate buffered saline (DPBS) mixed in equal volume to volume ratio with Titermax gold adjuvant (Sigma, St. Louis, Mo.). Subsequent injections of 10 ug of antigen per mouse occurred on days 5, 9, 12, 16, 19, 23, 26, 29, 30 and consisted of antigen in 20 uL of DPBS plus 5 uL of Adju-phos adjuvant (Accurate Chemical & Scientific Corp., Westbury, N.Y.) per mouse. The final boost injection on day 33 consisted of antigen diluted in DPBS alone. Fusion occurred on Day 37.

For generation of the D series MAbs mice were immunized as above with soluble insect cell expressed Pro104 recombinant protein, which corresponded to a region from Ile42 to Trp297 of the full length protein.

For the K series MAbs mice were immunized with a stably transfected CHO cell line expressing Pro104 on the cell surface. The cell surface expression of Pro104 ranged from 13.3 to 97.0%. In the first two injections, the mice were immunized with $1.25 \times 10^6$ cells/mouse, in injections 3-9, the mice were injected with $3.75 \times 10^6$ cells/mouse. The mice were given a final injection of $2.5 \times 10^6$ cells. Whole cells in HBSS (Hanks Balanced Salt Solution) with no adjuvants were used throughout the immunization series. The K series immunization schedule was the same one used for the C and D series above.

Hybridoma Fusions

Mice were sacrificed at the completion of the immunization protocol and draining lymph node (popliteal) tissue was collected by sterile dissection. Lymph node cells were dispersed using a Tenbroeck tissue grinder (Wheaton #357426, VWR, Brisbane, Calif.) followed by pressing through a sterile 40 uM sieve (VWR) into DMEM and removing T-cells via anti-CD90 (Thy1.2) coated magnetic beads (Miltenyl Biotech, Baraisch-Gladbach, Germany).

These primary B-cell enriched lymph node cells were then immortalized by electro-cell fusion (BTX, San Diego, Calif.) with the continuous myeloma cell line P3×63Ag8.653 (Kearney, J. F. et al., J. Immunology 123: 1548-1550, 1979). Successfully fused cells were selected by culturing in standard Hypoxanthine, Azaserine (HA) (Sigma, St. Louis, Mo.) containing selection medium (DMEM/15% FBS/0.5 ng/mL rIL-6 (Sigma, St. Louis, Mo.)/10% $P388D_1$ (ATCC, Manassas, Va.) conditioned medium). These fusion cultures were immediately distributed, 2 million cells per plate, into wells of 96 well culture plates (Costar Cat. #3585, VWR). Distributing the culture in 96 well culture plates, immediately following fusion, facilitated selection of a larger diversity of hybridoma clones producing single, specific antibodies. Supernatants from wells were screened by ELISA, for reactivity against Pro104 *E. coli* expressed protein, Pro104 insect expressed protein, and for no cross-reactivity with the serine protease Ovr115 extracellular domain (insect expressed).

Monoclonal cultures, consisting of the genetically uniform progeny from single cells, were established after the screening procedure above, by limiting dilution (Coller, H and Coller, B. Hybridoma 2: 91-6, 1983), or cell sorting of single viable cells into wells of two 96 well plates (VWR), using flow cytometry (Coulter Elite, Beckman Coulter, Miami, Fla.). The resulting murine B-cell hybridoma cultures were expanded using standard tissue culture techniques. Selected hybridomas were cryopreserved in fetal bovine serum (FBS) with 10% DMSO and stored in Liquid Nitrogen at −196° C. to assure maintenance of viable clone cultures.

Screening & Selection of Antibody Producing Hybridomas

Hybridoma cell lines were selected for production of Pro104 specific antibody by enzyme linked solid phase immunoassay (ELISA). Pro104 or Ovr115 proteins were nonspecifically adsorbed to wells of 96 well polystyrene EIA plates (VWR). One hundred uL volumes of Pro104 or Ovr115 proteins at approximately 1 ug/mL in (DPBS) were incubated overnight at 4° C. in wells of 96 well polystyrene EIA plates. Plates were washed twice with Tris buffered saline with 0.05% Tween 20, pH 7.4 (TBST). The plate wells were then emptied and nonspecific binding capacity was blocked by completely filling the assay wells with TBST/0.5% bovine serum albumin (TBST/BSA) and incubating for 30 minutes at room temperature (RT). The plate wells were then emptied, 100 uL of hybridoma culture medium samples diluted 1:1 with TBST/BSA was added to the wells and incubated for 1 hour at RT. The wells were then washed 3 times with (TBST). One hundred uL of alkaline phosphatase conjugated goat anti-mouse IgG (Fc) (Pierce Chemical Co., Rockford, Ill.), diluted 1:5000 in TBST/BSA, was then added to each well and incubated for 1 hour at RT. The wells were then washed 3 times with TBST. One hundred uL of alkaline phosphatase substrate para-nitrophenylphosphate (pNPP) (Sigma, St. Louis, Mo.) at 1 mg/mL in 1 M Diethanolamine buffer pH 8.9 (Pierce, Rockford, Ill.) was then added to each well and incubated for 20 min. at RT. Color development was stopped by addition of 50 uL of 2N NaOH/well. Bound alkaline phosphatase activity was indicated by the development of a visible yellow color. The enzymatic reaction was quantified by measuring the solution's absorbance at 405 nm wavelength. Cultures producing the highest absorbance values were chosen for expansion and further evaluation. Selected ELISA positive cultures from the original 96 well plates were transferred to new 96 well tissue culture plates (VWR).

ELISA Screening of Pro104 MAbs

Hybridomas were retested to confirm continued production of Pro104 specific MAbs. Hybridoma cultures with supernatants producing ELISA absorbance values greater than 1.0 with Pro104 and less than 0.2 with Ovr115 were expanded in tissue culture and cryopreserved, as described above. Selected Pro104 specific cultures were subcloned by limiting dilution or single cell sorting (Coulter Elite) to ensure genetically stable and uniform progeny.

Results from ELISA Screening of Cloned Pro104 MAbs

Clones Pro104.C13, Pro104.C18, Pro104.C25 and Pro104.C55 from the first immunization with *E. coli* expressed Pro104 were positive by ELISA with *E. coli* expressed Pro104, insect expressed Pro104, human 293T cell expressed Pro104 with and without the HA tag (Table 1 below) and did not react with the other human serine proteases pancreatic trypsin, lung tryptase and kallikrein (Cal Biochem, San Diego, Calif.) nor plasmin or urokinase (American Diagnostics, Greenwich, Conn.). Pro104.C13, Pro104.C18, Pro104.C19, Pro104.C25 and Pro104.C55 were subcloned and scaled up for further characterization by western blot, immunohistochemistry and immunofluorescence. MAbs Pro104.C37 and Pro104.C48 cross-reacted with human urokinase and were not evaluated further by immunohistochemistry or immunofluorescence.

Clones Pro104.D4, Pro104.D6, Pro104.D9, Pro104.D14, Pro104.D18, Pro104.D19, Pro104.D31, Pro104.D43, Pro104.D47, Pro104.D51, Pro104.D56, Pro104.D58, Pro104.D64, Pro104.D81, Pro104.D88, Pro104.D91 and Pro104.D94 from immunization with the insect expressed Pro104, were positive by ELISA with *E. coli* expressed Pro104, insect expressed Pro104, human 293T cell expressed Pro104 with and without the HA tag (Table 2) and did not react with the other human serine proteases pancreatic trypsin, lung tryptase, kallikrein, plasmin nor urokinase, see Table 2 below. Clones Pro104.D12, Pro104.D15, Pro104.D55, Pro104.D62, Pro104.D68 and Pro104.D106 were positive by ELISA with *E. coli* expressed Pro104, insect expressed Pro104 and were more weakly reactive (ELISA OD 405 nm from 0.3-0.8) with the human 293T cell expressed Pro104 (data not shown), but did not react with pancreatic trypsin, lung tryptase and kallikrein, plasmin or urokinase (Table 2). Pro104.D20 and Pro104.D21 were positive only with mammalian (293T) Pro104 protein. Pro104.D4, Pro104.D6, Pro104.D9, Pro104.D12, Pro104.D14, Pro104.D18, Pro104.D19, Pro104.D20, Pro104.D21, Pro104.D26, Pro104.D29, Pro104.D31, Pro104.D43, Pro104.D47, Pro104.D51, Pro104.D55, Pro104.D56, Pro104.D58, Pro104.D62, Pro104.D63, Pro104.D64, Pro104.D68, Pro104.D69, Pro104.D75, Pro104.D81, Pro104.D85, Pro104.D88, Pro104.D91, Pro104.D94, Pro104.D102 and Pro104.D106 were subcloned and scaled up for further characterization by western blot, immunohistochemistry and immunofluorescence. Pro104 MAbs cross-reacting with other human serine proteases (Pro104.D29 & Pro104.D31) were not evaluated further by immunohistochemistry or immunofluorescence.

FACS Screening for Cell Surface Binding of Pro104 C-Series MAbs

CAOV3 (RT-PCR positive for Pro104) and SKOV3 (RT-PCR negative for Pro104) ovarian carcinoma cell lines (ATCC) were grown in DMEM/10% FBS. Prior to staining, the cells were washed once with 10 ml $Ca^{+2}/Mg^{+2}$ free DPBS and then 7 ml of warm (37° C.) Cellstripper (Mediatech, Herndon, Va.) was added per 150 $cm^2$ flask. The cells were then incubated for 5 min. at 37° C. with tapping of the flask to remove tightly attached cells. The cells were removed and pipetted several times to break aggregates, then immediately placed in DMEM/10% FBS. The cells were then centrifuged for 5 minutes at 1300 rpm and resuspended in DMEM/10% FBS. The cells were then incubated at 37° C. for a 30 min. recovery period. Prior to staining, viability of the cells was measured using Guava Viacount (Guava Cytometers, Hayward, Calif.) and if >90% viable they were distributed into 96-well v-bottom plates (VWR) for staining with MAbs. Cells were aliquoted at $0.5$-$1.0 \times 10^6$ cells/well in 96-well v-bottom plates and centrifuged for 2 minutes at 1500 rpm. Supernatants were aspirated and plates briefly shaken on a vortex mixer to resuspend the cells, then a 200 ul volume of DPBS/3% FBS/0.01% Na Azide (FACS buffer) was added to each well. Centrifugation and aspiration was repeated, then 25 uL volumes of hybridoma supernatant or purified MAb were added to the cells. Plates were vortexed to resuspend cells, stored on ice for 15 min., then washed in 200 uL of FACS buffer and centrifuged as above. This washing procedure was repeated a twice and then 25 uL volumes of phycoerythrin (PE) conjugated donkey anti-mouse IgG Fc antibody (Jackson Immunoresearch Laboratories Inc., West Grove, Pa.) were added to cells. After 15 minutes on ice the cells were washed twice, as above and then resuspended in 250 uL of FACS buffer for analysis on the cell sorter or flow cytometer. In certain cases, for storage overnight at 4° C. prior to analysis, 133 ul volumes of FACS buffer and 67 uL of 1% paraformaldehyde/DPBS were added to wells, for fixation, then the volumes were increased to 250 uL with DPBS. Stained cells were analyzed on an Elite fluorescent activated cell sorter (FACS) (Beckman-Coulter, Miami, Fla.).

Results demonstrating cell surface binding of several of the C series MAbs by immunofluorescent FACS and microscopic analysis, are summarized in Table 1. Further immunofluorescence microscopy data with human tumor cell lines are presented below. The isotypes of the C series MAbs were determined using commercially available mouse monoclonal antibody isotyping immunoassay test kits (IsoStrip, Roche Diagnostic Corp., Indianapolis, Ind.). Results of the isotyping are listed in Table 1.

TABLE 1

ISOTYPE, ELISA, IMMUNOFLUORESCENCE FACS & MICROSCOPY RESULTS OF Pro104 C SERIES MAbs

| Pro104 MAb Clone | Isotype | Direct ELISA | | | | | FACS | | Microscopy Co-localization with HA on Pro104-HA Transfected 293T cells |
|---|---|---|---|---|---|---|---|---|---|
| | | Pur. *E. coli* expressed Full Lgth Pro 104 | Pur. insect expressed Pro104 | Insect Pro104 Crude Lysate | FL Pro104 293T Lysate | Pro104-HA 293T Lysate | CaOv-3 (RT-PCR+) | SkOv-3 (RT-PCR−) | |
| C4 | IgG1 k | + | + | + | + | + | − | − | 4* |
| C13 | IgG1 k | + | + | − | + | + | + | − | 3 |
| C18 | IgG1 k | + | + | + | + | + | − | − | 3 |
| C19 | IgG1 k | + | + | + | − | − | − | − | 4 |
| C25 | IgG1 k | + | + | + | + | + | + | + | 3 |
| C34 | IgG1 k | + | + | + | − | − | − | − | 4 |
| C37 | IgG1 k | + | + | + | + | + | + | − | 3 |
| C46 | IgG2b k | + | + | − | − | − | − | − | 2 |

TABLE 1-continued

ISOTYPE, ELISA, IMMUNOFLUORESCENCE FACS &
MICROSCOPY RESULTS OF Pro104 C SERIES MAbs

| | | Direct ELISA | | | | | FACS | | Microscopy Co-localization with HA on |
|---|---|---|---|---|---|---|---|---|---|
| Pro104 MAb Clone | Isotype | Pur. E. coli expressed Full Lgth Pro 104 | Pur. insect expressed Pro104 | Insect Pro104 Crude Lysate | FL Pro104 293T Lysate | Pro104-HA 293T Lysate | CaOv-3 (RT-PCR+) | SkOv-3 (RT-PCR−) | Pro104-HA Transfected 293T cells |
| C48 | IgG1 k | + | + | − | + | + | + | − | 3 |
| C50 | IgG2b k | + | + | − | − | − | − | − | 3 |
| C53 | IgG2b k | + | + | − | − | − | − | − | 3 |
| C54 | IgG2b k | + | + | + | − | − | − | − | 4 |
| C55 | IgG1 k | + | + | + | + | − | − | − | 4 |
| C57 | IgG2b k | + | + | − | − | − | + | − | 2 |
| C60 | IgG1 k | + | + | + | − | − | + | − | 4 |
| C66 | IgG1 k | + | + | − | − | − | − | − | 1 |
| C84 | IgG1 k | + | − | + | + | + | − | − | 1 |
| C1 | IgG2b k | + | − | − | − | − | + | + | 2 |
| C17 | IgG2b k | + | − | − | − | − | + | + | 2 |
| C24 | IgG2a k | + | − | − | − | − | + | − | 2 |
| C27 | IgG3 k | + | − | − | − | − | + | − | 3 |
| C49 | IgG2a k | + | + | − | − | − | + | − | 2 |
| C75 | IgG3 k | + | + | − | − | − | + | − | 3 |

*4 = Strong co-localization with HA with no background staining of non-transfected 293T cells,
3 = Strong co-localization with HA & background staining of non-transfected 293T cells,
2 = Partial co-localization with HA & background staining of non-transfected 293T cells,
1 = Weak HA staining (possibly blocked by test MAb) & high background staining of non-transfected 293T cells.

TABLE 2

RESULTS OF ELISA SCREENING OF THE Pro104 D SERIES MAbs

| Pro104 MAb Clone | Pro104 (Insect) | Pro104 (E. coli) | Ovr115 LMTK | Urokinase | Plasmin | Tryptase | Kallikrein | Trypsin | Pro104 293T lysate |
|---|---|---|---|---|---|---|---|---|---|
| D4  | + | + | − | − | − | − | − | − | + |
| D6  | + | + | − | − | − | − | − | − | + |
| D9  | + | + | − | − | − | − | − | − | + |
| D12 | + | + | − | − | − | − | − | − | + |
| D14 | + | + | − | − | − | − | − | − | + |
| D15 | + | + | − | − | − | − | − | − | + |
| D18 | + | + | − | − | − | − | − | − | + |
| D19 | + | + | − | − | − | − | − | − | + |
| D20 | − | − | − | − | − | − | − | − | + |
| D21 | − | − | − | − | − | − | − | − | + |
| D26 | + | + | − | | | | | | + |
| D29 | + | − | − | − | + | − | − | − | + |
| D31 | + | + | − | − | + | − | − | − | + |
| D43 | + | + | − | | | | | | + |
| D47 | + | + | − | | | | | | + |
| D51 | + | + | − | | | | | | + |
| D55 | + | − | − | − | − | − | − | − | + |
| D56 | + | + | − | | | | | | + |
| D58 | + | + | − | − | − | − | − | − | + |
| D62 | + | + | − | − | − | − | − | − | + |
| D63 | + | + | − | | | | | | + |
| D64 | + | + | − | | | | | | + |
| D68 | + | + | − | − | − | − | − | − | + |
| D69 | + | + | − | | | | | | + |
| D75 | − | − | − | | | | | | + |
| D81 | + | + | − | | | | | | + |
| D85 | + | + | − | | | | | | + |
| D88 | + | + | − | − | − | − | − | − | + |
| D91 | + | + | − | | | | | | + |
| D94 | + | + | − | | | | | | + |
| D102| + | + | − | | | | | | + |
| D106| + | + | − | − | − | − | − | − | + |

FACS Screening for Cell Surface Binding of Pro104 D-Series and K-Series MAbs

Fifty million 293F cells were transfected by a preparation of lipid-DNA complexes by performing a dilution of 50 µg of plasmid DNA in Opti-MEM I reduced serum medium (GIBCO) to a total volume of 1.5 ml followed by gentle mixing. A dilution of 75 µl of 293Fectin (Invitrogen) in Opti-MEM I to a total volume of 1.5 ml was mixed gently and incubated for 5 minutes at room temperature. After the 5 minute incubation, the diluted DNA was mixed with the diluted 293fectin. This mixture was allowed to incubate for 20-30 minutes at room temperature to allow the DNA-293fectin complexes to form. While the DNA-293fectin complexes incubated, an aliquot of 50 ml of cell suspension (1E6 viable cells/ml) was placed into a sterile, disposable flask. After the DNA-293fectin complex incubation was completed, they were transferred to each flask of cells. The flasks were incubated in a 37° C. incubator with shaking at 120 rpm. The cells were used for staining experiments at approximately 48 hours post-transfection.

The DNA sequence used for transfecting the 293F cells was the full length Pro104 sequence (met$^1$ to val$^{314}$), with no tags, See SEQ ID NO: 3 above.

Prior to staining, the viability of the 293F and control cells was measured using Guava Viacount (Guava Technologies, Hayward, Calif.) and if >90% were viable they were distributed into 96-well v-bottom plates (VWR) for staining with MAbs.

Cells were aliquoted at 0.5–1.0×10$^6$ cells/well in 96-well v-bottom plates and centrifuged for 2 minutes at 1500 rpm. Supernatants were aspirated and plates briefly shaken on a vortex mixer to resuspend the cells, then 200 ul of DPBS/3% FBS/0.01% Na Azide (FACS buffer) was added to each well. Centrifugation and aspiration was repeated, then 25 uL of hybridoma supernatant or 1 ug/million cells of purified MAb was added to the cells. Plates were stored on ice for 15 min., then washed and centrifuged as above, in 200 uL of FACS buffer. This washing procedure was repeated twice and then 25 uL of goat anti-mouse Ig (H+ L) biotin conjugated antibody (Caltag Laboratories, Burlingame, Calif.) was added to the wells for 15 minutes and washed as above. 25 ul of phycoerythrin Streptavidin (PESA) was added to cells. After 15 minutes on ice the cells were washed twice, as above and then resuspended in 250 uL of FACS buffer for analysis on the cell sorter or flow cytometer. Stained cells were analyzed on an Elite fluorescence activated cell sorter (Beckman-Coulter, Miami, Fla.).

Results demonstrating cell surface binding of many of the D-series and K-series MAbs by FACS analysis, are listed in Tables 3A, 3B, and 3C below. Results of representative experiments demonstrating cell surface expression by FACS analysis are depicted in FIG. 1 (A and B) and FIG. 2 (A and B).

Figure 1A:
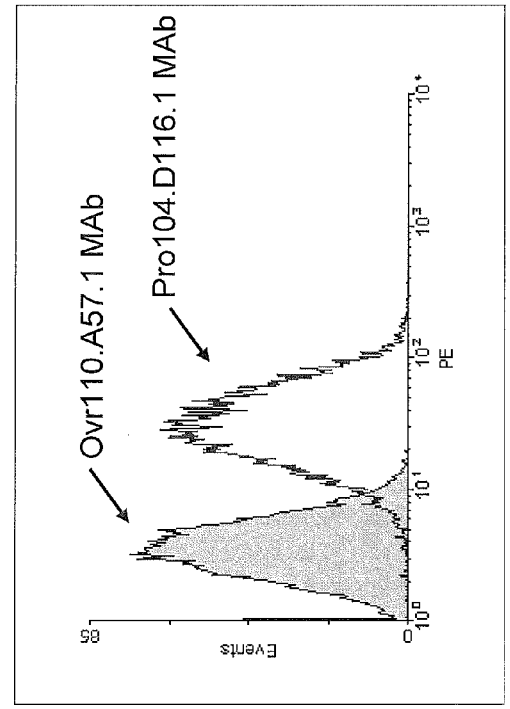
Figure 2B:
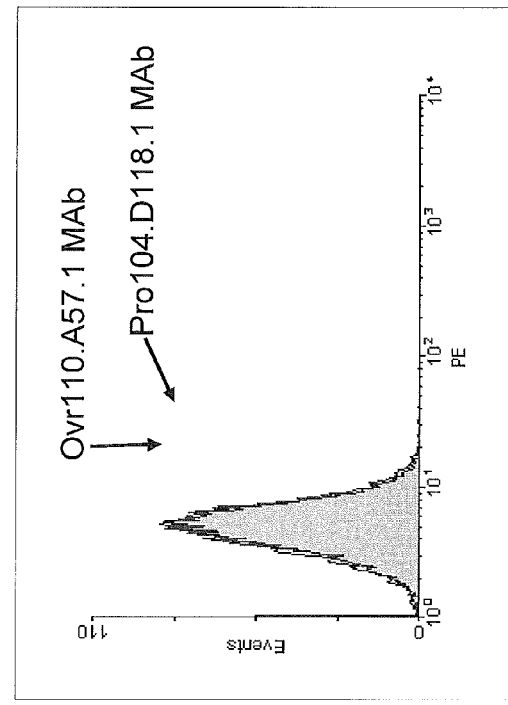
FIG. 2 shows that Pro104.D118.1 MAb Binds to 293F cells transiently transfected with Pro104 (FIG. 2A) and does not bind to 293F cells that do not express Pro104 (FIG. 2B).
Figure 2A:
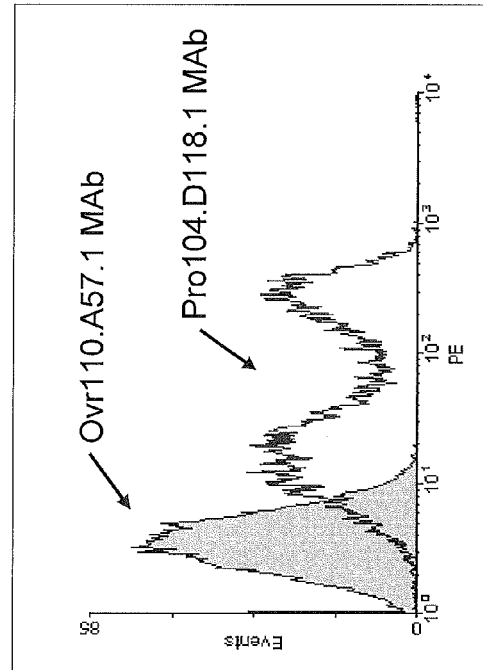

Specifically, FIG. 1A demonstrates cell surface binding of the Pro104.D116.1 antibody to transiently transfected 293F cells compared to a control antibody (Ovr110.A57.1). FIG. 1B indicates the binding observed in FIG. 1A is specific to Pro104. In addition, FIG. 2A demonstrates cell surface binding of the Pro104.D118.1 antibody to transiently transfected 293F cells compared to a control antibody (Ovr110.A57.1). FIG. 2B indicates the binding observed in FIG. 2A is specific to Pro104.

Binding of the MAb Pro104.D116.1 resulted in 85% of Pro104 transfected human 293F cells being positive, with a MFI (mean fluorescence intensity) 9-fold higher than cells stained with a control antibody (Ovr110.A57.1) alone. Binding of Pro104.D118.1 resulted in a bimodal distribution with 70% of the cells being positive for Pro104 and a mean fluorescence intensity 22-fold higher than the control antibody.

The other D-series antibodies that bound significantly to Pro104-293F transfected cells and not to untransfected 293F cells were Pro104.D9.1, Pro104.D112.1, Pro104.D113.1, Pro104.D114.1, Pro104.D115.1, Pro104.D119.1, Pro104.D120.1, Pro104.D121.1, Pro104.D122.1, Pro104.D123.1, Pro104.D124.1, Pro104.D125.1, Pro104.D126.1, Pro104.D127.1, Pro104.D129.1, Pro104.D130.1, Pro104.D131.1, Pro104.D132.1, Pro104.D133.1, Pro104.D134.1, Pro104.D135.1, Pro104.D136.1, Pro104.D137.1, Pro104.D138.1, and Pro104.D139.1 (see table 3A below).

TABLE 3A

Cell Surface Binding of Pro104 D-Series MAbs to Pro104 Transfected 293F Cells

| Sample | Pro104-Transfected 293F Cells | | Untransfected 293F Cells | |
|---|---|---|---|---|
| | % Cells Positive | MFI | % Cells Positive | MFI |
| No Stain | 1.6 | 0.429 | 1.5 | 0.465 |
| GAMBio SAPE | 4.5 | 0.421 | 1.7 | 0.538 |
| SAPE alone | 3.8 | 0.411 | 1.4 | 0.511 |
| Ovr110.A57.1 (negative control) | 3.1 | 0.372 | 1.6 | 0.504 |
| 5E9C11 (positive control) | 80.7 | 25 | 99.2 | 18.1 |
| Pro104.D9.1 | 38 | 2.63 | 9.2 | 0.802 |
| Pro104.D111.1 | 5.2 | 0.593 | 1.2 | 0.479 |
| Pro104.D112.1 | 28.7 | 2.38 | 1.4 | 0.515 |
| Pro104.D113.1 | 68.7 | 6.2 | 1.8 | 0.571 |
| Pro104.D114.1 | 51.5 | 4.18 | 1.7 | 0.509 |
| Pro104.D115.1 | 28.3 | 2.25 | 3.9 | 0.672 |
| Pro104.D116.1 | 84.8 | 3.88 | 1.9 | 0.594 |
| Pro104.D117.1 | 1.5 | 2.04 | 1.2 | 0.524 |
| Pro104.D118.1 | 69.9 | 9.01 | 1.6 | 0.524 |
| Pro104.D119.1 | 83.4 | 3.96 | 1.2 | 0.503 |
| Pro104.D120.1 | 36.4 | 2.68 | 1.8 | 0.531 |
| Pro104.D121.1 | 76.3 | 7.58 | 1.9 | 0.545 |
| Pro104.D122.1 | 21.3 | 2.41 | 1.3 | 0.513 |
| Pro104.D123.1 | 63 | 3.12 | 1.3 | 0.475 |
| Pro104.D124.1 | 74.5 | 3.41 | 2 | 0.595 |
| Pro104.D125.1 | 65.1 | 6.62 | 3 | 0.609 |
| Pro104.D126.1 | 62.5 | 3.16 | 1.5 | 0.483 |
| Pro104.D127.1 | 66.3 | 3.39 | 1.4 | 0.514 |
| Pro104.D128.1 | 1.9 | 2.06 | 1.3 | 0.504 |
| Pro104.D129.1 | 72.5 | 3.33 | 2.9 | 0.59 |
| Pro104.D130.1 | 56.7 | 6.26 | 3.7 | 0.65 |
| Pro104.D131.1 | 31.2 | 2.58 | 9.7 | 0.822 |
| Pro104.D132.1 | 61.2 | 3.1 | 2.4 | 0.614 |
| Pro104.D133.1 | 55 | 2.99 | 2.1 | 0.511 |
| Pro104.D134.1 | 14.2 | 2.19 | 2.3 | 0.561 |
| Pro104.D135.1 | 53.3 | 5.87 | 2.7 | 0.538 |
| Pro104.D136.1 | 40.2 | 2.52 | 2.3 | 0.52 |
| Pro104.D137.1 | 56.3 | 5.86 | 2.9 | 0.646 |
| Pro104.D138.1 | 68.3 | 6.23 | 3.1 | 0.624 |
| Pro104.D139.1 | 59.4 | 5.98 | 2.7 | 0.633 |

Pro104.K81 (from the K series) antibody also bound to 293F transiently transfected with Pro104. Approximately 54% of the cells were positive with a mean fluorescence intensity of 1.69 which was 3-fold over the negative control antibody.

The other K-series antibodies that bound significantly to Pro104-293F transfected cells and not to untransfected 293F cells were Pro104.K72, Pro104.K78, Pro104.K81, Pro104.K88, Pro104.K156, Pro104.K159, Pro104.K164 and Pro104.K176 (see table 3B below).

TABLE 3B

Cell Surface Binding of Pro104 K-Series MAbs to Pro104 Transfected 293F Cells

| Sample | Pro104-Transfected 293F Cells | | Untransfected 293F Cells | |
|---|---|---|---|---|
| | % Cells Positive | MFI | % Cells Positive | MFI |
| No Stain | 1.1 | 0.41 | 0.8 | 0.456 |
| GAMBio SAPE | 1.8 | 0.428 | 1.5 | 0.482 |
| SAPE | 1.4 | 0.397 | 0.8 | 0.459 |
| Pro104.D9.1 | 70.3 | 3 | 1.7 | 0.482 |
| Cln242.B53.1 (negative control) | 3.6 | 0.544 | 1.4 | 0.535 |
| Pro104.K15 | 18.1 | 0.919 | 3.2 | 0.557 |
| Pro104.K47 | 16.2 | 0.901 | 11.7 | 0.824 |
| Pro104.K71 | 18.1 | 0.963 | 1.8 | 0.479 |
| Pro104.K72 | 19.7 | 1.03 | 1.5 | 0.475 |
| Pro104.K75 | 99.2 | 15.5 | 13.4 | 0.816 |
| Pro104.K78 | 99 | 17.2 | 2.7 | 0.495 |
| Pro104.K81 | 54.2 | 1.69 | 3.1 | 0.56 |
| Pro104.K88 | 55.5 | 1.95 | 1.9 | 0.51 |
| Pro104.K156 | 98.7 | 18.7 | 7.7 | 0.907 |
| Pro104.K159 | 39.1 | 1.34 | 1.9 | 0.488 |
| Pro104.K164 | 81.8 | 3.75 | 4.2 | 0.581 |
| Pro104.K176 | 81.1 | 3.23 | 2.4 | 0.546 |

Pro104 D-series and K-series antibodies were also tested on cell lines that were QPCR positive for Pro104 transcript (HeLa) and QPCR negative for Pro104 transcript (HCT116). Pro104.K81 bound to 97% of HeLa and to 9% of HCT116 cells, with a 8-fold higher shift in mean fluorescence intensity. (See table 3C below).

TABLE 3C

Cell Surface Binding of Pro104 D-Series and K-Series MAbs to Pro104 QPCR Positive Cell Line HeLa

| Sample | Hela Cells | | HCT116 Cells | |
|---|---|---|---|---|
| | % Cells Positive | MFI | % Cells Positive | MFI |
| No Stain | 1.3 | 0.339 | 1.6 | 0.332 |
| GAMBio SAPE | 1.4 | 0.38 | 1.25 | 0.48 |
| SAPE | 1.3 | 0.333 | 1.4 | 0.423 |
| Ovr110.A57.1 (negative control) | 1.3 | 0.375 | 1.3 | 0.522 |
| anti-CD71 (positive control) | 99.8 | 49.6 | 99.9 | 38.9 |
| Pro104.D4.1 | 2 | 0.425 | 0.7 | 0.447 |
| Pro104.6.1 | 4.4 | 0.692 | 1.5 | 0.448 |
| Pro104.D9.1 | 3.3 | 0.694 | 0.5 | 0.408 |
| Pro104.D14.1 | 2.2 | 0.428 | 1 | 0.404 |
| Pro104.D18.1 | 2.3 | 0.486 | 1 | 0.421 |
| Pro104.D19.1 | 2.1 | 0.506 | 1.1 | 0.421 |
| Pro104.D31.1 | 6.9 | 0.634 | 3.6 | 0.527 |
| Pro104.D58.1 | 2 | 0.441 | 0.5 | 0.421 |
| Pro104.D116.1 | 5.5 | 0.738 | 0.6 | 0.428 |
| Pro104.D118.1 | 2 | 0.478 | 1.1 | 0.449 |
| Pro104.D119.1 | 6.3 | 0.801 | 0.8 | 0.425 |
| Pro104.D121.1 | 4.1 | 0.656 | 1 | 0.432 |
| Pro104.D123.1 | 3.8 | 0.696 | 0.6 | 0.416 |
| Pro104.D124.1 | 5.3 | 0.746 | 0.7 | 0.418 |
| Pro104.D126.1 | 4.6 | 0.711 | 0.8 | 0.428 |
| Pro104.D132.1 | 4.6 | 0.689 | 1.2 | 0.431 |
| Pro104.D133.1 | 5.2 | 0.706 | 0.8 | 0.408 |
| Pro104.K14 | 2.3 | 0.472 | 1 | 0.538 |
| Pro104.K15 | 92.6 | 5.84 | 80.2 | 3.29 |
| Pro104.K16 | 2.8 | 0.455 | 1.9 | 0.505 |
| Pro104.K47 | 51.8 | 1.6 | 69.5 | 2.09 |
| Pro104.K71 | 10.9 | 0.744 | 8.9 | 0.776 |

TABLE 3C-continued

Cell Surface Binding of Pro104 D-Series and K-Series MAbs to Pro104 QPCR Positive Cell Line HeLa

| Sample | Hela Cells | | HCT116 Cells | |
|---|---|---|---|---|
| | % Cells Positive | MFI | % Cells Positive | MFI |
| Pro104.K72 | 10.4 | 0.769 | 8.3 | 0.719 |
| Pro104.K74 | 1.6 | 0.442 | 0.2 | 0.465 |
| Pro104.K75 | 98.8 | 14.5 | 93 | 7.62 |
| Pro104.K76 | 2.2 | 0.42 | 1.3 | 0.485 |
| Pro104.K78 | 2.7 | 0.409 | 1 | 0.444 |
| Pro104.K81 | 96.9 | 6.51 | 8.9 | 0.772 |
| Pro104.K87 | 3.3 | 0.531 | 3.9 | 0.641 |
| Pro104.K88 | 99.3 | 10.2 | 96.7 | 10.1 |
| Pro104.K89 | 99.6 | 19.1 | 43.7 | 1.34 |
| Pro104.K155 | 1.5 | 0.413 | 0.4 | 0.468 |
| Pro104.K156 | 2.4 | 0.491 | 1.1 | 0.505 |
| Pro104.K157 | 97.4 | 10.3 | 92.9 | 6.47 |
| Pro104.K158 | 2.3 | 0.454 | 2.4 | 0.519 |
| Pro104.K159 | 15.8 | 0.87 | 22.3 | 0.908 |
| Pro104.K160 | 36.7 | 1.3 | 29 | 1.08 |
| Pro104.K163 | 4.1 | 0.49 | 13.9 | 0.751 |
| Pro104.K176 | 31.7 | 1.18 | 47 | 1.29 |
| Pro104.K217 | 11.9 | 0.767 | 25.4 | 0.949 |
| Pro104.K226 | 9.6 | 0.736 | 11.4 | 0.75 |
| Pro104.K227 | 42.4 | 1.42 | 65.5 | 2.19 |
| Pro104.K240 | 97.5 | 8 | 95.8 | 15.2 |
| Pro104.K274 | 23 | 0.923 | 15.1 | 0.622 |
| Pro104.K264 | 3.6 | 0.497 | 1.5 | 0.53 |
| Pro104.K281 | 55.2 | 2.08 | 70.7 | 3 |
| Pro104.K358 | 3.8 | 0.539 | 4.1 | 0.625 |
| Pro104.K362 | 3.9 | 0.534 | 3.2 | 0.61 |

These results indicate that the antibodies in Tables 3A, 3B and 3C and in particular, Pro104.K81 Mab are suitable for immunotherapy of tumors with or without conjugated drugs, toxins, enzymes, prodrug activating molecules or isotopes.

Pro104 MAb Affinity Analyses

Binding kinetics and affinity constants were calculated from surface plasmon resonance measurements using a BIACORE 3000 instrument (Biacore, Piscataway, N.J.). Experiments were designed to simultaneously generate on rate, off rate, and affinity values for the Pro104 MAbs.

Pro104 protein lot #060402 (diaDexus) was immobilized on flow cell 2 of a CM5 sensor chip (Biacore) by standard amine coupling (Biacore). Flow cell 1 was used as a blank surface for reference subtractions, and was activated and then inactivated with ethanolamine. Pro104 MAbs were diluted in HBS EP buffer (Biacore) and passed over flow cells 1 and 2 in series. MAbs were injected in duplicate, sequentially, for each of five concentrations: 200, 100, 50, 25, 12.5 ug/mL. Assuming a molecular weight for the MAbs of 158,000 kDa, the respective concentrations in nM were calculated to be: 1266, 633, 317, 158 and 79. MAbs were injected for 3 minutes at 30 uL/min followed by a dissociation time of 12 minutes. The regeneration of the chip surface, or removal of MAb between cycles, was performed by passing two injections of 100 mM Glycine pH 1.5 through the flow cells firstly for 30 seconds and then for 12 seconds, both at 100 uL/minute.

The above procedure was performed by using the Biacore's kinetic analysis wizard included in the Biacore control software. The resulting sensograms were fitted automatically, assuming a 1:1 Langmuir binding model. The results presented in Table 4 below were calculated using the wizard data processing function. The calculated affinities presented in Table 3 were all in the $10^{-9}$ M range except for Pro104.C34 and hence were sufficiently high to achieve a therapeutic dose in-vivo at less than or equal to 10 mg/kg, excepting for Pro104.C34.

TABLE 4

Pro104 C Series MAb Affinities
Pro104 Biacore Affinity Characterization

| Anti-Pro104 Antibody Clone | KA | KD | ka | Kd |
|---|---|---|---|---|
| C4  | 3.5E+08 | 2.9E−09 | 2.6E+04 | 7.4E−05 |
| C18 | 3.4E+08 | 2.9E−09 | 2.6E+04 | 7.5E−05 |
| C25 | 3.5E+08 | 2.8E−09 | 3.0E+04 | 8.5E−05 |
| C37 | 5.5E+08 | 1.8E−09 | 5.4E+45 | 9.7E−05 |
| C48 | 3.6E+08 | 2.8E−09 | 4.0E+04 | 1.1E−04 |
| C60 | 1.6E+08 | 6.4E−09 | 3.0E+04 | 1.9E−04 |
| C19 | 1.9E+08 | 5.2E−09 | 3.8E+04 | 2.0E−04 |
| C34 | 3.2E+08 | 3.0E−05 | 2.0E+01 | 6.2E−04 |
| C54 | 5.5E+08 | 1.8E−09 | 3.7E+04 | 6.7E−05 |
| C55 | 1.0E+08 | 9.8E−09 | 1.6E+04 | 1.5E−04 |

Western Blots

Protein extracts for western blot analysis were prepared in cell lysis buffer (1% NP-40/10 mM Sodium Phosphate pH 7.2/150 mM sodium chloride) from Pro104-293T transient transfectants and mammalian adenocarcinoma cell lines. Proteins were separated by electrophoresis on NuPAGE 4-12% Bis-Tris gels (Invitrogen Life Technologies, Carlsbad, Calif.) under denaturing conditions in a Novex-XCell II Minicell gel apparatus (Invitrogen Life Technologies, Carlsbad, Calif.) and subsequently transferred to PVDF membranes using an XCell II Blot Module (Invitrogen Life Technologies, Carlsbad, Calif.). Following the transfer of proteins, the membranes were blocked in 1% blocking reagent (Cat. #1 096 176, Roche Diagnostic Corp., Indianapolis, Ind.) and incubated overnight at 4° C. with purified primary antibodies Pro104.C4, Pro104.C13, Pro104.C18, Pro104.C19, Pro104.C25, Pro104.C34, Pro104.C37, Pro104.C48, Pro104.C55, Pro104.C60 or Pro104.C66, and then with horseradish-peroxidase conjugated goat anti-mouse IgG (Cat. #115-036-062, Jackson Immunoresearch Laboratories, Inc.). Bands were visualized by chemiluminescence using an ECL advance western blotting detection kit (Cat. #RPN2135, Amersham Biosciences, Piscataway, N.J.).

Deglycosylation experiments were performed on protein extracts from Pro104-293T transfectants, mammalian adenocarcinoma cell lines and normal human testis by treating with peptide N-glycosidase F (PNGaseF, Cat. #P0704S, New England Biolabs, Inc, Beverly, Mass.) as directed by the manufacturer. The deglycosylated samples were then analyzed by western blotting as described above. Briefly, 100 ug volumes of protein extracts were denatured in glycoprotein denaturing buffer (0.5% SDS/1% beta-mercaptoethanol), at 100° C. for 10 minutes. This was followed by the addition of kit reaction buffers (New England Biolabs) to a final concentration of 1% NP-40 and 50 mM sodium phosphate, addition of 100 units of PNGase F and incubation at 37° C. for 4 hours.

TABLE 5

RESULTS FROM WESTERN BLOTS USING PRO104 MABS WITH EXTRACTS FROM TRANSFECTED 293T CELLS & HUMAN ADENOCARCINOMA CELL LINES

| Pro104 MAb | Pro104-293T | Deglycosylated Pro104-293T | HeLa & CaOv3 (RT-PCR+) | Deglycosylated HeLa & CaOv3 | SkOv3 (RT-PCR−) |
|---|---|---|---|---|---|
| C4  | +Multiple bands 35-40 kDa | | | | |
| C13 | +Multiple bands 35-40 kDa | | | | |
| C18 | +Multiple bands 35-40 kDa | | | | |
| C19 | +Multiple bands 35-40 kDa | | | | |
| C25 | +Multiple bands 35-40 kDa | approx. 30 kDa | approx. 38 kDa | approx. 30 kDa | — |
| C34 | +Multiple bands 35-40 kDa | | | | |
| C37 | +Multiple bands 35-40 kDa | | approx. 38 kDa | | — |
| C48 | +Multiple bands 35-40 kDa | | | | |
| C55 | +Multiple bands 35-40 kDa | | approx. 38 kDa | | — |
| C60 | +Multiple bands 35-40 kDa | | | | |
| C66 | — | | | | |

Results of the western blot experiments are summarized in Table 5 above. In whole cell lysates from Pro104-293T transfectants, the MAbs Pro104.C4, Pro104.C13, Pro104.C18, Pro104.C19, Pro104.C25, Pro104.C34, Pro104.C37, Pro104.C48, Pro104.C55 and Pro104.C60 reacted specifically with several protein bands from approximately 35 kDa to 40 kDa, which were consistent with glycosylated forms of Pro104 formed after processing of full length Pro104/testisin. These bands were absent in the non-transfected 293T cell line sample. Pro104 MAb-C66 was not reactive by western blot analysis and was therefore eliminated from further studies. A protein eband at approximately 38 kDa was detected by MAbs Pro104.C25, Pro104.C55 and Pro104.C37 in lysates from Pro104 mRNA positive (RT-PCR+) cancer cell lines HeLa and CaOv3 (ATCC), but was absent as expected, in lysates from the RT-PCR negative ovarian cancer cell line SkOv3 (ATCC). Similarly, MAbs Pro104.C25 and Pro104.C55 detected a band of the predicted molecular weight (38 kDa), in lysate from normal human testis (data not shown). MAbs Pro104.C25 and Pro104.C55 also reacted with recombinant and native mouse testisin (data not shown), in western blots.

In western blots on deglycosylated lysates from Pro104 transfectants, RT-PCR positive cell lines and normal human testis, the migration of the Pro104 protein as detected by Pro104.C25, shifted from approximately 38-40 kDa (glycosylated) to approximately 30 kDa (non-glycosylated). This reduction in molecular weight of Pro104 is consistent with the prediction of three N-glycosylation sites on the catalytic subunit of Pro104 protein.

Example 2

Cell Surface Binding of Pro104 Mabs in Live Cancer Cells Demonstrated by Immunofluorescence The following cancer cell lines were used in this study and were obtained from the ATCC: Cervical (HeLa), Ovarian (Tov-112D, Tov-21G, CaOV-3 and SKOV-3), colon (HCT116) as well as the pancreatic (MIA Paca-2 and AsPC). HeLa, CaOV-3 cell lines express Pro104 RNA as determined by QPCR. Control HCT116 and SKOV-3 cells do not express Pro104 RNA.

The above cell lines were seeded onto sterile 18 mm glass coverslips and cultured at 37° C. in DMEM/10% FBS with penicillin and streptomycin for 48 hr prior to treatment with the primary antibodies (Pro104 MAbs). MAbs Pro104.C19.1, Pro104.C25.1, Pro104.C55.1 and Pro104.D9 were tested by immunofluorescence microscopy to determine which of these antibodies bound specifically to the cell surface of Pro104 expressing cancer cells. Primary MAbs were added to the medium at a final concentration of 10 ug/ml and incubated for one hour at 37° C. Following fixation with 3% formaldehyde in Phosphate Buffered Saline (PBS), the cells were incubated with a secondary Cy3-labeled donkey anti-mouse (Jackson Immunoresearch Laboratories, West Grove, Pa.) at a concentration of 5 ug/ml for 30 min. Following washing, the cells were mounted in Vectastain (Vector, Burlingame, Calif.), a medium containing DAPI to visualize the cell nuclei and observed in a Zeiss Axiophot fluorescence microscope (Carl Zeiss, Thornwood, N.Y.) equipped with the appropriate fluorescent filters. Micrographs were recorded using a CCD camera.

Pro104.C19.1, Pro104.C25.1, Pro104.C55.1 and Pro104.D9 all bound to Pro104 expressing cells. FIGS. 3A and 3B demonstrate the binding of Pro104.C19.1 to HeLa cells (FIG. 3A). Most of the cells in the field showed labeling for Pro104. Pro104.C19.1 could clearly be seen decorating the cell membrane of the cells (arrows). However, Pro104.C19.1 did not bind to the control negative (QPCR) SKOV-3 cancer cells (FIG. 3B, N indicates the position of the cell nuclei).

Binding and Internalization in Live Cancer Cells by Cy3 Conjugated Antibodies

This study was performed using directly conjugated fluorescent antibodies (MAbs). Using antibodies directly conjugated with the fluorescent dye Cy3, antibody binding and internalization can be visualized by fluorescence microscopy. This technology is well known in the art. SKOV-3 cells that do not express Pro104 (QPCR negative) were used as negative controls.

Cy3 Conjugation

Pro104.C19.1, Pro104.C25.1 and Pro104.A55.1 MAbs were each conjugated to Cy3. Cy3 conjugation was carried out according to standard procedures in the manufacturer's guidelines (Pierce). Briefly, 1 mg of antibody was dialyzed against 0.1M bicarbonate buffer (pH 9.3) for 60 min, mixed with Cy3 dye and incubated at RT for 2 hr, then transferred to a Slide-A Lyzer Dialysis cassette (Pierce) and dialyzed in 2 liters of PBS for 6 hr at 4° C. The dialysis buffer was replaced and dialysis was repeated 6 times. The Cy3 conjugated antibodies were recovered and concentration was measured in a spectrometer at 280 nm.

Cell Labeling

Cy3-Pro104.C19.1, Cy3-Pro104.C25.1 and Cy3-Pro104.A55.1 MAbs were incubated with the cells at a concentration of 10 ug/ml at 37° C. in water chambers for 60 min and then the coverslips with cells were washed in PBS and the cells were fixed with 3% formaldehyde in PBS for 10 min. Following fixation, the coverslips with the cells were mounted in a medium containing DAPI (Vectastain) to visualize cell nuclei and the cells observed using a Zeiss fluorescence Microscope Axiophot equipped with the appropriate fluorescent filters. Micrographs were obtained with a CCD camera.

Results

Immunofluorescence microscopy of cancer cells treated with Cy3-Pro104.C19.1, Cy3-Pro104.C25.1 and Cy3-Pro104.A55.1 indicated that ovarian and pancreatic cancer cells expressing Pro104 were able to bind and internalize the fluorescent antibodies. FIG. 4A shows the binding of Cy3-Pro104.C25.1 to the cell surface of HeLa cells (arrows), a cell line that expresses Pro104. The Cy3-Pro104.C25.1 antibody did not bind to the control cells SKOV-3 which do not express Pro104. See FIG. 4B, N indicates the nuclei of several unlabeled cells. FIG. 5 demonstrates that, following the binding to the cell membrane, Cy3-Pro104.C25.1 was internalized in live HeLa cells and that internalization vesicles could be observed in the cytoplasm of these cells. In particular, vesicles could be often visualized in close proximity to the cell nuclei (N) (arrow). FIG. 6A and FIG. 7A show the binding and internalization of Cy3-Pro104.19.1 and Cy3-Pro104.C55.1 in MIA-PaCa-2 cells, respectively. MIA-PaCa-2 cells are a pancreatic cell line that expresses Pro104. The internalization pattern was characterized by the presence of perinuclear vesicles likely to correspond to endosomes located in the proximity of the Golgi apparatus (arrows). Cy3-Pro104.C19.1 and Cy3-Pro104.C55.1 did not bind to the cells of the control cell line HCT-116 which does not express Pro104 (FIGS. 6B and 7B).

Cy3 conjugated MAbs Pro104.C19.1, Pro104.C25.1 and Pro104.A55.1 were all internalized upon binding to the cell surface of Pro104 expressing cancer cells, in-vitro. These results indicate anti-Pro104 antibodies, and in particular, Pro104.C19.1, Pro104.C25.1 and Pro104.A55.1 MAbs are suitable for immunotherapy of tumors with or without conjugated drugs, toxins, enzymes, prodrug activating molecules or isotopes.

Distribution of Pro104 in Tumors and Normal Tissues by Immunohistochemistry (IHC)

Formalin fixed paraffin embedded blocks of ovarian and pancreatic cancer and normal adjacent tissues were obtained from the National Disease Research Interchange (Philadelphia, Pa.). OCT embedded blocks of normal organs were obtained from Zoion (Hawthorne, N.Y.).

Immunohistochemical Staining for Formalin Fixed Paraffin Embedded Sections

Six μm thick sections cut from formalin fixed paraffin embedded blocks were heated at 45° C. for 15 min, deparaffinized in Histoclear (National Diagnostics, Atlanta, Ga.), deparaffinized in Histoclear and rehydrated through a series of reducing ethanol concentrations to PBS. Antigen retrieval was performed by boiling the section slides in 10 mM sodium citrate buffer (pH 6.0), at 120° C., 15-17 PSI in a decloaking chamber (Biocare, Walnut Creek, Calif.) for 10 min. Endogenous peroxidase activity was quenched by treating the sections with 3% hydrogen peroxide solution for 15 min. Slides were incubated with 1% BSA to block nonspecific antibody binding and then reacted with the primary Pro104 MAbs used at a concentration of 10 ug/ml for 1 hour at room temperature in a DAKO autostainer (Dako Co., Carpinteria, Calif.). After washing in Tris-Buffered Saline (TBS) with 0.5% Tween-20, slides were then incubated with anti-mouse IgG conjugated to horse radish peroxidase (HRP) (Immunovision technologies, Daly City, Calif.). After washing in TBS with 0.5% Tween-20, sections were treated by 3,3'-diaminobenzidine chromagen for 2-5 minutes (Immunovision Technologies) and counterstained with hematoxylin before mounting in Permount medium (American Master Tech Scientific, Inc, Lodi, Calif.) after dehydration. Normal mouse IgG at the same concentration as the primary antibody, served as negative a control for immunolabeling specificity. In additional control experiments, the Pro104 MAbs were incubated with the antigen Pro104 before being applied to the histological sections.

Immunohistochemical Staining for OCT Embedded Frozen Unfixed Sections

Slides were cut in the cryochamber at 5-8 um at an appropriate temperature, air dried for a minimum of thirty minutes at room temperature. Briefly, slides were rinsed in TBS to remove off OCT and incubated at room temperature. IHC was performed using the Immunovision Powervision Kit (Immunovision Technologies, Co. Daly City, Calif.). Briefly, slides were rinsed in TBS-T to remove off OCT and incubated with Pro104 primary antibodies for 1 hour at room temperature. They were then post-fixed in 4% paraformaldehyde fixative for 10 min at room temperature and treated as described above.

Results

Pro104.C25.1, Pro104.A55.1, Pro104.D9 and Pro104.D133 were used to immunolabel sections of ovarian and pancreatic cancer. Epithelial cells in the ovarian and pancreatic tumors but not in normal ovary and pancreas were labeled. Pro104.C25.1 labeled the cell surface of 10 out of 17 (58%) serous ovarian cancer and 11/11 (100%) pancreatic cancer clinical samples. Pro104.C55.1 labeled the cell surface of 6 out of 8 (75%) ovarian cancer and 3/3 (100%) pancreatic cancer clinical samples. Pro104.D9 labeled the cell surface in 1/4 ovarian cancer (25%). FIGS. 8A, 8B, 8C and 8D illustrate the IHC results obtained with Pro104.C25.1 in two ovarian cancer clinical samples (FIGS. 8A and 8C). Control normal ovaries were not labeled by the Pro104.C25.1 MAb (FIGS. 8B and 8D). FIG. 9 shows a higher magnification of an ovarian cancer histological section labeled with Pro104.C25.1. The labeling clearly localized to the cell membrane of the tumor epithelial cells (arrows).

FIG. 10 demonstrates that Pro104.D9 labeled the cell surface of ovarian cancer cells (arrow). Additionally, FIG. 11 shows that Pro104.D133 labeled the cell surface of serous ovarian cancer cells.

FIGS. 12A and 12C illustrate the immunolabeling pattern obtained with Pro104.C25.1 in clinical samples of pancreatic adenocarcinoma. Pro104 labeling was mostly restricted to the cell surface of epithelial cells (arrows) with occasional cytoplasmic labeling (FIG. 12C). Normal pancreatic cells were mostly devoid of specific labeling (FIGS. 12B and 12D). Additionally, FIG. 13 shows that no specific labeling was observed when normal mouse IgG was used instead of Pro104.C25 (FIG. 13A) or when Pro104.C25.1 was adsorbed with Pro104 antigen prior to processing for IHC (FIG. 13B).

Pro104 expression was also analyzed in normal organs. IHC on OCT frozen sections showed no detectable labeling on the cell surface in the cells of normal heart, liver, kidney, brain, colon, stomach, lung, prostate, ovary, pancreas and breast. However, the membrane of the germ cells in the testis showed strong Pro104 immunolabeling. This result was expected from data published in the scientific literature (J. D. Hooper et al. Testisin, a new human serine protease expressed by premeiotic testicular germ cells and lost in testicular germ cell tumors. *Cancer Research* 59:3199-3205 (1999)). See table 6 below for summary.

TABLE 6

Summary of IHC results for Pro104 D-Series MAbs
Pro104 D MAb Immunohistochemistry Results

| | | Unfixed OCT | | | | | | Formalin Fixed (FFPE) | |
|---|---|---|---|---|---|---|---|---|---|
| | | | Testis | | | Normal | Ovarian Cancers (no. | | Ovarian cancers |
| mAb Clone | Dilution (ug/ml) | Germ cell | Stroma | Smooth muscle | Other | vital organs* | positive/no. tested) | Testis | (Ratio positive/tested) |
| IgG1 Anti-Keratin | 10 ug/ml | – | – | – | – | | 3+ (5/5) | | 3+ (2/2) |
| D9 | 5 ug/ml | 3+ | – | – | – | – | 3+ (2/3) | 3+ | |
| D116 | 10 ug/ml | 3+ | – | – | – | – | 1+ (3/5) | | |
| D119 | 10 ug/ml | 3+ | – | – | – | – | 1+ (3/5) | | |

TABLE 6-continued

Summary of IHC results for Pro104 D-Series MAbs
Pro104 D MAb Immunohistochemistry Results

| | | Unfixed OCT | | | | | Formalin Fixed (FFPE) | |
|---|---|---|---|---|---|---|---|---|
| | | Testis | | | Normal | Ovarian Cancers (no. | | Ovarian cancers |
| mAb Clone | Dilution (ug/ml) | Germ cell | Stroma | Smooth muscle | Other | vital organs* | positive/no. tested) | Testis | (Ratio positive/tested) |
| D121 | 10 ug/ml | 3+ | – | – | – | 3+ (all 3) | 1+ (4/5) | | 2+ (3/3) |
| D124 | 10 ug/ml | 3+ | – | – | – | – | 1+ (3/5) | | |
| D123 | 10 ug/ml | 3+ | – | – | – | – | 2+ (2/5) | 3+ | 2+ (2/2) |
| D126 | 10 ug/ml | 3+ | – | – | – | +/– | 2+ (1/5) | 3+ | 1+ (2/2) |
| D132 | 10 ug/ml | 3+ | – | – | – | – | 2+ (1/5) | 3+ | 2+ (5/5) |
| D133 | 10 ug/ml | 3+ | – | – | – | – | 2+ (1/5) | 3+ | 2+ (2/2) |

*Normal vital organs include heart, liver and kidney.

The immunohistochemistry results above demonstrate Pro104 is expressed in a high percentage of ovarian and pancreatic cancer cases. The fact that Pro104 is expressed on the cell surface of cancer cells makes it an ideal target for antibody based therapy. Additionally, binding of anti-Pro104 antibodies to ovarian and pancreatic cancer cells demonstrated by IHC indicates anti-Pro104 antibodies, and in particular, Pro104.C25.1, Pro104.D9 and Pro104.D133 MAbs are suitable for immunotherapy of tumors with or without conjugated drugs, toxins, enzymes, prodrug activating molecules or isotopes.

Example 3

Mouse Monoclonal Sandwich ELISA Detection of Pro104

Pro104 Competitive Checkerboard ELISA

High binding polystyrene plates (Corning Life Sciences (MA)) were coated overnight at 4° C. with 1 μg/well of anti-Pro104 MAb. The coating solution was aspirated off and free binding sites were blocked by adding 300 μl/well of Superblock-TBS (Pierce Biotechnology, Illinois) for 1 hour at RT. After washing twice with Wash Buffer (1×TBS/0.05% Tween20), 100 μl volumes of Pro104 antigen were added to each well. Each pair was tested with 100 ng/ml and 0 ng/ml of recombinant Pro104 E. coli expressed protein diluted in Assay Buffer (1×TBS, 1% BSA/1% Mouse Serum/1% Calf Serum/0.1% Tween20). After addition, plates were incubated for 1 hour at RT with shaking, and washed 4× with 360 μl of Wash Buffer. Then 50 μl volumes of unlabeled coating MAb, at 20 μg/ml in Assay Buffer, were added and incubated with shaking at RT for 10 min. Afterwards, 50 μl volumes of biotinylated detecting MAb (2 μg/ml) were added to each well and plates were incubated for 1 hour at RT, with shaking. After washing, 100 μl volumes of alkaline phosphatase conjugated streptavidin (Jackson ImmunoResearch Laboratories, PA, 1:2000 dilution) were added to wells and plates were incubated for 30 min. at RT, with shaking. After washing, the plate was then developed using pNPP substrate in 1×DEA buffer (Pierce Biotechnology, Illinois) for 30 min. at RT. The reaction was stopped by adding 100 μl/well 1N NaOH, and plates were read at 405 nm using a Spectramax 190 plate reader (Molecular Devices, CA). OD readings at 405 nm were used to calculate signal to noise ratio (OD at 100 ng/mL divided by OD at 0 ng/mL) of each Ab pairs.

The results of the checkerboard ELISA testing 13 MAb are shown in Table 7 below. Each antibody was used as a coating as well as a detecting antibody in all possible combinations. All pairs were tested in duplicate on 100 and 0 ng of Pro104 E. coli protein in assay buffer (containing mouse serum, calf serum and BSA to be used as blank). The results are shown as specific signal/noise (assay buffer alone) ratio. During the incubation with detecting antibody, a 10-fold higher concentration of coating antibody was added to the wells to prevent self-pairing. Self-pairing may be observed when antigens are partly multimerized and may confound MAb pairing results. Performing the ELISA assay under competitive conditions ensures that antibodies cannot bind to the same or proximal epitopes when the antigen is aggregated.

The data suggest a minimum of five epitopes have been identified since steric hindrance may also be a contributing factor to the non-pairing of MAbs. The epitope map of the Pro104 MAbs derived from the results in Table 7 is shown in FIG. 14. More than 50% of the monoclonal antibodies (Pro104.C4, Pro104.C18, Pro104.C25, Pro104.C37, Pro104.C48 and Pro104.C60) reacted with one epitope or epitopes proximal enough to cause steric hindrance and so block MAb pairing in the assay. The MAbs Pro104.C34 and Pro104.C 13 both reacted with epitopes that were distinct from one another and distinct from the other epitopes or MAb groups. The MAbs Pro104.C55 and Pro104.C19 reacted with an epitope or two proximal epitopes which were sufficiently close to the epitope identified by Pro104.C66 to cause partial blocking. The MAbs Pro104.C55 and Pro104.C19 also reacted with an epitope or epitopes which were sufficiently close to the epitope or epitopes identified by the MAb group Pro104.C4, Pro104.C18, Pro104.C25, Pro104.C37, Pro104.C48 and Pro104.C60 to cause partial blocking. However, MAb Pro104.C66 reacted with an epitope which was sufficiently distant from the epitope or epitopes identified by Pro104.C4, Pro104.C18, Pro104.C25, Pro104.C37, Pro104.C48 and Pro104.C60 to allow pairing with MAbs of this group.

Several different MAb combinations were tested to establish a sandwich ELISA assay for the detection of native Pro104 from medium or lysates of cancer cell lines, transfected cell lines and cancer tissues. The pairs Pro104.C19/C48 and Pro104.C55/C34 performed best in the Sandwich ELISA with a sensitivity for recombinant Pro104 at approximately 1 ng/ml. Pro104 was detected by sandwich ELISA in CHAPS (Pierce) detergent lysates from RT-PCR positive CaOV3 ovarian cancer cells, RT-PCR positive HeLa cervical cancer cells and in lysates from Pro104 transfected 293T and LMTK cells, 48 hours post transfection. Pro104 was not detected in lysates from the prostate cancer cell line PC3 (ATCC) nor the colon cancer line HT29 (ATCC), which are Pro104 negative by RT-PCR. These results were also in agreement with immunofluorescence data. However, Pro104 protein could not be detected in the tissue culture medium from any of these cancer cell lines, or in the medium from Pro104 transfected cells, at 48 hours post transfection.

TABLE 7

Identification of Pro104 ELISA MAb Pairs by Competition ELISA

| | | Detecting Antibody | | | | | | | | | | |
|---|---|---|---|---|---|---|---|---|---|---|---|
| | | C4 | C13 | C18 | C25 | C37 | C48 | C60 | C66 | C19 | C34 | C55 |
| Coating Antibody | C4 | 4.3* | 50 | 4 | | 5.3 | 4.7 | 5.1 | 2.1 | 12 | | |
| | C13 | 33 | | 5.3 | 40 | 32 | 26.7 | 32 | 28 | 8.3 | 17 | 9 | 16 |
| | C18 | 3.2 | 43 | | 2.7 | 3.1 | 3.6 | 3.9 | 1.54 | 10 | | | |
| | C25 | 4 | 47 | 4.3 | | 5 | 5.6 | 5.1 | 1.67 | 1.3 | | | |
| | C37 | 4.2 | 46 | 4 | 4.3 | | 4.4 | 4.9 | 2.3 | 13 | | | |
| | C48 | 3 | 50 | 3.7 | 3.9 | 3.7 | | 3.8 | 1.9 | 14.7 | 1.3 | 19.5 | 1 |
| | C60 | 22 | 46 | 21 | 19 | 18 | 25 | | 4.38 | 7.8 | | | |
| | C66 | 31 | 30 | 34 | 23 | 19 | 22 | 13 | | 2 | 12 | 11 | 10 |
| | B8 | 22.8 | 22.4 | 21/40 | 16 | 13 | 17 | 7.8 | 2.6 | | 26 | 15.6 | 27 |
| | B11 | | 17 | 14 | 9.7 | 7.9 | 11 | 5.3 | 1.4 | | | | |
| | C19 | | 34 | 33 | | | 34 | | 14 | | 1.6 | 31 | 11 |
| | C34 | | 8.7 | 7.7 | | | 5.6 | | 1.9 | | 4.3 | 1.4 | 4.3 |
| | C55 | | 38 | 7.8 | | | 13.4 | | 13.6 | | 3 | 27 | 2.3 |

*Signal to noise (OD at 100 ng/mL divided by OD at 0 ng/mL (assay buffer alone)) ratio.

Example 4

Detection of Pro104 Protein and Phosphorylation of EGF Receptor

Detection of Pro104 Protein in Cell Lines and Ovarian Tumors by Western Blot

Rk3E, HeLa, AsPC1 and HT29 cells lines were evaluated for expression of Pro104. The RK3E and HT29 cell lines are negative for Pro104 mRNA. As a control RK3E was transfected with Pro104 (RK3E-104) using methods known in the art. As an additional control RK3E cells were also transfected with Alkaline Phosphatase (RK3E-AP). HeLa and AsPC1 are positive for Pro104 mRNA. In addition to the cell lines, ovarian tumor and normal adjacent tissue to the tumor was evaluated for the presence of Pro104.

Cell extracts were prepared on ice using modified RIPA buffer (1% NP40, 10 mM $Na_2PO_4$, 0.15M NaCl) plus a protease inhibitor cocktail (Roche Inc.). Between 20 and 50 ug of protein extract were used for each gel lane; protein equivalent concentrations were evaluated for protein level comparisons on the same gel. Clarified extracts were mixed with an equal volume of 2× concentrated Laemmli sample buffer (Invitrogen Life Technologies, Carlsbad, Calif.), heated to 70° C. for 10 minutes and then analyzed using pre-cast 4-12% SDS-polyacrylamide minigels (Nupage; Invitrogen Life Technologies, Carlsbad, Calif.) with MES running buffer (Nupage; Invitrogen Life Technologies, Carlsbad, Calif.). Gels were transferred to Immobilon-P PVDF membranes with a 0.45 µm pore size (Invitrogen Life Technologies, Carlsbad, Calif.) using 1× Nupage transfer buffer plus 10% Methanol. The membranes were rinsed and blocked for 1 hour at room temperature using 5% nonfat dry milk in PBS with 0.05% Tween-20. Membranes were incubated with primary antibody overnight in 5% nonfat dry milk in PBS with 0.05% Tween-20. A mouse monoclonal antibody directed against Pro104 was produced in house using recombinant bacterial Pro104 protein. The Pro104 monoclonal antibody was diluted 1:1000 for a final concentration of 1 ug/ml and a mouse monoclonal antibody against GAPDH (Chemicon Inc., Temecula, Calif.) was diluted 1:5000 (for a final concentration of 0.2 ug/ml). Following primary antibody incubation, membranes were washed four times at room temperature for 10 min. each in 1×PBS with 0.05% Tween-20. Horseradish peroxidase linked goat anti-mouse immunoglobulin (Jackson Lab Inc., Bar Harbor, Me.) was used (1:10,000 dilution) in 5% nonfat dry milk in PBS plus 0.05% Tween-20 for 1 hour at room temperature to detect the primary monoclonal antibody. Membranes were finally washed four times for 10 min. in 1×PBS plus 0.05% Tween-20 followed by detection using enhanced chemiluminescence (ECL) reagent per manufacturer's directions (Amersham, Piscataway, N.J.) and exposure to X-ray film (Kodak, Rochester, N.Y.). For the Western immunoblot experiment comparing RK3E cells infected with an AP (alkaline phosphatase)-expressing retrovirus with the same cells infected with a Pro104-expressing retrovirus, cells were plated in growth medium containing either 1% or 10% FBS for 48 hours. Cell extracts were prepared using modified RIPA buffer including a phosphatase inhibitor cocktail (Calbiochem) and 25 ug of clarified extract were evaluated by SDS-PAGE and Western immunoblot with a polyclonal antibody specific for the phosphorylated EGF receptor (BioSource International, Camarillo, Calif.).

FIG. 15A demonstrates by western blot Pro104 protein was detected in Pro104 transfected cells lines (RK3E-104) and cell lines natively expressing Pro104 (HeLa and AsPC1). Pro104 protein was not detected in AP transfected cell lines (Rk3E-AP) and mRNA negative cell lines (HT29). Additionally, FIG. 15B illustrated detection of Pro104 protein by western blot in ovarian tumor tissues but not in normal adjacent tissues.

The fact that Pro104 is detectable in cancer cell lines and ovarian tumor tissue makes it an ideal target for antibody based therapy. Anti-Pro104 antibodies are suitable for immunotherapy of tumors with or without conjugated drugs, toxins, enzymes, prodrug activating molecules or isotopes.

Phosphorylation of EGF Receptor

RK3E transfected cell lines overexpressing Pro104 (RK3E-Pro104) were evaluated for phosphorylation of the Epidermal Growth Factor (EGF) Receptor. As a control RK3E cells were also transfected with Alkaline Phosphatase (RK3E-AP). Using methods known in the art, phosphorylation of the EGF receptor was evaluated with 10% and 1% serum from RK3E-Pro104 and RK3E-AP cells.

Over expression of Pro104 was found lead to phosphorylation of EGF receptor. FIG. 16 is a western immunoblot against phosphorylated EGF Receptor which demonstrates EGF receptor is phosphorylated from overexpression of Pro104 compared to AP controls.

Example 5

Glycosylation, GPI-Linkage and Biotinylation of Pro104 Protein

Pro104 Glycosylation

Deglycosylation experiments were performed on protein extracts from HeLa cell lines (Pro104 mRNA positive) and ovarian cancer tumor samples using Peptide N-Glycosidase F (PNGaseF, Cat #P0704S, New England Biolabs, Inc, Beverly, Mass.) as per the directions provided by the manufacturer. The deglycosylated samples were then analyzed by western blotting as described above. Briefly, 100 ug of protein extract was denatured in glycoprotein denaturing buffer/0.5% SDS/1% beta-mercaptoethanol, at 100° C. for 10 minutes. This was followed by the addition of kit reaction buffers (New England Biolabs) at a final concentration of 1% NP-40 and 50 mM sodium phosphate before the addition of 100 units of PNGase F and incubated at 37° C. for 4 hours.

FIG. 17A illustrates a shift in the migration of Pro104 protein from both the HeLa cell line and ovarian cancer samples when treated with Pangs. These results demonstrate not only that Pro104 is glycosylated, but that anti-Pro104 antibodies are capable of detecting both glycosylated and deglycosylated forms of native Pro104.

Pro104 GPI-Linkage Characterization by PI-PLC

HeLa cells were seeded in 6 well plates. 48 hours later, at 90% confluence, the media were replaced with 1 ml fresh growth media, with and without 0.5 unit phosphatidylinositol-specific phospholipase C (PI-PLC, Sigma). After one hour incubation at 37° C., the media were harvested and briefly microfuged. 15 µl of unconcentrated media were analyzed by SDS-PAGE. Cells were solubilized for immunoblot analysis as described above.

Since human Pro104 was predicted to be a GPI-linked protein, this was tested by treating live HeLa cells with phosphatidylinositol-specific phospholipase C (PI-PLC) as described above. PI-PLC cleaves the membrane anchor from GPI-linked proteins and releases the protein into the medium. FIG. 17B demonstrated no Pro104 protein was shed into the medium of untreated HeLa cells, however, treatment with PI-PLC released Pro104 into the medium where it could be detected by immunoblot. The PI-PLC treatment did not release other non-GPI-linked membrane proteins indicating that the release of Pro104 was due to specific cleavage of the GPI-anchor by the PI-PLC. This experiment shows that Pro104 is localized to the surface of tumor cells via a GPI-linkage.

Pro104 Biotinylation

Attached Cells

Caco2, CaOV3, or HeLa cells were removed from a 37° C. incubator, place on ice, and remained on ice for duration of the experiment. Cells were washed 3 times with ice cold PBS (10 mM Na—P) at pH 7.4. Biotinylation reagent (Sulfo-NHS-SS-Biotin; Pierce, Rockford, Ill.) dissolved in ice cold PBS to final concentration of 0.5 mg/ml was added to cover the cells completely (approximately 200 µl) and incubated on ice for 30 minutes. Biotinylation reagent was removed and cells were washed with 1×PBS+25 mM Tris once followed by three washes with ice cold PBS. 500 µl of Lysis Buffer (1×PBS+1.0% Triton) with 1× protease inhibitors was added to cells and incubated on ice for 10 minutes. Resulting lysate was transferred into a microcentrifuge tube and spun for 2 minutes at 14,000 rpm at 4° C. 50 µl of supernatant was saved to be run on gels as total protein extract, while the remaining volume of supernatant was immunoprecipitated with 20 µl of Streptavidin Agarose beads (Pierce). After immunoprecipitation, the beads were washed three times with cell lysis buffer (1×PBS+1.0% Triton). 100 µl of 1×LDS Sample Buffer (NuPage; Invitrogen) and 1× Sample Reducing Agent (NuPage; Invitrogen) were added to each sample and incubated at 70° C. for 10 minutes prior to running on gel. A standard western blot was then performed as described above.

Detached Cells

Caco2, CaOV3, or HeLa cells were removed from a 37° C. incubator, place on ice, and remained on ice for duration of the experiment. Cells were detached and washed 3 times with ice cold PBS (10 mM Na—P) at pH 7.4 and resuspended in 500 µl PBS. Biotinylation reagent (Sulfo-NHS-SS-Biotin; Pierce, Rockford, Ill.) dissolved in ice cold PBS with a concentration of 1.0 mg/ml was added to the cells for a final concentration of 0.5 mg/ml and incubated on ice for 30 minutes. Cells were spun at 200 rpm for 5 minutes. Biotinylation reagent was removed and cells were washed with 1×PBS+25 mM Tris once followed by three washes with ice cold PBS. Cells were spun at 200 rpm for 5 minutes in between washings to remove buffer. 500 µl of Lysis Buffer (1×PBS+1.0% Triton) with 1× protease inhibitors was added to cells and incubated on ice for 10 minutes. Resulting lysate was transferred into a microcentrifuge tube and spun for 2 minutes at 14,000 rpm at 4° C. Supernatant was transferred to a new microcentrifuge tube and protein concentration was determined using the BCA assay (Pierce). 50 µl of supernatant was saved to be run on gels as total protein extract, while the remaining volume of supernatant was immunoprecipitated with 20 µl of Streptavidin Agarose beads (Pierce). After immunoprecipitation, the beads were washed three times with cell lysis buffer (1×PBS+1.0% Triton). 100 µl of 1×LDS Sample Buffer (NuPage; Invitrogen) and 1× Sample Reducing Agent (NuPage; Invitrogen) were added to each sample and incubated at 70° C. for 10 minutes prior to running on gel. A standard western blot was then performed as described above.

FIG. 18 demonstrates that native Pro104 is biotinylated on the cell surface compared to NaK-ATPase (positive control) and GAPDH (negative control).

The fact that Pro104 is located on the cell surface via GPI-Linkage in cell lines makes it an ideal target for antibody based therapy. Furthermore, binding of anti-Pro 104 antibodies to glycosylated and deglycosylated Pro104 on cell lines and ovarian cancer cells indicates anti-Pro104 antibodies are suitable for immunotherapy of tumors with or without conjugated drugs, toxins, enzymes, prodrug activating molecules or isotopes.

Example 6

Generation of Pro104 Expressing Cell Lines

Cells and Cell Cultures

SKOV3, RK3E, 293T, HeLa, CaOV3, NCIH522 and HCT116 cell lines were purchased from American Type Culture Collection (Manassas, Va.). Cells were grown in DMEM (Invitrogen Life Technologies, Carlsbad, Calif.) with L-glutamine plus 4.5 g/L glucose and supplemented with 10% FBS and 100 U/mL Penicillin/Streptomycin (Cellgro, Herndon, Va.). All cells were maintained in a humidified 37° C. incubator with 5% $CO_2$.

Expression Vector Construction

As a source for cloning of Pro104, human ovarian cancer cDNA was prepared from poly-A+ mRNA using a BD SMART PCR cDNA synthesis kit (BD Bioscience/Clontech, Palo Alto, Calif.). For construction of a retroviral expression vector encoding untagged Pro104 (pLXSN-Pro104), Pro104 cDNA was synthesized by PCR reaction using ovarian cancer 5'-RACE-ready cDNA as template and the following gene specific primers:

```
                                         (SEQ ID NO: 8)
5'-end:    5'-ATGGGCGCGCGCGGGGCGCTGCTGCTG-3'

(SEQ ID NO: 9)
3'-end:    5'-TTATCAGACCGGCCCCAGGAGTGGGAGAGCCCA-3'
```

The PCR fragment was cloned into the Hpa I cloning site of the pLXSN vector (BD Bioscience/Clontech) and sequence verified. The Genbank accession for pLXSN vector is #M28248.

For construction of a retroviral expression vector encoding Pro104 with an in-frame COOH-terminal hemagglutinin tag (pLXSN-Pro104HA), the same procedure was used except that the 3' primer used was:

```
3'-end (HA tag is bold):
                                        (SEQ ID NO: 10)
5'-TTATCACGCGTAGTCCGGCACGTCGTACGGGTAGCCGACCGGCCCCA

GGAGTGGGAGAGCCCA-3'
```

The pLXSN retrovirus vector utilizes a 5'Mo-MuSV (Moloney Murine Sarcoma Virus) LTR and 3'Mo-MuLV (Moloney Murine Leukemia Virus) LTR to drive expression of cDNA's cloned into the multiple cloning site and an SV40 promoter driving expression of a Neo$^r$ gene encoding G418 resistance. pLAPSN, a retroviral expression vector encoding alkaline phosphatase (AP), was purchased from BD Bioscience/Clontech (referred to as pLXSN-AP).

Virus Production

Ecotropic virus was used to infect RK3E cells and amphotropic virus to infect SKOV3 cells. For ecotropic virus packaging, one day prior to transfection, 293T cells were seeded at a density of $8\times10^5$ cells per well of a 6 well dish onto Biocoat collagen coated plates (BD). Cells were transfected with purified plasmid DNA's using Lipofectamine with the addition of PLUS reagent (Invitrogen Life Technologies, Carlsbad, Calif.). Per well of cells 0.8 μg of virus plasmid DNA: pLXSN-Pro104, pLXSN-Pro104HA or pLXSN-AP plus 0.8 μg pVpack-ECO and 0.8 μg pVpackGP (Stratagene, La Jolla, Calif.) were added to a stock of 125 μL DMEM without serum and 10 μL of PLUS reagent followed by incubation for 15 minutes at room temperature. Subsequently, 8 μL of lipofectamine diluted into 125 μL of DMEM medium were added to the DNA/PLUS reagent mixture and incubated for 15 minutes as room temperature. One ml of DMEM was added to the final Lipofectamine/DNA mixture and applied to the cell monolayer, already containing 1 ml DMEM without serum, followed by incubation at 37° C. for 3 hours. One mL of DMEM containing 20% FBS was added to the transfection mix after the 3 h incubation and grown overnight. Finally, the media was changed to DMEM supplemented with 10% FBS+ 100 U/mL Pen/Strep for virus collection. Virus-containing media were harvested 24 hours later and filtered through a 0.45 μm polysulfonic filter.

For amphotropic virus packaging the same procedure was followed except that the pVpackAmpho plasmid (Stratagene) was used instead of the pVpack Eco plasmid.

Virus Infection and Selection

Polybrene (Hexadimethrine Bromide; Sigma, St. Louis, Mo.) was added to fresh virus-containing medium at a final concentration of 4 μg/ml. RK3E or SKOV3 cells, plated the day before at a density of $3\times10^5$ cells per 100 mm$^2$ dish, were washed once with phosphate-buffered saline including Ca2+ and Mg2+ (Cellgro). The virus solution (6 ml per 100 mm2 dish) was applied directly to the cells and then incubated for 3 hours in a humidified 37° C. incubator with 5% $CO_2$ with occasional swirling. The virus-containing medium was replaced by fresh growth medium and the cells incubated at 37° C. for 60-72 hours at which point a final concentration of 350 ug/mL of G418 sulfate (Cellgro) was included in the growth medium to select for virus-infected cells. Cells were maintained between 70-80% confluence and G418-containing media was changed every 2 days. Following G418 selection, pools of cells were used for subsequent experiments including verification of Pro104 protein expression by Western immunoblot analysis where cells were extracted and analyzed as described above. Expression of AP by infected cell monolayers was monitored by staining whereby monolayers of cells were fixed for 10 minutes at room temperature with a solution of 0.5% glutaraldehyde, rinsed with PBS, heated to 65° C. for 30 minutes and AP visualized by incubation with BCIP/NBT liquid substrate (Sigma, St. Louis, Mo.) for 2-3 hours.

Results of Cell Line Virus Infection and Selection

SKOV3, RK3E, 293T, HeLa, CaOV3, NCIH522 and HCT116 cell lines underwent virus infection and selection to overexpress Pro104.

Retroviral-mediated overexpression of Pro104 protein in RK3E cells was confirmed by Western Immunoblot. FIG. 19 is a western immunoblot demonstrating Pro104 protein expression in retroviral packaging cell lines and virus infected RK3E cells.

Retroviral-mediated overexpression of Pro104 protein in SKOV3 cells was confirmed by Western Immunoblot. FIG. 20 is a western immunoblot demonstrating Pro104 protein expression in retroviral packaging cell lines and virus infected SKOV3 cells.

Example 7 siRNA Generation and Transfection siRNA Oligonucleotide Design and Preparation

To design Pro104 specific siRNA molecules, sequences were selected from the open reading frame of the Pro104 mRNA based on methods previously described (Elbashir et al., 2001, Nature 411:494-498A random "scrambled" siRNA sequence which should not generate knockdown of any known cellular mRNA was used as a negative control. As an additional negative control a siRNA targeting Emerin was used to demonstrate that knockdown of a non-essential mRNA did not affect Pro104 levels nor any of the biological endpoints studied. As a positive control for knockdown of an mRNA leading to apoptosis induction, a siRNA targeting either DAXX or OPA1 was used, based on published data. Michaelson et al., 2002, Journal of Cell Science, 116:345-352; Olichen et al., 2003, J Biol Chem., 278(10):7743-6. A BLAST search against the human genome was performed with each selected siRNA sequence to ensure that the siRNA was target-specific and would not function to knockdown other sequences. The siRNA sequences used to knockdown Emerin and DAXX were obtained from published papers. Michaelson et al., 2002; Harborth et al., 2001, Journal of Cell Science, 114:4557-4565.

All siRNA molecules (HPP purified grade) were chemically synthesized by Xeragon Inc. (Germantown, Md.). siRNA's were dissolved in sterile buffer, heated at 90° C. for 1 minute and then incubated at 37° C. for 1 hour prior to use. siRNA oligonucleotides with two thymidine residues (dTdT) at the 3' end of the sequence consisted of the following specific RNA sequences:

```
Pro104 #56: sense
5'-CACAUCCAGCCCAUCUGUC-3'     (SEQ ID NO: 11)

Pro104 #79: sense
5'-GAGGAUGAGGCACUGCCAU-3'     (SEQ ID NO: 12)

Pro104 #80: sense
5'-CUCUAUGUGCAACCACCUC-3'     (SEQ ID NO: 13)

Pro104 #81: sense
5'-GUACAGUUUCCGCAAGGAC-3'     (SEQ ID NO: 14)

Scrambled: sense
5'-UUCUCCGAACGUGUCACGU-3'     (SEQ ID NO: 15)

Emerin: sense
5'-CCGUGCUCCUGGGGCUGGG-3'     (SEQ ID NO: 16)

DAXX: sense
5'-GGAGUUGGAUCUCUCAGAA-3'     (SEQ ID NO: 17)

OPAI sense
5'-GUUAUCAGUCUGAGCCAGG-3'     (SEQ ID NO: 18)
```

Additional siRNA oligonucleotides specific for Pro104 with two thymidine residues (dTdT) at the 3' end of the sequence consisted of the following specific RNA sequences:

```
Pro104_siRNA#1:
gccggagucgcaggaggcg           (SEQ ID NO: 19)

Pro104_siRNA#2:
cucgggcguuggccgugge           (SEQ ID NO: 20)

Pro104_siRNA#3:
accuauagugaccuuagug           (SEQ ID NO: 21)

Pro104_siRNA#4:
ccuauagugaccuuaguga           (SEQ ID NO: 22)

Pro104_siRNA#5:
uucacccuaugacauugcc           (SEQ ID NO: 23)

Pro104_siRNA#6:
gcugucugcaccugucacc           (SEQ ID NO: 24)

Pro104_siRNA#7:
ccggacagacugcugggug           (SEQ ID NO: 25)

Pro104_siRNA#8:
agaggaugaggcacugcca           (SEQ ID NO: 26)

Pro104_siRNA#9:
guucaggucgccaucauaa           (SEQ ID NO: 27)

Pro104_siRNA#10:
ggacaucuuuggagacaug           (SEQ ID NO: 28)

Pro104_siRNA#11:
caagaauggacugugggau           (SEQ ID NO: 29)

Pro104_siRNA#12:
gaauggacugugguaucag           (SEQ ID NO: 30)

Pro104_siRNA#13:
uggacugugguaucagauu           (SEQ ID NO: 31)

Pro104_siRNA#14:
ucggccggugucuacacc            (SEQ ID NO: 32)

Pro104_siRNA#15:
uaucagccaccacuuugag           (SEQ ID NO: 33)

Pro104_siRNA#16:
gucaggcccugguucucuu           (SEQ ID NO: 34)

Pro104_siRNA#17:
uaaacacauuccaguugau           (SEQ ID NO: 35)

Pro104_siRNA#18:
uaaacacauuccaguugau           (SEQ ID NO: 36)

Pro104_siRNA#19:
acacauuccaguugaugcc           (SEQ ID NO: 37)

Pro104_siRNA#20:
cacauuccaguugaugccu           (SEQ ID NO: 38)
```

Transfection with siRNA Oligonucleotides

HeLa ($4\times10^4$ cells) and CaOV3 ($6\times10^4$ cells) cells expressing Pro104 were seeded in 12-well plates for 18-24 hours prior to transfection. Transient transfection was carried out using Oligofectamine reagent (Invitrogen Life Technologies, Carlsbad, Calif.) according to the manufacturer's protocol. A final concentration of 100 nM siRNA (except DAXX siRNA which was 200 nM) and 1.5 ul Oligofectamine were used per well of cells. Pro104, Scrambled, DAXX and Emerin siRNA's were transfected in triplicate for all experiments. Parallel wells of cells were evaluated 72 hours after transfection for changes in mRNA levels by quantitative real-time RT-PCR (QPCR), changes in protein levels by Western immunoblot and changes in apoptosis by two different assay systems (see below). All findings were confirmed with at least 2 additional experiments.

Example 8

SDS-PAGE and Western Immunoblot Analysis 72 hrs after transfection with siRNA, cell extracts were prepared on ice using modified RIPA buffer (1% NP40, 10 mM $Na_2PO_4$, 0.15M NaCl) plus a protease inhibitor cocktail (Roche Inc.). Between 20 and 50 ug of protein extract were used for each gel lane; protein equivalent concentrations were evaluated for protein level comparisons on the same gel. Clarified extracts were mixed with an equal volume of 2× concentrated Laemmli sample buffer (Invitrogen Life Technologies, Carlsbad, Calif.), heated to 70° C. for 10 minutes and then analyzed using pre-cast 4-12% SDS-polyacrylamide minigels (Nupage; Invitrogen Life Technologies, Carlsbad, Calif.) with MES running buffer (Nupage; Invitrogen Life Technologies, Carlsbad, Calif.). Gels were transferred to Immobilon-P PVDF membranes with a 0.45 µm pore size (Invitrogen Life Technologies, Carlsbad, Calif.) using 1× Nupage transfer buffer plus 10% Methanol. The membranes were rinsed and blocked for 1 hour at room temperature using 5% nonfat dry milk in PBS with 0.05% Tween-20. Membranes were incubated with primary antibody overnight in 5% nonfat dry milk in PBS with 0.05% Tween-20. A mouse monoclonal antibody directed against Pro104 was produced in house using recombinant bacterial Pro104 protein. The Pro104 monoclonal antibody was diluted 1:1000 for a final concentration of 1 ug/ml and a mouse monoclonal antibody against GAPDH (Chemicon Inc., Temecula, Calif.) was diluted 1:5000 (for a final concentration of 0.2 ug/ml). Following primary antibody incubation, membranes were washed four times at room temperature for 10 min. each in 1×PBS with 0.05% Tween-20. Horseradish peroxidase linked goat anti-mouse immunoglobulin (Jackson Lab Inc., Bar Harbor, Me.) was used (1:10,000 dilution) in 5% nonfat dry milk in PBS plus 0.05% Tween-20 for 1 hour at room temperature to detect the primary monoclonal antibody. Membranes were finally washed four times for 10 min. in 1×PBS plus 0.05% Tween-20 followed by detection using enhanced chemiluminescence (ECL) reagent per manufacturer's directions (Amersham, Piscataway, N.J.) and exposure to X-ray film (Kodak, Rochester, N.Y.). For the Western immunoblot experiment comparing RK3E cells infected with an AP (alkaline phosphatase)-expressing retrovirus with the same cells infected with a Pro104-expressing retrovirus, cells were plated in growth medium containing either 1% or 10% FBS for 48 hours. Cell extracts were prepared using modified RIPA buffer including a phosphatase inhibitor cocktail (Calbiochem) and 25 ug of clarified extract were evaluated by SDS-PAGE and Western immunoblot with a polyclonal antibody specific for the phosphorylated EGF receptor (BioSource International, Camarillo, Calif.).

Figure 22:
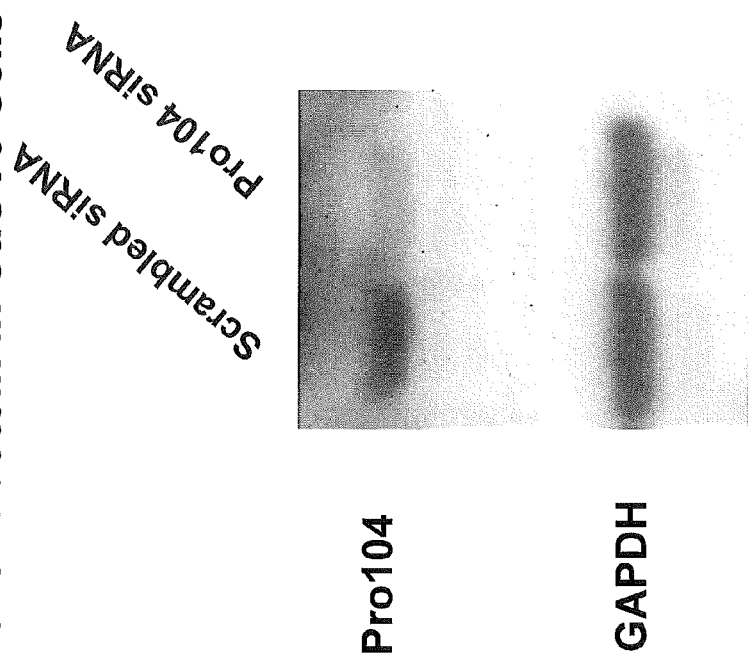
FIG. 22 shows siRNA mediates down-regulation of Pro104 protein in CaOV3 cells.

Effects of Pro104 specific siRNA on Pro104 protein was determined by western immunoblot. FIG. 21 shows siRNA Mediates Specific Down-Regulation of Pro104 Protein in HeLa Cells. A 60% knockdown ($\Delta$CT=1.3) of Pro104 protein was observed. These results were not confined to a single cell type. FIG. 22 shows siRNA Mediates Specific Down-Regulation of Pro104 Protein in CaOV3 Cells. A 55% knockdown ($\Delta$CT=1.2) of Pro104 protein was observed.

Example 9

Quantitative Real Time RT-PCR (QPCR)

A QuantiTech SYBR Green RT-PCR kit from Qiagen Inc. was used for QPCR evaluation. The final reaction volume was 20 ul, including 10 ul RT-PCR Master Mix, 2 ul forward primer (5 uM), 2 ul reverse primer (5 uM), QuantiTect RT mix 0.2 ul and RNase-free water. Between 20 and 40 ng of template RNA was used per reaction. QPCR was performed using a Taqman 7700 Sequence Detection system (Applied Biosystem Inc.) with the following cycle conditions: 50° C. for 30 min., 95° C. for 15 min., 40 cycles at 94° C. for 15 s, 55° C. for 30 s, 72° C. for 30 s, then held at 72° C. for 2 min.

The QPCR assay was used to determine the effect of Pro104 siRNA on gene transcription levels.

QPCR assays demonstrated Pro104 siRNA specifically knockdown Pro104 mRNA in CaOV3 cells. FIG. 23A shows that Pro104 siRNA do not knockdown non-Pro104 mRNA (GAPDH) compared to negative controls in CaOV3 cells. FIG. 23B demonstrates Pro104 siRNA knockdown Pro104 mRNA compared to negative controls in CaOV3 cells.

Specificity of Pro104 siRNA was not limited by cell type. QPCR assays further demonstrated Pro104 siRNA specifically knockdown Pro104 mRNA in HeLa cells. FIG. 24A shows that Pro104 siRNA do not knockdown non-Pro104 mRNA (GAPDH) compared to negative controls in HeLa cells. FIG. 24B demonstrates Pro104 siRNA knockdown Pro104 mRNA compared to negative controls in HeLa cells. A 75% knockdown ($\Delta$CT=2) of Pro104 was observed in HeLa cells.

Figure 25:
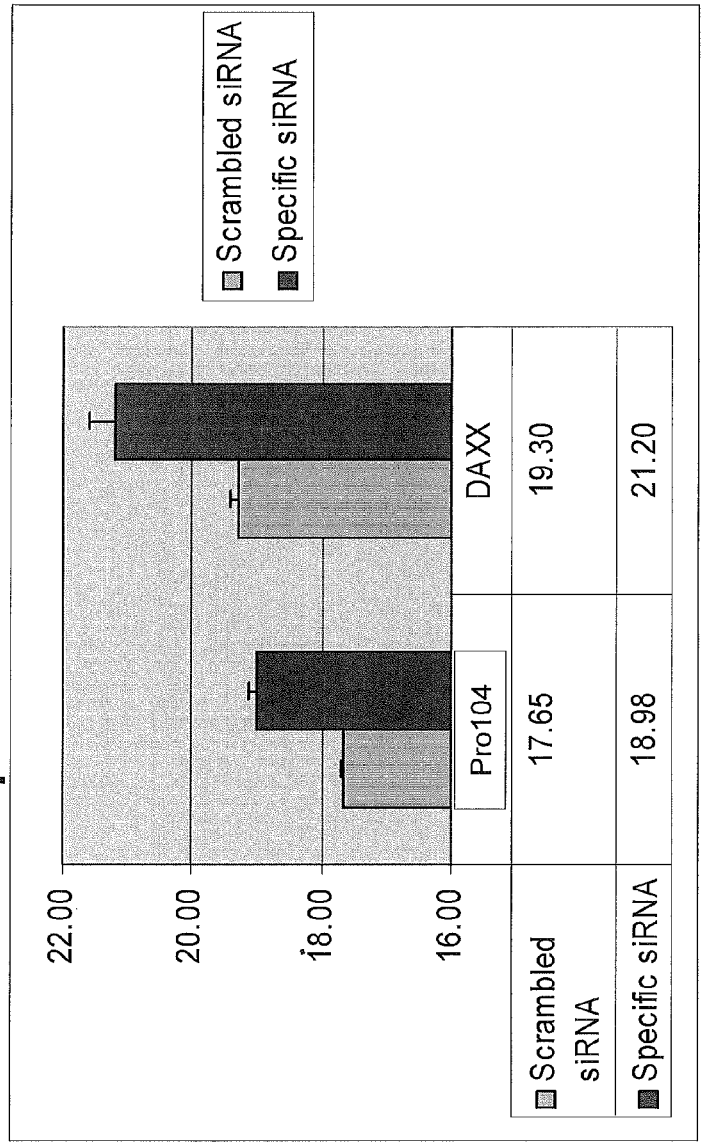
FIG. 25 shows Pro104 siRNA specific knockdown of Pro104 mRNA in HeLa cells, compared to a positive control.

Knockdown of essential mRNA such as DAXX leads to apoptosis induction. Michaelson 2002 supra; Olichen 2002, supra. QPCR experiments demonstrated that knockdown of Pro104 mRNA may lead to apoptosis induction as well. FIG. 25 shows Pro104 siRNA knockdown of Pro104 mRNA in HeLa cells compared to a positive control for apoptosis induction (DAXX).

Furthermore, QPCR assays confirmed that different Pro104 siRNA knockdown Pro104 mRNA in HeLa cells. FIG. 26B demonstrates that Pro104 siRNAs #56 (SEQ ID NO: 10), #79 (SEQ ID NO: 11), #80 (SEQ ID NO: 12) and #81 (SEQ ID NO: 13) knockdown Pro104 mRNA compared to the negative control (scrambled siRNA). Knockdown of Pro104 mRNA by four different siRNA specifically designed for Pro104 mRNA is indicative that siRNA designed to interfere with Pro104 mRNA may knockdown Pro104 mRNA and protein expression.

Example 10

Apoptosis Assays

Two different assay kits, Annexin V assay and Caspase assay, were used to evaluate the effects of siRNA on apoptosis.

With the "Apo-ONE Homogeneous Caspase-3/7 Assay" kit (Promega Inc., Madison, Wis.) the test cells were solubilized directly in the culture plate and caspase activity, reflected as a fluorescent readout, was measured according to supplier's instructions.

With the second kit, "Guava Nexin V-PE Kit" (Guava Technologies Inc.), treated cells were harvested by trypsinization and washing and approximately $10^5$ cells were resuspended in 40 ul provided buffer and 5 ul each Annexin V (+) and 7-AAD(−) were added. Following 20 minutes incubation on ice, cells were analyzed using the Guava PCA machine according to manufacturer's instructions.

Annexin V assay results demonstrates that different Pro104 siRNA which knockdown Pro104 mRNA induces apoptosis. FIG. 26A shows that Pro104 siRNAs #56 (SEQ ID NO: 10), #79 (SEQ ID NO: 11), #80 (SEQ ID NO: 12) and #81 (SEQ ID NO: 13) or DAXX siRNA induce apoptosis compared to scrambled siRNA (negative control) in HeLa cells.

Annexin V assay results also demonstrate specific knockdown of Pro104 mRNA with Pro104 siRNA induces cell death. FIG. 27A shows a greater percentage of HeLa cells are early apoptotic when transfected with Pro104 siRNA compared to negative controls (no siRNA, and scrambled siRNA). Additionally, FIG. 27B shows a greater percentage of HeLa cells are necrotic when transfected with Pro104 siRNA compared to negative controls (no siRNA, and scrambled siRNA).

Induction of apoptosis by knockdown of Pro104 mRNA by Pro104 siRNA was demonstrated by the Anexin V assay, and the Caspase assay. Results of Annexin V assay in FIG. 28A show a greater percentage HeLa cells are apoptotic when transfected with Pro104 siRNA, or DAXX siRNA (positive control) compared to scrambled siRNA (negative control). Results of Caspase assay in FIG. 28B show a greater percentage HeLa cells are apoptotic when transfected with Pro104 siRNA, or DAXX siRNA (positive control) compared to scrambled siRNA (negative control).

Figure 29:
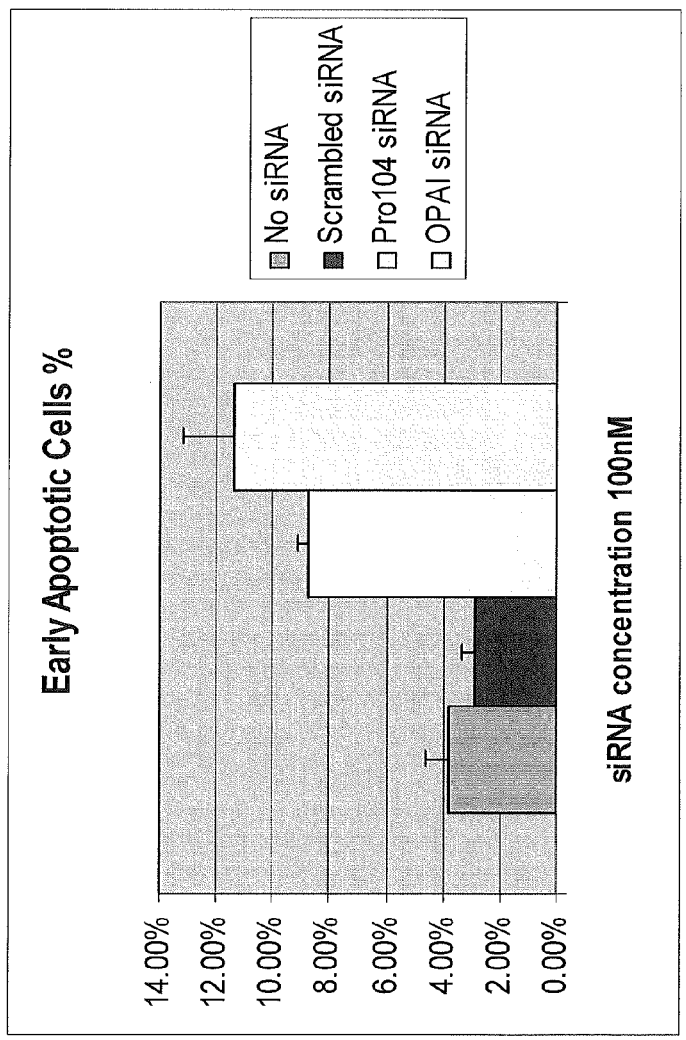
FIG. 29 shows specific knockdown of Pro104 mRNA in CaOV3 Cells inducing apoptosis.

Induction of apoptosis by Pro104 mRNA knockdown by Pro104 siRNA was not limited by cell type. Results of Annexin V assay in FIG. 29 show a greater percentage CaOV3 cells also are apoptotic when transfected with Pro104 siRNA, or OPAI siRNA (positive control) compared to scrambled siRNA (negative control) and no siRNA (negative control).

Induction of apoptosis by knockdown of Pro104 mRNA is due loss of Pro104 function. Pro104 siRNA does not induce apoptosis in cells that do not express Pro104. FIG. 30A demonstrates knockdown levels of Pro104 mRNA, Emerin mRNA (positive control, non-essential) and DAXX mRNA (positive control, essential) in SKBR3 cells which do not express Pro104 mRNA. There is no difference between knockdown levels of Pro104 mRNA due to scrambled siRNA and Pro104 specific siRNA while Emerin and DAXX mRNA levels are knocked-down, 50% and 65% respectively, by specific siRNA compared to scrambled siRNA.

Results from a Caspase assay in FIG. 30B demonstrate that SKBR3 cells which do not express Pro104 mRNA do not undergo apoptosis when transfected with Pro104 siRNA while apoptosis is induced by transfection by DAXX siRNA (positive control). Furthermore, SKBR3 cells which do not express Pro104 mRNA do not undergo apoptosis when transfected with Emerin siRNA (non-essential) or scrambled siRNA (negative control).

Results from FIGS. 30A and 30B serve as a negative control to show Pro104 siRNA transfection induces apoptosis by specifically knockdown of Pro104 mRNA and down-regulation of Pro104 protein.

Furthermore, Pro104 is shown to be essential to cell survival. FIGS. 30A and 30B demonstrate that knockdown of non-essential mRNA (Emerin) does not induce apoptosis compared to scrambled siRNA (negative control). Only knockdown of essential mRNA such as DAXX (positive control) and Pro104 will induce apoptosis.

Example 11

Soft Agar Assay

Soft agar assays were conducted using 6-well plates (Corning, VWR). The 2 ml bottom agar base layer consisted of 0.8% agar, 10% FBS in Iscove's medium (Invitrogen Life Technologies, Carlsbad, Calif.). Trypsinized cells were suspended in 0.4% agar, 10% FBS in Iscove's medium and applied in a 5 ml final volume on top of the solidified base layer. Three different viable cell numbers, $10^5$, $10^4$ and $5 \times 10^3$ cells, were seeded in agar per 6 cm well in duplicate. A final 2 ml layer consisting of 0.8% agar, 10% FBS in Iscove's medium was applied on top of the solidified cell layer. The agar plates were then incubated in a humidified 37° C. incubator with 5% $CO_2$ for approximately 2 weeks before colonies appeared. The soft agar was maintained by weekly feedings with growth medium. Colonies were counted between 2 and 4 weeks. 24 to 36 hours after siRNA transfection, HeLa cells were trypsinized and plated in soft agar at a density of $10^4$ cells per well as described above.

Soft agar assays were conducted to evaluate the effects of over-expression of Pro104, Pro104 protease activity and knockdown of Pro104 on cells.

FIG. 31 demonstrates that over expression of Pro104 induces cell growth in soft agar. Table 8 below shows the number of colonies observed in soft agar plates for each cell type in FIG. 31.

TABLE 8

Number of Colonies in Soft Agar Plates

| FIG. | Cell Type | Number of Colonies |
|---|---|---|
| 31A | RK3E-AP | 0 |
| 31B | RK3E-Pro104 | 60 |

TABLE 8-continued

Number of Colonies in Soft Agar Plates

| FIG. | Cell Type | Number of Colonies |
|---|---|---|
| 31C | RK3E-Pro104-HA | 68 |
| 31D | NCIH522 (− control) | 0 |
| 31E | HCT116 (+ control) | >200 |

Pro104 Protease Activity is Required for Cell Growth

RK3E cells were infected with retrovirus vectors expressing wild-type Pro104 protein (Pro104), with and without a C-terminal hemagglutinin tag (HA). Additionally, RK3E cells were infected with retrovirus vectors expressing Pro104 protein lacking enzymatic activity with a point mutation within the catalytic triad (Pro104-mut) or Alkaline Phosphatase (AP-control). Retroviral infection was followed by G418 selection for infected cells.

Expression of Pro104 proteins in the G418-selected cell pools was verified by immunoblot with a monoclonal antibody directed against Pro104, FIG. 32A. Expression of AP in the G418-selected cells was evaluated by staining cell monolayers for AP activity which showed that essentially all of the cells were positive (FIG. 32B) and, therefore, most of the G418-selected cells were expressing the gene of interest. The virus-infected, selected cells were then plated in soft agar and monitored for colony formation. The parental RK3E cells did not form any colonies under the conditions used for the assay nor did the AP-expressing cells (FIG. 32C, 32D). However, cells expressing either HA-tagged (Pro104-HA) or untagged Pro104 protein formed colonies demonstrating that ectopic expression of the protein can promote transformation (FIG. 32C, 32D). The mutant Pro104 (Pro104-mut) protein was unable to induce soft agar growth of RK3E cells (FIG. 32C, 32D) indicating that the catalytic function of Pro104 is required for transformation.

Knockdown of Pro104 mRNA by siRNA Inhibits Cell Growth

As shown above, specific knockdown of Pro104 mRNA and protein in Hela cells led to an increase in apoptosis, measured by two different methods. We next examined whether knockdown of Pro104 could affect the ability of HeLa cells to form colonies in soft agar. HeLa cells were treated with scrambled, Pro104- or DAXX-specific siRNA and subsequently plated in soft agar to evaluate colony formation. Scrambled siRNA served as a negative control while DAXX-specific siRNA served as positive control for inducing apoptosis. HeLa cells form numerous large colonies in agar and this was not affected by the scrambled siRNA as demonstrated in FIGS. 33C and 33F. In contrast, both Pro104- and DAXX-specific siRNA's inhibited the number of colonies formed by approximately 88% and 80%, respectively (FIGS. 33A and 33B, respectively). Furthermore, the size and morphology of colonies formed by cells treated with Pro104- and DAXX-specific siRNAs was smaller and restricted (FIGS. 33D and 33E, respectively).

QPCR performed after transfection with siRNA showed that the Pro104, DAXX and Emerin mRNA levels were decreased compared to transfection with scrambled siRNA (FIG. 34A). In this experiment the Pro104 and DAXX siRNA's were again able to induce caspase activity whereas the scrambled and Emerin-specific siRNA did not (FIG. 34B). A siRNA against emerin had no effect on the ability of the Hela cells to form colonies.

Results

Figure 33:
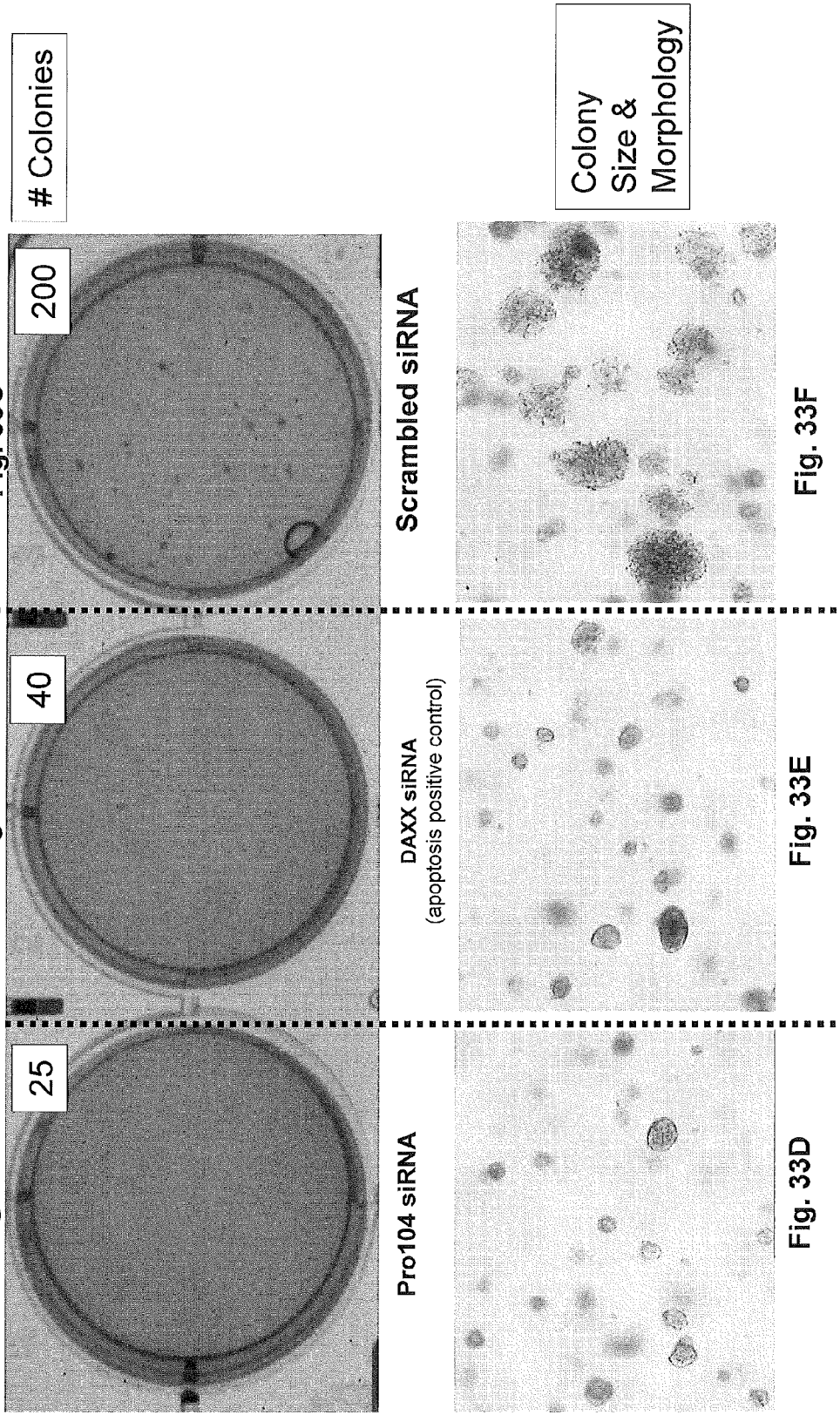
FIG. 33 shows knockdown of Pro104 mRNA (FIG. 33A and FIG. 33D), positive control DAXX mRNA (FIG. 33B and FIG. 33E) and scrambled siRNA (FIG. 33C and FIG. 33F) by siRNA inhibiting growth of HeLa cells in soft agar.

These assays confirm that Pro104 is essential to cell survival and over-expression induces cell growth (FIG. 31). Knockdown of Pro104 mRNA by siRNA (FIGS. 23-26) reduces protein expression (FIGS. 21, 22) which induces apoptosis (FIGS. 27-30). This in turn results in fewer colonies and colony size and morphology indicative of apoptosis in soft agar (FIG. 33). Mutated Pro104 lacking protease activity does not induce cell growth confirming Pro104 activity is essential for cell growth (FIG. 32).

Example 12

Tumor Xenograft Experiment

To further evaluate the transforming ability of Pro104, RK3E cells expressing Pro104 or AP were implanted subcutaneously into Nude or SCID/Beige mice and tumor formation was monitored.

Increased Growth of Ovarian Tumor Cells Over-Expressing Pro104 in Nude Mice

Retrovirus-infected, G418-selected pools of SKOV3 or RK3E cells expressing either AP or Pro104 were injected subcutaneously into nude mice. Parental SKOV3 cells were also used for comparison. For SKOV3 cells, $10^7$ of each type were implanted with matrigel into each of 6 mice. For RK3E cells, $5 \times 10^6$ cells were implanted into each of 8 mice without matrigel. Tumor formation was monitored by palpation and caliper measurement where possible every 4 days for a period of 4 weeks.

An animal model demonstrated growth of human ovarian tumor cells over-expressing Pro104. SKOV3 cells over-expressing Pro104 increased in volume compared to Parental SKOV3 cells (control) or AP expressing SKOV3 cells (non-growth inducing control).

Additionally, table 9 below shows over-expression of Pro104 promotes tumor formation in subcutaneous cell xenografts in nude mice.

TABLE 9

Tumor formation in subcutaneous cell xenografts.
RK3E Cell Line

| $5 \times 10^6$ cells implanted | # mice with nodules* or tumor** by 4 weeks |
|---|---|
| AP (negative control) | 0/8 |
| Pro104 | 8/8* |
| V-Ras (positive control) | 8/8** |

These animal models demonstrate that Pro104 overexpressing cells grow and form nodules.

Increased Growth of Ovarian Tumor Cells Over-Expressing Pro104 in SCID Mice

Retrovirus-infected, G418-selected pools of SKOV3 or RK3E cells expressing either AP or Pro104 were injected subcutaneously into SCID/Beige mice (Charles River Laboratories). Nine or ten mice were used per group as indicated. For SKOV3 cells, $10^7$ cells in 100 ul PBS were implanted with matrigel and for RK3E cells, $5 \times 10^6$ cells in PBS were implanted without using matrigel. Tumor formation was monitored by palpation and caliper measurement and tumor volume was calculated using the formula: (length×width$^2$)/2. The graphs shown in FIGS. 36A and 36C plot mean group tumor volume over time. All animal experiments were performed in complete compliance with institutional guidelines.

For the SKOV3 xenograft studies a single factor ANOVA was performed to test whether on the last day of measurement the tumor volumes between control and Pro104 groups differed. The results indicated a >99.0% probability that the two groups do not have the same tumor volume. Furthermore, Pairwise Two-Sample t-Tests Assuming Unequal Variances with Bonferroni Correction analysis were performed comparing the SKOV3-testisin tumors to the SKOV3-control tumors. Analysis of data from the last day of measurement revealed that the SKOV3-Pro104 tumors had significantly larger volumes than SKOV3-control tumors at a 99.0% confidence level.

KR3E-Pro104 Tumor Cell Growth

Nine out of nine mice implanted with Pro104 expressing RK3E cells developed large tumors whereas none of the mice implanted with AP-expressing cells formed tumors (FIG. 35A). At the conclusion of the xenograft study tumors were harvested and evaluated by immunoblot for the presence of Pro104 protein. The tumors maintained expression of Pro104 protein at a level similar to that observed in the infected RK3E cells prior to implantation (FIG. 35B).

SKOV3-Pro104 Tumor Cell Growth

We next evaluated the effect of ectopic Pro104 expression on tumor formation by the human SKOV3 ovarian cancer cell line which was chosen for this purpose since it does not express endogenous Pro104 mRNA nor Pro104 protein (evaluated by immunoblot-FIG. 35D). SKOV3 cells were infected with either a retrovirus expressing Pro104 or the AP control followed by G418-selection. Expression of Pro104 protein in the selected cells was verified by immunoblot (FIG. 35D). AP control and Pro104-expressing SKOV3 cells were implanted subcutaneously into SCID/Beige mice and monitored for tumor formation. SKOV3 cancer cells are known to form tumors as xenografts in mice. As expected, the AP control-expressing SKOV3 cells were also capable of growth as xenografts where 10 out of 10 mice implanted formed tumors (FIG. 35C). However, cells expressing ectopic Pro104 protein formed larger tumors throughout the time course when compared to the AP-control cells (FIG. 35C). Statistical analysis of the data showed that the increased size of SKOV3-Pro104 tumors compared to AP control-SKOV3 tumors was significant.

Example 13

Anti-Pro104 Molecules in Combination with Anti-Angiogenesis and Anti-Vascular Molecules Angiogenesis plays a critical role in many physiological processes, such as embryogenesis, wound healing, and menstruation and in certain pathological events, such as solid tumor growth and metastasis, arthritis, psoriasis, and diabetic retinopathy as described above.

Additionally, vascular targeting agents, which selectively destroy tumor blood vessels, may be attractive agents for the treatment of solid tumors. They differ from anti-angiogenic agents in that they target the mature, blood-conducting vessels of the tumors. They are better suited for larger tumors where angiogenesis can occur less frequently. Vascular targeting agents include antibodies which bind to specific targets or complexes. For application in man, target molecules are needed that are selectively expressed on the vascular endothelium of tumors.

In addition to targeting Pro104 to modulate growth of Pro104 expressing tumors, targeting of angiogenesis associated molecules or vascular associated molecules and complexes may be used to enhance anti-Pro104 therapies. Specifically, anti-Pro104 antibodies may be used in combination with antibodies which specifically target angiogenesis associated molecules or vascular associated molecules and complexes to slow, stop, regress, reverse or inhibit growth or metastasis of Pro104 expressing tumors.

See Feng D., et al. J Histochem Cytochem. 2000 April; 48(4):545-56; Brekken R A., et al. Cancer Res. 2000 Sep. 15; 60(18):5117-24; Brekken R A., et al., Anticancer Res. 2001 November-December; 21(6B):4221-9; and Brekken R A., et al., *Int J Cancer.* 2002 Jul. 10; 100(2):123-30.

Anti-Pro104 Antibodies in Combination with Anti-VEGF Antibodies

Vascular permeability factor/vascular endothelial growth factor (VPF/VEGF) is a potent multifunctional cytokine that permeabilizes vascular endothelium to plasma proteins and reprograms endothelial cell gene expression so as to induce angiogenesis. VPF/VEGF is secreted by many tumors and by activated macrophages, keratinocytes, synovial cells, various embryonic cells, and cultured epithelial and mesenchymal cell lines. There are at least five splice variants of VEGF, encoding proteins of 121, 145, 165, 189, and 206 amino acids. The smaller versions having 121, 145, or 165 amino acids are secreted from cells. Secreted VEGF is an obligate dimer of between Mr 38,000 and Mr 46,000 in which the monomers are linked by two disulfide bonds. The VEGF dimer binds to one of two well-characterized receptors, VEGFR1 (FLT-1) and VEGFR2 (KDR/Flk-1), that are selectively expressed on endothelial cells. A recently identified third cell surface protein, neuropilin-1, binds VEGF165 with high affinity. VPF/VEGF induces its biological effects by binding to these receptors which are selectively expressed in vascular endothelium.

Anti-Pro104 antibodies may be used in combination with anti-VEGF antibodies to slow, stop, regress, reverse or inhibit growth or metastasis of Pro104 expressing tumors.

Anti-Pro104 Antibodies in Combination with Anti-VEGF Receptor Antibodies

VEGFR1 and VEGFR2 are members of the type III receptor tyrosine kinase family that is characterized by seven extracellular IgG-like repeats, a single spanning transmembrane domain, and an intracellular split tyrosine kinase domain. Both receptors are strikingly upregulated in tumors, wounds, and in certain types of inflammation (e.g., rheumatoid arthritis, psoriasis) in which VPF/VEGF is overexpressed. The complex that forms between tumor-secreted VPF/VEGF and its receptors has been recognized as an attractive potential target for antiangiogenesis therapy. VEGF binds to VEGFR1 and VEGFR2 with high affinities having a Kd (dissociation constant) of 15-100 pM and 400-800 pM, respectively. VEGFR2 appears to be the dominant signaling receptor in VEGF-induced mitogenesis and permeability.

Expression of both VEGFR-1 and VEGFR-2 has been localized by in situ hybridization to microvascular endothelium of normal kidneys and to tumors, healing wounds, and inflammatory sites. VEGFR-2 has also been identified in the blood vessels of human placentas, breast cancers, and gastric carcinomas by light microscopic immunohistochemistry. See Anti-Pro104 antibodies may be used in combination with antibodies against VEGFR-1, VEGFR-2 or neuropilin-1, to slow, stop, regress, reverse or inhibit growth or metastasis of Pro104 expressing tumors.

Anti-Pro104 Antibodies in Combination with Anti-Vascular Targeting Antibodies

Vascular targeting antibodies specifically bind to vascular associated markers. Such markers include the complexes that are formed when vascular endothelial growth factor (VEGF) binds to its receptors (VEGFR). VEGF production by tumor cells is induced by oncogenic gene mutations and by the hypoxic conditions within the tumor mass. The receptors, VEGFR1 (FLT-1) and VEGFR2 (KDR/Flk-1), are upregulated on vascular endothelial cells in tumors by hypoxia and by the increased local concentration of VEGF. Consequently, there is a high concentration of occupied receptors on tumor vascular endothelium.

Vascular targeting with monoclonal antibodies that bind to VEGF: VEGFR complexes and their use as tumor vascular targeting agents are known to those of skill in the art. Antibodies which blocks VEGF from binding to VEGFR2 but not VEGFR1 might have dual activity as an anti-angiogenic agent by inhibiting VEGFR2 activity and as a vascular targeting agent for selective drug delivery to tumor vessels.

Anti-Pro104 antibodies may be used in combination with antibodies against VEGF:VEGFR complexes to slow, stop, regress, reverse or inhibit growth or metastasis of Pro104 expressing tumors. Examples of antibodies include but are not limited to anti-Pro104, Pro104.C1, Pro104.C4, Pro104.C13, Pro104.C17, Pro104.C18, Pro104.C19, Pro104.C24, Pro104.C25, Pro104.C27, Pro104.C34, Pro104.C37, Pro104.C46, Pro104.C48, Pro104.C49, Pro104.C50, Pro104.C53, Pro104.C54, Pro104.C55, Pro104.C57, Pro104.C60, Pro104.C66, Pro104.C75, Pro104.C84, Pro104.D4, Pro104.D6, Pro104.D9, Pro104.D12, Pro104.D14, Pro104.D18, Pro104.D19, Pro104.D20, Pro104.D21, Pro104.D26, Pro104.D29, Pro104.D31, Pro04.D43, Pro104.D47, Pro104.D51, Pro104.D55, Pro104.D56, Pro104.D58, Pro104.D62, Pro104.D63, Pro104.D64, Pro104.D68, Pro104.D69, Pro104.D75, Pro104.D81, Pro104.D85, Pro104.D88, Pro104.D91, Pro104.D94, Pro104.D102, Pro104.D106, Pro104.D111, Pro104.D112, Pro104.D113, Pro104.D114, Pro104.D115, Pro104.D116, Pro104.D117, Pro104.D118, Pro104.D119, Pro104.D120, Pro104.D121, Pro104.D122, Pro104.D123, Pro104.D, Pro104.D124, Pro104.D125, Pro104.D126, Pro104.D127, Pro104.D, Pro104.D128, Pro104.D129, Pro104.D130, Pro104.D131, Pro104.D132, Pro104.D133, Pro104.D134, Pro104.D135, Pro104.D136, Pro104.D137, Pro104.D138, Pro104.D139, Pro104.K14, Pro104.K15, Pro104.K16, Pro104.K47, Pro104.K71, Pro104.K72, Pro104.K74, Pro104.K75, Pro104.K76, Pro104.K78, Pro104.K81, Pro104.K87, Pro104.K88, Pro104.K89, Pro104.K155, Pro104.K156, Pro104.K157, Pro104.K158, Pro104.K159, Pro104.K160, Pro104.K163, Pro104.K164, Pro104.K176, Pro104.K217, Pro104.K226, Pro104.K227, Pro104.K240, Pro104.K274, Pro104.K264, Pro104.K281, Pro104.K358 or Pro104.K362; anti-VEGF, bevacizumab (Avastin; Genentech Inc., South San Francisco, Calif.; Rini et al. Clin Cancer Res. 2004 Apr. 15; 10(8):2584-6), infliximab (Canete et al. Arthritis Rheum. 2004 May; 50(5):1636-41, Klimiuk et al. Arch Immunol Ther Exp (Warsz). 2004 January-February; 52(1):36-42); anti-VEGF-R, vatalanib (Manley et al. Biochim Biophys Acta. 2004 Mar. 11; 1697(1-2):17-27); anti-VEGF-R2, DC101 (Tong et al. Cancer Res. 2004 Jun. 1; 64(11):3731-6, Kiessling et al. Neoplasia. 2004 May-June; 6(3):213-23); anti-VEGF-3, hF4-3C5 (Persaud et al. J Cell Sci. 2004 Jun. 1; 117(Pt 13): 2745-56). In addition, combination therapy for EGFR may be used e.g. anti-EGFR, cetuximab, C225 (Andre et al. Bull Cancer. 2004 January; 91(1):75-80), gefitinib, ZD1839 (Ciardiello et al. Clin Cancer Res. 2004 Jan. 15; 10(2):784-93).

Example 14

Deposit of Cell Lines and DNA

Hybridoma cell lines were deposited with the American Type Culture Collection (ATCC) located at 10801 University Boulevard, Manassas, Va. 20110-2209, U.S.A., and accorded accession numbers.

The following hybridoma cell lines were deposited with ATCC, Pro104.C55.1, Pro104.C25.1, Pro104.D9.1 and Pro104.K81.15. The names of the deposited hybridoma cell lines above may be shortened for convenience of reference. E.g. A01.1 corresponds to Pro104.A01.1. Additionally, the names of the deposited hybridoma cell lines may or may not contain the period punctuation mark separating "Pro104" from the hybridoma clone. E.g. Pro104 C55.1 corresponds to Pro104.C55.1. These hybridomas correspond to the clones (with their full names) deposited with the ATCC. Table 10 lists the hybridoma clone deposited with the ATCC, the accorded ATCC accession number, and the date of deposit.

TABLE 10

ATCC deposits

| Hybridoma | ATCC Accession No. | Deposit Date |
| --- | --- | --- |
| Pro104.C55.1 | PTA-5277 | 23 Jun. 2003 |
| Pro104.C25.1 | PTA-6076 | 15 Jun. 2004 |
| Pro104.D9.1 | PTA-6077 | 15 Jun. 2004 |
| Pro104.K81.15 | PTA-6078 | 15 Jun. 2004 |

These deposits were made under the provisions of the Budapest Treaty on the International Recognition of the Deposit of Microorganisms for the Purpose of Patent Procedure and the Regulations there under (Budapest Treaty). This assures maintenance of viable cultures for 30 years from the date of deposit. The organisms will be made available by ATCC under the terms of the Budapest Treaty, and subject to an agreement between diaDexus, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 3 7 CFR §1.14 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited strains are not to be construed as a license to practice the invention in contravention of the rights granted under the authority of any government in accordance with its patent laws. The making of these deposits is by no means an admission that deposits are required to enable the invention

We claim:

1. An isolated Pro104 specific siRNA, wherein the Pro104 specific siRNA is selected from the group comprising SEQ ID NO:11-14, SEQ ID NO:19-33 or SEQ ID NO: 37-38.

2. The Pro104 specific siRNA of claim 1 which knocksdown Pro104 mRNA.

3. The Pro104 specific siRNA of claim 1 which down regulates Pro104 protein expression.

4. The Pro104 specific siRNA of claim 1 which induces apoptosis.

5. The Pro104 specific siRNA of claim 1 further comprising two thymidine residues (dTdT) at the 3' end of the sequence.

6. An isolated Pro104 specific siRNA, wherein the Pro104 specific siRNA comprises a sequence selected from the group consisting of SEQ ID NO:11-14, SEQ ID NO:19-33 and SEQ ID NO: 37-38.

7. The Pro104 specific siRNA of claim 6 which knocksdown Pro104 mRNA.

8. The Pro104 specific siRNA of claim 6 which down regulates Pro104 protein expression.

9. The Pro104 specific siRNA of claim 6 which induces apoptosis.

10. The Pro104 specific siRNA of claim 6 further comprising two thymidine residues (dTdT) at the 3' end of the sequence.

11. An isolated Pro104 specific siRNA consisting of SEQ ID NO:34.

12. An isolated Pro104 specific siRNA consisting of SEQ ID NO:34 with two thymidine residues (dTdT) at the 3' end of the sequence.

* * * * *

UNITED STATES PATENT AND TRADEMARK OFFICE
CERTIFICATE OF CORRECTION

PATENT NO. : 8,080,650 B2
APPLICATION NO. : 12/354047
DATED : December 20, 2011
INVENTOR(S) : Jackie Papkoff It is certified that error appears in the above-identified patent and that said Letters Patent is hereby corrected as shown below:

At item (63), please delete "PCT/JP2004/020741"

At item (63), please insert --PCT/US2004/020741--

Signed and Sealed this
Twenty-fifth Day of December, 2012

David J. Kappos
*Director of the United States Patent and Trademark Office*

SEQUENCE LISTING

```
<160> NUMBER OF SEQ ID NOS: 38

<210> SEQ ID NO 1
<211> LENGTH: 288
<212> TYPE: PRT
<213> ORGANISM: Homo sapiens

<400> SEQUENCE: 1

Met Ala Lys Pro Glu Ser Gln Glu Ala Ala Pro Leu Ser Gly Pro Cys
1               5                   10                  15

Gly Arg Arg Val Ile Thr Ser Arg Ile Val Gly Gly Glu Asp Ala Glu
            20                  25                  30

Leu Gly Arg Trp Pro Trp Gln Gly Ser Leu Arg Leu Trp Asp Ser His
        35                  40                  45

Val Cys Gly Val Ser Leu Leu Ser His Arg Trp Ala Leu Thr Ala Ala
    50                  55                  60

His Cys Phe Glu Thr Tyr Ser Asp Leu Ser Asp Pro Ser Gly Trp Met
65                  70                  75                  80

Val Gln Phe Gly Gln Leu Thr Ser Met Pro Ser Phe Trp Ser Leu Gln
                85                  90                  95

Ala Tyr Tyr Thr Arg Tyr Phe Val Ser Asn Ile Tyr Leu Ser Pro Arg
            100                 105                 110

Tyr Leu Gly Asn Ser Pro Tyr Asp Ile Ala Leu Val Lys Leu Ser Ala
        115                 120                 125

Pro Val Thr Tyr Thr Lys His Ile Gln Pro Ile Cys Leu Gln Ala Ser
    130                 135                 140

Thr Phe Glu Phe Glu Asn Arg Thr Asp Cys Trp Val Thr Gly Trp Gly
145                 150                 155                 160

Tyr Ile Lys Glu Asp Glu Ala Leu Pro Ser Pro His Thr Leu Gln Glu
                165                 170                 175

Val Gln Val Ala Ile Ile Asn Asn Ser Met Cys Asn His Leu Phe Leu
            180                 185                 190
```

```
Lys Tyr Ser Phe Arg Lys Asp Ile Phe Gly Asp Met Val Cys Ala Gly
        195                 200                 205

Asn Ala Gln Gly Gly Lys Asp Ala Cys Phe Gly Asp Ser Gly Gly Pro
        210                 215                 220

Leu Ala Cys Asn Lys Asn Gly Leu Trp Tyr Gln Ile Gly Val Val Ser
225                 230                 235                 240

Trp Gly Val Gly Cys Gly Arg Pro Asn Arg Pro Gly Val Tyr Thr Asn
                245                 250                 255

Ile Ser His His Phe Glu Trp Ile Gln Lys Leu Met Ala Gln Ser Gly
            260                 265                 270

Met Ser Gln Pro Asp Pro Ser Trp Leu Glu His His His His His
        275                 280                 285
```

<210> SEQ ID NO 2
<211> LENGTH: 287
<212> TYPE: PRT
<213> ORGANISM: Homo sapiens

<400> SEQUENCE: 2

```
Met Lys Phe Leu Val Asn Val Ala Leu Val Phe Met Val Val Tyr Ile
1               5                   10                  15

Ser Tyr Ile Tyr Ala Asp Pro Met Ala Ile Val Gly Gly Glu Asp Ala
            20                  25                  30

Glu Leu Gly Arg Trp Pro Trp Gln Gly Ser Leu Arg Leu Trp Asp Ser
        35                  40                  45

His Val Cys Gly Val Ser Leu Leu Ser His Arg Trp Ala Leu Thr Ala
    50                  55                  60

Ala His Cys Phe Glu Thr Tyr Ser Asp Leu Ser Asp Pro Ser Gly Trp
65                  70                  75                  80

Met Val Gln Phe Gly Gln Leu Thr Ser Met Pro Ser Phe Trp Ser Leu
                85                  90                  95

Gln Ala Tyr Tyr Thr Arg Tyr Phe Val Ser Asn Ile Tyr Leu Ser Pro
            100                 105                 110

Arg Tyr Leu Gly Asn Ser Pro Tyr Asp Ile Ala Leu Val Lys Leu Ser
        115                 120                 125

Ala Pro Val Thr Tyr Thr Lys His Ile Gln Pro Ile Cys Leu Gln Ala
    130                 135                 140

Ser Thr Phe Glu Phe Glu Asn Arg Thr Asp Cys Trp Val Thr Gly Trp
145                 150                 155                 160

Gly Tyr Ile Lys Glu Asp Glu Ala Leu Pro Ser Pro His Thr Leu Gln
                165                 170                 175

Glu Val Gln Val Ala Ile Ile Asn Asn Ser Met Cys Asn His Leu Phe
            180                 185                 190

Leu Lys Tyr Ser Phe Arg Lys Asp Ile Phe Gly Asp Met Val Cys Ala
        195                 200                 205

Gly Asn Ala Gln Gly Gly Lys Asp Ala Cys Phe Gly Asp Ser Gly Gly
    210                 215                 220

Pro Leu Ala Cys Asn Lys Asn Gly Leu Trp Tyr Gln Ile Gly Val Val
225                 230                 235                 240

Ser Trp Gly Val Gly Cys Gly Arg Pro Asn Arg Pro Gly Val Tyr Thr
                245                 250                 255

Asn Ile Ser His His Phe Glu Trp Ile Gln Lys Leu Met Ala Gln Ser
            260                 265                 270

Gly Met Ser Gln Pro Asp Pro Ser Trp His His His His His
        275                 280                 285
```

```
<210> SEQ ID NO 3
<211> LENGTH: 340
<212> TYPE: PRT
<213> ORGANISM: Homo sapiens

<400> SEQUENCE: 3

Met Gly Ala Arg Gly Ala Leu Leu Ala Leu Leu Ala Arg Ala
1               5                   10                  15

Gly Leu Arg Lys Pro Glu Ser Gln Glu Ala Ala Pro Leu Ser Gly Pro
            20                  25                  30

Cys Gly Arg Arg Val Ile Thr Ser Arg Ile Val Gly Gly Glu Asp Ala
        35                  40                  45

Glu Leu Gly Arg Trp Pro Trp Gln Gly Ser Leu Arg Leu Trp Asp Ser
50                  55                  60

His Val Cys Gly Val Ser Leu Leu Ser His Arg Trp Ala Leu Thr Ala
65                  70                  75                  80

Ala His Cys Phe Glu Thr Tyr Ser Asp Leu Ser Asp Pro Ser Gly Trp
                85                  90                  95

Met Val Gln Phe Gly Gln Leu Thr Ser Met Pro Ser Phe Trp Ser Leu
            100                 105                 110

Gln Ala Tyr Tyr Thr Arg Tyr Phe Val Ser Asn Ile Tyr Leu Ser Pro
        115                 120                 125

Arg Tyr Leu Gly Asn Ser Pro Tyr Asp Ile Ala Leu Val Lys Leu Ser
130                 135                 140

Ala Pro Val Thr Tyr Thr Lys His Ile Gln Pro Ile Cys Leu Gln Ala
145                 150                 155                 160

Ser Thr Phe Glu Phe Glu Asn Arg Thr Asp Cys Trp Val Thr Gly Trp
                165                 170                 175

Gly Tyr Ile Lys Glu Asp Glu Ala Leu Pro Ser Pro His Thr Leu Gln
            180                 185                 190

Glu Val Gln Val Ala Ile Ile Asn Asn Ser Met Cys Asn His Leu Phe
        195                 200                 205

Leu Lys Tyr Ser Phe Arg Lys Asp Ile Phe Gly Asp Met Val Cys Ala
210                 215                 220

Gly Asn Ala Gln Gly Gly Lys Asp Ala Cys Phe Gly Asp Ser Gly Gly
225                 230                 235                 240

Pro Leu Ala Cys Asn Lys Asn Gly Leu Trp Tyr Gln Ile Gly Val Val
                245                 250                 255

Ser Trp Gly Val Gly Cys Gly Arg Pro Asn Arg Pro Gly Val Tyr Thr
            260                 265                 270

Asn Ile Ser His His Phe Glu Trp Ile Gln Lys Leu Met Ala Gln Ser
        275                 280                 285

Gly Met Ser Gln Pro Asp Pro Ser Trp Pro Leu Leu Phe Phe Pro Leu
290                 295                 300

Leu Trp Ala Leu Pro Leu Leu Gly Pro Val Asp Pro Ala Phe Leu Tyr
305                 310                 315                 320

Lys Val Val Arg Ser Arg Met Ala Ser Tyr Pro Tyr Asp Val Pro Asp
                325                 330                 335

Tyr Ala Ser Leu
            340

<210> SEQ ID NO 4
<211> LENGTH: 314
<212> TYPE: PRT
<213> ORGANISM: Homo sapiens
```

<400> SEQUENCE: 4

Met Gly Ala Arg Gly Ala Leu Leu Ala Leu Leu Ala Arg Ala
1               5                   10                  15

Gly Leu Arg Lys Pro Glu Ser Gln Glu Ala Ala Pro Leu Ser Gly Pro
            20                  25                  30

Cys Gly Arg Arg Val Ile Thr Ser Arg Ile Val Gly Gly Glu Asp Ala
        35                  40                  45

Glu Leu Gly Arg Trp Pro Trp Gln Gly Ser Leu Arg Leu Trp Asp Ser
    50                  55                  60

His Val Cys Gly Val Ser Leu Leu Ser His Arg Trp Ala Leu Thr Ala
65                  70                  75                  80

Ala His Cys Phe Glu Thr Tyr Ser Asp Leu Ser Asp Pro Ser Gly Trp
                85                  90                  95

Met Val Gln Phe Gly Gln Leu Thr Ser Met Pro Ser Phe Trp Ser Leu
            100                 105                 110

Gln Ala Tyr Tyr Thr Arg Tyr Phe Val Ser Asn Ile Tyr Leu Ser Pro
        115                 120                 125

Arg Tyr Leu Gly Asn Ser Pro Tyr Asp Ile Ala Leu Val Lys Leu Ser
130                 135                 140

Ala Pro Val Thr Tyr Thr Lys His Ile Gln Pro Ile Cys Leu Gln Ala
145                 150                 155                 160

Ser Thr Phe Glu Phe Glu Asn Arg Thr Asp Cys Trp Val Thr Gly Trp
                165                 170                 175

Gly Tyr Ile Lys Glu Asp Glu Ala Leu Pro Ser Pro His Thr Leu Gln
            180                 185                 190

Glu Val Gln Val Ala Ile Ile Asn Asn Ser Met Cys Asn His Leu Phe
        195                 200                 205

Leu Lys Tyr Ser Phe Arg Lys Asp Ile Phe Gly Asp Met Val Cys Ala
210                 215                 220

Gly Asn Ala Gln Gly Gly Lys Asp Ala Cys Phe Gly Asp Ser Gly Gly
225                 230                 235                 240

Pro Leu Ala Cys Asn Lys Asn Gly Leu Trp Tyr Gln Ile Gly Val Val
                245                 250                 255

Ser Trp Gly Val Gly Cys Gly Arg Pro Asn Arg Pro Gly Val Tyr Thr
            260                 265                 270

Asn Ile Ser His His Phe Glu Trp Ile Gln Lys Leu Met Ala Gln Ser
        275                 280                 285

Gly Met Ser Gln Pro Asp Pro Ser Trp Pro Leu Leu Phe Phe Pro Leu
    290                 295                 300

Leu Trp Ala Leu Pro Leu Leu Gly Pro Val
305                 310

<210> SEQ ID NO 5
<211> LENGTH: 486
<212> TYPE: PRT
<213> ORGANISM: Homo sapiens

<400> SEQUENCE: 5

Met Ala Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys

```
                50                    55                   60
Leu Thr Gln Ser Met Ala Ile Ile Arg Tyr Ile Ala Asp Lys His Asn
 65                  70                   75                   80

Met Leu Gly Gly Cys Pro Lys Glu Arg Ala Glu Ile Ser Met Leu Glu
                     85                   90                   95

Gly Ala Val Leu Asp Ile Arg Tyr Gly Val Ser Arg Ile Ala Tyr Ser
                    100                  105                  110

Lys Asp Phe Glu Thr Leu Lys Val Asp Phe Leu Ser Lys Leu Pro Glu
                115                  120                  125

Met Leu Lys Met Phe Glu Asp Arg Leu Cys His Lys Thr Tyr Leu Asn
130                  135                  140

Gly Asp His Val Thr His Pro Asp Phe Met Leu Tyr Asp Ala Leu Asp
145                  150                  155                  160

Val Val Leu Tyr Met Asp Pro Met Cys Leu Asp Ala Phe Pro Lys Leu
                    165                  170                  175

Val Cys Phe Lys Lys Arg Ile Glu Ala Ile Pro Gln Ile Asp Lys Tyr
                    180                  185                  190

Leu Lys Ser Ser Lys Tyr Ile Ala Trp Pro Leu Gln Gly Trp Gln Ala
                    195                  200                  205

Thr Phe Gly Gly Gly Asp His Pro Pro Lys Ser Asp Leu Val Pro Arg
210                  215                  220

His Asn Gln Thr Ser Leu Tyr Lys Lys Ala Gly Phe Glu Asn Leu Tyr
225                  230                  235                  240

Phe Gln Gly Val Val Gly Gly Glu Ala Ser Val Asp Ser Trp Pro
                    245                  250                  255

Trp Gln Val Ser Ile Gln Tyr Asp Lys Gln His Val Cys Gly Gly Ser
                    260                  265                  270

Ile Leu Asp Pro His Trp Val Leu Thr Ala Ala His Cys Phe Arg Lys
                    275                  280                  285

His Thr Asp Val Phe Asn Trp Lys Val Arg Ala Gly Ser Asp Lys Leu
                    290                  295                  300

Gly Ser Phe Pro Ser Leu Ala Val Ala Lys Ile Ile Ile Glu Phe
305                  310                  315                  320

Asn Pro Met Tyr Pro Lys Asp Asn Asp Ile Ala Leu Met Lys Leu Gln
                    325                  330                  335

Phe Pro Leu Thr Phe Ser Gly Thr Val Arg Pro Ile Cys Leu Pro Phe
                    340                  345                  350

Phe Asp Glu Glu Leu Thr Pro Ala Thr Pro Leu Trp Ile Ile Gly Trp
                    355                  360                  365

Gly Phe Thr Lys Gln Asn Gly Gly Lys Met Ser Asp Ile Leu Leu Gln
                    370                  375                  380

Ala Ser Val Gln Val Ile Asp Ser Thr Arg Cys Asn Ala Asp Asp Ala
385                  390                  395                  400

Tyr Gln Gly Glu Val Thr Glu Lys Met Met Cys Ala Gly Ile Pro Glu
                    405                  410                  415

Gly Gly Val Asp Thr Cys Gln Gly Asp Ser Gly Gly Pro Leu Met Tyr
                    420                  425                  430

Gln Ser Asp Gln Trp His Val Val Gly Ile Val Ser Trp Gly Tyr Gly
                    435                  440                  445

Cys Gly Gly Pro Ser Thr Pro Gly Val Tyr Thr Lys Val Ser Ala Tyr
                    450                  455                  460

Leu Asn Trp Ile Tyr Asn Val Trp Lys Ala Glu Leu Ser Asn Trp Ser
465                  470                  475                  480
```

His Pro Gln Phe Glu Lys
            485

<210> SEQ ID NO 6
<211> LENGTH: 391
<212> TYPE: PRT
<213> ORGANISM: Homo sapiens

<400> SEQUENCE: 6

Met Lys Val Ile Leu Asp Lys Tyr Tyr Phe Leu Cys Gly Gln Pro Leu
1               5                   10                  15

His Phe Ile Pro Arg Lys Gln Leu Cys Asp Gly Glu Leu Asp Cys Pro
            20                  25                  30

Leu Gly Glu Asp Glu His Cys Val Lys Ser Phe Pro Glu Gly Pro
        35                  40                  45

Ala Val Ala Val Arg Leu Ser Lys Asp Arg Ser Thr Leu Gln Val Leu
    50                  55                  60

Asp Ser Ala Thr Gly Asn Trp Phe Ser Ala Cys Phe Asn Phe Thr
65                  70                  75                  80

Glu Ala Leu Ala Glu Thr Ala Cys Arg Gln Met Gly Tyr Ser Ser Lys
                85                  90                  95

Pro Thr Phe Arg Ala Val Glu Ile Gly Pro Asp Gln Asp Leu Asp Val
            100                 105                 110

Val Glu Ile Thr Glu Asn Ser Gln Glu Leu Arg Met Arg Asn Ser Ser
        115                 120                 125

Gly Pro Cys Leu Ser Gly Ser Leu Val Ser Leu His Cys Leu Ala Cys
    130                 135                 140

Gly Lys Ser Leu Lys Thr Pro Arg Val Val Gly Gly Glu Glu Ala Ser
145                 150                 155                 160

Val Asp Ser Trp Pro Trp Gln Val Ser Ile Gln Tyr Asp Lys Gln His
                165                 170                 175

Val Cys Gly Gly Ser Ile Leu Asp Pro His Trp Val Leu Thr Ala Ala
            180                 185                 190

His Cys Phe Arg Lys His Thr Asp Val Phe Asn Trp Lys Val Arg Ala
        195                 200                 205

Gly Ser Asp Lys Leu Gly Ser Phe Pro Ser Leu Ala Val Ala Lys Ile
    210                 215                 220

Ile Ile Ile Glu Phe Asn Pro Met Tyr Pro Lys Asp Asn Asp Ile Ala
225                 230                 235                 240

Leu Met Lys Leu Gln Phe Pro Leu Thr Phe Ser Gly Thr Val Arg Pro
                245                 250                 255

Ile Cys Leu Pro Phe Phe Asp Glu Glu Leu Thr Pro Ala Thr Pro Leu
            260                 265                 270

Trp Ile Ile Gly Trp Gly Phe Thr Lys Gln Asn Gly Gly Lys Met Ser
        275                 280                 285

Asp Ile Leu Leu Gln Ala Ser Val Gln Val Ile Asp Ser Thr Arg Cys
    290                 295                 300

Asn Ala Asp Asp Ala Tyr Gln Gly Glu Val Thr Glu Lys Met Met Cys
305                 310                 315                 320

Ala Gly Ile Pro Glu Gly Gly Val Asp Thr Cys Gln Gly Asp Ser Gly
                325                 330                 335

Gly Pro Leu Met Tyr Gln Ser Asp Gln Trp His Val Val Gly Ile Val
            340                 345                 350

Ser Trp Gly Tyr Gly Cys Gly Gly Pro Ser Thr Pro Gly Val Tyr Thr
        355                 360                 365

Lys Val Ser Ala Tyr Leu Asn Trp Ile Tyr Asn Val Trp Lys Ala Glu
370                 375                 380

Leu His His His His His
385                 390

<210> SEQ ID NO 7
<211> LENGTH: 461
<212> TYPE: PRT
<213> ORGANISM: Homo sapiens

<400> SEQUENCE: 7

Met Asp Pro Asp Ser Asp Gln Pro Leu Asn Ser Leu Asp Val Lys Pro
1               5                   10                  15

Leu Arg Lys Pro Arg Ile Pro Met Glu Thr Phe Arg Lys Val Gly Ile
                20                  25                  30

Pro Ile Ile Ile Ala Leu Leu Ser Leu Ala Ser Ile Ile Val Val
            35                  40                  45

Val Leu Ile Lys Val Ile Leu Asp Lys Tyr Tyr Phe Leu Cys Gly Gln
    50                  55                  60

Pro Leu His Phe Ile Pro Arg Lys Gln Leu Cys Asp Gly Glu Leu Asp
65                  70                  75                  80

Cys Pro Leu Gly Glu Asp Glu His Cys Val Lys Ser Phe Pro Glu
                85                  90                  95

Gly Pro Ala Val Ala Val Arg Leu Ser Lys Asp Arg Ser Thr Leu Gln
            100                 105                 110

Val Leu Asp Ser Ala Thr Gly Asn Trp Phe Ser Ala Cys Phe Asp Asn
    115                 120                 125

Phe Thr Glu Ala Leu Ala Glu Thr Ala Cys Arg Gln Met Gly Tyr Ser
130                 135                 140

Ser Lys Pro Thr Phe Arg Ala Val Glu Ile Gly Pro Asp Gln Asp Leu
145                 150                 155                 160

Asp Val Val Glu Ile Thr Glu Asn Ser Gln Leu Arg Met Arg Asn
                165                 170                 175

Ser Ser Gly Pro Cys Leu Ser Gly Ser Leu Val Ser Leu His Cys Leu
            180                 185                 190

Ala Cys Gly Lys Ser Leu Lys Thr Pro Arg Val Val Gly Gly Glu Glu
    195                 200                 205

Ala Ser Val Asp Ser Trp Pro Trp Gln Val Ser Ile Gln Tyr Asp Lys
210                 215                 220

Gln His Val Cys Gly Gly Ser Ile Leu Asp Pro His Trp Val Leu Thr
225                 230                 235                 240

Ala Ala His Cys Phe Arg Lys His Thr Asp Val Phe Asn Trp Lys Val
                245                 250                 255

Arg Ala Gly Ser Asp Lys Leu Gly Ser Phe Pro Ser Leu Ala Val Ala
            260                 265                 270

Lys Ile Ile Ile Glu Phe Asn Pro Met Tyr Pro Lys Asp Asn Asp
    275                 280                 285

Ile Ala Leu Met Lys Leu Gln Phe Pro Leu Thr Phe Ser Gly Thr Val
290                 295                 300

Arg Pro Ile Cys Leu Pro Phe Phe Asp Glu Glu Leu Thr Pro Ala Thr
305                 310                 315                 320

Pro Leu Trp Ile Ile Gly Trp Gly Phe Thr Lys Gln Asn Gly Gly Lys
                325                 330                 335

Met Ser Asp Ile Leu Leu Gln Ala Ser Val Gln Val Ile Asp Ser Thr
            340                 345                 350

```
Arg Cys Asn Ala Asp Asp Ala Tyr Gln Gly Glu Val Thr Glu Lys Met
        355                 360                 365

Met Cys Ala Gly Ile Pro Glu Gly Gly Val Asp Thr Cys Gln Gly Asp
    370                 375                 380

Ser Gly Gly Pro Leu Met Tyr Gln Ser Asp Gln Trp His Val Val Gly
385                 390                 395                 400

Ile Val Ser Trp Gly Tyr Gly Cys Gly Gly Pro Ser Thr Pro Gly Val
                405                 410                 415

Tyr Thr Lys Val Ser Ala Tyr Leu Asn Trp Ile Tyr Asn Val Trp Lys
                420                 425                 430

Ala Glu Leu Asp Pro Ala Phe Leu Tyr Lys Val Val Arg Ser Arg Met
        435                 440                 445

Ala Ser Tyr Pro Tyr Asp Val Pro Asp Tyr Ala Ser Leu
    450                 455                 460

<210> SEQ ID NO 8
<211> LENGTH: 27
<212> TYPE: DNA
<213> ORGANISM: Artificial sequence
<220> FEATURE:
<223> OTHER INFORMATION: Synthetic

<400> SEQUENCE: 8
atgggcgcgc gcggggcgct gctgctg                                           27

<210> SEQ ID NO 9
<211> LENGTH: 33
<212> TYPE: DNA
<213> ORGANISM: Artificial sequence
<220> FEATURE:
<223> OTHER INFORMATION: Synthetic

<400> SEQUENCE: 9
ttatcagacc ggccccagga gtgggagagc cca                                    33

<210> SEQ ID NO 10
<211> LENGTH: 63
<212> TYPE: DNA
<213> ORGANISM: Artificial sequence
<220> FEATURE:
<223> OTHER INFORMATION: Synthetic

<400> SEQUENCE: 10
ttatcacgcg tagtccggca cgtcgtacgg gtagccgacc ggccccagga gtgggagagc       60
cca                                                                     63

<210> SEQ ID NO 11
<211> LENGTH: 19
<212> TYPE: RNA
<213> ORGANISM: Artificial sequence
<220> FEATURE:
<223> OTHER INFORMATION: Synthetic

<400> SEQUENCE: 11
cacauccagc ccaucuguc                                                    19

<210> SEQ ID NO 12
<211> LENGTH: 19
<212> TYPE: RNA
<213> ORGANISM: Artificial sequence
<220> FEATURE:
<223> OTHER INFORMATION: Synthetic

<400> SEQUENCE: 12
```
gaggaugagg cacugccau					19

<210> SEQ ID NO 13
<211> LENGTH: 19
<212> TYPE: RNA
<213> ORGANISM: Artificial sequence
<220> FEATURE:
<223> OTHER INFORMATION: Synthetic

<400> SEQUENCE: 13
cucuaugugc aaccaccuc					19

<210> SEQ ID NO 14
<211> LENGTH: 19
<212> TYPE: RNA
<213> ORGANISM: Artificial sequence
<220> FEATURE:
<223> OTHER INFORMATION: Synthetic

<400> SEQUENCE: 14
guacaguuuc cgcaaggac					19

<210> SEQ ID NO 15
<211> LENGTH: 19
<212> TYPE: RNA
<213> ORGANISM: Artificial sequence
<220> FEATURE:
<223> OTHER INFORMATION: Synthetic

<400> SEQUENCE: 15
uucuccgaac gugucacgu					19

<210> SEQ ID NO 16
<211> LENGTH: 19
<212> TYPE: RNA
<213> ORGANISM: Artificial sequence
<220> FEATURE:
<223> OTHER INFORMATION: Synthetic

<400> SEQUENCE: 16
ccgugcuccu ggggcuggg					19

<210> SEQ ID NO 17
<211> LENGTH: 19
<212> TYPE: RNA
<213> ORGANISM: Artificial sequence
<220> FEATURE:
<223> OTHER INFORMATION: Synthetic

<400> SEQUENCE: 17
ggaguuggau cucucagaa					19

<210> SEQ ID NO 18
<211> LENGTH: 19
<212> TYPE: RNA
<213> ORGANISM: Artificial sequence
<220> FEATURE:
<223> OTHER INFORMATION: Synthetic

<400> SEQUENCE: 18
guuaucaguc ugagccagg					19

<210> SEQ ID NO 19
<211> LENGTH: 19
<212> TYPE: RNA
<213> ORGANISM: Artificial sequence

```
<220> FEATURE:
<223> OTHER INFORMATION: Synthetic

<400> SEQUENCE: 19
gccggagucg caggaggcg                                                    19

<210> SEQ ID NO 20
<211> LENGTH: 19
<212> TYPE: RNA
<213> ORGANISM: Artificial sequence
<220> FEATURE:
<223> OTHER INFORMATION: Synthetic

<400> SEQUENCE: 20
cucgggcguu ggccguggc                                                    19

<210> SEQ ID NO 21
<211> LENGTH: 19
<212> TYPE: RNA
<213> ORGANISM: Artificial sequence
<220> FEATURE:
<223> OTHER INFORMATION: Synthetic

<400> SEQUENCE: 21
accuauagug accuuagug                                                    19

<210> SEQ ID NO 22
<211> LENGTH: 19
<212> TYPE: RNA
<213> ORGANISM: Artificial sequence
<220> FEATURE:
<223> OTHER INFORMATION: Synthetic

<400> SEQUENCE: 22
ccuauaguga ccuuaguga                                                    19

<210> SEQ ID NO 23
<211> LENGTH: 19
<212> TYPE: RNA
<213> ORGANISM: Artificial sequence
<220> FEATURE:
<223> OTHER INFORMATION: Synthetic

<400> SEQUENCE: 23
uucacccuau gacauugcc                                                    19

<210> SEQ ID NO 24
<211> LENGTH: 19
<212> TYPE: RNA
<213> ORGANISM: Artificial sequence
<220> FEATURE:
<223> OTHER INFORMATION: Synthetic

<400> SEQUENCE: 24
gcugucugca ccugucacc                                                    19

<210> SEQ ID NO 25
<211> LENGTH: 19
<212> TYPE: RNA
<213> ORGANISM: Artificial sequence
<220> FEATURE:
<223> OTHER INFORMATION: Synthetic

<400> SEQUENCE: 25
ccggacagac ugcugggug                                                    19
```

```
<210> SEQ ID NO 26
<211> LENGTH: 19
<212> TYPE: RNA
<213> ORGANISM: Artificial sequence
<220> FEATURE:
<223> OTHER INFORMATION: Synthetic

<400> SEQUENCE: 26
agaggaugag gcacugcca                                               19

<210> SEQ ID NO 27
<211> LENGTH: 19
<212> TYPE: RNA
<213> ORGANISM: Artificial sequence
<220> FEATURE:
<223> OTHER INFORMATION: Synthetic

<400> SEQUENCE: 27
guucaggucg ccaucauaa                                               19

<210> SEQ ID NO 28
<211> LENGTH: 19
<212> TYPE: RNA
<213> ORGANISM: Artificial sequence
<220> FEATURE:
<223> OTHER INFORMATION: Synthetic

<400> SEQUENCE: 28
ggacaucuuu ggagacaug                                               19

<210> SEQ ID NO 29
<211> LENGTH: 19
<212> TYPE: RNA
<213> ORGANISM: Artificial sequence
<220> FEATURE:
<223> OTHER INFORMATION: Synthetic

<400> SEQUENCE: 29
caagaaugga cugugguau                                               19

<210> SEQ ID NO 30
<211> LENGTH: 19
<212> TYPE: RNA
<213> ORGANISM: Artificial sequence
<220> FEATURE:
<223> OTHER INFORMATION: Synthetic

<400> SEQUENCE: 30
gaauggacug ugguaucag                                               19

<210> SEQ ID NO 31
<211> LENGTH: 19
<212> TYPE: RNA
<213> ORGANISM: Artificial sequence
<220> FEATURE:
<223> OTHER INFORMATION: Synthetic

<400> SEQUENCE: 31
uggacugugg uaucagauu                                               19

<210> SEQ ID NO 32
<211> LENGTH: 19
<212> TYPE: RNA
<213> ORGANISM: Artificial sequence
<220> FEATURE:
<223> OTHER INFORMATION: Synthetic

<400> SEQUENCE: 32
```
ucggcccggu gucuacacc                                                19

<210> SEQ ID NO 33
<211> LENGTH: 19
<212> TYPE: RNA
<213> ORGANISM: Artificial sequence
<220> FEATURE:
<223> OTHER INFORMATION: Synthetic

<400> SEQUENCE: 33
uaucagccac cacuuugag                                                19

<210> SEQ ID NO 34
<211> LENGTH: 19
<212> TYPE: RNA
<213> ORGANISM: Artificial sequence
<220> FEATURE:
<223> OTHER INFORMATION: Synthetic

<400> SEQUENCE: 34
gucaggcccu gguucucuu                                                19

<210> SEQ ID NO 35
<211> LENGTH: 19
<212> TYPE: RNA
<213> ORGANISM: Artificial sequence
<220> FEATURE:
<223> OTHER INFORMATION: Synthetic

<400> SEQUENCE: 35
uaaacacauu ccaguugau                                                19

<210> SEQ ID NO 36
<211> LENGTH: 19
<212> TYPE: RNA
<213> ORGANISM: Artificial sequence
<220> FEATURE:
<223> OTHER INFORMATION: Synthetic

<400> SEQUENCE: 36
uaaacacauu ccaguugau                                                19

<210> SEQ ID NO 37
<211> LENGTH: 19
<212> TYPE: RNA
<213> ORGANISM: Artificial sequence
<220> FEATURE:
<223> OTHER INFORMATION: Synthetic

<400> SEQUENCE: 37
acacauucca guugaugcc                                                19

<210> SEQ ID NO 38
<211> LENGTH: 19
<212> TYPE: RNA
<213> ORGANISM: Artificial sequence
<220> FEATURE:
<223> OTHER INFORMATION: Synthetic

<400> SEQUENCE: 38
cacauuccag uugaugccu                                                19